US012686726B2

(12) United States Patent
Ostertag et al.

(10) Patent No.: US 12,686,726 B2
(45) Date of Patent: Jul. 21, 2026

(54) ANTI-MUC1 COMPOSITIONS AND METHODS OF USE

(71) Applicant: Poseida Therapeutics, Inc., San Diego, CA (US)

(72) Inventors: Eric M. Ostertag, San Diego, CA (US); Devon Shedlock, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 990 days.

(21) Appl. No.: 17/785,825

(22) PCT Filed: Dec. 18, 2020

(86) PCT No.: PCT/US2020/066121
§ 371 (c)(1),
(2) Date: Jun. 15, 2022

(87) PCT Pub. No.: WO2021/127505
PCT Pub. Date: Jun. 24, 2021

(65) Prior Publication Data
US 2023/0079955 A1     Mar. 16, 2023

Related U.S. Application Data

(60) Provisional application No. 62/951,257, filed on Dec. 20, 2019.

(51) Int. Cl.
| | |
|---|---|
| *C07K 16/30* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 5/0783* | (2010.01) |
| *C12N 15/62* | (2006.01) |
| *A61K 38/00* | (2006.01) |

(52) U.S. Cl.
CPC .......... *C07K 16/3092* (2013.01); *A61K 40/11* (2025.01); *A61K 40/31* (2025.01); *A61K 40/4257* (2025.01); *A61P 35/00* (2018.01); *C07K 14/7051* (2013.01); *C07K 14/70517* (2013.01); *C07K 14/70564* (2013.01); *C07K 14/70578* (2013.01); *C07K 14/70589* (2013.01); *C12N 5/0636* (2013.01); *C12N 15/625* (2013.01); *A61K 38/00* (2013.01); *A61K 2239/31* (2023.05); *A61K 2239/38* (2023.05); *A61K 2239/49* (2023.05); *C07K 2317/24* (2013.01); *C07K 2317/622* (2013.01)

(58) Field of Classification Search
CPC ............ C07K 16/3092; C07K 14/7051; C07K 14/70517; C07K 14/70564; C07K 14/70578; C07K 14/70589; C07K 2317/24; C07K 2317/622; C07K 2317/73; C07K 2317/565; C07K 2317/567; C07K 2319/03; C07K 14/70575; A61K 40/11; A61K 40/31; A61K 40/4257; A61K 38/00; A61K 2239/31; A61K 2239/38; A61K 2239/49; A61K 2039/505; A61K 35/17; A61K 39/00117; A61P 35/00; C12N 5/0636; C12N 15/625; C12N 2800/90
See application file for complete search history.

(56) References Cited

U.S. PATENT DOCUMENTS

| | | | |
|---|---|---|---|
| 3,773,919 | A | 11/1973 | Boswell et al. |
| 4,239,754 | A | 12/1980 | Sache et al. |
| 4,309,989 | A | 1/1982 | Fahim |
| 4,544,101 | A | 10/1985 | Hahn et al. |
| 4,656,134 | A | 4/1987 | Ringold |
| 4,668,218 | A | 5/1987 | Virtanen |
| 4,683,195 | A | 7/1987 | Mullis et al. |
| 4,683,202 | A | 7/1987 | Mullis |
| 4,704,692 | A | 11/1987 | Ladner |
| 4,766,067 | A | 8/1988 | Biswas |
| 4,767,402 | A | 8/1988 | Kost et al. |
| 4,795,699 | A | 1/1989 | Tabor et al. |
| 4,800,159 | A | 1/1989 | Mullis et al. |
| 4,818,542 | A | 4/1989 | DeLuca et al. |
| 4,889,818 | A | 12/1989 | Gelfand et al. |
| 4,921,794 | A | 5/1990 | Tabor et al. |
| 4,925,673 | A | 5/1990 | Steiner et al. |
| 4,939,666 | A | 7/1990 | Hardman |

(Continued)

FOREIGN PATENT DOCUMENTS

| | | |
|---|---|---|
| CN | 102421902 A | 4/2012 |
| CN | 105384825 A | 3/2016 |

(Continued)

OTHER PUBLICATIONS

US 5,733,746 A, 03/1998, Treco et al. (withdrawn)

(Continued)

*Primary Examiner* — Julie Wu

*Assistant Examiner* — John J Skoko, III

(74) *Attorney, Agent, or Firm* — Roberto K. Rodriguez; Genentech, Inc.

(57)     ABSTRACT

Disclosed are antibodies against MUC1, MUC1-CAR compositions and methods for use of these antibodies and compositions to target a MUC1 protein, wherein a cell expressing the MUC1 protein may be targeted and killed by, for instance, a cytotoxic T cell.

34 Claims, 10 Drawing Sheets

Specification includes a Sequence Listing.

(56) References Cited

U.S. PATENT DOCUMENTS

| | | | |
|---|---|---|---|
| 4,946,778 | A | 8/1990 | Ladner et al. |
| 4,965,188 | A | 10/1990 | Mullis et al. |
| 4,994,370 | A | 2/1991 | Silver et al. |
| 5,066,584 | A | 11/1991 | Gyllensten et al. |
| 5,091,310 | A | 2/1992 | Innis |
| 5,122,464 | A | 6/1992 | Wilson et al. |
| 5,130,238 | A | 7/1992 | Malek et al. |
| 5,142,033 | A | 8/1992 | Innis |
| 5,168,062 | A | 12/1992 | Stinski |
| 5,223,409 | A | 6/1993 | Ladner et al. |
| 5,260,203 | A | 11/1993 | Ladner et al. |
| 5,266,491 | A | 11/1993 | Nagata et al. |
| 5,385,839 | A | 1/1995 | Stinski |
| 5,403,484 | A | 4/1995 | Ladner et al. |
| 5,404,871 | A | 4/1995 | Goodman et al. |
| 5,427,908 | A | 6/1995 | Dower et al. |
| 5,455,030 | A | 10/1995 | Ladner et al. |
| 5,458,135 | A | 10/1995 | Patton et al. |
| 5,514,670 | A | 5/1996 | Friedman et al. |
| 5,518,889 | A | 5/1996 | Ladner et al. |
| 5,534,621 | A | 7/1996 | Ladner et al. |
| 5,571,698 | A | 11/1996 | Ladner et al. |
| 5,576,195 | A | 11/1996 | Robinson et al. |
| 5,580,717 | A | 12/1996 | Dower et al. |
| 5,580,734 | A | 12/1996 | Treco et al. |
| 5,595,898 | A | 1/1997 | Robinson et al. |
| 5,618,920 | A | 4/1997 | Robinson et al. |
| 5,641,670 | A | 6/1997 | Treco et al. |
| 5,643,768 | A | 7/1997 | Kawasaki |
| 5,656,730 | A | 8/1997 | Lee |
| 5,658,754 | A | 8/1997 | Kawasaki |
| 5,693,493 | A | 12/1997 | Robinson et al. |
| 5,698,417 | A | 12/1997 | Robinson et al. |
| 5,698,435 | A | 12/1997 | Robinson et al. |
| 5,733,761 | A | 3/1998 | Treco et al. |
| 5,750,373 | A | 5/1998 | Garrard et al. |
| 5,763,733 | A | 6/1998 | Whitlow et al. |
| 5,767,260 | A | 6/1998 | Whitlow et al. |
| 5,770,222 | A | 6/1998 | Unger et al. |
| 5,770,359 | A | 6/1998 | Wilson et al. |
| 5,814,599 | A | 9/1998 | Mitragotri et al. |
| 5,827,739 | A | 10/1998 | Wilson et al. |
| 5,837,500 | A | 11/1998 | Ladner et al. |
| 5,839,446 | A | 11/1998 | Waner et al. |
| 5,849,695 | A | 12/1998 | Cohen et al. |
| 5,851,198 | A | 12/1998 | Castellano et al. |
| 5,856,456 | A | 1/1999 | Whitlow et al. |
| 5,871,753 | A | 2/1999 | Crabtree et al. |
| 5,879,681 | A | 3/1999 | Leone-Bay et al. |
| 5,885,793 | A | 3/1999 | Griffiths et al. |
| 6,019,968 | A | 2/2000 | Platz et al. |
| 6,218,185 | B1 | 4/2001 | Shirk et al. |
| 6,309,663 | B1 | 10/2001 | Patel et al. |
| 6,835,394 | B1 | 12/2004 | Discher et al. |
| 6,962,810 | B2 | 11/2005 | Fraser et al. |
| 7,217,427 | B2 | 5/2007 | Discher et al. |
| 7,867,512 | B2 | 1/2011 | Discher et al. |
| 8,399,643 | B2 | 3/2013 | Ostertag et al. |
| 8,808,748 | B2 | 8/2014 | Ghoroghchian et al. |
| 9,228,180 | B2 | 1/2016 | Izsvak et al. |
| 9,393,292 | B2 | 7/2016 | Brenner |
| 9,913,882 | B2 | 3/2018 | Slawin et al. |
| 10,041,077 | B2 | 8/2018 | Minshull et al. |
| 10,329,543 | B2 | 6/2019 | Ostertag et al. |
| 10,415,024 | B2 | 9/2019 | Ostertag et al. |
| 10,456,452 | B2 | 10/2019 | Ghoroghchian et al. |
| 2014/0363496 | A1 | 12/2014 | Ghoroghchian |
| 2016/0130357 | A1 | 5/2016 | Mukherjee |
| 2016/0145343 | A1 | 5/2016 | Schoen et al. |
| 2016/0340442 | A1 | 11/2016 | Kufe et al. |
| 2017/0000743 | A1 | 1/2017 | Ghoroghchian et al. |
| 2017/0107541 | A1 | 4/2017 | Ostertag et al. |
| 2017/0114149 | A1 | 4/2017 | Ostertag et al. |
| 2018/0036441 | A1 | 2/2018 | Kufe et al. |
| 2018/0187185 | A1 | 7/2018 | Ostertag et al. |
| 2019/0225667 | A1 | 7/2019 | Ostertag et al. |
| 2019/0255191 | A1 | 8/2019 | Ghoroghchian et al. |
| 2019/0328784 | A1 | 10/2019 | Ostertag et al. |

FOREIGN PATENT DOCUMENTS

| | | | | |
|---|---|---|---|---|
| EP | | 0237507 | B1 | 12/1991 |
| KR | | 20200137320 | A | 12/2020 |
| WO | | WO-9117271 | A1 | 11/1991 |
| WO | | WO-9118980 | A1 | 12/1991 |
| WO | | WO-9119818 | A1 | 12/1991 |
| WO | | WO-9205258 | A1 | 4/1992 |
| WO | | WO-9214843 | A1 | 9/1992 |
| WO | | WO-9216221 | A1 | 10/1992 |
| WO | | WO-9308278 | A1 | 4/1993 |
| WO | | WO-9406498 | A1 | 3/1994 |
| WO | | WO-9408552 | A2 | 4/1994 |
| WO | | WO-9416970 | A1 | 8/1994 |
| WO | | WO-9619256 | A1 | 6/1996 |
| WO | | WO-9722376 | A1 | 6/1997 |
| WO | | WO-9725086 | A2 | 7/1997 |
| WO | | WO-9835888 | A1 | 8/1998 |
| WO | | WO-9853847 | A1 | 12/1998 |
| WO | | WO-9916419 | A1 | 4/1999 |
| WO | | WO-2006133398 | A2 | 12/2006 |
| WO | | WO-2010099296 | A1 | 9/2010 |
| WO | | WO-2010099301 | A2 | 9/2010 |
| WO | | WO-2013023162 | A2 | 2/2013 |
| WO | | WO-2013049275 | A1 | 4/2013 |
| WO | | WO-2015009740 | A2 | 1/2015 |
| WO | | WO-2015095895 | A1 | 6/2015 |
| WO | | WO-2015116753 | A1 | 8/2015 |
| WO | | WO-2016016341 | A1 | 2/2016 |
| WO | | WO-2017120525 | A1 | 7/2017 |
| WO | | WO-2018014039 | A1 | 1/2018 |
| WO | | WO-2018224844 | A1 * | 12/2018 ......... C07K 16/2809 |
| WO | | WO-2018231759 | A1 | 12/2018 |
| WO | | WO-2018234759 | A1 | 12/2018 |
| WO | | WO-2019126589 | A1 | 6/2019 |
| WO | | WO-2019173636 | A1 | 9/2019 |
| WO | | WO-2019241315 | A1 | 12/2019 |
| WO | | WO-2020051374 | A1 | 3/2020 |
| WO | | WO-2020132396 | A1 | 6/2020 |
| WO | | WO-2020252472 | A2 | 12/2020 |
| WO | | WO-2021127505 | A1 | 6/2021 |

OTHER PUBLICATIONS

Leslie M et al. Engineered natural killer cells may be the next great cancer immunotherapy. (Science Sep. 13, 2018 doi: 10.1126/science. aav4154) (Year: 2018).*

Xu D et al. The development of CAR design for tumor CAR-T cell therapy. (Oncotarget. 2018; 9:13991-14004) (Year: 2018).*

Chiu ML et al. Antibody Structure and Function: The Basis for Engineering Therapeutics. (Antibodies 2019, 8(4), 55) (Year: 2019).*

Anonymous (Aug. 12, 2015) "Janssen and Poseida partner to use Centyrin technology to develop CAR therapies—Pharmaceutical Technology" [online]. Retrieved from the Internet: http://www. pharmaceutical-technology.com/news/newsjanssen-poseida-partner-to-use-centyrin-technology-to-develop-car-therapies-4645132, retrieved on Sep. 5, 2017, 3 printed pages.

Arcone, R. et al. (1988) "Identification of sequences responsible for acute-phase induction of human C-reactive protein" Nucl Acids Res, 16:3195-3207.

Berry, M.J. et al. (1992) "Substitution of Cysteine for Selenocysteine in Type 1 Iodothyronine Deiodinase Reduces the Catalytic Efficiency of the Protein but Enhances its Translation" Endocrinology, 131:1848-1852.

Bojak, A. et al. (2002) "Muscle specific versus ubiquitous expression of Gag based HIV-1 DNA vaccines: a comparative analysis" Vaccine, 20:1975-1979.

Bridgeman, J.S. et al. (2010) "The Optimal Antigen Response of Chimeric Antigen Receptors Harboring the CD3ζ Transmembrane Domain Is Dependent upon Incorporation of the Receptor into the Endogenous TCR/CD3 Complex" J Immunol, 184(12):6938-6949, DOI: https://doi.org/10.4049/jimmunol.0901766.

(56) References Cited

OTHER PUBLICATIONS

Burns, W.R. et al. (2010) "A high molecular weight-melanoma associated antigen-specific chimeric antigen receptor redirects lymphocytes to target human melanomas" Cancer Research, 70(8):3027-3033.

Capellas, M. et al. (1997) "Enzymatic Condensation of Cholecystokinin CCK-8 (4-6) and CCK-8 (7-8) Peptide Fragments in Organic Media" Biotechnol. Bioeng., 56(4):456-463.

CAS Registry No. 195514-63-7, "2-Piperidinecarboxylic acid, 1-[(2S)-1-oxo-2-(3,4,5-trimethoxyphenyl)butyl]-, 2,2'-[1,2-ethanediylbis[imino(2-oxo-2,1-ethanediyl)oxy-3,1-phenylene[(1R)-3-(3,4-dimethoxyphenyl)propylidene]]]ester, (2S,2'S)-" (CA Index Name). STN International, entered Oct. 17, 1997; 3 printed pages.

CAS Registry No. 195514-80-8, "2-Piperidinecarboxylic acid, 1-[(2S)-1-oxo-2-(3,4,5-trimethoxyphenyl)butyl]-, 2,2'-[2-[(dimethylamino)methyl]-1,3-propanediyl]bis[imino(2-oxo-2,1-ethanediyl)oxy-3, 1-phenylene[(1R)-3-(3,4-dimethoxyphenyl)propylidene]]] ester, (2S,2'S)-" (CA Index Name). STN International, entered Oct. 17, 1997; 3 printed pages.

Cazeaux, N. et al. (2002) "Comparative study of immune responses induced after immunization with plasmids encoding the HIV-1 Nef protein under the control of the CMV-IE or the muscle-specific desmin promoter" Vaccine, 20:3322-3331.

Chen, X. et al. (2013) "Fusion protein linkers: property, design and functionality" Advanced Drug Delivery Reviews, 65(10):1357-1369.

Chmielewski, M. et al. (Nov. 2013) "Antigen-specific T-cell activation independently of the MHC: chimeric antigen receptor-redirected T cells" Front Immunol, 4(Article 371), 7 pages.

Colman, P. M. (1994) "Effects of amino acid sequence changes on antibody-antigen interactions" Research in Immunology, 145(1):33-36.

Cordoba, S.P. et al. (2013) "The large ectodomains of CD45 and CD148 regulate their segregation from and inhibition of ligated T-cell receptor" Blood, 121(21):4295-4302.

Cunningham, B.C. and Wells, J.A. (Jun. 2, 1989) "High-Resolution Epitope Mapping of hGH-Receptor Interactions by Alanine-Scanning Mutagenesis" Science, 244(4908):1081-1085.

De Vos, A.M. et al. (1992) "Human Growth Hormone and Extracellular Domain of Its Receptor: Crystal Structure of the Complex" Science, 255:306-312.

Diem, M.D. et al. (20 14) "Selection of high-affinity Centyrin FN3 domains from a simple library diversified at a combination of strand and loop positions" Protein Eng Des Sel, 27(10):419-429.

Dolezal, O. et al. (2000) "ScFv multimers of the anti-neuraminidase antibody NC10: shortening of the linker in single-chain Fv fragment assembled in VL to VH orientation drives the formation of dimers, trimers, tetramers and higher molecular mass multimers" Protein Engineering, 13(8):565-574.

Donnelly, J.J. et al. (1997) "DNA Vaccines" Annu Rev Immunol, 15:617-648.

Fisch, I. et al. (1992) "Site-Specific Modification of a Fragment of a Chimeric Monoclonal Antibody Using Reverse Proteolysis" Bioconjugate Chem, 3:147-153.

Gasser, B. and D. Mattanovich (2007) "Antibody production with yeasts and filamentous fungi: on the road to large scale?" Biotechnol Lett, 29:201-212.

GenPept Accession No. AAA87375.2 (Oct. 15, 2002) "unknown protein [Trichoplusia ni]" U.S. National Library of Medicine, National Center for Biotechnology Information [online]. Retrieved from: https://www.ncbi.nlm.nih.gov/protein/AAA87375, 2 printed pages.

GenPept Accession No. BAD11135.1 (Sep. 15, 2007) "putative transposase yabusame-1 [Bombyx mori]" Bethesda (MD): National Library of Medicine (US), National Center for Biotechnology Information [online]. Retrieved from: https://www.ncbi.nlm.nih.gov/protein/BAD11135.1, 1 page.

GenPept Accession No. NP_001191215.1 (Apr. 17, 2020) "mucin-1 isoform 10 precursor [Homo sapiens]" U.S. National Library of Medicine, National Center for Biotechnology Information [online]. Retrieved from: https://www.ncbi.nlm.nih.gov/protein/NP_001191215.1, 3 pages.

Golubovskaya et al. (Mar. 15, 2016) "Different Subsets of T Cells, Memory, Effector Functions, and CAR-T Immunotherapy", Cancers, 8(3):36, 12 pages DOI: 10.3390/cancers8030036.

Gossen, M. et al. (Jun. 1992) "Tight control of gene expression in mammalian cells by tetracycline-responsive promoters" Proc Natl Acad Sci USA, 89:5547-5551.

Gossen, M. et al. (Jun. 2, 19953) "Transcriptional activation by tetracyclkines in mammalian cells" Science, 268(5218):1766-1769.

Hinoda, Y. et al. (2003) "Increased expression of MUC1 in advanced pancreatic cancer" J Gastroenterol, 38:1162-1166.

Itoh, K. et al. (1996) "Application of Inverse Substrates to Trypsin-Catalyzed Peptide Synthesis" Bioorg Chem, 24(1):59-68.

Iuliucci, J.D. et al. (2001) "Intravenous Safety and Pharmacokinetics of a Novel Dimerizer Drug, AP1903, in Healthy Volunteers" J Clin Pharmacol, 41:870-879.

Jamnani, F.R. et al. (Jan. 2014) "T cells expressing VHH-directed oligoclonal chimeric HER2 antigen receptors: Towards tumor-directed oligoclonal T cell therapy" Biochim Biophys Acta, 1840(1):378-386.

Junginger, H.E. et al. (1994) "Visualization of Drug Transport Across Human Skin and the Influence of Penetration Enhancers" in Drug Permeation Enhancement. Hsieh, D.S. (Ed.); New York: Marcel Dekker, Inc., pp. 59-89.

Kageyama, R. et al. (Feb. 15, 1987) "Differing Utilization of Homologous Transcription Initiation Sites of Rat K and T Kininogen Genes Under Inflammation Condition" J Biol Chem, 262(5):2345-2351.

Kufe, D.W. (2013) "MUC1-C oncoprotein as a target in breast cancer: activation of signaling pathways and therapeutic approaches" Oncogene, 32(9):1073-1081.

Kumaran, S. et al. (1997) "Conformationally driven protease-catalyzed splicing of peptide segments: V8 protease-mediated synthesis of fragments derived from thermolysin and ribonuclease A" Protein Sci, 6(10):2233-2241.

Kyte, J. and R.F. Doolittle (May 5, 1982) "A simple method for displaying the hydropathic character of a protein" J Mol Biol, 157(1):105-132.

Maeda, et al., "Engineering of Functional Chimeric Protein G-Vargula Luciferase". Analytical Biochemistry (Jul. 1, 1997); 249(2): 147-152.

Maher, J. and S. Wilkie (Jun. 1, 2009) "CAR mechanics: driving T cells into the MUC of cancer" Cancer Research, 69(11):4559-4562.

Maus, M.V. et al. (2014) "Antibody-modified T cells: CARs take the front seat for hematologic malignancies" Blood, 123(17):2625-2635.

Olimpieri et al. (Oct. 9, 2014) "Tabhu: tools for antibody humanization" Bioinformatics, 31(3):434-435.

Oliviero, S. et al. (1987) "The human haptoglobin gene: transcriptional regulation during development and acute phase induction" The EMBO Journal, 6(7):1905-1912.

Philip, B. et al. (2014) "A highly compact epitope-based marker/suicide gene for easier and safer T-cell therapy" Blood, 124(8):1277-1287.

Poli, V. et al. (Nov. 1989) "Interleukin 6 induces a liver-specific nuclear protein that binds to the promoter of acute-phase genes" Proc Natl Acad Sci USA, 86:8202-8206.

Poseida Therapeutics, Inc. (Aug. 11, 2015) "Poseida Therapeutics, Inc. Announces Worldwide License Agreement with Janssen to Apply Centyrin Technology in the Development of Chimeric Antigen Receptor (CAR) Therapies" Global Newswire [online]. Retrieved from: https://www.globenewswire.com/news-release/2015/08/11/759596/0/en/Poseida-Therapeutics-Inc-Announces-Worldwide-License-Agreement-With-Janssen-to-Apply-Centyrin-Technology-in-the-Development-of-Chimeric-Antigen-Receptor-CAR-Therapies.html?print=1; 2 pages.

Prowse, K.R. and H. Baumann (Jan. 1988) "Hepatocyte-Stimulating Factor, 2 Interferon, and Interleukin-1 Enhance Expression of the Rat 1-Acid Glycoprotein Gene via a Distal Upstream Regulatory Region" Mol Cell Biol, 8(1):42-51.

(56) References Cited

OTHER PUBLICATIONS

Quntarelli, C. et al. (Oct. 15, 2007) "Co-expression of cytokine and suicide genes to enhance the activity and safety of tumor-specific cytotoxic T lymphocytes" Blood, 110(8):2793-2802 [online]. Retrieved from the Internet: www.ncbi.nlm.nih.gov/pmc/articles/PMC2018664/?report=printable; retrieved on Apr. 1, 2019, 22 printed pages.
Ron, D. et al. (May 1991) "Angiotensinogen Gene-Inducible Enhancer-Binding Protein 1, a Member of a New Family of Large Nuclear Proteins That Recognize Nuclear Factor kappaB-Binding Sites through a Zinc Finger Motif" Mol Cell Biol, 11(5):2887-2895.
Safdari, Y. et al. (2013) "Antibody humanization methods—a review and update" Biotechnology and Genetic Engineering Reviews, 29(2):175-186.
Smith, L.J. et al. (1992) "Human Interleukin 4. The Solution Structure of a Four-helix Bundle Protein" J Mol Biol, 244:899-904.
Sprague, J. et al. (Feb. 1983) "Expression of a Recombinant DNA Gene Coding for the Vesicular Stomatitis Virus Nucleocapsid Protein" J Virol, 45(2):773-781.
Stepanov, A.V. et al. (2015) "Modelling of the Receptor-Ligand Interaction in a Single Cell Mode" Biological Membranes: Journal of Membrane and Cell Biology, 32(2):102-109 [in Russian, with English abstract on p. 109].

Straathof, K.C. et al. (2005) "An inducible caspase 9 safety switch for T-cell therapy" Blood, 105:4247-4254.
Tatusova et al., "Blast 2 Sequences—a new tool for comparing protein and nucleotide sequences." FEMS Microbiol Lett. 174:247-250 (1999).
Teplyakov, A. et al. (2014). Antibody modeling assessment II. Structures and models, Proteins: Structure, Function, and Bioinformatics 82:1563-1582.
Werlen, R.C. et al. (1994) "Site-Specific Conjugation of an Enzyme and an Antibody Fragment" Bioconjugate Chem., 5:411-417.
Wilson, D.R. et al. (Dec. 1990) "A 58-Base-Pair Region of the Human C3 Gene Confers Synergistic Inducibility by Interleukin-1 and Interleukin-6" Mol Cell Biol, 10(12):6181-6191.
You, F. et al. (Mar. 7, 2016) "Phase 1 clinical trial demonstrated that MUC1 positive metastatic seminal vesicle cancer can be effectively eradicated by modified Anti-MUC1 chimeric antigen receptor transduced T cells" Zhongguo Kexue Zazhische [Science China Life Sciences], 59(4):386-397.
Zechner, R. et al. (Jun. 1988) "Recombinant Human Cachectin/Tumor Necrosis Factor but Not Interleukin-1 Downregulates Lipoprotein Lipase Gene Expression at the Transcriptional Level in Mouse 3T3-L1 Adipocytes" Mol Cell Biol, 8(6):2394-2401.

* cited by examiner

CD8a Signal Peptide

Light Chain

Linker

Heavy Chain

CD8a Hinge

CD8a TM 4-1BB ICS

CD3z ICS

Humanized MUC1-C CAR Structure (485 aa)

Heavy Chain Amino Acid Sequence Alignment

FIG. 5A

Light Chain Amino Acid Sequence Alignment

FIG. 5B

ANTI-MUC1 COMPOSITIONS AND METHODS OF USE

RELATED APPLICATIONS

This application is a U.S. National Phase application, filed under 35 U.S.C. § 371, of International Application No. PCT/US2020/066121, filed Dec. 18, 2020, which claims priority to, and the benefit of, U.S. Provisional Application No. 62/951,257, filed Dec. 20, 2019. The contents of each of which are incorporated herein by reference in their entireties.

FIELD OF THE INVENTION

The disclosure is directed to molecular biology, and more, specifically, to antibodies and chimeric antigen receptors that bind specifically to a target protein with high affinity and avidity.

INCORPORATION-BY-REFERENCE OF SEQUENCE LISTING

This contents of the file named "POTH-040 NO1US SeqList.txt", which was created on Jun. 13, 2022, and is 412 KB in size are hereby incorporated by reference in their entirety.

BACKGROUND OF THE INVENTION

The discovery of agents capable of recognizing and binding to a specific target protein with high affinity and avidity has been a focus of the biopharmaceutical industry. There remains a need for more efficacious agents that are smaller, more soluble and more stable than the available options.

SUMMARY OF THE INVENTION

The present disclosure provides an isolated antibody comprising a heavy chain variable region comprising the amino acid sequence of QVQLVQS-GAEVKKPGSSVKXiSCKTSGYAFSNF WMNWVX$_2$QX$_3$PGQGLEWIGQIYP GDGDTNYNX$_4$KFKGRX$_5$TLTADKSX$_6$STAYMEL SSLRSEX$_7$TAVYFCARSYYRSAWF AYWGQGTLVTVSS (SEQ ID NO:1), wherein X1 of SEQ ID NO: 1 is V or I, wherein X2 of SEQ ID NO: 1 is R or K, wherein X3 of SEQ ID NO: 1 is A or R, wherein X4 of SEQ ID NO: 1 is G or A, wherein X5 of SEQ ID NO: 1 is V or A, wherein X6 of SEQ ID NO: 1 is T or S, and wherein X7 of SEQ ID NO: 1 is D or A; and a light chain variable region comprising the amino acid sequence of EILLTQSPDFQSVTPKEKVTFT-CRASQSIGTSIHWYQQKPNQSPKLLIKYASESISGVPS RFSGSGSGTDFTLX$_1$INSX$_2$ESEDIAX$_3$YYCQ QSNNWPLTFGQGTKLEIK (SEQ ID NO:2), wherein X1 of SEQ ID NO: 2 is T or S, wherein X2 of SEQ ID NO: 2 is L or V, and wherein X3 of SEQ ID NO: 2 is T or D.

The isolated antibody can be humanized. The isolated antibody can be an IgG. The isolated antibody can bind to human MUC1-C. The isolated antibody can be a monoclonal antibody, a chimeric antibody, a single domain antibody, a VHH, a VH, a single chain variable fragment (scFv), a Fab or a Fab fragment. Preferably, the isolated antibody is an scFv.

The heavy chain variable region comprises the amino acid sequence of SEQ ID NO:3, SEQ ID NO:4, SEQ ID NO:5, SEQ ID NO:6, SEQ ID NO:7, or SEQ ID NO:8. The light chain variable region comprises the amino acid sequence of SEQ ID NO:9, SEQ ID NO:10, or SEQ ID NO:11.

The scFv can comprise a linker between the heavy chain variable region and the light chain variable region. In an aspect, the linker comprises the amino acid sequence of SEQ ID NO: 59.

The scFv can comprise of SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140 or SEQ ID NO: 141. In on aspect, the scFv comprises an amino acid sequence of SEQ ID NO: 125.

The present disclosure also provides a chimeric antigen receptor (CAR) comprising an antibody as disclosed herein. Preferably, the CAR comprises an scFv as disclosed herein.

The CAR can comprise (a) an ectodomain comprising antigen recognition region, wherein the antigen recognition region comprises at least one anti-MUC1 single chain variable fragment (scFv); (b) a transmembrane domain, and (c) an endodomain comprising at least one costimulatory domain; wherein the scFv comprises a heavy chain variable region comprising the amino acid sequence of QVQLVQS-GAEVKKPGSSVKXiSCKTSGYAF SNFWMNWVX$_2$QX$_3$PGQGLEWIGQIYP GDGDTNYNX$_4$KFKGRX$_5$TLTADKSX$_6$STAYMEL SSLRSEX$_7$TAVYFCARSYYRSAWF AYWGQGTLVTVSS (SEQ ID NO:1), wherein X1 of SEQ ID NO: 1 is V or I, wherein X2 of SEQ ID NO: 1 is R or K, wherein X3 of SEQ ID NO: 1 is A or R, wherein X4 of SEQ ID NO: 1 is G or A, wherein X5 of SEQ ID NO: 1 is V or A, wherein X6 of SEQ ID NO: 1 is T or S, and wherein X7 of SEQ ID NO: 1 is D or A; and a light chain variable region comprising the amino acid sequence of EILLTQSPDFQSVTPKEKVTFT-CRASQSIGTSIHWYQQKPNQSPKLLIKYASESISGVPS RFSGSGSGTDFTLX$_1$INSX$_2$ESEDIAX$_3$YYC QQSNNWPLTFGQGTKLEIK (SEQ ID NO:2), wherein X1 of SEQ ID NO: 2 is T or S, wherein X2 of SEQ ID NO: 2 is L or V, and wherein X3 of SEQ ID NO: 2 is T or D.

The heavy chain variable region of the CAR can comprise the amino acid sequence of SEQ ID NO:3, SEQ ID NO:4, SEQ ID NO:5, SEQ ID NO:6, SEQ ID NO:7, or SEQ ID NO:8. The light chain variable region of the CAR can comprise the amino acid sequence of SEQ ID NO:9, SEQ ID NO:10, or SEQ ID NO:11.

The heavy chain variable region of the CAR can comprise the amino acid sequence of SEQ ID NO:3 and the light chain variable region of the CAR can comprise the amino acid sequence of SEQ ID NO:9. The heavy chain variable region of the CAR can comprise the amino acid sequence of SEQ ID NO:4 and the light chain variable region of the CAR can comprise the amino acid sequence of SEQ ID NO:9. The heavy chain variable region of the CAR can comprise the amino acid sequence of SEQ ID NO:5 and the light chain variable region of the CAR can comprise the amino acid sequence of SEQ ID NO:9. The heavy chain variable region of the CAR can comprise the amino acid sequence of SEQ ID NO:6 and the light chain variable region of the CAR can comprise the amino acid sequence of SEQ ID NO:9. The heavy chain variable region of the CAR can comprise the amino acid sequence of SEQ ID NO:7 and the light chain variable region of the CAR can comprise the amino acid sequence of SEQ ID NO:9. The heavy chain variable region of the CAR can comprise the amino acid sequence of SEQ ID NO:8 and the light chain variable region of the CAR can comprise the amino acid sequence of SEQ ID NO:9. The heavy chain variable region of the CAR can comprise the amino acid sequence of SEQ ID NO:3 and the light chain variable region of the CAR can comprise the amino acid sequence of SEQ ID NO:10. The heavy chain variable region of the CAR can comprise the amino acid sequence of SEQ ID NO:4 and the light chain variable region of the CAR can comprise the amino acid sequence of SEQ ID NO:10. The heavy chain variable region of the CAR can comprise the amino acid sequence of SEQ ID NO:5 and the light chain variable region of the CAR can comprise the amino acid sequence of SEQ ID NO: 10. The heavy chain variable region of the CAR can comprise the amino acid sequence of SEQ ID NO:6 and the light chain variable region of the CAR can comprise the amino acid sequence of SEQ ID NO:10. The heavy chain variable region of the CAR can comprise the amino acid sequence of SEQ ID NO:7 and the light chain variable region of the CAR can comprise the amino acid sequence of SEQ ID NO:10. The heavy chain variable region of the CAR can comprise the amino acid sequence of SEQ ID NO:8 and the light chain variable region of the CAR can comprise the amino acid sequence of SEQ ID NO:10. The heavy chain variable region of the CAR can comprise the amino acid sequence of SEQ ID NO:3 and the light chain variable region of the CAR can comprise the amino acid sequence of SEQ ID NO:11. The heavy chain variable region of the CAR can comprise the amino acid sequence of SEQ ID NO:4 and the light chain variable region of the CAR can comprise the amino acid sequence of SEQ ID NO:11. The heavy chain variable region of the CAR can comprise the amino acid sequence of SEQ ID NO:5 and the light chain variable region of the CAR can comprise the amino acid sequence of SEQ ID NO:11. The heavy chain variable region of the CAR can comprise the amino acid sequence of SEQ ID NO:6 and the light chain variable region of the CAR can comprise the amino acid sequence of SEQ ID NO: 11. The heavy chain variable region of the CAR can comprise the amino acid sequence of SEQ ID NO:7 and the light chain variable region of the CAR can comprise the amino acid sequence of SEQ ID NO:11. The heavy chain variable region of the CAR can comprise the amino acid sequence of SEQ ID NO:8 and the light chain variable region of the CAR can comprise the amino acid sequence of SEQ ID NO:11. The scFv can comprise a linker between the heavy chain variable region and the light chain variable region. Preferably, the linker comprises the amino acid sequence of SEQ ID NO: 59. The scFv can comprise of SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140 or SEQ ID NO: 141. In on aspect, the scFv comprises an amino acid sequence of SEQ ID NO: 125. The ectodomain can further comprise a signal peptide. Preferably, the signal peptide comprises the amino acid sequence of SEQ ID NO: 57. The CAR can further comprise a hinge region between the antigen recognition region and the transmembrane domain. Preferably, the hinge region comprises the amino acid sequence of SEQ ID NO: 61. The transmembrane domain can comprise a sequence encoding a CD8 transmembrane domain. Preferably, the CD8 transmembrane domain comprises the amino acid sequence of SEQ ID NO: 63. The at least one costimulatory domain can comprise a CD3$\zeta$ costimulatory domain, a 4-1BB costimulatory domain, or a combination thereof. In an aspect, the at least one costimulatory domain comprises a CD3$\zeta$ costimulatory domain and a 4-1BB costimulatory domain, and wherein the 4-1BB costimulatory domain is located between the transmembrane domain and the CD3$\zeta$ costimulatory domain. Preferably, the 4-1BB costimulatory domain comprises the amino acid sequence of SEQ ID NO: 65. Preferably, the CD3$\zeta$ costimulatory domain comprises the amino acid sequence of SEQ ID NO: 67.

The present disclosure also provides a chimeric antigen receptor (CAR) comprising (a) an ectodomain comprising antigen recognition region, wherein the antigen recognition region comprises at least one anti-MUC1 single chain variable fragment (scFv); (b) a transmembrane domain, and (c) an endodomain comprising at least one costimulatory domain; wherein the scFv comprises a heavy chain variable region comprising the amino acid sequence of QVQLVQS-GAEVKKPGSSVKXiSCKTSGYAFSN FWMNWVX$_2$QX$_3$PGQGLEWIGQIYP GDGDTNYNX$_4$KFKGRX$_5$TLTADKSX$_6$ STAYMELSSLRSEX$_7$TAVYFCARSYYRSAWF AYWGQGTLVTVSS (SEQ ID NO:1), wherein X1 of SEQ ID NO: 1 is V or I, wherein X2 of SEQ ID NO: 1 is R or K, wherein X3 of SEQ ID NO: 1 is A or R, wherein X4 of SEQ ID NO: 1 is G or A, wherein X5 of SEQ ID NO: 1 is V or A, wherein X6 of SEQ ID NO: 1 is T or S, and wherein X7 of SEQ ID NO: 1 is D or A; and a light chain variable region comprising the amino acid sequence of EILLTQSPDFQSVTPKEKVTFT-CRASQSIGTSIHWYQQKPNQSPKLLIKYASESISGVPS RFSGSGSGTDFTLX$_1$INSX$_2$ESEDIAX$_3$YY CQQSNNWPLTFGQGTKLEIK (SEQ ID NO:2), wherein X1 of SEQ ID NO: 2 is T or S, wherein X2 of SEQ ID NO: 2 is L or V, and wherein X3 of SEQ ID NO: 2 is T or D, wherein the scFv comprises a linker between the heavy chain variable region and the light chain variable region, wherein the ectodomain comprises a signal peptide, wherein the CAR further comprises a hinge region between the antigen recognition region and the transmembrane domain, wherein the transmembrane domain comprises a sequence comprising a CD8 transmembrane domain; and wherein the at least one costimulatory domain comprises a CD3$\zeta$ costimulatory domain and a 4-1BB costimulatory domain, and wherein the 4-1BB costimulatory domain is located between the transmembrane domain and the CD3$\zeta$ costimulatory domain.

In some aspects, the scFv comprises an amino acid sequence of SEQ ID NO: 125, the signal peptide comprises SEQ ID NO: 57, the hinge region comprises SEQ ID NO: 61, the CD8 transmembrane domain comprises SEQ ID NO: 63, the 4-1BB costimulatory domain comprises SEQ ID NO: 65; and the CD3$\zeta$ costimulatory domain comprises SEQ ID NO: 67.

In some aspects, the CAR comprises the amino acid sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, or SEQ ID NO: 29. In some aspects, the CAR comprises the amino acid sequence of SEQ ID NO: 13. In some aspects, the amino acid sequence of the CAR is encoded by a polynucleotide comprising the nucleic acid sequence of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO; 167. In some aspects, the amino acid sequence of the CAR is encoded by a polynucleotide comprising the nucleic acid sequence of SEQ ID NO: 167.

The present disclosure also provides a polynucleotide comprising a nucleic acid sequence encoding an antibody as disclosed herein; a polynucleotide comprising a nucleic acid sequence encoding an scFv as disclosed herein; and/or a polynucleotide comprising a nucleic acid sequence encoding a CAR as disclosed herein.

The present disclosure also provides a transposon comprising a nucleic acid encoding a CAR as disclosed herein. In some aspects, the nucleic acid sequence comprises the CAR comprising an amino acid sequence of SEQ ID NO: 13. The transposon can further comprise a nucleic acid encoding an inducible caspase polypeptide, a nucleic acid encoding a chimeric stimulatory receptor, a nucleic acid encoding a selection gene, a nucleic acid encoding a therapeutic agent, or a combination thereof. The selection gene can comprise a DI-FR resistance gene. Preferably, the transposon is a piggyBac transposon. In some aspects, the transposon comprises a nucleic acid sequence of SEQ ID NO: 172. The present disclosure also provides a plasmid or vector comprising any of the polynucleotides disclosed herein or any of the transposons disclosed herein.

The present disclosure also provides a cell comprising any of an antibody, an scFv, a CAR or a transposon as disclosed herein. The present disclosure also provides a population of cells, wherein a plurality of the population are modified to express any of an antibody, an scFv, a CAR or a transposon as disclosed herein. In an aspect, the plurality of modified cells is a plurality of modified immune cells. In an aspect, the plurality of modified cells is a plurality of modified T-cells. In an aspect, the plurality of the population of cells comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% of cells that express the CAR. In an aspect, CAR comprises an amino acid sequence of SEQ ID NO: 13. In an aspect, In an aspect, at least 50% of plurality of modified T-cells express one or more cell-surface marker(s) comprising CD45RA and CD62L and do not express one or more cell-surface marker(s) comprising CD45RO.

The present disclosure also provides a composition comprising any of an antibody, an scFv, a CAR, a transposon, a cell or a population of cells as disclosed herein. In an aspect, the composition is a pharmaceutical composition and further comprises a pharmaceutically acceptable carrier.

The present disclosure also provides a method of treating a proliferation disorder in a subject in need thereof by administering a therapeutically effective amount of any of an antibody, an scFv, a CAR, a transposon, a cell, a population of cells, a composition or a pharmaceutical composition as disclosed herein. In an aspect, the proliferation disorder is cancer. In an aspect, the cancer can be MUC1-positive cancer. In an aspect, the cancer is a MUC1-C positive cancer. The cancer can be a primary tumor, a metastatic cancer, a multiply resistant cancer, a progressive tumor or recurrent cancer. The cancer can be a solid tumor. The cancer can be lung cancer, a brain cancer, a head and neck cancer, a breast cancer, a skin cancer, a liver cancer, a pancreatic cancer, a stomach cancer, a colon cancer, a rectal cancer, a uterine cancer, a cervical cancer, an ovarian cancer, a prostate cancer, a testicular cancer, a skin cancer or an esophageal cancer.

BRIEF DESCRIPTION OF THE DRAWINGS

FIG. 1A depicts MUC1 undergoing autoproteolysis at a SEA domain (a sea-urchin sperm protein, enterokinase and agrin domain) to generate two subunits that consequently form a stable noncovalent heterodimer. The MUC1-N and MUC1-C nomenclature is used to designate positioning of the subunits after cleavage and to distinguish them from genetic isoforms that are subclassified with Greek characters. FIG. 1B provides detail of the MUC1-C subunit. The MUC1-C 58 amino acid extracellular domain is glycosylated on asparagine at position 36, which is an $N^{36}LT$ site. The amino acid sequence of the extracellular domain of the C-terminal of MUC1-C (MUC1-C/ECD) is shown (SEQ ID NO: 77). The MUC1-C 72 amino acid cytoplasmic domain interacts with multiple effectors and is sufficient to induce oncogenic transformation. FIG. 1A-1B are reproduced from Kufe D W, Oncogene, 32(9):1073.

FIG. 5A-5B are diagrams depicting amino acid sequence alignment of heavy chain variable and light chain variable regions of humanized anti-MUC-1C antibodies of the disclosure.

Raji cells. Mock-transposed T cells did not kill either Raji nor engineered Raji target cell lines.

Figure 10:
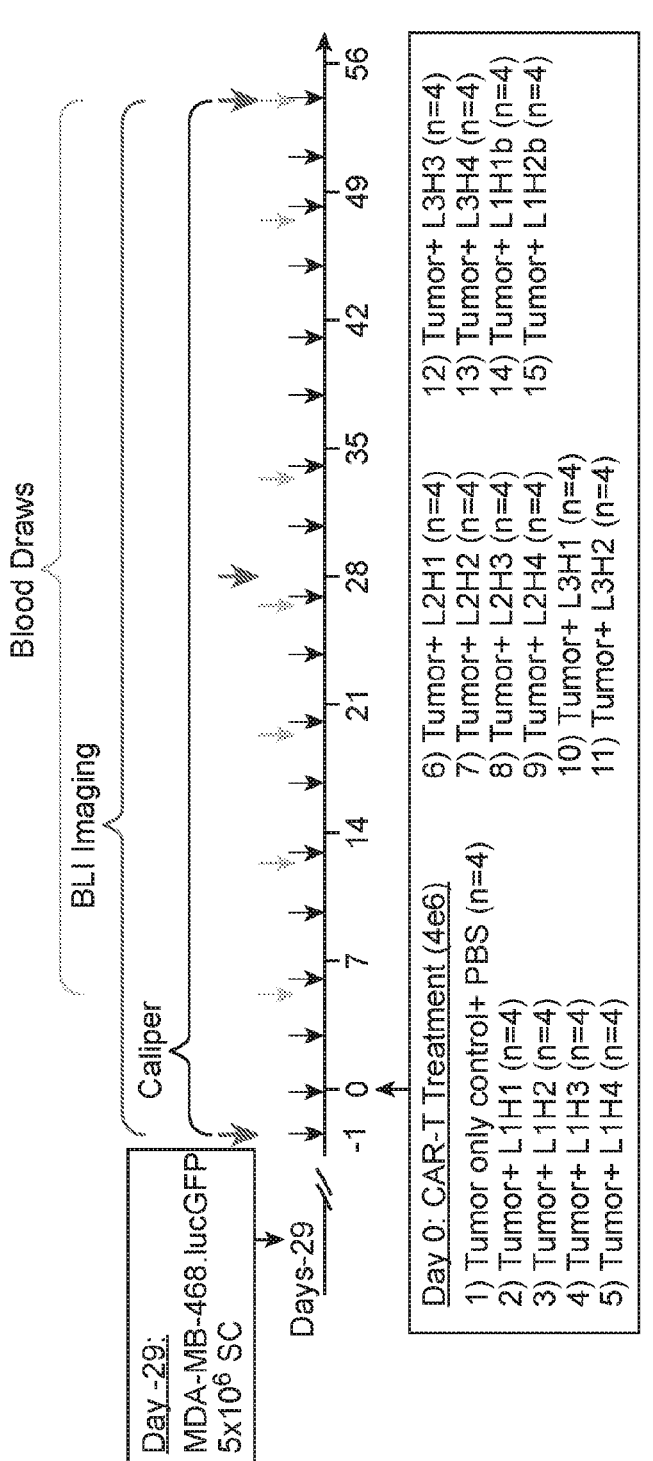

FIG. 10 is a schematic diagram of a study design for preclinical evaluation of candidate humanized MUC1-C CAR-T cells at 'stress' doses using the Murine Xenograft Model.

All documents cited herein, including any cross referenced or related patent or application is hereby incorporated herein by reference in its entirety for all purposes, unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

DETAILED DESCRIPTION OF THE INVENTION

The present disclosure provides compositions and methods for using these compositions to recognize and bind to a specific target protein, a Mucin 1, cell surface associated (MUC1) protein, with high affinity and avidity.
MUC1

MUC1 is an extensively O-glycosylated mucin protein predominantly expressed by epithelial cells. The secreted and membrane-bound MUC1 forms a physical barrier that protects the apical borders of epithelial cells from damage induced by toxins, microorganisms and other forms of stress that occur at the interface with the external environment. Aberrant overexpression of MUC1, as found in most human carcinomas, confers anchorage-independent growth and tumorigenicity. Overexpression of MUC1 confers resistance to apoptosis induced by oxidative stress and genotoxic anti-cancer agents.

Human MUC1 is heterodimeric glycoprotein, translated as a single polypeptide and cleaved into N- and C-terminal subunits (MUC1-N and MUC1-C) in the endoplasmic reticulum. The cleavage may be mediated by an autocatalytic process. The >250 kDa MUC1 N-terminal (MUC1 N-ter or MUC1-N) subunit contains variable numbers of 20 amino acid tandem repeats that are imperfect with highly conserved variations and are modified by 0-linked glycans. MUC1-N is tethered to the cell surface by dimerization with the approximately 23 kDa C-terminal subunit (MUC1 C-ter or MUC1-C), which includes a 58 amino acid extracellular region, a 28 amino acid transmembrane domain and a 72-amino acid cytoplasmic domain (CD) (FIG. 1i). MUC1-C comprises the amino acid sequence of (SEQ ID NO: 76):

SVVVQLTLAFREGTINVHDVETQFNQYKTEAASRYNLTISDVS

VSDVPFPFSAQSGAGVPGWGIALLVLVCVLVALAIVYLIALAV

*CQCRRKNYGQLDIFP*ARDTYHPMSEYPTYHTHGRYVPPSSTDR

SPYEKVSAGNGGSSLSYTNPAVAATSANL .

The compositions of the present disclosure can bind to the underlined 58 amino acid portion of the MUC1-C/ECD. The bold sequence indicates the CD, and the italicized portion is an oligomer-inhibiting peptide. With transformation of normal epithelia to carcinomas, MUC1 is aberrantly overexpressed in the cytosol and over the entire cell membrane. Cell membrane-associated MUC1 is targeted to endosomes by clathrin-mediated endocytosis. In addition, MUC1-C, but not MUC1-N, is targeted to the nucleus and mitochondria.

Compositions of the disclosure can selectively bind to one or more amino acids of an "epitope" MUC1-C/extracellular domain (MUC1-C/ECD). Epitopes can be linear or conformational. As used herein, the term "epitope" is meant to refer to a one or more amino acids to which the disclosed compositions specifically bind. The one or more amino acids of the epitopes of the disclosure may be arranged in a linear, non-linear, continuous, or discontinuous manner. Epitopes of the disclosure may be "conformational", meaning that the protein scaffold bind to the one or more amino acids of the epitope with greater affinity or greater selectivity when the amino acids are presented in the conformation of a properly folded peptide, protein, or protein complex. In certain aspects, compositions that bind to conformational epitopes may not bind to linear epitopes.

Compositions of the disclosure can selectively bind to one or more amino acids of the MUC1-C/extracellular domain (MUC1-C/ECD) defined by the amino acid sequence of SVVVQLTLAFREGTINVHDVETQFNQYKTEAAS-RYNLTISDVSVSDVPFPFSAQSGA G (SEQ ID NO: 77) (see FIG. 1i). Alternatively, or in addition, the compositions bind selectively to one or more amino acids of a variant MUC1-C/extracellular domain (MUC1-C/ECD). Variant MUC1-C/ECD peptides of the disclosure may include, but are not limited to, MUC1-C/ECD-L6A, MUC1-C/ECD-L8A, MUC1-C/ECD-L6,8A, MUC1-C/ECD-Q23V, MUC1-C/ECD-Q26V, MUC1-C/ECD-N36A, as numbered in accordance with SEQ ID NO: 76 or SEQ ID NO: 77.

The compositions of the disclosure can selectively bind to one or more amino acids of the following peptides derived from the MUC1-C/extracellular domain (MUC1-C/ECD):

```
                        ("peptide 1", SEQ ID NO: 78)
        SVVVQLTLAFREGTINVHDVET, ("peptide 2", SEQ ID NO: 79)
        VETQFNQYKTEAASRYNLTISD,
        or ("peptide 3", SEQ ID NO: 80)
        TISDVSVSDVPFPFSAQSGAG.
```

The compositions of the disclosure can selectively bind to an alpha3 (a3) helix or an alpha4 (a4) helix in MUC1-C/ED. In some embodiments, the MUC1-C/ECD comprises the amino acid sequence of SVVVQLTLAFREGTINVHD-VETQFNQYKTEAAS-RYNLTISDVSVSDVPFPFSAQSGA G (SEQ ID NO: 77); a3 helix bolded and a4 helix bolded and italicized). The MUC1-C/ED a3 helix can comprise, consist essential of, or consist of the amino acid sequence of VHDVETQFNQ (SEQ ID NO: 81). The MUC1-C/ED a4 helix can comprise, consist essential of, or consist of the amino acid sequence of EAASRYN(SEQ ID NO: 82). The epitope of the composition of the disclosure can comprises, consists essential of, or consists of the amino acid sequences of SEQ ID NO: 81 or SEQ ID NO: 82. The epitope can be linear or conformational. In some aspects, the epitope is discontinuous, optionally, comprising, consisting essentially of, or consisting of two or more discontinuous amino acids of the amino acid sequences of SEQ ID NO: 81 or SEQ ID NO: 82.

Compositions of the Disclosure

The present disclosure provides an antibody comprising a heavy chain variable region comprising, consisting essentially of, or consisting of an amino acid sequence at least 95%, 96%, 97%, 98%, 99% or 100% (or any percentage in between) identical to QVQLVQSGAEVKKPGSSVKXiS-CKTSGY AFSNFWMNWVX₂QX₃PGQGLEWIGQIYP GDGDTNYNX₄KFKGRX₅TLTADKSX₆STAYMEL SSLRSEX₇TAVYFCARSYYRSAWF AYWGQGTLVTVSS (SEQ ID NO: 1), wherein X1 of SEQ ID NO: 1 is V or I, wherein X2 of SEQ ID NO: 1 is R or K, wherein X3 of SEQ ID NO: 1 is A or R, wherein X4 of SEQ ID NO: 1 is G or A, wherein X5 of SEQ ID NO: 1 is V or A, wherein X6 of SEQ ID NO: 1 is T or S, and wherein X7 of SEQ ID NO: 1 is D or A; and a light chain variable region comprising, consisting essentially of, or consisting of an amino acid sequence at least 95%, 96%, 97%, 98%, 99% or 100% (or any percentage in between) identical to EILLTQSPDFQSVTPKEKVTFT-CRASQSIGTSIHWYQQKPNQSPKLLIKYASESISGVPS RFSGSGSGTDFTLX₁INSX₂ESEDIAX₃YYCQQ SNNWPLTFGQGTKLEIK (SEQ ID NO:2), wherein X1 of SEQ ID NO: 2 is T or S, wherein X2 of SEQ ID NO: 2 is L or V, and wherein X3 of SEQ ID NO: 2 is T or D.

Preferably, the heavy variable chain variable region comprises the amino acid sequence of SEQ ID NO:1, wherein X2 is R or K, wherein X3 is A or R, wherein X4 is G or A, wherein X5 is V or A, wherein X6 is T or S, and wherein X7 1 is D or A. Preferably, the light variable chain variable region comprises the amino acid sequence of SEQ ID NO:2, wherein X1 is T or S, wherein X2 is L or V, and wherein X3 is T or D.

In some aspects, the antibody binds to human MUC1 polypeptide (UniProt Accession Number P15941-1) comprising, consisting essential of, or consisting of SEQ ID NO: 160. In one aspect, the antibody binds to human MUC1-C polypeptide that comprises, consists essentially of, or consists of SEQ ID NO: 76. In another aspect, the antibody binds to human MUC1-N polypeptide (subunit of MUC1 receptor also known as alpha chain, mature chain) that comprises, consists essentially of, or consists of SEQ ID NO: 161.

In some aspects, the antibody binds to human MUC1-C extracellular domain (ED) that comprises, consisting essentially of or consisting of SEQ ID NO: 77. In some aspects, the antibody binds to MUC1-C ED (SEQ ID NO: 77) with a higher affinity than human full length MUC1 polypeptide (SEQ ID NO: 160). In some aspects, the antibody binds to human MUC1-C ED (SEQ ID NO: 77) with a higher affinity than MUC1-N polypeptide (SEQ ID NO: 161). In some aspects, the antibody binds to MUC1-C ED (SEQ ID NO: 77) and does not bind to human full length MUC1 polypep-tide (SEQ ID NO: 160). In some aspects, the antibody binds to human MUC1-C ED (SEQ ID NO: 77) and does not bind to MUC1-N polypeptide (SEQ ID NO: 161).

In some embodiments, the human variable heavy chain framework acceptor comprises, consists essentially of, or consists of the polypeptide of IGHV1-69 08 of SEQ ID NO: 162. In some aspects, the human variable light chain frame-work acceptor comprises, consists essentially of or consists of the polypeptide of IGKV6-21 02 of SEQ ID NO: 163.

The heavy chain variable region comprises a complemen-tary determining region 1 (CDRH1) comprising SEQ ID NO: 69. The heavy chain variable region comprises a CDRH2 comprising SEQ ID NO: 70 or SEQ ID NO: 75. The heavy chain variable region comprises a CDRH3 comprising SEQ ID NO: 71.

The light chain variable region comprises a complemen-tary determining region 1 (CDRL1) comprising SEQ ID NO: 72. The light chain variable region comprises a CDRL2 comprising SEQ ID NO: 73. The light chain variable region comprises a CDRL3 comprising SEQ ID NO: 74.

The heavy chain variable region comprises, consists essentially of, or consists of the amino acid sequence at least 95%, 96%, 97%, 98%, 99% or 100% (or any percentage in between) identical to SEQ ID NO: 3, SEQ ID NO: 4, SEQ ID NO: 5, SEQ ID NO: 6, SEQ ID NO: 7 or SEQ ID NO: 8. In a preferred aspect, the heavy chain variable region comprises, consists essentially of, or consists of the amino acid sequence of SEQ ID NO: 3, SEQ ID NO: 4, SEQ ID NO: 5, SEQ ID NO: 6, SEQ ID NO: 7 or SEQ ID NO: 8.

The heavy chain variable region is encoded by a poly-nucleotide comprising, consisting essentially of or consist-ing of the nucleic acid sequence at least 95%, 96%, 97%, 98%, 99% or 100% (or any percentage in between) identical to SEQ ID NO: 48, SEQ ID NO: 49, SEQ ID NO: 50, SEQ ID NO: 51, SEQ ID NO: 52, SEQ ID NO: 53 or SEQ ID NO: 164.

In a preferred aspect, the heavy chain variable region is encoded by a polynucleotide comprising, consisting essen-tially of or consisting of the nucleic acid sequence of SEQ ID NO: 48, SEQ ID NO: 49, SEQ ID NO: 50, SEQ ID NO: 51, SEQ ID NO: 52, SEQ ID NO: 53 or SEQ ID NO: 164.

The light chain variable region comprises, consists essen-tially of, or consists of the amino acid sequence at least 95%, 96%, 97%, 98%, 99% or 100% (or any percentage in between) identical to the amino acid sequence of SEQ ID NO: 9, SEQ ID NO: 10 or SEQ ID NO: 11. In a preferred aspect, the light chain variable region comprises, consists essentially of, or consists of the amino acid sequence of SEQ ID NO: 9, SEQ ID NO: 10 or SEQ ID NO: 11.

The light chain variable region is encoded by a polynucle-otide comprising, consisting essentially of or consisting of the nucleic acid sequence at least 95%, 96%, 97%, 98%, 99% or 100% (or any percentage in between) identical to SEQ ID NO: 54, SEQ ID NO: 55, SEQ ID NO: 56 or SEQ ID NO: 165. In a preferred aspect, the light chain variable region is encoded by a polynucleotide comprising, consist-ing essentially of or consisting of the nucleic acid sequence of SEQ ID NO: 54, SEQ ID NO: 55, SEQ ID NO: 56 or SEQ ID NO: 165.

The heavy chain variable region of the antibody can comprise the amino acid sequence of SEQ ID NO: 3 and the light chain variable region of the antibody can comprise the amino acid sequence of SEQ ID NO: 9. The heavy chain variable region of the antibody can comprise the amino acid sequence of SEQ ID NO: 4 and the light chain variable region of the antibody can comprise the amino acid sequence of SEQ ID NO: 9. The heavy chain variable region of the antibody can comprise the amino acid sequence of SEQ ID NO: 5 and the light chain variable region of the antibody can comprise the amino acid sequence of SEQ ID NO: 9. The heavy chain variable region of the antibody can comprise the amino acid sequence of SEQ ID NO: 6 and the light chain variable region of the antibody can comprise the amino acid sequence of SEQ ID NO: 9. The heavy chain variable region of the antibody can comprise the amino acid sequence of SEQ ID NO: 7 and the light chain variable region of the antibody can comprise the amino acid sequence of SEQ ID NO: 9. The heavy chain variable region of the antibody can comprise the amino acid sequence of SEQ ID NO: 8 and the light chain variable region of the antibody can comprise the amino acid sequence of SEQ ID NO: 9.

The heavy chain variable region of the antibody can comprise the amino acid sequence of SEQ ID NO: 3 and the light chain variable region of the antibody can comprise the amino acid sequence of SEQ ID NO: 10. The heavy chain variable region of the antibody can comprise the amino acid sequence of SEQ ID NO: 4 and the light chain variable region of the antibody can comprise the amino acid sequence of SEQ ID NO: 10. The heavy chain variable region of the antibody can comprise the amino acid sequence of SEQ ID NO: 5 and the light chain variable region of the antibody can comprise the amino acid sequence of SEQ ID NO: 10. The heavy chain variable region of the antibody can comprise the amino acid sequence of SEQ ID NO: 6 and the light chain variable region of the antibody can comprise the amino acid sequence of SEQ ID NO: 10. The heavy chain variable region of the antibody can comprise the amino acid sequence of SEQ ID NO: 7 and the light chain variable region of the antibody can comprise the amino acid sequence of SEQ ID NO: 10. The heavy chain variable region of the antibody can comprise the amino acid sequence of SEQ ID NO: 8 and the light chain variable region of the antibody can comprise the amino acid sequence of SEQ ID NO: 10.

The heavy chain variable region of the antibody can comprise the amino acid sequence of SEQ ID NO: 3 and the light chain variable region of the antibody can comprise the amino acid sequence of SEQ ID NO: 11. The heavy chain variable region of the antibody can comprise the amino acid sequence of SEQ ID NO: 4 and the light chain variable region of the antibody can comprise the amino acid sequence of SEQ ID NO: 11. The heavy chain variable region of the antibody can comprise the amino acid sequence of SEQ ID NO: 5 and the light chain variable region of the antibody can comprise the amino acid sequence of SEQ ID NO: 11. The heavy chain variable region of the antibody can comprise the amino acid sequence of SEQ ID NO: 6 and the light chain variable region of the antibody can comprise the amino acid sequence of SEQ ID NO: 11. The heavy chain variable region of the antibody can comprise the amino acid sequence of SEQ ID NO: 7 and the light chain variable region of the antibody can comprise the amino acid sequence of SEQ ID NO: 11. The heavy chain variable region of the antibody can comprise the amino acid sequence of SEQ ID NO: 8 and the light chain variable region of the antibody can comprise the amino acid sequence of SEQ ID NO: 11.

In some aspects, the antibody comprises a human or humanized sequence. In some aspects, a CDR comprises the humanized sequence. In some aspects, a variable region comprises the humanized sequence. In some aspects, a framework region comprises the humanized sequence. The framework region can further comprise one or more sequence variation to decrease immunogenicity or to improve production of the antibody. In some aspects, the antibody is an IgG.

The antibody can be a monoclonal antibody, a chimeric antibody, a single domain antibody, a VHH, a VH, a single chain variable fragment (scFv), an antigen-binding fragment (Fab) or a Fab fragment. In a preferred aspect, the antibody is an scFv.

The disclosure provides scFv compositions and methods for using these compositions to recognize and bind to a specific target protein (e.g., MUC1) with high affinity and avidity. The scFv compositions can comprise a heavy chain variable region and a light chain variable region of an anti-MUC1 antibody.

The scFv can comprise a linker polypeptide between the heavy chain variable region and the light chain variable region. In some embodiments, the linker polypeptide comprises, consists essentially of, or consists of the amino acid sequence of SEQ ID NO: 59. The linker polypeptide can be encoded by a polynucleotide comprising, consisting essentially of, or consists of the nucleic acid sequence of SEQ ID NO: 60.

The scFv comprises, consists essentially of, or consists of the amino acid sequence at least 95%, 96%, 97%, 98%, 99% or 100% (or any percentage in between) identical to SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 or SEQ ID NO: 29. In a preferred aspect, the scFv comprises, consists essentially of, or consists of the amino acid sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 or SEQ ID NO: 29.

The scFv is encoded by a polynucleotide comprising, consisting essentially of, or consisting of the nucleic acid sequence at least 95%, 96%, 97%, 98%, 99% or 100% (or any percentage in between) identical to SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO: 166. In a preferred aspect, the scFv is encoded by a nucleic acid comprising, consisting essentially of or consisting of the nucleic acid sequence of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 or SEQ ID NO: 166.

The present disclosure also provides a chimeric antigen receptor (CAR) comprising an ectodomain comprising antigen recognition region, wherein the antigen recognition region comprises at least one anti-MUC1 single chain variable fragment (scFv) of the disclosure; a transmembrane domain, and an endodomain comprising at least one costimulatory domain. The CAR can further comprise a hinge region between the antigen recognition domain and the transmembrane domain. The antigen recognition region can comprise at least two anti-MUC1 scFv. The antigen recognition region can comprise at least three anti-MUC1 scFv. In one aspect, a CAR of the disclosure is a bi-specific CAR comprising at least two scFvs that specifically bind two distinct antigens.

The ectodomain can comprise a signal peptide. The signal peptide can comprise a sequence encoding a human CD2, CD3δ, CD3ε, CD3γ, CD3ζ, CD4, CD8α, CD19, CD28, 4-1BB or GM-CSFR signal peptide. In a preferred aspect, the signal peptide comprises, consists essentially of, or consists of a human CD8 alpha (CD8α) signal peptide (SP) or a portion thereof. The human CD8a SP comprises, consists essentially of, or consists of an amino acid sequence at least 75%, 80%, 85%, 90%, 95%, 96%, 97%, 98%, 99% or 100% (or any percentage in between) identical to SEQ ID NO: 57. Preferably, the human CD8a SP comprises, consists essentially of, or consists of the amino acid sequence of SEQ ID NO: 57.

The human CD8a SP is encoded by a polynucleotide comprising, consisting essentially of or consisting of a nucleic acid sequence at least 75%, 80%, 85%, 90%, 95%, 96%, 97%, 98%, 99% or 100% (or any percentage in between) identical to SEQ ID NO: 58. Preferably, the human CD8a SP is encoded by a polynucleotide comprising, consisting essentially of, or consisting of the amino acid sequence of SEQ ID NO: 58.

The hinge domain or hinge region can comprise a human CD8α, IgG4, CD4 sequence, or a combination thereof. In a preferred aspect, the hinge can comprise, consist essentially of, or consist of a human CD8 alpha (CD8α) hinge or a portion thereof. The human CD8a hinge comprises, consists essentially, of or consists of an amino acid sequence at least 75%, 80%, 85%, 90%, 95%, 96%, 97%, 98%, 99% or 100% (or any percentage in between) identical to SEQ ID NO: 61. Preferably, the human CD8a hinge domain comprises, consists essentially of, or consists of the amino acid sequence of SEQ ID NO: 61.

The human CD8a hinge is encoded by a polynucleotide comprising, consisting essentially of or consisting of a nucleic acid sequence at least 75%, 80%, 85%, 90%, 95%, 96%, 97%, 98%, 99% or 100% (or any percentage in between) identical to SEQ ID NO: 62 or SEQ ID NO: 168. Preferably, the human CD8a hinge domain is encoded by a polynucleotide comprising, consisting essentially of or consisting of the nucleic acid sequence of SEQ ID NO: 62 or SEQ ID NO: 168.

The transmembrane domain can comprise, consist essentially of, or consist of a sequence encoding a human CD2, CD3δ, CD3F, CD3γ, CD3ζ, CD4, CD8α, CD19, CD28, 4-1BB or GM-CSFR transmembrane domain. Preferably, the transmembrane domain can comprise, consist essentially of, or consist of a human CD8 alpha (CD8α) transmembrane domain, or a portion thereof. The CD8a transmembrane domain comprises, consists essentially of or consists of an amino acid sequence at least 75%, 80%, 85%, 90%, 95%, 96%, 97%, 98%, 99% or 100% (or any percentage in between) identical to SEQ ID NO: 63. Preferably, the human CD8a transmembrane domain comprises, consists essentially of, or consists of the amino acid sequence of SEQ ID NO: 63.

The CD8a transmembrane domain is encoded by a polynucleotide comprising, consisting essentially of, or consisting of a nucleic acid sequence at least 75%, 80%, 85%, 90%, 95%, 96%, 97%, 98%, 99% or 100% (or any percentage in between) identical to SEQ ID NO: 64 or SEQ ID NO: 169. Preferably, the CD8a transmembrane domain is encoded by a polynucleotide comprising, consisting essentially of, or consisting of the nucleic acid sequence of SEQ ID NO: 64 or SEQ ID NO: 169.

The at least one costimulatory domain can comprise, consist essentially of, or consist of a human 4-1BB, CD28, CD3 zeta (CD3ζ), CD40, ICOS, MyD88, OX-40 intracellular domain, or any combination thereof. Preferably, the at least one costimulatory domain comprises a CD3ζ, a 4-1BB costimulatory domain, or a combination thereof.

The 4-1BB intracellular domain comprises, consists essentially of, or consists of an amino acid sequence at least 75%, 80%, 85%, 90%, 95%, 96%, 97%, 98%, 99% or 100% (or any percentage in between) identical to SEQ ID NO: 65.

Preferably, the 4-1BB intracellular domain comprises, consists essentially of, or consists of the amino acid sequence of SEQ ID NO: 65.

The 4-1BB intracellular domain is encoded by a polynucleotide comprising, consisting essentially of, or consisting of a nucleic acid sequence at least 75%, 80%, 85%, 90%, 95%, 96%, 97%, 98%, 99% or 100% (or any percentage in between) identical to SEQ ID NO: 66 or SEQ ID NO: 170. Preferably, the 4-1BB intracellular domain is encoded by a polynucleotide comprising, consisting essentially of or consisting of the nucleic acid sequence of SEQ ID NO: 66 or SEQ ID NO: 170.

The CD3ζ intracellular domain comprises, consists essentially of, or consists of an amino acid sequence at least 75%, 80%, 85%, 90%, 95%, 96%, 97%, 98%, 99% or 100% (or any percentage in between) identical to SEQ ID NO: 67. Preferably, the CD3ζ intracellular domain comprises, consists essentially of, or consists of the amino acid sequence of SEQ ID NO: 67.

The CD3ζ intracellular domain is encoded by a polynucleotide comprising, consisting essentially of, or consisting of a nucleic acid sequence at least 75%, 80%, 85%, 90%, 95%, 96%, 97%, 98%, 99% or 100% (or any percentage in between) identical to SEQ ID NO: 68 or SEQ ID NO: 171. Preferably, the CD3ζ intracellular domain is encoded by a polynucleotide comprising, consisting essentially of, or consisting of the nucleic acid sequence of SEQ ID NO: 68 or SEQ ID NO: 171.

A composition of the present disclosure (e.g., an anti-MUC1 scFv, CAR comprising an anti-MUC1 scFv) may bind human MUC1 with at least one affinity selected from a $K_D$ of less than or equal to $10^{-9}$M, less than or equal to $10^{-10}$M, less than or equal to $10^{-11}$M, less than or equal to $10^{-12}$M, less than or equal to $10^{-13}$M, less than or equal to $10^{-14}$M, and less than or equal to $10^{-15}$M. The $K_D$ may be determined by any means, including, but not limited to, surface plasmon resonance.

Compositions comprising an anti-MUC1 scFv or a CAR comprising an anti-MUC1 scFv can be incorporated into a cell delivery composition (e.g., transposon or vector) as described in detail herein, and, optionally, can be incorporated into a cell.

Cells modified (e.g., immune cells and cytotoxic immune cells) by contact and/or incorporation of a composition of the disclosure can specifically target MUC1-expressing cells. Preferred aspects of the methods of the disclosure use a MUC1-C scFv binder to redirect a cytotoxic cell type to mediate the destruction of a cell expressing MUC1-C (MUC1-C+ cell). For example, to treat a proliferation disorder, such as cancer. Modified cells expressing an anti-MUC1 scFv or a CAR comprising an anti-MUC1 scFv of the disclosure demonstrate improved in vivo persistence and anti-tumor efficacy. In some aspects, modified cells expressing an anti-MUC1 scFv or a CAR comprising an anti-MUC1 scFv of the disclosure demonstrate improved potency and reduced immunogenicity in comparison to cells that express a murine anti-MUC1 scFv or a CAR comprising a murine anti-MUC1 scFv. In some aspects, modified cells expressing an anti-MUC1 scFv or a CAR comprising an anti-MUC1 scFv of the disclosure demonstrate improved potency and reduced immunogenicity in comparison to cells that express an scFv comprising a heavy variable region of SEQ ID NO: 176 and a light variable region of SEQ ID NO: 177 or a CAR comprising the scFv. In some aspects, modified cells expressing an anti-MUC1 scFv or a CAR comprising an anti-MUC1 scFv of the disclosure demonstrate improved potency and reduced immunogenicity in comparison to cells that express an scFv comprising a heavy variable region of SEQ ID NO: 178 and a light variable region of SEQ ID NO: 179 or a CAR comprising the scFv. In some aspects, modified cells expressing an anti-MUC1 scFv or a CAR comprising an anti-MUC1 scFv of the disclosure demonstrate improved potency and reduced immunogenicity in comparison to cells that express an scFv comprising a heavy variable region of SEQ ID NO: 180 and a light variable region of SEQ ID NO: 181 or a CAR comprising the same.

A "L1H1" scFv comprises a light chain variable region "L1" having the amino acid sequence of SEQ ID NO: 9 encoded by the nucleic acid sequence of SEQ ID NO: 54; and comprises a heavy chain variable region "H1" having the amino acid sequence of SEQ ID NO: 3, encoded by the nucleic acid sequence of SEQ ID NO: 48. A "L1H1" scFv comprises an amino acid sequence of SEQ ID NO: 124 encoded by the nucleic acid sequence of SEQ ID NO: 142. A "L1H1" CAR comprises an amino acid sequence of SEQ ID NO: 12, encoded by the nucleic acid sequence of SEQ ID NO: 30.

A "L1H1B" scFv comprises a light chain variable region "L1" having the amino acid sequence of SEQ ID NO: 9 encoded by the nucleic acid sequence of SEQ ID NO: 54 or SEQ ID NO: 165; and comprises a heavy chain variable region "H1B" having the amino acid sequence of SEQ ID NO: 4, encoded by the nucleic acid sequence of SEQ ID NO: 49 or SEQ ID NO: 164. A "L1H1B" scFv comprises an amino acid sequence of SEQ ID NO: 125 encoded by the nucleic acid sequence of SEQ ID NO: 143 or SEQ ID NO: 166. A "L1H1B" CAR comprises an amino acid sequence of SEQ ID NO: 13, encoded by the nucleic acid sequence of SEQ ID NO: 31 or SEQ ID NO: 167.

A "L1H2" scFv comprises a light chain variable region "L1" having the amino acid sequence of SEQ ID NO: 9 encoded by the nucleic acid sequence of SEQ ID NO: 54; and comprises a heavy chain variable region "H2" having the amino acid sequence of SEQ ID NO: 5, encoded by the nucleic acid sequence of SEQ ID NO: 50. A "L1H2" scFv comprises an amino acid sequence of SEQ ID NO: 126 encoded by the nucleic acid sequence of SEQ ID NO: 144. A "L1H2" CAR comprises an amino acid sequence of SEQ ID NO: 14, encoded by the nucleic acid sequence of SEQ ID NO: 32.

A "L1H2B" scFv comprises a light chain variable region "L1" having the amino acid sequence of SEQ ID NO: 9 encoded by the nucleic acid sequence of SEQ ID NO: 54; and comprises a heavy chain variable region "H2B" having the amino acid sequence of SEQ ID NO: 6, encoded by the nucleic acid sequence of SEQ ID NO: 51. A "L1H2B" scFv comprises an amino acid sequence of SEQ ID NO: 127 encoded by the nucleic acid sequence of SEQ ID NO: 145. A "L1H2B" CAR comprises an amino acid sequence of SEQ ID NO: 15, encoded by the nucleic acid sequence of SEQ ID NO: 33.

A "L1H3" scFv comprises a light chain variable region "L1" having the amino acid sequence of SEQ ID NO: 9 encoded by the nucleic acid sequence of SEQ ID NO: 54; and comprises a heavy chain variable region "H3" having the amino acid sequence of SEQ ID NO: 7, encoded by the nucleic acid sequence of SEQ ID NO: 52. A "L1H3" scFv comprises an amino acid sequence of SEQ ID NO: 128 encoded by the nucleic acid sequence of SEQ ID NO: 146. A "L1H3" CAR comprises an amino acid sequence of SEQ ID NO: 16, encoded by the nucleic acid sequence of SEQ ID NO: 34.

A "L1H4" scFv comprises a light chain variable region "L1" having the amino acid sequence of SEQ ID NO: 9 encoded by the nucleic acid sequence of SEQ ID NO: 54; and comprises a heavy chain variable region "H4" having the amino acid sequence of SEQ ID NO: 8, encoded by the nucleic acid sequence of SEQ ID NO: 53. A "L1H4" scFv comprises an amino acid sequence of SEQ ID NO: 129 encoded by the nucleic acid sequence of SEQ ID NO: 147. A "L1H4" CAR comprises an amino acid sequence of SEQ ID NO: 17, encoded by the nucleic acid sequence of SEQ ID NO: 35.

A "L2H1" scFv comprises a light chain variable region "L2" having the amino acid sequence of SEQ ID NO: 10 encoded by the nucleic acid sequence of SEQ ID NO: 55; and comprises a heavy chain variable region "H1" having the amino acid sequence of SEQ ID NO: 3, encoded by the nucleic acid sequence of SEQ ID NO: 48. A "L2H1" scFv comprises an amino acid sequence of SEQ ID NO: 130 encoded by the nucleic acid sequence of SEQ ID NO: 148. A "L2H1" CAR comprises an amino acid sequence of SEQ ID NO: 18, encoded by the nucleic acid sequence of SEQ ID NO: 36.

A "L2H1B" scFv comprises a light chain variable region "L2" having the amino acid sequence of SEQ ID NO: 10 encoded by the nucleic acid sequence of SEQ ID NO: 55; and comprises a heavy chain variable region "H1B" having the amino acid sequence of SEQ ID NO: 4, encoded by the nucleic acid sequence of SEQ ID NO: 49. A "L2H1B" scFv comprises an amino acid sequence of SEQ ID NO: 131 encoded by the nucleic acid sequence of SEQ ID NO: 149. A "L2H1B" CAR comprises an amino acid sequence of SEQ ID NO: 19, encoded by the nucleic acid sequence of SEQ ID NO: 37.

A "L2H2" scFv comprises a light chain variable region "L2" having the amino acid sequence of SEQ ID NO: 10 encoded by the nucleic acid sequence of SEQ ID NO: 55; and comprises a heavy chain variable region "H2" having the amino acid sequence of SEQ ID NO: 5, encoded by the nucleic acid sequence of SEQ ID NO: 50. A "L2H2" scFv comprises an amino acid sequence of SEQ ID NO: 132 encoded by the nucleic acid sequence of SEQ ID NO: 150. A "L2H2" CAR comprises an amino acid sequence of SEQ ID NO: 20, encoded by the nucleic acid sequence of SEQ ID NO: 38.

A "L2H2B" scFv comprises a light chain variable region "L2" having the amino acid sequence of SEQ ID NO: 10 encoded by the nucleic acid sequence of SEQ ID NO: 55; and comprises a heavy chain variable region "H2B" having the amino acid sequence of SEQ ID NO: 6, encoded by the nucleic acid sequence of SEQ ID NO: 51. A "L2H2B" scFv comprises an amino acid sequence of SEQ ID NO: 133 encoded by the nucleic acid sequence of SEQ ID NO: 151. A "L2H2B" CAR comprises an amino acid sequence of SEQ ID NO: 21, encoded by the nucleic acid sequence of SEQ ID NO: 39.

A "L2H3" scFv comprises a light chain variable region "L2" having the amino acid sequence of SEQ ID NO: 10 encoded by the nucleic acid sequence of SEQ ID NO: 55; and comprises a heavy chain variable region "H3" having the amino acid sequence of SEQ ID NO: 7, encoded by the nucleic acid sequence of SEQ ID NO: 52. A "L2H3" scFv comprises an amino acid sequence of SEQ ID NO: 134 encoded by the nucleic acid sequence of SEQ ID NO: 152. A "L2H3" CAR comprises an amino acid sequence of SEQ ID NO: 22, encoded by the nucleic acid sequence of SEQ ID NO: 40.

A "L2H4" scFv comprises a light chain variable region "L2" having the amino acid sequence of SEQ ID NO: 10 encoded by the nucleic acid sequence of SEQ ID NO: 55;

and comprises a heavy chain variable region "H4" having the amino acid sequence of SEQ ID NO: 8, encoded by the nucleic acid sequence of SEQ ID NO: 53. A "L2H4" scFv comprises an amino acid sequence of SEQ ID NO: 135 encoded by the nucleic acid sequence of SEQ ID NO: 153. A "L2H4" CAR comprises an amino acid sequence of SEQ ID NO: 23, encoded by the nucleic acid sequence of SEQ ID NO: 41.

A "L3H1" scFv comprises a light chain variable region "L3" having the amino acid sequence of SEQ ID NO: 11 encoded by the nucleic acid sequence of SEQ ID NO: 56; and comprises a heavy chain variable region "H1" having the amino acid sequence of SEQ ID NO: 3, encoded by the nucleic acid sequence of SEQ ID NO: 48. A "L3H1" scFv comprises an amino acid sequence of SEQ ID NO: 136 encoded by the nucleic acid sequence of SEQ ID NO: 154. A "L3H1" CAR comprises an amino acid sequence of SEQ ID NO: 24, encoded by the nucleic acid sequence of SEQ ID NO: 42.

A "L3H1B" scFv comprises a light chain variable region "L3" having the amino acid sequence of SEQ ID NO: 11 encoded by the nucleic acid sequence of SEQ ID NO: 56; and comprises a heavy chain variable region "H1B" having the amino acid sequence of SEQ ID NO: 4, encoded by the nucleic acid sequence of SEQ ID NO: 49. A "L3H1B" scFv comprises an amino acid sequence of SEQ ID NO: 137 encoded by the nucleic acid sequence of SEQ ID NO: 155. A "L3H1B" CAR comprises an amino acid sequence of SEQ ID NO: 25, encoded by the nucleic acid sequence of SEQ ID NO: 43.

A "L3H2" scFv comprises a light chain variable region "L3" having the amino acid sequence of SEQ ID NO: 11 encoded by the nucleic acid sequence of SEQ ID NO: 56; and comprises a heavy chain variable region "H2" having the amino acid sequence of SEQ ID NO: 5, encoded by the nucleic acid sequence of SEQ ID NO: 50. A "L3H2" scFv comprises an amino acid sequence of SEQ ID NO: 138 encoded by the nucleic acid sequence of SEQ ID NO: 156.

A "L3H2" CAR comprises an amino acid sequence of SEQ ID NO: 26, encoded by the nucleic acid sequence of SEQ ID NO: 44.

A "L3H2B" scFv comprises a light chain variable region "L3" having the amino acid sequence of SEQ ID NO: 11 encoded by the nucleic acid sequence of SEQ ID NO: 56; and comprises a heavy chain variable region "H2B" having the amino acid sequence of SEQ ID NO: 6, encoded by the nucleic acid sequence of SEQ ID NO: 51. A "L3H2B" scFv comprises an amino acid sequence of SEQ ID NO: 139 encoded by the nucleic acid sequence of SEQ ID NO: 157. A "L3H2B" CAR comprises an amino acid sequence of SEQ ID NO: 27, encoded by the nucleic acid sequence of SEQ ID NO: 45.

A "L3H3" scFv comprises a light chain variable region "L3" having the amino acid sequence of SEQ ID NO: 11 encoded by the nucleic acid sequence of SEQ ID NO: 56; and comprises a heavy chain variable region "H3" having the amino acid sequence of SEQ ID NO: 7, encoded by the nucleic acid sequence of SEQ ID NO: 52. A "L3H3" scFv comprises an amino acid sequence of SEQ ID NO: 140 encoded by the nucleic acid sequence of SEQ ID NO: 158. A "L3H3" CAR comprises an amino acid sequence of SEQ ID NO: 28, encoded by the nucleic acid sequence of SEQ ID NO: 46.

A "L3H4" scFv comprises a light chain variable region "L3" having the amino acid sequence of SEQ ID NO: 11 encoded by the nucleic acid sequence of SEQ ID NO: 56; and comprises a heavy chain variable region "H4" having the amino acid sequence of SEQ ID NO: 8, encoded by the nucleic acid sequence of SEQ ID NO: 53. A "L3H4" scFv comprises an amino acid sequence of SEQ ID NO: 141 encoded by the nucleic acid sequence of SEQ ID NO: 159. A "L3H4" CAR comprises an amino acid sequence of SEQ ID NO: 29, encoded by the nucleic acid sequence of SEQ ID NO: 47.

Table 1A and Table 1B show exemplary MUC-1C CAR components and sequences of the disclosure.

TABLE 1

| MUC-1C CAR Components and Amino Acid Sequences of the Disclosure | | |
|---|---|---|
| MUC1C CAR Components | Amino acid sequence | SEQ ID NOs: |
| complementary determining region 1 (CDRH1) | NFWMN | 69 |
| complementary determining region 2 (CDRH2) | QIYPGDGDTNYNGKFKG | 70 |
| complementary determining region 2 (CDRH2) | QIYPGDGDTNYNAKFKG | 75 |
| complementary determining region 3 (CDRH3) | SYYRSAWFAY | 71 |
| complementary determining region 1 (CDRL1) | RASQSIGTSIH | 72 |

TABLE 1-continued

MUC-1C CAR Components and
Amino Acid Sequences of the Disclosure

| MUC1C CAR Components | Amino acid sequence | SEQ ID NOs: |
|---|---|---|
| complementary determining region 2 (CDRL2) | YASESIS | 73 |
| complementary determining region 3 (CDRL3) | QQSNNWPLT | 74 |
| "H1" humanized heavy chain variable region | QVQLVQSGAEVKKPGSSVKVSCKTSGYAFSNFWMNWVRQAPG QGLEWIGQIYPGDGDTNYNGKFKGRVTLTADKSTSTAYMELS SLRSEDTAVYFCARSYYRSAWFAYWGQGTLVTVSS | 3 |
| "H1B" humanized heavy chain variable region | QVQLVQSGAEVKKPGSSVKVSCKTSGYAFSNFWMNWVRQAPG QGLEWIGQIYPGDGDTNYNAKFKGRVTLTADKSTSTAYMELS SLRSEDTAVYFCARSYYRSAWFAYWGQGTLVTVSS | 4 |
| "H2" humanized heavy chain variable region | QVQLVQSGAEVKKPGSSVKISCKTSGYAFSNFWMNWVRQAPG QGLEWIGQIYPGDGDTNYNGKFKGRVTLTADKSTSTAYMELS SLRSEATAVYFCARSYYRSAWFAYWGQGTLVTVSS | 5 |
| "H2B" humanized heavy chain variable region | QVQLVQSGAEVKKPGSSVKISCKTSGYAFSNFWMNWVRQAPG QGLEWIGQIYPGDGDTNYNAKFKGRVTLTADKSTSTAYMELS SLRSEATAVYFCARSYYRSAWFAYWGQGTLVTVSS | 6 |
| "H3" humanized heavy chain variable region | QVQLVQSGAEVKKPGSSVKISCKTSGYAFSNFWMNWVKQRPG QGLEWIGQIYPGDGDTNYNGKFKGRATLTADKSTSTAYMELS SLRSEATAVYFCARSYYRSAWFAYWGQGTLVTVSS | 7 |
| "H4" humanized heavy chain variable region | QVQLVQSGAEVKKPGSSVKISCKTSGYAFSNFWMNWVKQRPG QGLEWIGQIYPGDGDTNYNGKFKGRATLTADKSSSTAYMELS SLRSEATAVYFCARSYYRSAWFAYWGQGTLVTVSS | 8 |
| "L1" humanized light chain variable region | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIK | 9 |
| "L2" humanized light chain variable region | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIK | 10 |
| "L3" humanized light chain variable region | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIK | 11 |
| "L1H1" scFv | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIKGGGGSGGGGSGGGGSQVQL VQSGAEVKKPGSSVKVSCKTSGYAFSNFWMNWVRQAPGQGLE WIGQIYPGDGDTNYNGKFKGRVTLTADKSTSTAYMELSSLRS EDTAVYFCARSYYRSAWFAYWGQGTLVTVSS | 124 |
| "L1H1B" scFv | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIKGGGGSGGGGSGGGGSQVQL VQSGAEVKKPGSSVKVSCKTSGYAFSNFWMNWVRQAPGQGLE WIGQIYPGDGDTNYNAKFKGRVTLTADKSTSTAYMELSSLRS EDTAVYFCARSYYRSAWFAYWGQGTLVTVSS | 125 |
| "L1H2" scFv | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIKGGGGSGGGGSGGGGSQVQL VQSGAEVKKPGSSVKISCKTSGYAFSNFWMNWVRQAPGQGLE WIGQIYPGDGDTNYNGKFKGRVTLTADKSTSTAYMELSSLRS EATAVYFCARSYYRSAWFAYWGQGTLVTVSS | 126 |

TABLE 1-continued

MUC-1C CAR Components and
Amino Acid Sequences of the Disclosure

| MUC1C CAR Components | Amino acid sequence | SEQ ID NOs: |
|---|---|---|
| "L1H2B" scFv | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIKGGGGSGGGGSGGGGSQVQL VQSGAEVKKPGSSVKISCKTSGYAFSNFWMNWVRQAPGQGLE WIGQIYPGDGDTNYNAKFKGRVTLTADKSTSTAYMELSSLRS EATAVYFCARSYYRSAWFAYWGQGTLVTVSS | 127 |
| "L1H3" scFv | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIKGGGGSGGGGSGGGGSQVQL VQSGAEVKKPGSSVKISCKTSGYAFSNFWMNWVKQRPGQGLE WIGQIYPGDGDTNYNGKFKGRATLTADKSTSTAYMELSSLRS EATAVYFCARSYYRSAWFAYWGQGTLVTVSS | 128 |
| "L1H4" scFv | EILLTQSPDFQSVTPKEKVTFTCRASQSIGTSIHWYQQKPNQ SPKLLIKYASESISGVPSRFSGSGSGTDFTLTINSLESEDIA TYYCQQSNNWPLTFGQGTKLEIKGGGGSGGGGSGGGGSQVQL VQSGAEVKKPGSSVKISCKTSGYAFSNFWMNWVKQRPGQGLE WIGQIYPGDGDTNYNGKFKGRATLTADKSSSTAYMELSSLRS EATAVYFCARSYYRSAWFAYWGQGTLVTVSS | 129 |
| "L2H1" scFv | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIKGGGGSGGGGSGGGGSQVQL VQSGAEVKKPGSSVKVSCKTSGYAFSNFWMNWVRQAPGQGLE WIGQIYPGDGDTNYNGKFKGRVTLTADKSTSTAYMELSSLRS EDTAVYFCARSYYRSAWFAYWGQGTLVTVSS | 130 |
| "L2H1B" scFv | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIKGGGGSGGGGSGGGGSQVQL VQSGAEVKKPGSSVKVSCKTSGYAFSNFWMNWVRQAPGQGLE WIGQIYPGDGDTNYNAKFKGRVTLTADKSTSTAYMELSSLRS EDTAVYFCARSYYRSAWFAYWGQGTLVTVSS | 131 |
| "L2H2" scFv | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIKGGGGSGGGGSGGGGSQVQL VQSGAEVKKPGSSVKISCKTSGYAFSNFWMNWVRQAPGQGLE WIGQIYPGDGDTNYNGKFKGRVTLTADKSTSTAYMELSSLRS EATAVYFCARSYYRSAWFAYWGQGTLVTVSS | 132 |
| "L2H2B" scFv | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIKGGGGSGGGGSGGGGSQVQL VQSGAEVKKPGSSVKISCKTSGYAFSNFWMNWVRQAPGQGLE WIGQIYPGDGDTNYNAKFKGRVTLTADKSTSTAYMELSSLRS EATAVYFCARSYYRSAWFAYWGQGTLVTVSS | 133 |
| "L2H3" scFv | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIKGGGGSGGGGSGGGGSQVQL VQSGAEVKKPGSSVKISCKTSGYAFSNFWMNWVKQRPGQGLE WIGQIYPGDGDTNYNGKFKGRATLTADKSTSTAYMELSSLRS EATAVYFCARSYYRSAWFAYWGQGTLVTVSS | 134 |
| "L2H4" scFv | EILLTQSPDFQSVTPKEKVTFTCRASQSIGTSIHWYQQKPNQ SPKLLIKYASESISGVPSRFSGSGSGTDFTLTINSVESEDIA DYYCQQSNNWPLTFGQGTKLEIKGGGGSGGGGSGGGGSQVQL VQSGAEVKKPGSSVKISCKTSGYAFSNFWMNWVKQRPGQGLE WIGQIYPGDGDTNYNGKFKGRATLTADKSSSTAYMELSSLRS EATAVYFCARSYYRSAWFAYWGQGTLVTVSS | 135 |
| "L3H1" scFv | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIKGGGGSGGGGSGGGGSQVQL VQSGAEVKKPGSSVKVSCKTSGYAFSNFWMNWVRQAPGQGLE WIGQIYPGDGDTNYNGKFKGRVTLTADKSTSTAYMELSSLRS EDTAVYFCARSYYRSAWFAYWGQGTLVTVSS | 136 |
| "L3H1B" scFv | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIKGGGGSGGGGSGGGGSQVQL | 137 |

TABLE 1-continued

MUC-1C CAR Components and
Amino Acid Sequences of the Disclosure

| MUC1C CAR Components | Amino acid sequence | SEQ ID NOs: |
|---|---|---|
| | VQSGAEVKKPGSSVKVSCKTSGYAFSNFWMNWVRQAPGQGLE WIGQIYPGDGDTNYNAKFKGRVTLTADKSTSTAYMELSSLRS EDTAVYFCARSYYRSAWFAYWGQGTLVTVSS | |
| "L3H2" scFv | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIKGGGGSGGGGSGGGGSQVQL VQSGAEVKKPGSSVKISCKTSGYAFSNFWMNWVRQAPGQGLE WIGQIYPGDGDTNYNGKFKGRVTLTADKSTSTAYMELSSLRS EATAVYFCARSYYRSAWFAYWGQGTLVTVSS | 138 |
| "L3H2B" scFv | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIKGGGGSGGGGSGGGGSQVQL VQSGAEVKKPGSSVKISCKTSGYAFSNFWMNWVRQAPGQGLE WIGQIYPGDGDTNYNAKFKGRVTLTADKSTSTAYMELSSLRS EATAVYFCARSYYRSAWFAYWGQGTLVTVSS | 139 |
| "L3H3" scFv | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIKGGGGSGGGGSGGGGSQVQL VQSGAEVKKPGSSVKISCKTSGYAFSNFWMNWVKQRPGQGLE WIGQIYPGDGDTNYNGKFKGRATLTADKSTSTAYMELSSLRS EATAVYFCARSYYRSAWFAYWGQGTLVTVSS | 140 |
| "L3H4" scFv | EILLTQSPDFQSVTPKEKVTFTCRASQSIGTSIHWYQQKPNQ SPKLLIKYASESISGVPSRFSGSGSGTDFTLSINSVESEDIA DYYCQQSNNWPLTFGQGTKLEIKGGGGSGGGGSGGGGSQVQL VQSGAEVKKPGSSVKISCKTSGYAFSNFWMNWVKQRPGQGLE WIGQIYPGDGDTNYNGKFKGRATLTADKSSSTAYMELSSLRS EATAVYFCARSYYRSAWFAYWGQGTLVTVSS | 141 |
| "L1H1" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSLESEDIATYYCQQSNNWPLTFGQGTKLE IKGGGGSGGGGSGGGGSQVQLVQSGAEVKKPGSSVKVSCKTS GYAFSNFWMNWVRQAPGQGLEWIGQIYPGDGDTNYNGKFKGR VTLTADKSTSTAYMELSSLRSEDTAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 12 |
| "LlHlB" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSLESEDIATYYCQQSNNWPLTFGQGTKLE IKGGGGSGGGGSGGGGSQVQLVQSGAEVKKPGSSVKVSCKTS GYAFSNFWMNWVRQAPGQGLEWIGQIYPGDGDTNYNAKFKGR VTLTADKSTSTAYMELSSLRSEDTAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 13 |
| "L1H2" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSLESEDIATYYCQQSNNWPLTFGQGTKLE IKGGGGSGGGGSGGGGSQVQLVQSGAEVKKPGSSVKISCKTS GYAFSNFWMNWVRQAPGQGLEWIGQIYPGDGDTNYNGKFKGR VTLTADKSTSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 14 |
| "L1H2B" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSLESEDIATYYCQQSNNWPLTFGQGTKLE | 15 |

TABLE 1-continued

MUC-1C CAR Components and
Amino Acid Sequences of the Disclosure

| MUC1C CAR Components | Amino acid sequence | SEQ ID NOs: |
|---|---|---|
| | IKGGGGSGGGGSGGGGSQVQLVQSGAEVKKPGSSVKISCKTS GYAFSNFWMNWVRQAPGQGLEWIGQIYPGDGDTNYNAKFKGR VTLTADKSTSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPEMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | |
| "L1H3" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSLESEDIATYYCQQSNNWPLTFGQGTKLE IKGGGGSGGGGSGGGGSQVQLVQSGAEVKKPGSSVKISCKTS GYAFSNFWMNWVKQRPGQGLEWIGQIYPGDGDTNYNGKFKGR ATLTADKSTSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 16 |
| "L1H4" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSLESEDIATYYCQQSNNWPLTFGQGTKLE IKGGGGSGGGGSGGGGSQVQLVQSGAEVKKPGSSVKISCKTS GYAFSNFWMNWVKQRPGQGLEWIGQIYPGDGDTNYNGKFKGR ATLTADKSSSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 17 |
| "L2H1" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSVESEDIADYYCQQSNNWPLTFGQGTKLE IKGGGGSGGGGSGGGGSQVQLVQSGAEVKKPGSSVKVSCKTS GYAFSNFWMNWVRQAPGQGLEWIGQIYPGDGDTNYNGKFKGR VTLTADKSTSTAYMELSSLRSEDTAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 18 |
| "L2H1B" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSVESEDIADYYCQQSNNWPLTFGQGTKLE IKGGGGSGGGGSGGGGSQVQLVQSGAEVKKPGSSVKVSCKTS GYAFSNFWMNWVRQAPGQGLEWIGQIYPGDGDTNYNAKFKGR VTLTADKSTSTAYMELSSLRSEDTAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 19 |
| "L2H2" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLTINSVESEDIADYYCQQSNNWPLTFGQGTKLE IKGGGGSGGGGSGGGGSQVQLVQSGAEVKKPGSSVKISCKTS GYAFSNFWMNWVRQAPGQGLEWIGQIYPGDGDTNYNGKFKGR VTLTADKSTSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 20 |

TABLE 1-continued

MUC-1C CAR Components and
Amino Acid Sequences of the Disclosure

| MUC1C CAR Components | Amino acid sequence | SEQ ID NOs: |
|---|---|---|
| "L2H2B" CAR | MALPVTALLLPLALLLHAARPEILLTQSPDFQSVTPKEKVTF<br>TCRASQSIGTSIHWYQQKPNQSPKLLIKYASESISGVPSRFS<br>GSGSGTDFTLTINSVESEDIADYYCQQSNNWPLTFGQGTKLE<br>IKGGGGSGGGGSGGGGSQVQLVQSGAEVKKPGSSVKISCKTS<br>GYAFSNFWMNWVRQAPGQGLEWIGQIYPGDGDTNYNAKFKGR<br>VTLTADKSTSTAYMELSSLRSEATAVYFCARSYYRSAWFAYW<br>GQGTLVTVSSTTTPAPRPPTPAPTIASQPLSLRPEACRPAAG<br>GAVHTRGLDFACDIYIWAPLAGTCGVLLLSLVITLYCKRGRK<br>KLLYIFKQPFMRPVQTTQEEDGCSCRFPEEEEGGCELRVKFS<br>RSADAPAYKQGQNQLYNELNLGRREEYDVLDKRRGRDPEMGG<br>KPRRKNPQEGLYNELQKDKMAEAYSEIGMKGERRRGKGHDGL<br>YQGLSTATKDTYDALHMQALPPR | 21 |
| "L2H3" CAR | MALPVTALLLPLALLLHAARPEILLTQSPDFQSVTPKEKVTF<br>TCRASQSIGTSIHWYQQKPNQSPKLLIKYASESISGVPSRFS<br>GSGSGTDFTLTINSVESEDIADYYCQQSNNWPLTFGQGTKLE<br>IKGGGGSGGGGSGGGGSQVQLVQSGAEVKKPGSSVKISCKTS<br>GYAFSNFWMNWVKQRPGQGLEWIGQIYPGDGDTNYNGKFKGR<br>ATLTADKSTSTAYMELSSLRSEATAVYFCARSYYRSAWFAYW<br>GQGTLVTVSSTTTPAPRPPTPAPTIASQPLSLRPEACRPAAG<br>GAVHTRGLDFACDIYIWAPLAGTCGVLLLSLVITLYCKRGRK<br>KLLYIFKQPFMRPVQTTQEEDGCSCRFPEEEEGGCELRVKFS<br>RSADAPAYKQGQNQLYNELNLGRREEYDVLDKRRGRDPEMGG<br>KPRRKNPQEGLYNELQKDKMAEAYSEIGMKGERRRGKGHDGL<br>YQGLSTATKDTYDALHMQALPPR | 22 |
| "L2H4" CAR | MALPVTALLLPLALLLHAARPEILLTQSPDFQSVTPKEKVTF<br>TCRASQSIGTSIHWYQQKPNQSPKLLIKYASESISGVPSRFS<br>GSGSGTDFTLTINSVESEDIADYYCQQSNNWPLTFGQGTKLE<br>IKGGGGSGGGGSGGGGSQVQLVQSGAEVKKPGSSVKISCKTS<br>GYAFSNFWMNWVKQRPGQGLEWIGQIYPGDGDTNYNGKFKGR<br>ATLTADKSSSTAYMELSSLRSEATAVYFCARSYYRSAWFAYW<br>GQGTLVTVSSTTTPAPRPPTPAPTIASQPLSLRPEACRPAAG<br>GAVHTRGLDFACDIYIWAPLAGTCGVLLLSLVITLYCKRGRK<br>KLLYIFKQPFMRPVQTTQEEDGCSCRFPEEEEGGCELRVKFS<br>RSADAPAYKQGQNQLYNELNLGRREEYDVLDKRRGRDPEMGG<br>KPRRKNPQEGLYNELQKDKMAEAYSEIGMKGERRRGKGHDGL<br>YQGLSTATKDTYDALHMQALPPR | 23 |
| "L3H1" CAR | MALPVTALLLPLALLLHAARPEILLTQSPDFQSVTPKEKVTF<br>TCRASQSIGTSIHWYQQKPNQSPKLLIKYASESISGVPSRFS<br>GSGSGTDFTLSINSVESEDIADYYCQQSNNWPLTFGQGTKLE<br>IKGGGGSGGGGSGGGGSQVQLVQSGAEVKKPGSSVKVSCKTS<br>GYAFSNFWMNWVRQAPGQGLEWIGQIYPGDGDTNYNGKFKGR<br>VTLTADKSTSTAYMELSSLRSEDTAVYFCARSYYRSAWFAYW<br>GQGTLVTVSSTTTPAPRPPTPAPTIASQPLSLRPEACRPAAG<br>GAVHTRGLDFACDIYIWAPLAGTCGVLLLSLVITLYCKRGRK<br>KLLYIFKQPFMRPVQTTQEEDGCSCRFPEEEEGGCELRVKFS<br>RSADAPAYKQGQNQLYNELNLGRREEYDVLDKRRGRDPEMGG<br>KPRRKNPQEGLYNELQKDKMAEAYSEIGMKGERRRGKGHDGL<br>YQGLSTATKDTYDALHMQALPPR | 24 |
| "L3H1B" CAR | MALPVTALLLPLALLLHAARPEILLTQSPDFQSVTPKEKVTF<br>TCRASQSIGTSIHWYQQKPNQSPKLLIKYASESISGVPSRFS<br>GSGSGTDFTLSINSVESEDIADYYCQQSNNWPLTFGQGTKLE<br>IKGGGGSGGGGSGGGGSQVQLVQSGAEVKKPGSSVKVSCKTS<br>GYAFSNFWMNWVRQAPGQGLEWIGQIYPGDGDTNYNAKFKGR<br>VTLTADKSTSTAYMELSSLRSEDTAVYFCARSYYRSAWFAYW<br>GQGTLVTVSSTTTPAPRPPTPAPTIASQPLSLRPEACRPAAG<br>GAVHTRGLDFACDIYIWAPLAGTCGVLLLSLVITLYCKRGRK<br>KLLYIFKQPFMRPVQTTQEEDGCSCRFPEEEEGGCELRVKFS<br>RSADAPAYKQGQNQLYNELNLGRREEYDVLDKRRGRDPEMGG<br>KPRRKNPQEGLYNELQKDKMAEAYSEIGMKGERRRGKGHDGL<br>YQGLSTATKDTYDALHMQALPPR | 25 |
| "L3H2" CAR | MALPVTALLLPLALLLHAARPEILLTQSPDFQSVTPKEKVTF<br>TCRASQSIGTSIHWYQQKPNQSPKLLIKYASESISGVPSRFS<br>GSGSGTDFTLSINSVESEDIADYYCQQSNNWPLTFGQGTKLE<br>IKGGGGSGGGGSGGGGSQVQLVQSGAEVKKPGSSVKISCKTS<br>GYAFSNFWMNWVRQAPGQGLEWIGQIYPGDGDTNYNGKFKGR<br>VTLTADKSTSTAYMELSSLRSEATAVYFCARSYYRSAWFAYW<br>GQGTLVTVSSTTTPAPRPPTPAPTIASQPLSLRPEACRPAAG<br>GAVHTRGLDFACDIYIWAPLAGTCGVLLLSLVITLYCKRGRK | 26 |

TABLE 1-continued

MUC-1C CAR Components and
Amino Acid Sequences of the Disclosure

| MUC1C CAR Components | Amino acid sequence | SEQ ID NOs: |
|---|---|---|
| | KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | |
| "L3H2B" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLSINSVESEDIADYYCQQSNNWPLTFGQGTKLE IKGGGGSGGGGSGGGGSQVQLVQSGAEVKKPGSSVKISCKTS GYAFSNFWMNWVRQAPGQGLEWIGQIYPGDGDTNYNAKFKGR VTLTADKSTSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 27 |
| "L3H3" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLSINSVESEDIADYYCQQSNNWPLTFGQGTKLE IKGGGGSGGGGSGGGGSQVQLVQSGAEVKKPGSSVKISCKTS GYAFSNFWMNWVKQRPGQGLEWIGQIYPGDGDTNYNGKFKGR ATLTADKSTSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 28 |
| "L3H4" CAR | MALPVTALLLPLALLLHAARPEILLTQSPDFQSVTPKEKVTF TCRASQSIGTSIHWYQQKPNQSPKLLIKYASESISGVPSRFS GSGSGTDFTLSINSVESEDIADYYCQQSNNWPLTFGQGTKLE IKGGGGSGGGGSGGGGSQVQLVQSGAEVKKPGSSVKISCKTS GYAFSNFWMNWVKQRPGQGLEWIGQIYPGDGDTNYNGKFKGR ATLTADKSSSTAYMELSSLRSEATAVYFCARSYYRSAWFAYW GQGTLVTVSSTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFS RSADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR | 29 |
| CD8a signal peptide | MALPVTALLLPLALLLHAARP | 57 |
| linker sequence | GGGGSGGGGSGGGGS | 59 |
| CD8a hinge | TTTPAPRPPTPAPTIASQPLSLRPEACRPAAGGAVHTRGLDF ACD | 61 |
| CD8a transmembrane domain | IYIWAPLAGTCGVLLLSLVITLYC | 63 |
| 41BB ICS | KRGRKKLLYIFKQPFMRPVQTTQEEDGCSCRFPEEEEGGCEL | 65 |
| CD3z ICS | RVKFSRSADAPAYKQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR | 67 |

TABLE 1B

MUC-1C CAR Components and Nucleic
Acid Sequences of the Disclosure

| MUC1C CAR Components | SEQ ID NOs: |
|---|---|
| "H1" humanized heavy chain variable region | 48 |
| "H1B" humanized heavy chain variable region | 49, 164 |

TABLE 1B-continued

MUC-1C CAR Components and Nucleic
Acid Sequences of the Disclosure

| MUC1C CAR Components | SEQ ID NOs: |
|---|---|
| "H2" humanized heavy chain variable region | 50 |
| "H2B" humanized heavy chain variable region | 51 |

TABLE 1B-continued

MUC-1C CAR Components and Nucleic
Acid Sequences of the Disclosure

| MUC1C CAR Components | SEQ ID NOs: |
| --- | --- |
| "H3" humanized heavy chain variable region | 52 |
| "H4" humanized heavy chain variable region | 53 |
| "L1" humanized light chain variable region | 54, 165 |
| "L2" humanized light chain variable region | 55 |
| "L3" humanized light chain variable region | 56 |
| "L1H1" scFv | 142 |
| "L1H1B" scFv | 143, 166 |
| "L1H2" scFv | 144 |
| "L1H2B" scFv | 145 |
| "L1H3" scFv | 146 |
| "L1H4" scFv | 147 |
| "L2H1" scFv | 148 |
| "L2H1B" scFv | 149 |
| "L2H2" scFv | 150 |
| "L2H2B" scFv | 151 |
| "L2H3" scFv | 152 |
| "L2H4" scFv | 153 |
| "L3H1" scFv | 154 |
| "L3H1B" scFv | 155 |
| "L3H2" scFv | 156 |
| "L3H2B" scFv | 157 |
| "L3H3" scFv | 158 |
| "L3H4" scFv | 159 |
| "L1H1" CAR | 30 |
| "L1H1B" CAR | 31, 167 |
| "L1H2" CAR | 32 |
| "L1H2B" CAR | 33 |
| "L1H3" CAR | 34 |
| "L1H4" CAR | 35 |
| "L2H1" CAR | 36 |
| "L2H1B" CAR | 37 |
| "L2H2" CAR | 38 |
| "L2H2B" CAR | 39 |
| "L2H3" CAR | 40 |
| "L2H4" CAR | 41 |
| "L3H1" CAR | 42 |
| "L3H1B" CAR | 43 |
| "L3H2" CAR | 44 |
| "L3H2B" CAR | 45 |
| "L3H3" CAR | 46 |
| "L3H4" CAR | 47 |
| CD8a signal peptide | 58 |
| linker sequence | 60 |
| CD8a hinge | 62, 168 |
| CD8a transmembrane domain | 64, 169 |
| 41BB ICS | 66, 170 |
| CD3z ICS | 68, 171 |
| "L1H1B" CAR transposon sequence | 175 |

Cells and Modified Cells of the Disclosure

Cells and modified cells of the disclosure can be mammalian cells. Preferably, the cells and modified cells are human cells. Cells and modified cells of the disclosure can be immune cells. The immune cells of the disclosure can comprise lymphoid progenitor cells, natural killer (NK) cells, T lymphocytes (T-cell), stem memory T cells ($T_{SCM}$ cells), central memory T cells ($T_{CM}$), stem cell-like T cells, B lymphocytes (B-cells), antigen presenting cells (APCs), cytokine induced killer (CIK) cells, myeloid progenitor cells, neutrophils, basophils, eosinophils, monocytes, macrophages, platelets, erythrocytes, red blood cells (RBCs), megakaryocytes or osteoclasts.

The immune precursor cells can comprise any cells which can differentiate into one or more types of immune cells. The immune precursor cells can comprise multipotent stem cells that can self-renew and develop into immune cells. The immune precursor cells can comprise hematopoietic stem cells (HSCs) or descendants thereof. The immune precursor cells can comprise precursor cells that can develop into immune cells. The immune precursor cells can comprise hematopoietic progenitor cells (HPCs).

Hematopoietic stem cells (HSCs) are multipotent, self-renewing cells. All differentiated blood cells from the lymphoid and myeloid lineages arise from HSCs. HSCs can be found in adult bone marrow, peripheral blood, mobilized peripheral blood, peritoneal dialysis effluent and umbilical cord blood.

HSCs can be isolated or derived from a primary or cultured stem cell. HSCs can be isolated or derived from an embryonic stem cell, a multipotent stem cell, a pluripotent stem cell, an adult stem cell, or an induced pluripotent stem cell (iPSC).

Immune precursor cells can comprise an HSC or an HSC descendent cell. Non-limiting examples of HSC descendent cells include multipotent stem cells, lymphoid progenitor cells, natural killer (NK) cells, T lymphocyte cells (T-cells), B lymphocyte cells (B-cells), myeloid progenitor cells, neutrophils, basophils, eosinophils, monocytes and macrophages.

HSCs produced by the disclosed methods can retain features of "primitive" stem cells that, while isolated or derived from an adult stem cell and while committed to a single lineage, share characteristics of embryonic stem cells. For example, the "primitive" HSCs produced by the disclosed methods retain their "stemness" following division and do not differentiate. Consequently, as an adoptive cell therapy, the "primitive" HSCs produced by the disclosed methods not only replenish their numbers, but expand in vivo. "Primitive" HSCs produced by disclosed the methods can be therapeutically-effective when administered as a single dose.

Primitive HSCs can be CD34+. Primitive HSCs can be CD34+ and CD38−. Primitive HSCs can be CD34+, CD38− and CD90+. Primitive HSCs can be CD34+, CD38−, CD90+ and CD45RA−. Primitive HSCs can be CD34+, CD38−, CD90+, CD45RA−, and CD49f+. Primitive HSCs can be CD34+, CD38−, CD90+, CD45RA−, and CD49f+.

Primitive HSCs, HSCs, and/or HSC descendent cells can be modified according to the disclosed methods to express an exogenous sequence (e.g., a chimeric antigen receptor or therapeutic protein). Modified primitive HSCs, modified HSCs, and/or modified HSC descendent cells can be forward differentiated to produce a modified immune cell including, but not limited to, a modified T cell, a modified natural killer cell and/or a modified B-cell.

The modified immune or immune precursor cells can be NK cells. The NK cells can be cytotoxic lymphocytes that differentiate from lymphoid progenitor cells. Modified NK cells can be derived from modified hematopoietic stem and progenitor cells (HSPCs) or modified HSCs. In some aspects, non-activated NK cells are derived from CD3-depleted leukapheresis (containing CD14/CD19/CD56+ cells).

The modified immune or immune precursor cells can be B cells. B cells are a type of lymphocyte that express B cell receptors on the cell surface. B cell receptors bind to specific antigens. Modified B cells can be derived from modified hematopoietic stem and progenitor cells (HSPCs) or modified HSCs.

Modified T cells of the disclosure may be derived from modified hematopoietic stem and progenitor cells (HSPCs) or modified HSCs. Unlike traditional biologics and chemotherapeutics, the disclosed modified-T cells the capacity to rapidly reproduce upon antigen recognition, thereby potentially obviating the need for repeat treatments. To achieve this, in some embodiments, modified-T cells not only drive an initial response, but also persist in the patient as a stable population of viable memory T cells to prevent potential relapses. Alternatively, in some aspects, when it is not desired, the modified-T cells do not persist in the patient.

Intensive efforts have been focused on the development of antigen receptor molecules that do not cause T cell exhaustion through antigen-independent (tonic) signaling, as well as of a modified-T cell product containing early memory T cells, especially stem cell memory (TSCM) or stem cell-like T cells. Stem cell-like modified-T cells of the disclosure exhibit the greatest capacity for self-renewal and multipotent capacity to derive central memory ($T_{CM}$) T cells or $T_{CM}$ like cells, effector memory ($T_{EM}$) and effector T cells ($T_E$), thereby producing better tumor eradication and long-term modified-T cell engraftment. A linear pathway of differentiation may be responsible for generating these cells: Naïve T cells ($T_N$)$>T_{SCM}$$>T_{CM}$$>T_{EM}$$>T_E$$>T_{TE}$, whereby $T_N$ is the parent precursor cell that directly gives rise to TSCM, which then, in turn, directly gives rise to $T_{CM}$, etc. Compositions of T cells of the disclosure can comprise one or more of each parental T cell subset with $T_{SCM}$ cells being the most abundant (e.g., $T_{SCM}$$>T_{CM}$$>T_{EM}$$>T_E$$>T_{TE}$).

The immune cell precursor can be differentiated into or is capable of differentiating into an early memory T cell, a stem cell like T-cell, a Naïve T cells ($T_N$), a TSCM, a $T_{CM}$, a $T_{EM}$, a $T_E$, or a $T_{TE}$. The immune cell precursor can be a primitive HSC, an HSC, or a HSC descendent cell of the disclosure. The immune cell can be an early memory T cell, a stem cell like T-cell, a Naïve T cells ($T_N$), a TSCM, a $T_{CM}$, a $T_{EM}$, a $T_E$, or a $T_{TE}$.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of a plurality of modified T cells in the population expresses one or more cell-surface marker(s) of an early memory T cell. The population of modified early memory T cells comprises a plurality of modified stem cell-like T cells. The population of modified early memory T cells comprises a plurality of modified $T_{SCM}$ cells. The population of modified early memory T cells comprises a plurality of modified $T_{CM}$ cells.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of a stem cell-like T cell. The population of modified stem cell-like T cells comprises a plurality of modified $T_{SCM}$ cells. The population of modified stem cell-like T cells comprises a plurality of modified $T_{CM}$ cells.

In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% or any percentage in between of the plurality of modified T cells in the population expresses one or more cell-surface marker(s) of a stem memory T cell (TSCM) or a $T_{SCM}$-like cell; and wherein the one or more cell-surface marker(s) comprise CD45RA and CD62L. The cell-surface markers can comprise one or more of CD62L, CD45RA, CD28, CCR7, CD127, CD45RO, CD95, CD95 and IL-2Rβ. The cell-surface markers can comprise one or more of CD45RA, CD95, IL-2Rβ, CCR7, and CD62L.

In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the plurality of modified T cells in the population expresses one or more cell-surface marker(s) of a central memory T cell ($T_{CM}$) or a $T_{CM}$-like cell; and wherein the one or more cell-surface marker(s) comprise CD45RO and CD62L. The cell-surface markers can comprise one or more of CD45RO, CD95, IL-2Rβ, CCR7, and CD62L.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of a naïve T cell ($T_N$). The cell-surface markers can comprise one or more of CD45RA, CCR7 and CD62L.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of an effector T-cell (modified TEFF). The cell-surface markers can comprise one or more of CD45RA, CD95, and IL-2Rβ.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells of the population expresses one or more cell-surface marker(s) of a stem cell-like T cell, a stem memory T cell (TSCM) or a central memory T cell ($T_{CM}$).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells of the population expresses one or more cell-surface marker(s) of a stem cell-like T cell, a stem memory T cell (TSCM) or a central memory T cell ($T_{CM}$). In some aspects, the CAR comprises an amino acid sequence of SEQ ID NO: 13, encoded by the nucleic acid sequence of SEQ ID NO: 31 or SEQ ID NO: 167.

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 or wherein at least about 70% to about 99%, about 75% to about 95% or about 85% to about 95% of the population of modified cells express one or more cell-surface marker(s) comprising CD34 (e.g., comprise the cell-surface marker phenotype CD34+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and do not express one or more cell-surface marker(s) comprising CD38, or wherein at least about 45% to about 90%, about 50% to about 80% or about 65% to about 75% of the population of modified cells express one or more cell-surface marker(s) comprising CD34 and do not express one or more cell-surface marker(s) comprising CD38 (e.g., comprise the cell-surface marker phenotype CD34+ and CD38–).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD38, or wherein at least about 0.2% to about 40%, about 0.2% to about 30%, about 0.2% to about 2% or 0.5% to about 1.5% of the population of modified cells express one or more cell-surface marker(s) comprising CD34 and CD90 and do not express one or more cell-surface marker(s) comprising CD38 (e.g., comprise the cell-surface marker phenotype CD34+, CD38– and CD90+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD38 and CD45RA, or wherein at least about 0.2% to about 40%, about 0.2% to about 30%, about 0.2% to about 2% or 0.5% to about 1.5% of the population of modified cells express one or more cell-surface marker(s) comprising CD34 and CD90 and do not express one or more cell-surface marker(s) comprising CD38 and CD45RA (e.g., comprise the cell-surface marker phenotype CD34+, CD38–, CD90+, CD45RA–).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34, CD90 and CD49f and do not express one or more cell-surface marker(s) comprising CD38 and CD45RA, or wherein at least about 0.02% to about 30%, about 0.02% to about 2%, about 0.04% to about 2% or about 0.04% to about 1% of the population of modified cells express one or more cell-surface marker(s) comprising CD34, CD90 and CD49f and do not express one or more cell-surface marker(s) comprising CD38 and CD45RA (e.g., comprise the cell-surface marker phenotype CD34+, CD38–, CD90+, CD45RA- and CD49f+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD45RA, or wherein at least about 0.2% to about 5%, about 0.2% to about 3% or about 0.4% to about 3% of the population of modified cells express one or more cell-surface marker(s) comprising CD34 and CD90 and do not express one or more cell-surface marker(s) comprising CD45RA (e.g., comprise the cell-surface marker phenotype CD34+, CD90+ and CD45RA−).

Compositions and methods of producing and/or expanding the immune cells or immune precursor cells (e.g., the disclosed modified T-cells) and buffers for maintaining or enhancing a level of cell viability and/or a stem-like phenotype of the immune cells or immune precursor cells (e.g., the disclosed modified T-cells) are disclosed elsewhere herein and are disclosed in more detail in U.S. Pat. No. 10,329,543 and PCT Publication No. WO 2019/173636.

Cells and modified cells of the disclosure can be somatic cells. Cells and modified cells of the disclosure can be differentiated cells. Cells and modified cells of the disclosure can be autologous cells or allogenic cells. Allogeneic cells are engineered to prevent adverse reactions to engraftment following administration to a subject. Allogeneic cells may be any type of cell. Allogenic cells can be stem cells or can be derived from stem cells. Allogeneic cells can be differentiated somatic cells.

Methods of Expressing a Chimeric Antigen Receptor

The disclosure provides methods of expressing a CAR on the surface of a cell. The method comprises (a) obtaining a cell population; (b) contacting the cell population to a composition comprising a CAR or a sequence encoding the CAR, under conditions sufficient to transfer the CAR across a cell membrane of at least one cell in the cell population, thereby generating a modified cell population; (c) culturing the modified cell population under conditions suitable for integration of the sequence encoding the CAR; and (d) expanding and/or selecting at least one cell from the modified cell population that express the CAR on the cell surface.

In some aspects, the cell population can comprise leukocytes and/or CD4+ and CD8+ leukocytes. The cell population can comprise CD4+ and CD8+ leukocytes in an optimized ratio. The optimized ratio of CD4+ to CD8+ leukocytes does not naturally occur in vivo. The cell population can comprise a tumor cell.

In some aspects, the conditions sufficient to transfer the CAR or the sequence encoding the CAR, transposon, or vector across a cell membrane of at least one cell in the cell population comprises at least one of an application of one or more pulses of electricity at a specified voltage, a buffer, and one or more supplemental factor(s). In some aspects, the conditions suitable for integration of the sequence encoding the CAR comprise at least one of a buffer and one or more supplemental factor(s).

The buffer can comprise PBS, HBSS, OptiMEM, BTX-press, Amaxa Nucleofector, Human T cell nucleofection buffer or any combination thereof. The one or more supplemental factor(s) can comprise (a) a recombinant human cytokine, a chemokine, an interleukin or any combination thereof; (b) a salt, a mineral, a metabolite or any combination thereof; (c) a cell medium; (d) an inhibitor of cellular DNA sensing, metabolism, differentiation, signal transduction, one or more apoptotic pathway(s) or combinations thereof; and (e) a reagent that modifies or stabilizes one or more nucleic acids. The recombinant human cytokine, the chemokine, the interleukin or any combination thereof can comprise IL2, IL7, IL12, IL15, IL21, IL1, IL3, IL4, IL5, IL6, IL8, CXCL8, IL9, IL10, IL11, IL13, IL14, IL16, IL17, IL18, IL19, IL20, IL22, IL23, IL25, IL26, IL27, IL28, IL29, IL30, IL31, IL32, IL33, IL35, IL36, GM-CSF, IFN-gamma, IL-1 alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L or any combination thereof. The salt, the mineral, the metabolite or any combination thereof can comprise HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, antibiotics, pH adjusters, Earle's Salts, 2-Mercaptoethanol, Human transferrin, Recombinant human insulin, Human serum albumin, Nucleofector PLUS Supplement, KCL, $MgCl_2$, $Na_2HPO_4$, $NAH_2PO_4$, Sodium lactobionate, Mannitol, Sodium succinate, Sodium Chloride, CINa, Glucose, $Ca(NO_3)_2$, Tris/HCl, $K_2HPO_4$, $KH_2PO_4$, Polyethylenimine, Poly-ethylene-glycol, Poloxamer 188, Poloxamer 181, Poloxamer 407, Poly-vinylpyrrolidone, Pop313, Crown-5, or any combination thereof. The cell medium can comprise PBS, HBSS, OptiMEM, DMEM, RPMI 1640, AIM-V, X-VIVO 15, CellGro DC Medium, CTS OpTimizer T Cell Expansion SFM, TexMACS Medium, PRIME-XV T Cell Expansion Medium, ImmunoCult-XF T Cell Expansion Medium or any combination thereof. The inhibitor of cellular DNA sensing, metabolism, differentiation, signal transduction, one or more apoptotic pathway(s) or combinations thereof comprise inhibitors of TLR9, MyD88, IRAK, TRAF6, TRAF3, IRF-7, NF-KB, Type 1 Interferons, pro-inflammatory cytokines, cGAS, STING, Sec5, TBK1, IRF-3, RNA pol III, RIG-1, IPS-1, FADD, RIP1, TRAF3, AIM2, ASC, Caspasel, Pro-IL1B, PI3K, Akt, Wnt3A, inhibitors of glycogen synthase kinase-3β (GSK-3 β) (e.g. TWS119), or any combination thereof. Examples of such inhibitors can include Bafilomycin, Chloroquine, Quinacrine, AC-YVAD-CMK, Z-VAD-FMK, Z-IETD-FMK or any combination thereof. The reagent that modifies or stabilizes one or more nucleic acids comprises a pH modifier, a DNA-binding protein, a lipid, a phospholipid, CaPO4, a net neutral charge DNA binding peptide with or without a NLS sequence, a TREX1 enzyme or any combination thereof.

The expansion and selection steps can occur concurrently or sequentially. The expansion can occur prior to selection. The expansion can occur following selection, and, optionally, a further (i.e. second) selection can occur following expansion. Concurrent expansion and selection can be simultaneous. The expansion and/or selection steps can proceed for a period of 10 to 14 days, inclusive of the endpoints.

The expansion can comprise contacting at least one cell of the modified cell population with an antigen to stimulate the at least one cell through the CAR, thereby generating an expanded cell population. The antigen can be presented on the surface of a substrate. The substrate can have any form, including, but not limited to a surface, a well, a bead or a plurality thereof, and a matrix. The substrate can further comprise a paramagnetic or magnetic component. The antigen can be presented on the surface of a substrate, wherein the substrate is a magnetic bead, and wherein a magnet can be used to remove or separate the magnetic beads from the modified and expanded cell population. The antigen can be presented on the surface of a cell or an artificial antigen presenting cell. Artificial antigen presenting cells can include, but are not limited to, tumor cells and stem cells.

In some aspects wherein the transposon or vector comprises a selection gene, the selection step comprises contacting at least one cell of the modified cell population with a compound to which the selection gene confers resistance, thereby identifying a cell expressing the selection gene as surviving the selection and identifying a cell failing to express the selection gene as failing to survive the selection step.

The disclosure provides a composition comprising the modified, expanded and selected cell population of the methods described herein.

A more detailed description of methods for expressing a CAR on the surface of a cell is disclosed in PCT Publication No. WO 2019/049816 and PCT/US2019/049816.

The present disclosure provides a cell or a population of cells wherein the cell comprises a composition comprising (a) an inducible transgene construct, comprising a sequence encoding an inducible promoter and a sequence encoding a transgene, and (b) a receptor construct, comprising a sequence encoding a constitutive promoter and a sequence encoding an exogenous receptor, such as a CAR, wherein, upon integration of the construct of (a) and the construct of (b) into a genomic sequence of a cell, the exogenous receptor is expressed, and wherein the exogenous receptor, upon binding a ligand or antigen, transduces an intracellular signal that targets directly or indirectly the inducible promoter regulating expression of the inducible transgene (a) to modify gene expression.

The composition can modify gene expression by decreasing gene expression. The composition can modify gene expression by transiently modifying gene expression (e.g., for the duration of binding of the ligand to the exogenous receptor). The composition can modify gene expression acutely (e.g., the ligand reversibly binds to the exogenous receptor). The composition can modify gene expression chronically (e.g., the ligand irreversibly binds to the exogenous receptor).

The exogenous receptor can comprise an endogenous receptor with respect to the genomic sequence of the cell. Exemplary receptors include, but are not limited to, intracellular receptors, cell-surface receptors, transmembrane receptors, ligand-gated ion channels, and G-protein coupled receptors.

The exogenous receptor can comprise a non-naturally occurring receptor. The non-naturally occurring receptor can be a synthetic, modified, recombinant, mutant or chimeric receptor. The non-naturally occurring receptor can comprise one or more sequences isolated or derived from a T-cell receptor (TCR). The non-naturally occurring receptor can comprise one or more sequences isolated or derived from a scaffold protein. In some aspects, including those wherein the non-naturally occurring receptor does not comprise a transmembrane domain, the non-naturally occurring receptor interacts with a second transmembrane, membrane-bound and/or an intracellular receptor that, following contact with the non-naturally occurring receptor, transduces an intracellular signal. The non-naturally occurring receptor can comprise a transmembrane domain. The non-naturally occurring receptor can interact with an intracellular receptor that transduces an intracellular signal. The non-naturally occurring receptor can comprise an intracellular signaling domain. The non-naturally occurring receptor can be a chimeric ligand receptor (CLR). The CLR can be a chimeric antigen receptor (CAR).

The sequence encoding the inducible promoter of comprises a sequence encoding an NFκB promoter, a sequence encoding an interferon (IFN) promoter or a sequence encoding an interleukin-2 promoter. In some aspects, the IFN promoter is an IFNγ promoter. The inducible promoter can be isolated or derived from the promoter of a cytokine or a chemokine. The cytokine or chemokine can comprise IL2, TL3, IL4, IL5, IL6, IL10, IL12, IL13, IL17A/F, IL21, IL22, IL23, transforming growth factor beta (TGFβ), colony stimulating factor 2 (GM-CSF), interferon gamma (IFNγ), Tumor necrosis factor alpha (TNFα), LTα, perforin, Granzyme C (Gzmc), Granzyme B (Gzmb), C—C motif chemokine ligand 5 (CCL5), C—C motif chemokine ligand 4 (Ccl4), C—C motif chemokine ligand 3 (Ccl3), X—C motif chemokine ligand 1 (Xcl1) or LIF interleukin 6 family cytokine (Lif).

The inducible promoter can be isolated or derived from the promoter of a gene comprising a surface protein involved in cell differentiation, activation, exhaustion and function. In some aspects, the gene comprises CD69, CD71, CTLA4, PD-1, TIGIT, LAG3, TIM-3, GITR, MHCII, COX-2, FASL or 4-1BB.

The inducible promoter can be isolated or derived from the promoter of a gene involved in CD metabolism and differentiation. The inducible promoter can be isolated or derived from the promoter of Nr4a1, Nr4a3, Tnfrsf9 (4-1BB), Sema7a, Zfp3612, Gadd45b, Dusp5, Dusp6 and Neto2.

In some aspects, the inducible transgene construct comprises or drives expression of a signaling component downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene. Non-limiting examples of which are disclosed in PCT Publication No. WO 2019/173636 and PCT Application No. PCT/US2019/049816.

The present disclosure provides a method of producing a population of modified T-cells comprising, consisting essential of, or consisting of introducing into a plurality of primary human T-cells a composition comprising the CAR of the present disclosure or a sequence encoding the same to produce a plurality of modified T-cells. The present disclosure provides a composition comprising a population of modified T-cells produced by the method. In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the population expresses the CAR of the present disclosure.

Armored Cells

The modified cells of disclosure (e.g., CAR T-cells) can be further modified to enhance their therapeutic potential. Alternatively, or in addition, the modified cells may be further modified to render them less sensitive to immunologic and/or metabolic checkpoints. Modifications of this type "armor" the cells, which, following the modification, may be referred to here as "armored" cells (e.g., armored T-cells). Armored cells may be produced by, for example, blocking and/or diluting specific checkpoint signals delivered to the cells (e.g., checkpoint inhibition) naturally, within the tumor immunosuppressive microenvironment.

An armored cell of the disclosure can be derived from any cell, for example, a T cell, a NK cell, a hematopoietic progenitor cell, a peripheral blood (PB) derived T cell (including a T cell isolated or derived from G-CSF-mobilized peripheral blood), or an umbilical cord blood (UCB) derived T cell. An armored cell (e.g., armored T-cell) can comprise one or more of a chimeric ligand receptor (CLR comprising a protein scaffold, an antibody, an ScFv, or an antibody mimetic)/chimeric antigen receptor (CAR comprising a protein scaffold, an antibody, an ScFv, or an antibody mimetic), a CARTyrin (a CAR comprising a Centyrin), and/or a VCAR (a CAR comprising a camelid VHH or a single domain VH). An armored cell (e.g., armored T-cell) can comprise an inducible proapoptotic polypeptide as disclosed herein. An armored cell (e.g., armored T-cell) can comprise an exogenous sequence. The exogenous sequence can comprise a sequence encoding a therapeutic protein. Exemplary therapeutic proteins may be nuclear, cytoplasmic, intracellular, transmembrane, cell-surface bound, or secreted proteins. Exemplary therapeutic proteins expressed by the armored cell (e.g., armored T-cell) may modify an activity of the armored cell or may modify an activity of a second cell. An armored cell (e.g., armored T-cell) can comprise a selection gene or a selection marker. An armored cell (e.g., armored T-cell) can comprise a synthetic gene expression cassette (also referred to herein as an inducible transgene construct).

The modified cells of disclosure (e.g., CAR T-cells) can be further modified to silence or reduce expression one or more gene(s) encoding receptor(s) of inhibitory checkpoint signals to produce an armored cell (e.g., armored CAR T-cell). Receptors of inhibitory checkpoint signals are expressed on the cell surface or within the cytoplasm of a cell. Silencing or reducing expressing of the gene encoding the receptor of the inhibitory checkpoint signal results a loss of protein expression of the inhibitory checkpoint receptors on the surface or within the cytoplasm of an armored cell. Thus, armored cells having silenced or reduced expression of one or more genes encoding an inhibitory checkpoint receptor is resistant, non-receptive or insensitive to checkpoint signals. The resistance or decreased sensitivity of the armored cell to inhibitory checkpoint signals enhances the therapeutic potential of the armored cell in the presence of these inhibitory checkpoint signals. Non-limiting examples of inhibitory checkpoint signals (and proteins that induce immunosuppression) are disclosed in PCT Publication No. WO 2019/173636. Preferred examples of inhibitory checkpoint signals that may be silenced include, but are not limited to, PD-1 and TGFβRII.

The modified cells of disclosure (e.g., CAR T-cells) can be further modified to silence or reduce expression of one or more gene(s) encoding intracellular proteins involved in checkpoint signaling to produce an armored cell (e.g., armored CAR T-cell). The activity of the modified cells may be enhanced by targeting any intracellular signaling protein involved in a checkpoint signaling pathway, thereby achieving checkpoint inhibition or interference to one or more checkpoint pathways. Non-limiting examples of intracellular signaling proteins involved in checkpoint signaling are disclosed in PCT Publication No. WO 2019/173636.

The modified cells of disclosure (e.g., CAR T-cells) can be further modified to silence or reduce expression of one or more gene(s) encoding a transcription factor that hinders the efficacy of a therapy to produce an armored cell (e.g., armored CAR T-cell). The activity of modified cells may be enhanced or modulated by silencing or reducing expression (or repressing a function) of a transcription factor that hinders the efficacy of a therapy. Non-limiting examples of transcription factors that may be modified to silence or reduce expression or to repress a function thereof include, but are not limited to, the exemplary transcription factors are disclosed in PCT Publication No. WO 2019/173636.

The modified cells of disclosure (e.g., CAR T-cells) can be further modified to silence or reduce expression of one or more gene(s) encoding a cell death or cell apoptosis receptor to produce an armored cell (e.g., armored CAR T-cell). Interaction of a death receptor and its endogenous ligand results in the initiation of apoptosis. Disruption of an expression, an activity, or an interaction of a cell death and/or cell apoptosis receptor and/or ligand render a modified cell less receptive to death signals, consequently, making the armored cell more efficacious in a tumor environment. Non-limiting examples of cell death and/or cell apoptosis receptors and ligands are disclosed in PCT Publication No. WO 2019/173636. A preferred example of cell death receptor which may be modified is Fas (CD95).

The modified cells of disclosure (e.g., CAR T-cells) can be further modified to silence or reduce expression of one or more gene(s) encoding a metabolic sensing protein to produce an armored cell (e.g., armored CAR T-cell). Disruption to the metabolic sensing of the immunosuppressive tumor microenvironment (characterized by low levels of oxygen, pH, glucose and other molecules) by a modified cell leads to extended retention of T-cell function and, consequently, more tumor cells killed per cell. Non-limiting examples of metabolic sensing genes and proteins are disclosed in PCT Publication No. WO 2019/173636. A preferred example, HIF1a and VHL play a role in T-cell function while in a hypoxic environment. An armored T-cell may have silenced or reduced expression of one or more genes encoding HIF1a or VHL.

The modified cells of disclosure (e.g., CAR T-cells) can be further modified to silence or reduce expression of one or more gene(s) encoding proteins that that confer sensitivity to a cancer therapy, including a monoclonal antibody, to produce an armored cell (e.g., armored CAR T-cell). Thus, an armored cell can function and may demonstrate superior function or efficacy whilst in the presence of a cancer therapy (e.g., a chemotherapy, a monoclonal antibody therapy, or another anti-tumor treatment). Non-limiting examples of proteins involved in conferring sensitivity to a cancer therapy are disclosed in PCT Publication No. WO 2019/173636.

The modified cells of disclosure (e.g., CAR T-cells) can be further modified to silence or reduce expression of one or more gene(s) encoding a growth advantage factor to produce an armored cell (e.g., armored CAR T-cell). Silencing or reducing expression of an oncogene can confer a growth advantage for the cell. For example, silencing or reducing expression (e.g., disrupting expression) of a TET2 gene during a CAR T-cell manufacturing process results in the generation of an armored CAR T-cell with a significant capacity for expansion and subsequent eradication of a tumor when compared to a non-armored CAR T-cell lacking this capacity for expansion. This strategy may be coupled to a safety switch (e.g., an iC9 safety switch described herein), which permits the targeted disruption of an armored CAR T-cell in the event of an adverse reaction from a subject or uncontrolled growth of the armored CAR T-cell. Non-limiting examples of growth advantage factors are disclosed in PCT Publication No. WO 2019/173636.

The modified cells of disclosure (e.g., CAR T-cells) can be further modified to express a modified/chimeric checkpoint receptor to produce an armored T-cell of the disclosure.

The modified/chimeric checkpoint receptor can comprise a null receptor, decoy receptor or dominant negative receptor. A null receptor, decoy receptor or dominant negative receptor can be modified/chimeric receptor/protein. A null receptor, decoy receptor or dominant negative receptor can be truncated for expression of the intracellular signaling domain. Alternatively, or in addition, a null receptor, decoy receptor or dominant negative receptor can be mutated within an intracellular signaling domain at one or more amino acid positions that are determinative or required for effective signaling. Truncation or mutation of null receptor, decoy receptor or dominant negative receptor can result in loss of the receptor's capacity to convey or transduce a checkpoint signal to the cell or within the cell.

For example, a dilution or a blockage of an immunosuppressive checkpoint signal from a PD-L1 receptor expressed on the surface of a tumor cell may be achieved by expressing a modified/chimeric PD-1 null receptor on the surface of an armored cell (e.g., armored CAR T-cell), which effectively competes with the endogenous (non-modified) PD-1 receptors also expressed on the surface of the armored cell to reduce or inhibit the transduction of the immunosuppressive checkpoint signal through endogenous PD-1 receptors of the armored cell. In this non-limiting example, competition between the two different receptors for binding to PD-L1 expressed on the tumor cell reduces or diminishes a level of effective checkpoint signaling, thereby enhancing a therapeutic potential of the armored cell expressing the PD-1 null receptor.

The modified/chimeric checkpoint receptor can comprise a null receptor, decoy receptor or dominant negative receptor that is a transmembrane receptor, a membrane-associated or membrane-linked receptor/protein or an intracellular receptor/protein. Exemplary null, decoy, or dominant negative intracellular receptors/proteins include, but are not limited to, signaling components downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene. Non-limiting examples of cytokines, cytokine receptors, chemokines and chemokine receptors are disclosed in PCT Publication No. WO 2019/173636.

The modified/chimeric checkpoint receptor can comprise a switch receptor. Exemplary switch receptors comprise a modified/chimeric receptor/protein wherein a native or wild type intracellular signaling domain is switched or replaced with a different intracellular signaling domain that is either non-native to the protein and/or not a wild-type domain. For example, replacement of an inhibitory signaling domain with a stimulatory signaling domain would switch an immunosuppressive signal into an immunostimulatory signal. Alternatively, replacement of an inhibitory signaling domain with a different inhibitory domain can reduce or enhance the level of inhibitory signaling. Expression or overexpression, of a switch receptor can result in the dilution and/or blockage of a cognate checkpoint signal via competition with an endogenous wild-type checkpoint receptor (not a switch receptor) for binding to the cognate checkpoint receptor expressed within the immunosuppressive tumor microenvironment. Armored cells (e.g., armored CAR T-cells) can comprise a sequence encoding a switch receptor, leading to the expression of one or more switch receptors, and consequently, altering an activity of an armored cell. Armored cells (e.g., armored CAR T-cells) can express a switch receptor that targets an intracellularly expressed protein downstream of a checkpoint receptor, a transcription factor, a cytokine receptor, a death receptor, a metabolic sensing molecule, a cancer therapy, an oncogene, and/or a tumor suppressor protein or gene.

Exemplary switch receptors can comprise or can be derived from a protein including, but are not limited to, the signaling components downstream of an inhibitory check-point signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene.

The modified cells of disclosure (e.g., CAR T-cells) can be further modified to express a CLR/CAR that mediates conditional gene expression to produce an armored T-cell. The combination of the CLR/CAR and the condition gene expression system in the nucleus of the armored T-cell constitutes a synthetic gene expression system that is conditionally activated upon binding of cognate ligand(s) with CLR or cognate antigen(s) with CAR. This system may help to 'armor' or enhance therapeutic potential of modified T-cells by reducing or limiting synthetic gene expression at the site of ligand or antigen binding, at or within the tumor environment for example.

Gene Editing Compositions and Methods

A modified cell be produced by introducing a transgene into the cell. The introducing step may comprise delivery of a nucleic acid sequence, a transgene, and/or a genomic editing construct via a non-transposition delivery system.

Introducing a nucleic acid sequence, transgene and/or a genomic editing construct into a cell ex vivo, in vivo, in vitro or in situ can comprise one or more of topical delivery, adsorption, absorption, electroporation, spin-fection, co-culture, transfection, mechanical delivery, sonic delivery, vibrational delivery, magnetofection or by nanoparticle-mediated delivery. Introducing a nucleic acid sequence, a transgene and/or a genomic editing construct into a cell ex vivo, in vivo, in vitro or in situ can comprise liposomal transfection, calcium phosphate transfection, fugene transfection, and dendrimer-mediated transfection. Introducing a nucleic acid sequence, a transgene, and/or a genomic editing construct into a cell ex vivo, in vivo, in vitro or in situ by mechanical transfection can comprise cell squeezing, cell bombardment, or gene gun techniques. Introducing a nucleic acid sequence, transgene and/or a genomic editing construct into a cell ex vivo, in vivo, in vitro or in situ by nanoparticle-mediated transfection can comprise liposomal delivery, delivery by micelles, and delivery by polymerosomes.

Introducing a nucleic acid sequence, transgene and/or a genomic editing construct into a cell ex vivo, in vivo, in vitro or in situ can comprise a non-viral vector. The non-viral vector can comprise a nucleic acid. The non-viral vector can comprise plasmid DNA, linear double-stranded DNA (dsDNA), linear single-stranded DNA (ssDNA), Doggy-Bone™ DNA, nanoplasmids, minicircle DNA, single-stranded oligodeoxynucleotides (ssODN), DDNA oligo-nucleotides, single-stranded mRNA (ssRNA), and double-stranded mRNA (dsRNA). The non-viral vector can comprise a transposon as described herein.

Introducing a nucleic acid sequence, transgene and/or a genomic editing construct into a cell ex vivo, in vivo, in vitro or in situ can comprise a viral vector. The viral vector can be a non-integrating non-chromosomal vector. Non-limiting examples of non-integrating non-chromosomal vectors include adeno-associated virus (AAV), adenovirus, and herpes viruses. The viral vector can be an integrating chromosomal vector. Non-limiting examples of integrating chromosomal vectors include adeno-associated vectors (AAV), Lentiviruses, and gamma-retroviruses.

Introducing a nucleic acid sequence, transgene and/or a genomic editing construct into a cell ex vivo, in vivo, in vitro or in situ can comprise a combination of vectors. Non-limiting examples of vector combinations include viral and non-viral vectors, a plurality of non-viral vectors, or a plurality of viral vectors. Non-limiting examples of vector combinations include a combination of a DNA-derived and an RNA-derived vector, a combination of an RNA and a reverse transcriptase, a combination of a transposon and a transposase, a combination of a non-viral vector and an endonuclease, and a combination of a viral vector and an endonuclease.

Genome modification can comprise introducing a nucleic acid sequence, transgene and/or a genomic editing construct into a cell ex vivo, in vivo, in vitro or in situ to stably integrate a nucleic acid sequence, transiently integrate a nucleic acid sequence, produce site-specific integration of a nucleic acid sequence, or produce a biased integration of a nucleic acid sequence. The nucleic acid sequence can be a transgene.

Genome modification can comprise introducing a nucleic acid sequence, transgene and/or a genomic editing construct into a cell ex vivo, in vivo, in vitro or in situ to stably integrate a nucleic acid sequence. The stable chromosomal integration can be a random integration, a site-specific integration, or a biased integration. The site-specific integration can be non-assisted or assisted. The assisted site-specific integration is co-delivered with a site-directed nuclease. The site-directed nuclease comprises a transgene with 5' and 3' nucleotide sequence extensions that contain a percentage homology to upstream and downstream regions of the site of genomic integration. The transgene with homologous nucleotide extensions enable genomic integration by homologous recombination, microhomology-mediated end joining, or nonhomologous end-joining. The site-specific integration can occur at a safe harbor site. Genomic safe harbor sites are able to accommodate the integration of new genetic material in a manner that ensures that the newly inserted genetic elements function reliably (for example, are expressed at a therapeutically effective level of expression) and do not cause deleterious alterations to the host genome that cause a risk to the host organism. Non-limiting examples of potential genomic safe harbors include intronic sequences of the human albumin gene, the adeno-associated virus site 1 (AAVS1), a naturally occurring site of integration of AAV virus on chromosome 19, the site of the chemokine (C—C motif) receptor 5 (CCR5) gene and the site of the human ortholog of the mouse Rosa26 locus.

The site-specific transgene integration can occur at a site that disrupts expression of a target gene. Disruption of target gene expression can occur by site-specific integration at introns, exons, promoters, genetic elements, enhancers, suppressors, start codons, stop codons, and response elements. Non-limiting examples of target genes targeted by site-specific integration include TRAC, TRAB, PDI, any immunosuppressive gene, and genes involved in allo-rejection.

The site-specific transgene integration can occur at a site that results in enhanced expression of a target gene. Enhancement of target gene expression can occur by site-specific integration at introns, exons, promoters, genetic elements, enhancers, suppressors, start codons, stop codons, and response elements.

Enzymes can be used to create strand breaks in the host genome to facilitate delivery or integration of the transgene. Enzymes can create single-strand breaks or double-strand breaks. Non-limiting examples of break-inducing enzymes include transposases, integrases, endonucleases, CRISPR-Cas9, transcription activator-like effector nucleases (TALEN), zinc finger nucleases (ZFN), Cas-CLOVER™, and CPF1. Break-inducing enzymes can be delivered to the cell encoded in DNA, encoded in mRNA, as a protein, or as a nucleoprotein complex with a guide RNA (gRNA).

The site-specific transgene integration can be controlled by a vector-mediated integration site bias. Vector-mediated integration site bias can controlled by the chosen lentiviral vector or by the chosen gamma-retroviral vector.

The site-specific transgene integration site can be a non-stable chromosomal insertion. The integrated transgene can be become silenced, removed, excised, or further modified. The genome modification can be a non-stable integration of a transgene. The non-stable integration can be a transient non-chromosomal integration, a semi-stable non chromosomal integration, a semi-persistent non-chromosomal insertion, or a non-stable chromosomal insertion. The transient non-chromosomal insertion can be epi-chromosomal or cytoplasmic. In one aspect, the transient non-chromosomal insertion of a transgene does not integrate into a chromosome and the modified genetic material is not replicated during cell division.

The genome modification can be a semi-stable or persistent non-chromosomal integration of a transgene. A DNA vector encodes a Scaffold/matrix attachment region (S-MAR) module that binds to nuclear matrix proteins for episomal retention of a non-viral vector allowing for autonomous replication in the nucleus of dividing cells.

The genome modification can be a non-stable chromosomal integration of a transgene. The integrated transgene can become silenced, removed, excised, or further modified.

The modification to the genome by transgene insertion can occur via host cell-directed double-strand breakage repair (homology-directed repair) by homologous recombination (HR), microhomology-mediated end joining (MMEJ), nonhomologous end joining (NHEJ), transposase enzyme-mediated modification, integrase enzyme-mediated modification, endonuclease enzyme-mediated modification, or recombinant enzyme-mediated modification. The modification to the genome by transgene insertion can occur via CRISPR-Cas9, TALEN, ZFNs, Cas-CLOVER™, and cpf1.

In gene editing systems that involve inserting new or existing nucleotides/nucleic acids, insertion tools (e.g., DNA template vectors, transposable elements (transposons or retrotransposons) must be delivered to the cell in addition to the cutting enzyme (e.g., a nuclease, recombinase, integrase or transposase). Examples of such insertion tools for a recombinase may include a DNA vector. Other gene editing systems require the delivery of an integrase along with an insertion vector, a transposase along with a transposon/retrotransposon, etc. An example recombinase that may be used as a cutting enzyme is the CRE recombinase. Non-limiting examples of integrases that may be used in insertion tools include viral based enzymes taken from any of a number of viruses including AAV, gamma retrovirus, and lentivirus. Examples transposons/retrotransposons that may be used in insertion tools are described in more detail herein.

A cell with an ex vivo, in vivo, in vitro or in situ genomic modification can be a germline cell or a somatic cell. The modified cell can be a human, non-human, mammalian, rat, mouse, or dog cell. The modified cell can be differentiated, undifferentiated, or immortalized. The modified undifferentiated cell can be a stem cell. The modified undifferentiated cell can be an induced pluripotent stem cell. The modified cell can be an immune cell. The modified cell can be a T cell, a hematopoietic stem cell, a natural killer cell, a macrophage, a dendritic cell, a monocyte, a megakaryocyte, or an osteoclast. The modified cell can be modified while the cell is quiescent, in an activated state, resting, in interphase, in prophase, in metaphase, in anaphase, or in telophase. The modified cell can be fresh, cryopreserved, bulk, sorted into sub-populations, from whole blood, from leukapheresis, or from an immortalized cell line. A detailed description for isolating cells from a leukapheresis product or blood is disclosed in in PCT Publication No. WO 2019/173636 and PCT/US2019/049816.

The present disclosure provides a gene editing composition and/or a cell comprising the gene editing composition. The gene editing composition can comprise a sequence encoding a DNA binding domain and a sequence encoding a nuclease protein or a nuclease domain thereof. The sequence encoding a nuclease protein or the sequence encoding a nuclease domain thereof can comprise a DNA sequence, an RNA sequence, or a combination thereof. The nuclease or the nuclease domain thereof can comprise one or more of a CRISPR/Cas protein, a Transcription Activator-Like Effector Nuclease (TALEN), a Zinc Finger Nuclease (ZFN), and an endonuclease.

The nuclease or the nuclease domain thereof can comprise a nuclease-inactivated Cas (dCas) protein and an endonuclease. The endonuclease can comprise a Clo051 nuclease or a nuclease domain thereof. The gene editing composition can comprise a fusion protein. The fusion protein can comprise a nuclease-inactivated Cas9 (dCas9) protein and a Clo051 nuclease or a Clo051 nuclease domain. The gene editing composition can further comprise a guide sequence. The guide sequence comprises an RNA sequence.

The disclosure provides compositions comprising a small, Cas9 (Cas9) operatively-linked to an effector. The disclosure provides a fusion protein comprising, consisting essentially of or consisting of a DNA localization component and an effector molecule, wherein the effector comprises a small, Cas9 (Cas9). A small Cas9 construct of the disclosure can comprise an effector comprising a type IIS endonuclease. A *Staphylococcus aureus* Cas9 with an active catalytic site comprises the amino acid sequence of SEQ ID NO: 83.

The disclosure provides compositions comprising an inactivated, small, Cas9 (dSaCas9) operatively-linked to an effector. The disclosure provides a fusion protein comprising, consisting essentially of or consisting of a DNA localization component and an effector molecule, wherein the effector comprises a small, inactivated Cas9 (dSaCas9). A small, inactivated Cas9 (dSaCas9) construct of the disclosure can comprise an effector comprising a type IIS endonuclease. A dSaCas9 comprises the amino acid sequence of SEQ ID NO: 84, which includes a D10A and a N580A mutation to inactivate the catalytic site.

The disclosure provides compositions comprising an inactivated Cas9 (dCas9) operatively-linked to an effector. The disclosure provides a fusion protein comprising, consisting essentially of or consisting of a DNA localization component and an effector molecule, wherein the effector comprises an inactivated Cas9 (dCas9). An inactivated Cas9 (dCas9) construct of the disclosure can comprise an effector comprising a type IIS endonuclease.

The dCas9 can be isolated or derived from Streptococcus pyogenes. The dCas9 can comprise a dCas9 with substitutions at amino acid positions 10 and 840, which inactivate the catalytic site. In some aspects, these substitutions are D10A and H840A. The dCas9 can comprise the amino acid sequence of SEQ ID NO: 85 or SEQ ID NO: 86.

An exemplary Clo051 nuclease domain comprises, consists essentially of or consists of, the amino acid sequence of SEQ ID NO: 87.

An exemplary dCas9-Clo051 (Cas-CLOVER) fusion protein can comprise, consist essentially of, or consist of, the amino acid sequence of SEQ ID NO: 88. The exemplary dCas9-Clo051 fusion protein can be encoded by a poly-nucleotide which comprises, consists essentially of, or consists of, the nucleic acid sequence of SEQ ID NO: 89. The nucleic acid encoding the dCas9-Clo051 fusion protein can be DNA or RNA.

An exemplary dCas9-Clo051 (Cas-CLOVER) fusion protein can comprise, consist essentially of, or consist of, the amino acid sequence of SEQ ID NO: 90. The exemplary dCas9-Clo051 fusion protein can be encoded by a poly-nucleotide which comprises, consists essentially of, or consists of, the nucleic acid sequence of SEQ ID NO: 91. The nucleic acid encoding the dCas9-Clo051 fusion protein can be DNA or RNA.

A cell comprising the gene editing composition can express the gene editing composition stably or transiently. Preferably, the gene editing composition is expressed transiently. The guide RNA can comprise a sequence complementary to a target sequence within a genomic DNA sequence. The target sequence within a genomic DNA sequence can be a target sequence within a safe harbor site of a genomic DNA sequence.

Gene editing compositions, including Cas-CLOVER, and methods of using these compositions for gene editing are described in detail in U.S. Patent Publication Nos. 2017/0107541, 2017/0114149, 2018/0187185 and U.S. Pat. No. 10,415,024.

Gene editing tools can also be delivered to cells using one or more poly(histidine)-based micelles. Poly(histidine) (e.g., poly(L-histidine)), is a pH-sensitive polymer due to the imidazole ring providing an electron lone pair on the unsaturated nitrogen. That is, poly(histidine) has amphoteric properties through protonation-deprotonation. In particular, at certain pHs, poly(histidine)-containing triblock copolymers may assemble into a micelle with positively charged poly (histidine) units on the surface, thereby enabling complexing with the negatively-charged gene editing molecule(s). Using these nanoparticles to bind and release proteins and/or nucleic acids in a pH-dependent manner may provide an efficient and selective mechanism to perform a desired gene modification. In particular, this micelle-based delivery system provides substantial flexibility with respect to the charged materials, as well as a large payload capacity, and targeted release of the nanoparticle payload. In one example, site-specific cleavage of the double stranded DNA is enabled by delivery of a nuclease using the poly(histidine)-based micelles. Without wishing to be bound by a particular theory, it is believed that believed that in the micelles that are formed by the various triblock copolymers, the hydrophobic blocks aggregate to form a core, leaving the hydrophilic blocks and poly(histidine) blocks on the ends to form one or more surrounding layer.

In an aspect, the disclosure provides triblock copolymers made of a hydrophilic block, a hydrophobic block, and a charged block. In some aspects, the hydrophilic block may be poly(ethylene oxide) (PEO), and the charged block may be poly(L-histidine). An example triblock copolymer that can be used is a PEO-b-PLA-b-PHIS, with variable numbers of repeating units in each block varying by design.

Diblock copolymers that can be used as intermediates for making triblock copolymers can have hydrophilic biocompatible poly(ethylene oxide) (PEO), which is chemically synonymous with PEG, coupled to various hydrophobic aliphatic poly(anhydrides), poly(nucleic acids), poly(esters), poly(ortho esters), poly(peptides), poly(phosphazenes) and poly(saccharides), including but not limited by poly(lactide) (PLA), poly(glycolide) (PLGA), poly(lactic-co-glycolic acid) (PLGA), poly(F-caprolactone) (PCL), and poly(trim-ethylene carbonate) (PTMC). Polymeric micelles comprised of 100% PEGylated surfaces possess improved in vitro chemical stability, augmented in vivo bioavailablity, and prolonged blood circulatory half-lives.

Polymeric vesicles, polymersomes and poly(Histidine)-based micelles, including those that comprise triblock copolymers, and methods of making the same, are described in further detail in U.S. Pat. Nos. 7,217,427; 7,868,512; 6,835,394; 8,808,748; 10,456,452; U.S. Publication Nos. 2014/0363496; 2017/0000743; and 2019/0255191; and PCT Publication No. WO 2019/126589.

Transposon and Vector Compositions

The present disclosure provides compositions and methods for delivering an antibody (e.g., scFv) or a CAR (e.g., comprising an scFv) to a cell or a population of cells. Non-limiting examples of compositions for delivery of a composition of the disclosure to a cell or a population of cells include a transposon or a vector. Thus, the present disclosure provides a transposon comprising an antibody (e.g., scFv) or a CAR (e.g., comprising an scFv) or a vector comprising an antibody (e.g., scFv) or a CAR (e.g., comprising an scFv).

A transposon comprising a CAR of the disclosure or a vector comprising a CAR of the disclosure can further comprise a sequence encoding an inducible proapoptotic polypeptide. Alternatively, or in addition, one transposon or one vector can comprise a CAR of the disclosure and a second transposon or second vector can comprise a sequence encoding an inducible proapoptotic polypeptide of the disclosure. Inducible proapoptotic polypeptides are described in more detail herein.

A transposon comprising a CAR of the disclosure or a vector comprising a CAR of the disclosure can further comprise a sequence encoding a chimeric stimulatory receptor (CSR). Alternatively, or in addition, one transposon or one vector can comprise a CAR of the disclosure and a second transposon or a second vector can comprise a sequence encoding a CSR of the disclosure. Chimeric stimulatory receptors are described in more detail herein.

A transposon comprising a CAR of the disclosure or a vector comprising a CAR of the disclosure can further comprise a sequence encoding a recombinant HLA-E polypeptide. Alternatively, or in addition, one transposon or one vector can comprise a CAR of the disclosure and a second transposon or a second vector can comprise a sequence encoding a recombinant HLA-E polypeptide. Recombinant HLA-E polypeptide are described in more detail herein.

A transposon comprising a CAR of the disclosure or a vector comprising a CAR of the disclosure can further comprise a selection gene. The selection gene can encode a gene product essential for cell viability and survival. The selection gene can encode a gene product essential for cell viability and survival when challenged by selective cell culture conditions. Selective cell culture conditions may comprise a compound harmful to cell viability or survival and wherein the gene product confers resistance to the compound. Non-limiting examples of selection genes include neo (conferring resistance to neomycin), DI-FR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2), or any combination thereof.

In a preferred aspect, the selection gene encodes a DIFR mutein enzyme. The DIFR mutein enzyme comprises, consists essentially of, or consists of the amino acid sequence of SEQ ID NO: 92. The DIFR mutein enzyme is encoded by a polynucleotide comprising, consisting essential of, or consisting of the nucleic acid sequence of SEQ ID NO: 93 or SEQ ID NO: 174. The amino acid sequence of the DI-FR mutein enzyme can further comprise a mutation at one or more of positions 80, 113, or 153. The amino acid sequence of the DHFR mutein enzyme can comprise one or more of a substitution of a Phenylalanine (F) or a Leucine (L) at position 80, a substitution of a Leucine (L) or a Valine (V) at position 113, and a substitution of a Valine (V) or an Aspartic Acid (D) at position 153.

A transposon comprising a CAR of the disclosure or a vector comprising a CAR of the disclosure can further comprise at least one self-cleaving peptide. For example, a self-cleaving peptide can be located between a CAR (e.g., comprising an scFv) and an inducible proapoptotic polypeptide; or, a self-cleaving peptide can be located between a CAR (e.g., comprising an scFv) and protein encoded by a selection gene.

A transposon comprising a CAR of the disclosure or a vector comprising a CAR of the disclosure can further comprise at least two self-cleaving peptides. For example, a first self-cleaving peptide is located upstream or immediately upstream of a CAR and a second self-cleaving peptide is located downstream or immediately downstream of a CAR; or, the first self-cleaving peptide and the second self-cleaving peptide flank a CAR. For example, a first self-cleaving peptide is located upstream or immediately upstream of an inducible proapoptotic polypeptide and a second self-cleaving peptide is located downstream or immediately downstream of an inducible proapoptotic polypeptide; or, the first self-cleaving peptide and the second self-cleaving peptide flank an inducible proapoptotic polypeptide. For example, a first self-cleaving peptide is located upstream or immediately upstream of protein encoded by a selection gene and a second self-cleaving peptide is located downstream or immediately downstream of a protein encoded by a selection gene; or, the first self-cleaving peptide and the second self-cleaving peptide flank a protein encoded by a selection gene.

Non-limiting examples of self-cleaving peptides include a T2A peptide, GSG-T2A peptide, an E2A peptide, a GSG-E2A peptide, an F2A peptide, a GSG-F2A peptide, a P2A peptide, or a GSG-P2A peptide. A T2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 94. A GSG-T2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 95. A GSG-T2A polypeptide is encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 96. A E2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 97. A GSG-E2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 98. A F2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 99. A GSG-F2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 100. A P2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 101. A GSG-P2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 102.

In some aspects, the transposon of the disclosure comprises a nucleic acid encoding a CAR of SEQ ID NO: 13. In some aspects, the nucleic acid encoding the CAR is flanked by a nucleic acid encoding T2A peptide of SEQ ID NO: 95. In some aspects, the transposon further comprises a nucleic acid encoding a DI-FR enzyme of SEQ ID NO: 92. In some aspects, the transposon further comprises a nucleic acid encoding an ic9 safety switch peptide of SEQ ID NO: 172.

In some aspects, the transposon of the disclosure comprises, consists essentially of, or consists of a nucleic acid sequence at least 75%, 80%, 85%, 90%, 95%, 96%, 97%, 98%, 99% or 100% (or any percentage in between) identical to SEQ ID NO: 175.

Transposition Systems

The present disclosure provides a transposon comprising a protein scaffold as disclosed herein or the present disclosure provides a transposon comprising an antibody (e.g., scFv) or a CAR (e.g., comprising an scFv) as disclosed herein. In a preferred aspect, the transposon is a plasmid DNA transposon comprising a nucleotide sequence encoding a scFv or CAR (e.g., comprising an scFv) as disclosed herein flanked by two cis-regulatory insulator elements. The present disclosure also provides a composition comprising a transposon. In a preferred aspect, the composition comprising the transposon further comprises a plasmid comprising a nucleotide sequence encoding a transposase. The nucleotide sequence encoding the transposase may be a DNA sequence or an RNA sequence. Preferably, the sequence encoding the transposase is an mRNA sequence.

A transposon of the present disclosure can be a piggy-Bac™ (PB) transposon. In some aspects when the transposon is a PB transposon, the transposase is a piggyBac™ (PB) transposase a piggyBac-like (PBL) transposase or a Super piggyBac™ (SPB) transposase. The sequence encoding the SPB transposase is an mRNA sequence.

Non-limiting examples of PB transposons and PB, PBL and SPB transposases are described in detail in U.S. Pat. Nos. 6,218,182; 6,962,810; 8,399,643 and PCT Publication No. WO 2010/099296.

The PB, PBL and SPB transposases recognize transposon-specific inverted terminal repeat sequences (ITRs) on the ends of the transposon, and inserts the contents between the ITRs at the sequence 5'-TTAT-3' within a chromosomal site (a TTAT target sequence) or at the sequence 5'-TTAA-3' within a chromosomal site (a TTAA target sequence). The target sequence of the PB or PBL transposon can comprise or consist of 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. The PB or PBL transposon system has no payload limit for the genes of interest that can be included between the ITRs.

Exemplary amino acid sequence for one or more PB, PBL and SPB transposases are disclosed in U.S. Pat. Nos. 6,218, 185; 6,962,810 and 8,399,643. In a preferred aspect, the PB transposase comprises or consists of an amino acid sequence at least 75%, 80%, 85%, 90%, 95%, 96%, 97%, 98%, 99% or 100% (or any percentage in between) identical to SEQ ID NO: 103.

The PB or PBL transposase can comprise or consist of an amino acid sequence having an amino acid substitution at two or more, at three or more or at each of positions 30, 165, 282, or 538 of the sequence of SEQ ID NO: 103. The transposase can be a SPB transposase that comprises or consists of the amino acid sequence of the sequence of SEQ ID NO: 103 wherein the amino acid substitution at position 30 can be a substitution of a valine (V) for an isoleucine (I), the amino acid substitution at position 165 can be a substitution of a serine (S) for a glycine (G), the amino acid substitution at position 282 can be a substitution of a valine (V) for a methionine (M), and the amino acid substitution at position 538 can be a substitution of a lysine (K) for an asparagine (N). In a preferred aspect, the SPB transposase comprises or consists of an amino acid sequence at least 75%, 80%, 85%, 90%, 95%, 96%, 97%, 98%, 99% or 100% (or any percentage in between) identical to SEQ ID NO: 104.

In certain aspects wherein the transposase comprises the above-described mutations at positions 30, 165, 282 and/or 538, the PB, PBL and SPB transposases can further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 103 or SEQ ID NO: 104 are described in more detail in PCT Publication No. WO 2019/173636 and PCT/US2019/049816.

The PB, PBL or SPB transposases can be isolated or derived from an insect, vertebrate, crustacean or urochordate as described in more detail in PCT Publication No. WO 2019/173636 and PCT/US2019/049816. In preferred aspects, the PB, PBL or SPB transposases is be isolated or derived from the insect Trichoplusia ni (GenBank Accession No. AAA87375) or Bombyx mori (GenBank Accession No. BAD11135).

A hyperactive PB or PBL transposase is a transposase that is more active than the naturally occurring variant from which it is derived. In a preferred aspect, a hyperactive PB or PBL transposase is isolated or derived from Bombyx mori or Xenopus tropicalis. Examples of hyperactive PB or PBL transposases are disclosed in U.S. Pat. Nos. 6,218,185; 6,962,810, 8,399,643 and WO 2019/173636. A list of hyperactive amino acid substitutions is disclosed in U.S. Pat. No. 10,041,077.

In some aspects, the PB or PBL transposase is integration deficient. An integration deficient PB or PBL transposase is a transposase that can excise its corresponding transposon, but that integrates the excised transposon at a lower frequency than a corresponding wild type transposase. Examples of integration deficient PB or PBL transposases are disclosed in U.S. Pat. Nos. 6,218,185; 6,962,810, 8,399, 643 and WO 2019/173636. A list of integration deficient amino acid substitutions is disclosed in U.S. Pat. No. 10,041, 077.

In some aspects, the PB or PBL transposase is fused to a nuclear localization signal. Examples of PB or PBL transposases fused to a nuclear localization signal are disclosed in U.S. Pat. Nos. 6,218,185; 6,962,810, 8,399,643 and WO 2019/173636.

A transposon of the present disclosure can be a Sleeping Beauty transposon. In some aspects, when the transposon is a Sleeping Beauty transposon, the transposase is a Sleeping Beauty transposase (for example as disclosed in U.S. Pat. No. 9,228,180) or a hyperactive Sleeping Beauty (SB100X) transposase. In a preferred aspect, the Sleeping Beauty transposase comprises or consists of an amino acid sequence at least 75%, 80%, 85%, 90%, 95%, 96%, 97%, 98%, 99% or 100% (or any percentage in between) identical to SEQ ID NO: 105. In a preferred aspect, hyperactive Sleeping Beauty (SB100X) transposase comprises or consists of an amino acid sequence at least 75%, 80%, 85%, 90%, 95%, 96%, 97%, 98%, 99% or 100% (or any percentage in between) identical to SEQ ID NO: 106.

A transposon of the present disclosure can be a Helraiser transposon. An exemplary Helraiser transposon includes Helibat1, which comprises or consists of a nucleic acid sequence at least 75%, 80%, 85%, 90%, 95%, 96%, 97%, 98%, 99% or 100% (or any percentage in between) identical to SEQ ID NO: 107. In some aspects, when the transposon is a Helraiser transposon, the transposase is a Helitron transposase (for example, as disclosed in WO 2019/173636). In a preferred aspect, Helitron transposase comprises or consists of an amino acid sequence at least 75%, 80%, 85%, 90%, 95%, 96%, 97%, 98%, 99% or 100% (or any percentage in between) identical to SEQ ID NO: 108.

A transposon of the present disclosure can be a Tol2 transposon. An exemplary Tol2 transposon, including inverted repeats, subterminal sequences and the Tol2 transposase, comprises or consists of a nucleic acid sequence at least 75%, 80%, 85%, 90%, 95%, 96%, 97%, 98%, 99% or 100% (or any percentage in between) identical to SEQ ID NO: 109. In some aspects, when the transposon is a Tol2 transposon, the transposase is a Tol2 transposase (for example, as disclosed in WO 2019/173636). In a preferred aspect, Tol2 transposase comprises or consists of an amino acid sequence at least 75%, 80%, 85%, 90%, 95%, 96%, 97%, 98%, 99% or 100% (or any percentage in between) identical to SEQ ID NO: 110.

A transposon of the present disclosure can be a TcBuster transposon. In some aspects, when the transposon is a TcBuster transposon, the transposase is a TcBuster transposase or a hyperactive TcBuster transposase (for example, as disclosed in WO 2019/173636). The TcBuster transposase can comprise or consist of a naturally occurring amino acid sequence or a non-naturally occurring amino acid sequence. In a preferred aspect, a TcBuster transposase comprises or consists of an amino acid sequence at least 75%, 80%, 85%, 90%, 95%, 96%, 97%, 98%, 99% or 100% (or any percentage in between) identical to SEQ ID NO: 111. The polynucleotide encoding a TcBuster transposase can comprise or consist of a naturally occurring nucleic acid sequence or a non-naturally occurring nucleic acid sequence. In a preferred aspect, a TcBuster transposase is encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 112.

In some aspects, a mutant TcBuster transposase comprises one or more sequence variations when compared to a wild type TcBuster transposase as described in more detail in PCT Publication No. WO 2019/173636 and PCT/US2019/049816.

The transposon can be a nanotransposon. A nanotransposon can comprise, consist essential of, or consist of (a) a sequence encoding a transposon insert, comprising a sequence encoding a first inverted terminal repeat (ITR), a sequence encoding a second inverted terminal repeat (ITR), and an intra-ITR sequence; (b) a sequence encoding a backbone, wherein the sequence encoding the backbone comprises a sequence encoding an origin of replication having between 1 and 450 nucleotides, inclusive of the endpoints, and a sequence encoding a selectable marker having between 1 and 200 nucleotides, inclusive of the endpoints, and (c) an inter-ITR sequence. In some aspects, the inter-ITR sequence of (c) comprises the sequence of (b). In some aspects, the intra-ITR sequence of (a) comprises the sequence of (b).

The sequence encoding the backbone can comprise between 1 and 600 nucleotides, inclusive of the endpoints. In some aspects, the sequence encoding the backbone consists of between 1 and 50 nucleotides, between 50 and 100 nucleotides, between 100 and 150 nucleotides, between 150 and 200 nucleotides, between 200 and 250 nucleotides, between 250 and 300 nucleotides, between 300 and 350 nucleotides, between 350 and 400 nucleotides, between 400 and 450 nucleotides, between 450 and 500 nucleotides, between 500 and 550 nucleotides, between 550 and 600 nucleotides, each range inclusive of the endpoints.

The inter-ITR sequence can comprise between 1 and 1000 nucleotides, inclusive of the endpoints. In some aspects, the inter-ITR sequence consists of between 1 and 50 nucleotides, between 50 and 100 nucleotides, between 100 and 150 nucleotides, between 150 and 200 nucleotides, between 200 and 250 nucleotides, between 250 and 300 nucleotides, between 300 and 350 nucleotides, between 350 and 400 nucleotides, between 400 and 450 nucleotides, between 450 and 500 nucleotides, between 500 and 550 nucleotides, between 550 and 600 nucleotides, between 600 and 650 nucleotides, between 650 and 700 nucleotides, between 700 and 750 nucleotides, between 750 and 800 nucleotides, between 800 and 850 nucleotides, between 850 and 900 nucleotides, between 900 and 950 nucleotides, or between 950 and 1000 nucleotides, each range inclusive of the endpoints.

The nanotransposon can be a short nanotransposon (SNT) wherein the inter-ITR sequence comprises between 1 and 200 nucleotides, inclusive of the endpoints. The inter-ITR sequence can consist of between 1 and 10 nucleotides, between 10 and 20 nucleotides, between 20 and 30 nucleotides, between 30 and 40 nucleotides, between 40 and 50 nucleotides, between 50 and 60 nucleotides, between 60 and 70 nucleotides, between 70 and 80 nucleotides, between 80 and 90 nucleotides, or between 90 and 100 nucleotides, each range inclusive of the endpoints.

The selectable marker having between 1 and 200 nucleotides, inclusive of the endpoints, can comprise a sequence encoding a sucrose-selectable marker. The sequence encoding a sucrose-selectable marker can comprise a sequence encoding an RNA-OUT sequence. The sequence encoding an RNA-OUT sequence can comprise or consist of 137 base pairs (bp). The selectable marker having between 1 and 200 nucleotides, inclusive of the endpoints, can comprise a sequence encoding a fluorescent marker. The selectable marker having between 1 and 200 nucleotides, inclusive of the endpoints, can comprise a sequence encoding a cell surface marker.

The sequence encoding an origin of replication having between 1 and 450 nucleotides, inclusive of the endpoints, can comprise a sequence encoding a mini origin of replication. In some aspects, the sequence encoding an origin of replication having between 1 and 450 nucleotides, inclusive of the endpoints, comprises a sequence encoding an R6K origin of replication. The R6K origin of replication can comprise an R6K gamma origin of replication. The R6K origin of replication can comprise an R6K mini origin of replication. The R6K origin of replication can comprise an R6K gamma mini origin of replication. The R6K gamma mini origin of replication can comprise or consist of 281 base pairs (bp).

In some aspects of the nanotransposon, the sequence encoding the backbone does not comprise a recombination site, an excision site, a ligation site or a combination thereof. In some aspects, neither the nanotransposon nor the sequence encoding the backbone comprises a product of a recombination site, an excision site, a ligation site or a combination thereof. In some aspects, neither the nanotransposon nor the sequence encoding the backbone is derived from a recombination site, an excision site, a ligation site or a combination thereof.

In some aspects of the nanotransposon, a recombination site comprises a sequence resulting from a recombination event. In some aspects, a recombination site comprises a sequence that is a product of a recombination event. In some aspects, the recombination event comprises an activity of a recombinase (e.g., a recombinase site).

In some aspects of the nanotransposon, the sequence encoding the backbone does not further comprise a sequence encoding foreign DNA.

In some aspects of the nanotransposon, the inter-ITR sequence does not comprise a recombination site, an excision site, a ligation site or a combination thereof. In some aspects, the inter-ITR sequence does not comprise a product of a recombination event, an excision event, a ligation event or a combination thereof. In some aspects, the inter-ITR sequence is not derived from a recombination event, an excision event, a ligation event or a combination thereof. In some aspects, the inter-ITR sequence comprises a sequence encoding foreign DNA. In some aspects, the intra-ITR sequence comprises at least one sequence encoding an insulator and a sequence encoding a promoter capable of expressing an exogenous sequence in a mammalian cell. The mammalian cell can be a human cell. In some aspects, the intra-ITR sequence comprises a first sequence encoding an insulator, a sequence encoding a promoter capable of expressing an exogenous sequence in a mammalian cell and a second sequence encoding an insulator. In some aspects, the intra-ITR sequence comprises a first sequence encoding an insulator, a sequence encoding a promoter capable of expressing an exogenous sequence in a mammalian cell, a polyadenosine (polyA) sequence and a second sequence encoding an insulator. In some aspects, the intra-ITR sequence comprises a first sequence encoding an insulator, a sequence encoding a promoter capable of expressing an exogenous sequence in a mammalian cell, at least one exogenous sequence, a polyadenosine (polyA) sequence and a second sequence encoding an insulator.

Nanotransposons are described in more detail in PCT/US2019/067758.

Vector Systems

A vector of the present disclose can be a viral vector or a recombinant vector. Viral vectors can comprise a sequence isolated or derived from a retrovirus, a lentivirus, an adenovirus, an adeno-associated virus or any combination thereof.

The viral vector may comprise a sequence isolated or derived from an adeno-associated virus (AAV). The viral vector may comprise a recombinant AAV (rAAV). Exemplary adeno-associated viruses and recombinant adeno-associated viruses comprise two or more inverted terminal repeat (ITR) sequences located in cis next to a sequence encoding an scFv or a CAR of the disclosure. Exemplary adeno-associated viruses and recombinant adeno-associated viruses include, but are not limited to all serotypes (e.g., AAV1, AAV2, AAV3, AAV4, AAV5, AAV6, AAV7, AAV8, and AAV9). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03.

A vector of the present disclose can be a nanoparticle. Non-limiting examples of nanoparticle vectors include nucleic acids (e.g., RNA, DNA, synthetic nucleotides, modified nucleotides or any combination thereof), amino acids (L-amino acids, D-amino acids, synthetic amino acids, modified amino acids, or any combination thereof), polymers (e.g., polymersomes), micelles, lipids (e.g., liposomes), organic molecules (e.g., carbon atoms, sheets, fibers, tubes), inorganic molecules (e.g., calcium phosphate or gold) or any combination thereof. A nanoparticle vector can be passively or actively transported across a cell membrane.

The cell delivery compositions (e.g., transposons, vectors) disclosed herein can comprise a nucleic acid encoding a therapeutic protein or therapeutic agent. Examples of therapeutic proteins include those disclosed in PCT Publication No. WO 2019/173636 and PCT/US2019/049816.

Inducible Proapontotic Polypeptides

The inducible proapoptotic polypeptides disclosed herein are superior to existing inducible polypeptides because the inducible proapoptotic polypeptides of the disclosure are far less immunogenic. The inducible proapoptotic polypeptides are recombinant polypeptides, and, therefore, non-naturally occurring. Further, the sequences that are recombined to produce inducible proapoptotic polypeptides that do not comprise non-human sequences that the host human immune system could recognize as "non-self" and, consequently, induce an immune response in the subject receiving the inducible proapoptotic polypeptide, a cell comprising the inducible proapoptotic polypeptide or a composition comprising the inducible proapoptotic polypeptide or the cell comprising the inducible proapoptotic polypeptide.

The disclosure provides inducible proapoptotic polypeptides comprising a ligand binding region, a linker, and a proapoptotic peptide, wherein the inducible proapoptotic polypeptide does not comprise a non-human sequence. In certain aspects, the non-human sequence comprises a restriction site. In certain aspects, the ligand binding region can be a multimeric ligand binding region. In certain aspects, the proapoptotic peptide is a caspase polypeptide. Non-limiting examples of caspase polypeptides include caspase 1, caspase 2, caspase 3, caspase 4, caspase 5, caspase 6, caspase 7, caspase 8, caspase 9, caspase 10, caspase 11, caspase 12, and caspase 14. Preferably, the caspase polypeptide is a caspase 9 polypeptide. The caspase 9 polypeptide can be a truncated caspase 9 polypeptide. Inducible proapoptotic polypeptides can be non-naturally occurring. When the caspase is caspase 9 or a truncated caspase 9, the inducible proapoptotic polypeptides can also be referred to as an "iC9 safety switch".

An inducible caspase polypeptide can comprise (a) a ligand binding region, (b) a linker, and (c) a caspase polypeptide, wherein the inducible proapoptotic polypeptide does not comprise a non-human sequence. In certain aspects, an inducible caspase polypeptide comprises (a) a ligand binding region, (b) a linker, and (c) a truncated caspase 9 polypeptide, wherein the inducible proapoptotic polypeptide does not comprise a non-human sequence.

The ligand binding region can comprise a FK506 binding protein 12 (FKBP12) polypeptide. The amino acid sequence of the ligand binding region that comprises a FK506 binding protein 12 (FKBP12) polypeptide can comprise a modification at position 36 of the sequence. The modification can be a substitution of valine (V) for phenylalanine (F) at position 36 (F36V). The FKBP12 polypeptide can comprise, consist essential of, or consist of, the amino acid sequence at least 75%, 80%, 85%, 90%, 95%, 96%, 97%, 98%, 99% or 100% (or any percentage in between) identical to SEQ ID NO: 113. The FKBP12 polypeptide can be encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 114.

The linker region can comprise, consist essential of, or consist of, the amino acid sequence at least 75%, 80%, 85%, 90%, 95%, 96%, 97%, 98%, 99% or 100% (or any percentage in between) identical to SEQ ID NO: 115 or the linker region can be encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 116. In some aspects, the nucleic acid sequence encoding the linker does not comprise a restriction site.

The truncated caspase 9 polypeptide can comprise an amino acid sequence that does not comprise an arginine (R) at position 87 of the sequence. Alternatively, or in addition, the truncated caspase 9 polypeptide can comprise an amino acid sequence that does not comprise an alanine (A) at position 282 the sequence. The truncated caspase 9 polypeptide can comprise, consist essential of, or consist of, the amino acid sequence at least 75%, 80%, 85%, 90%, 95%, 96%, 97%, 98%, 99% or 100% (or any percentage in between) identical to SEQ ID NO: 117 or the truncated caspase 9 polypeptide can be encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 118.

In certain aspects when the polypeptide comprises a truncated caspase 9 polypeptide, the inducible proapoptotic polypeptide comprises, consists essential of, or consists of, the amino acid sequence at least 75%, 80%, 85%, 90%, 95%, 96%, 97%, 98%, 99% or 100% (or any percentage in between) identical to SEQ ID NO: 119 or the inducible proapoptotic polypeptide is encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 120.

In certain aspects when the polypeptide comprises a truncated caspase 9 polypeptide, the inducible proapoptotic polypeptide comprises, consists essential of, or consists of, the amino acid sequence at least 75%, 80%, 85%, 90%, 95%, 96%, 97%, 98%, 99% or 100% (or any percentage in between) identical to SEQ ID NO: 172 or the inducible proapoptotic polypeptide is encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 173.

Inducible proapoptotic polypeptides can be expressed in a cell under the transcriptional regulation of any promoter known in the art that is capable of initiating and/or regulating the expression of an inducible proapoptotic polypeptide in that cell.

Activation of inducible proapoptotic polypeptides can be accomplished through, for example, chemically induced dimerization (CID) mediated by an induction agent to produce a conditionally controlled protein or polypeptide. Proapoptotic polypeptides not only inducible, but the induction of these polypeptides is also reversible, due to the degradation of the labile dimerizing agent or administration of a monomeric competitive inhibitor.

In certain aspects when the ligand binding region comprises a FKBP12 polypeptide having a substitution of valine (V) for phenylalanine (F) at position 36 (F36V), the induction agent can comprise AP1903, a synthetic drug (CAS Index Name: 2-Piperidinecarboxylic acid, 1-[(2S)-1-oxo-2-(3,4,5-trimethoxyphenyl)butyl]-, 1,2-ethanediylbis[imino (2-oxo-2,1-ethanediyl)oxy-3,1-phenylene[(1R)-3-(3,4-di-methoxyphenyl)propylidene]]ester, [2S-[1(R*),2R*[S*[S* [1(R*),2R*]]]]]-(9Cl) CAS Registry Number: 195514-63-7; Molecular Formula: C78H98N4O20; Molecular Weight: 1411.65)); AP20187 (CAS Registry Number: 195514-80-8 and Molecular Formula: C82H107N5O20) or an AP20187 analog, such as, for example, AP1510. As used herein, the induction agents AP20187, AP1903 and AP1510 can be used interchangeably.

Inducible proapoptotic peptides and methods of inducing these peptides are described in detail in U.S. Patent Publication No. WO 2019/0225667 and PCT Publication No. WO 2018/068022.

Chimeric Stimulator Receptors and Recombinant HLA-E Polypeptides

Adoptive cell compositions that are "universally" safe for administration to any patient requires a significant reduction or elimination of alloreactivity. Towards this end, cells of the disclosure (e.g., allogenic cells) can be modified to interrupt expression or function of a T-cell Receptor (TCR) and/or a class of Major Histocompatibility Complex (MHC). The TCR mediates graft vs host (GvH) reactions whereas the MHC mediates host vs graft (HvG) reactions. In preferred aspects, any expression and/or function of the TCR is eliminated to prevent T-cell mediated GvH that could cause death to the subject. Thus, in a preferred aspect, the disclosure provides a pure TCR-negative allogeneic T-cell composition (e.g., each cell of the composition expresses at a level so low as to either be undetectable or non-existent).

Expression and/or function of MHC class I (MHC-I, specifically, HLA-A, HLA-B, and HLA-C) is reduced or eliminated to prevent HvG and, consequently, to improve engraftment of cells in a subject. Improved engraftment results in longer persistence of the cells, and, therefore, a larger therapeutic window for the subject. Specifically, expression and/or function of a structural element of MHC-I, Beta-2-Microglobulin (B2M), is reduced or eliminated.

The above strategies induce further challenges. T Cell Receptor (TCR) knockout (KO) in T cells results in loss of expression of CD3-zeta (CD3z or CD3ζ), which is part of the TCR complex. The loss of CD3ζ in TCR-KO T-cells dramatically reduces the ability of optimally activating and expanding these cells using standard stimulation/activation reagents, including, but not limited to, agonist anti-CD3 mAb. When the expression or function of any one component of the TCR complex is interrupted, all components of the complex are lost, including TCR-alpha (TCRα), TCR-beta (TCRβ), CD3-gamma (CD3γ), CD3-epsilon (CD3ε), CD3-delta (CD3δ), and CD3-zeta (CD3ζ). Both CD3ε and CD3ζ are required for T cell activation and expansion. Agonist anti-CD3 mAbs typically recognize CD3ε and possibly another protein within the complex which, in turn, signals to CD3ζ. CD3ζ provides the primary stimulus for T cell activation (along with a secondary co-stimulatory signal) for optimal activation and expansion. Under normal conditions, full T-cell activation depends on the engagement of the TCR in conjunction with a second signal mediated by one or more co-stimulatory receptors (e.g., CD28, CD2, 4-1BBL) that boost the immune response. However, when the TCR is not present, T cell expansion is severely reduced when stimulated using standard activation/stimulation reagents, including agonist anti-CD3 mAb. In fact, T cell expansion is reduced to only 20-40% of the normal level of expansion when stimulated using standard activation/stimulation reagents, including agonist anti-CD3 mAb.

Thus, the present disclosure provides a non-naturally occurring chimeric stimulatory receptor (CSR) comprising: (a) an ectodomain comprising a activation component, wherein the activation component is isolated or derived from a first protein; (b) a transmembrane domain; and (c) an endodomain comprising at least one signal transduction domain, wherein the at least one signal transduction domain is isolated or derived from a second protein; wherein the first protein and the second protein are not identical.

The activation component can comprise a portion of one or more of a component of a T-cell Receptor (TCR), a component of a TCR complex, a component of a TCR co-receptor, a component of a TCR co-stimulatory protein, a component of a TCR inhibitory protein, a cytokine receptor, and a chemokine receptor to which an agonist of the activation component binds. The activation component can comprise a CD2 extracellular domain or a portion thereof to which an agonist binds.

The signal transduction domain can comprise one or more of a component of a human signal transduction domain, T-cell Receptor (TCR), a component of a TCR complex, a component of a TCR co-receptor, a component of a TCR co-stimulatory protein, a component of a TCR inhibitory protein, a cytokine receptor, and a chemokine receptor. The signal transduction domain can comprise a CD3 protein or a portion thereof. The CD3 protein can comprise a CD3ζ protein or a portion thereof.

The endodomain can further comprise a cytoplasmic domain. The cytoplasmic domain can be isolated or derived from a third protein. The first protein and the third protein can be identical. The ectodomain can further comprise a signal peptide. The signal peptide can be derived from a fourth protein. The first protein and the fourth protein can be identical. The transmembrane domain can be isolated or derived from a fifth protein. The first protein and the fifth protein can be identical.

In some aspects, the activation component does not bind a naturally-occurring molecule. In some aspects, the activation component binds a naturally-occurring molecule but the CSR does not transduce a signal upon binding of the activation component to a naturally-occurring molecule. In some aspects, the activation component binds to a non-naturally occurring molecule. In some aspects, the activation component does not bind a naturally-occurring molecule but binds a non-naturally occurring molecule. The CSR can selectively transduces a signal upon binding of the activation component to a non-naturally occurring molecule.

In a preferred aspect, the present disclosure provides a non-naturally occurring chimeric stimulatory receptor (CSR) comprising: (a) an ectodomain comprising a signal peptide and an activation component, wherein the signal peptide comprises a CD2 signal peptide or a portion thereof and wherein the activation component comprises a CD2 extracellular domain or a portion thereof to which an agonist binds; (b) a transmembrane domain, wherein the transmembrane domain comprises a CD2 transmembrane domain or a portion thereof, and (c) an endodomain comprising a cytoplasmic domain and at least one signal transduction domain, wherein the cytoplasmic domain comprises a CD2 cytoplasmic domain or a portion thereof and wherein the at least one signal transduction domain comprises a CD3ζ protein or a portion thereof. In some aspects, the non-naturally CSR comprises an amino acid sequence at least 75%, 80%, 85%, 90%, 95%, 96%, 97%, 98%, 99% or 100% (or any percentage in between) identical to SEQ ID NO: 121. In a preferred aspect, the non-naturally occurring CSR comprises an amino acid sequence of SEQ ID NO: 121.

The present disclosure also provides a non-naturally occurring chimeric stimulatory receptor (CSR) wherein the ectodomain comprises a modification. The modification can comprise a mutation or a truncation of the amino acid sequence of the activation component or the first protein when compared to a wild type sequence of the activation component or the first protein. The mutation or a truncation of the amino acid sequence of the activation component can comprise a mutation or truncation of a CD2 extracellular domain or a portion thereof to which an agonist binds. The mutation or truncation of the CD2 extracellular domain can reduce or eliminate binding with naturally occurring CD58. In some aspects, the CD2 extracellular domain comprising the mutation or truncation comprises an amino acid sequence at least 75%, 80%, 85%, 90%, 95%, 96%, 97%, 98%, 99% or 100% (or any percentage in between) identical to SEQ ID NO: 122. In a preferred aspect, the CD2 extracellular domain comprising the mutation or truncation comprises an amino acid sequence of SEQ ID NO: 122.

In a preferred aspect, the present disclosure provides non-naturally occurring chimeric stimulatory receptor (CSR) comprising: (a) an ectodomain comprising a signal peptide and an activation component, wherein the signal peptide comprises a CD2 signal peptide or a portion thereof and wherein the activation component comprises a CD2 extracellular domain or a portion thereof to which an agonist binds and wherein the CD2 extracellular domain or a portion thereof to which an agonist binds comprises a mutation or truncation; (b) a transmembrane domain, wherein the transmembrane domain comprises a CD2 transmembrane domain or a portion thereof, and (c) an endodomain comprising a cytoplasmic domain and at least one signal transduction domain, wherein the cytoplasmic domain comprises a CD2 cytoplasmic domain or a portion thereof and wherein the at least one signal transduction domain comprises a CD3ζ protein or a portion thereof. In some aspects, the non-naturally CSR comprises an amino acid sequence at least 75%, 80%, 85%, 90%, 95%, 96%, 97%, 98%, 99% or 100% (or any percentage in between) identical to SEQ ID NO: 123. In a preferred aspect, the non-naturally occurring CSR comprises an amino acid sequence of SEQ ID NO: 123.

The present disclosure provides a nucleic acid sequence encoding any CSR disclosed herein. The present disclosure provides a transposon or a vector comprising a nucleic acid sequence encoding any CSR disclosed herein.

The present disclosure provides a cell comprising any CSR disclosed herein. The present disclosure provides a cell comprising a nucleic acid sequence encoding any CSR disclosed herein. The present disclosure provides a cell comprising a vector comprising a nucleic acid sequence encoding any CSR disclosed herein. The present disclosure provides a cell comprising a transposon comprising a nucleic acid sequence encoding any CSR disclosed herein.

A modified cell disclosed herein can be an allogeneic cell or an autologous cell. In some preferred aspects, the modified cell is an allogeneic cell. In some aspects, the modified cell is an autologous T-cell or a modified autologous CAR T-cell. In some preferred aspects, the modified cell is an allogeneic T-cell or a modified allogeneic CAR T-cell.

The present disclosure provides a composition comprising any CSR disclosed herein. The present disclosure provides a composition comprising a nucleic acid sequence encoding any CSR disclosed herein. The present disclosure provides a composition comprising a vector comprising a nucleic acid sequence encoding any CSR disclosed herein. The present disclosure provides a composition comprising a transposon comprising a nucleic acid sequence encoding any CSR disclosed herein. The present disclosure provides a composition comprising a modified cell disclosed herein or a composition comprising a plurality of modified cells disclosed herein.

The present disclosure provides a modified T lymphocyte (T-cell), comprising: (a) a modification of an endogenous sequence encoding a T-cell Receptor (TCR), wherein the modification reduces or eliminates a level of expression or activity of the TCR; and (b) a chimeric stimulatory receptor (CSR) comprising: (i) an ectodomain comprising an activation component, wherein the activation component is isolated or derived from a first protein; (ii) a transmembrane domain; and (iii) an endodomain comprising at least one signal transduction domain, wherein the at least one signal transduction domain is isolated or derived from a second protein; wherein the first protein and the second protein are not identical.

The modified T-cell can further comprise an inducible proapoptotic polypeptide. The modified T-cell can further comprise a modification of an endogenous sequence encoding Beta-2-Microglobulin (B2M), wherein the modification reduces or eliminates a level of expression or activity of a major histocompatibility complex (MHC) class I (MHC-I).

The modified T-cell can further comprise a non-naturally occurring polypeptide comprising an HLA class I histocompatibility antigen, alpha chain E (HLA-E) polypeptide. The non-naturally occurring polypeptide comprising a HLA-E polypeptide can further comprise a B2M signal peptide. The non-naturally occurring polypeptide comprising a HLA-E polypeptide can further comprise a B2M polypeptide. The non-naturally occurring polypeptide comprising an HLA-E polypeptide can further comprise a linker, wherein the linker is positioned between the B2M polypeptide and the HLA-E polypeptide. The non-naturally occurring polypeptide comprising an HLA-E polypeptide can further comprise a peptide and a B2M polypeptide. The non-naturally occurring polypeptide comprising an HLA-E can further comprise a first linker positioned between the B2M signal peptide and the peptide, and a second linker positioned between the B2M polypeptide and the peptide encoding the HLA-E.

The modified T-cell can further comprise a non-naturally occurring antigen receptor, a sequence encoding a therapeutic polypeptide, or a combination thereof. The non-naturally occurring antigen receptor can comprise a chimeric antigen receptor (CAR).

The CSR can be transiently expressed in the modified T-cell. The CSR can be stably expressed in the modified T-cell. The polypeptide comprising the HLA-E polypeptide can be transiently expressed in the modified T-cell. The polypeptide comprising the HLA-E polypeptide can be stably expressed in the modified T-cell. The inducible proapoptotic polypeptide can be transiently expressed in the modified T-cell. The inducible proapoptotic polypeptide can be stably expressed in the modified T-cell. The non-naturally occurring antigen receptor or a sequence encoding a therapeutic protein can be transiently expressed in the modified T-cell. The non-naturally occurring antigen receptor or a sequence encoding a therapeutic protein can be stably expressed in the modified T-cell.

Gene editing compositions, including but not limited to, RNA-guided fusion proteins comprising dCas9-Clo051, as described in detail herein, can be used to target and decrease or eliminate expression of an endogenous T-cell receptor. In preferred aspects, the gene editing compositions target and delete a gene, a portion of a gene, or a regulatory element of a gene (such as a promoter) encoding an endogenous T-cell receptor. Non-limiting examples of primers (including a T7 promoter, genome target sequence, and gRNA scaffold) for the generation of guide RNA (gRNA) templates for targeting and deleting TCR-alpha (TCR-α), targeting and deleting TCR-beta (TCR-β), and targeting and deleting beta-2-microglobulin (β2M) are disclosed in PCT Application No. PCT/US2019/049816.

Gene editing compositions, including but not limited to, RNA-guided fusion proteins comprising dCas9-Clo051, can be used to target and decrease or eliminate expression of an endogenous MHCI, MHCII, or MHC activator. In preferred aspects, the gene editing compositions target and delete a gene, a portion of a gene, or a regulatory element of a gene (such as a promoter) encoding one or more components of an endogenous MHCI, MHCII, or MHC activator. Non-limiting examples of guide RNAs (gRNAs) for targeting and deleting MHC activators are disclosed in PCT Application No. PCT/US2019/049816.

A detailed description of non-naturally occurring chimeric stimulatory receptors, genetic modifications of endogenous sequences encoding TCR-alpha (TCR-α), TCR-beta (TCR-β), and/or Beta-2-Microglobulin (β2M), and non-naturally occurring polypeptides comprising an HLA class I histocompatibility antigen, alpha chain E (HLA-E) polypeptide is disclosed in PCT Application No. PCT/US2019/049816.

Formulations, Dosages and Modes of Administration

The present disclosure provides formulations, dosages and methods for administration of the compositions described herein.

The disclosed compositions and pharmaceutical compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the "Physician's Desk Reference", 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

Non-limiting examples of pharmaceutical excipients and additives suitable for use include proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin, such as human serum albumin (HSA), recombinant human albumin (rHA), gelatin, casein, and the like. Representative amino acid/protein components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Non-limiting examples of carbohydrate excipients suitable for use include monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferably, the carbohydrate excipients are mannitol, trehalose, and/or raffinose.

The compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers are organic acid salts, such as citrate.

Additionally, the disclosed compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

Many known and developed modes can be used for administering therapeutically effective amounts of the compositions or pharmaceutical compositions disclosed herein. Non-limiting examples of modes of administration include bolus, buccal, infusion, intrarticular, intrabronchial, intraabdominal, intracapsular, intracartilaginous, intracavitary, intracelial, intracerebellar, intracerebroventricular, intracolic, intracervical, intragastric, intrahepatic, intralesional, intramuscular, intramyocardial, intranasal, intraocular, intraosseous, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intratumoral, intravenous, intravesical, oral, parenteral, rectal, sublingual, subcutaneous, transdermal or vaginal means.

A composition of the disclosure can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

For parenteral administration, any composition disclosed herein can be formulated as a solution, suspension, emulsion, particle, powder, or lyophilized powder in association, or separately provided, with a pharmaceutically acceptable parenteral vehicle. Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and protein scaffolds and a combination of at least two surfactants intended for oral, buccal, mucosal, nasal, pulmonary, vaginal transmembrane, or rectal administration are described in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 and used to deliver biologically active agents orally are known in the art.

For pulmonary administration, preferably, a composition or pharmaceutical composition described herein is delivered in a particle size effective for reaching the lower airways of the lung or sinuses. The composition or pharmaceutical composition can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers (e.g., jet nebulizer, ultrasonic nebulizer), dry powder generators, sprayers, and the like. All such devices can use formulations suitable for the administration for the dispensing of a composition or pharmaceutical composition described herein in an aerosol. Such aerosols can be comprised of either solutions (both aqueous and non-aqueous) or solid particles. Additionally, a spray including a composition or pharmaceutical composition described herein can be produced by forcing a suspension or solution of at least one protein scaffold through a nozzle under pressure. In a metered dose inhaler (MDI), a propellant, a composition or pharmaceutical composition described herein, and any excipients or other additives are contained in a canister as a mixture including a liquefied compressed gas. Actuation of the metering valve releases the mixture as an aerosol, preferably containing particles in the size range of less than about 10 m, preferably, about 1 m to about 5 m, and, most preferably, about 2 m to about 3 m. A more detailed description of pulmonary administration, formulations and related devices is disclosed in PCT Publication No. WO 2019/049816.

For absorption through mucosal surfaces, compositions include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670).

Mucous surfaces suitable for application of the emulsions of the disclosure can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695). A more detailed description of mucosal administration and formulations is disclosed in PCT Publication No. WO 2019/049816.

For transdermal administration, a composition or pharmaceutical composition disclosed herein is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599). A more detailed description of transdermal administration, formulations and suitable devices is disclosed in PCT Publication No. WO 2019/049816.

It can be desirable to deliver the disclosed compounds to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the disclosed compounds or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J. Preferred doses can optionally include about 0.1-99 and/or 100-500 mg/kg/administration, or any range, value or fraction thereof, or to achieve a serum concentration of about 0.1-5000 μg/ml serum concentration per single or multiple administration, or any range, value or fraction thereof. A preferred dosage range for the compositions or pharmaceutical compositions disclosed herein is from about 1 mg/kg, up to about 3, about 6 or about 12 mg/kg of body weight of the subject.

Alternatively, the dosage administered can vary depending upon known factors, such as the pharmacodynamic characteristics of the particular agent, and its mode and route of administration; age, health, and weight of the recipient;

nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably, 0.1 to 10 milligrams per kilogram per administration or in sustained release form is effective to obtain desired results.

As a non-limiting example, treatment of humans or animals can be provided as a one-time or periodic dosage of the compositions or pharmaceutical compositions disclosed herein about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

An effective amount can comprise an amount of about 0.001 to about 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

In aspects where the compositions to be administered to a subject in need thereof are modified cells as disclosed herein, the cells can be administered between about $1\times10^3$ and $1\times10^{15}$ cells; about $1\times10^4$ and $1\times10^{12}$ cells; about $1\times10^5$ and $1\times10^{10}$ cells; about $1\times10^6$ and $1\times10^9$ cells; about $1\times10^6$ and $1\times10^8$ cells; about $1\times10^6$ and $1\times10^7$ cells; or about $1\times10^6$ and $25\times10^6$ cells. In one aspect the cells are administered between about $5\times10^6$ and $25\times10^6$ cells.

A more detailed description of pharmaceutically acceptable excipients, formulations, dosages and methods of administration of the disclosed compositions and pharmaceutical compositions is disclosed in PCT Publication No. WO 2019/049816.

Methods of Using the Compositions of the Disclosure

The disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms "subject" and "patient" are used interchangeably herein.

The disclosure provides a method for modulating or treating at least one malignant disease or disorder in a cell, tissue, organ, animal or subject. Preferably, the malignant disease is cancer. Non-limiting examples of a malignant disease or disorder include leukemia, acute leukemia, acute lymphoblastic leukemia (ALL), acute lymphocytic leukemia, B-cell, T-cell or FAB ALL, acute myeloid leukemia (AML), acute myelogenous leukemia, chronic myelocytic leukemia (CML), chronic lymphocytic leukemia (CLL), hairy cell leukemia, myelodysplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

In preferred aspects, the treatment of a malignant disease or disorder comprises adoptive cell therapy. For example, in one aspect, the disclosure provides modified cells that express at least one disclosed antibody (e.g., scFv) and/or CAR comprising an antibody (e.g., scFv) that have been selected and/or expanded for administration to a subject in need thereof. Modified cells can be formulated for storage at any temperature including room temperature and body temperature. Modified cells can be formulated for cryopreservation and subsequent thawing. Modified cells can be formulated in a pharmaceutically acceptable carrier for direct administration to a subject from sterile packaging. Modified cells can be formulated in a pharmaceutically acceptable carrier with an indicator of cell viability and/or CAR expression level to ensure a minimal level of cell function and CAR expression. Modified cells can be formulated in a pharmaceutically acceptable carrier at a prescribed density with one or more reagents to inhibit further expansion and/or prevent cell death.

Any can comprise administering an effective amount of any composition or pharmaceutical composition disclosed herein to a cell, tissue, organ, animal or subject in need of such modulation, treatment or therapy. Such a method can optionally further comprise co-administration or combination therapy for treating such diseases or disorders, wherein the administering of any composition or pharmaceutical composition disclosed herein, further comprises administering, before concurrently, and/or after, at least one chemotherapeutic agent (e.g., an alkylating agent, an a mitotic inhibitor, a radiopharmaceutical).

In some aspects, the subject does not develop graft vs. host (GvH) and/or host vs. graft (HvG) following administration. In one aspect, the administration is systemic. Systemic administration can be any means known in the art and described in detail herein. Preferably, systemic administration is by an intravenous injection or an intravenous infusion. In one aspect, the administration is local. Local administration can be any means known in the art and described in detail herein. Preferably, local administration is by intratumoral injection or infusion, intraspinal injection or infusion, intracerebroventricular injection or infusion, intraocular injection or infusion, or intraosseous injection or infusion.

In some aspects, the therapeutically effective dose is a single dose. In some aspects, the single dose is one of at least 2, 5, 10, 15, 20, 25, 30, 35, 40, 45, 50, 55, 60, 65, 70, 75, 80, 85, 90, 95, 100 or any number of doses in between that are manufactured simultaneously. In some aspects, where the composition is autologous cells or allogeneic cells, the dose is an amount sufficient for the cells to engraft and/or persist for a sufficient time to treat the disease or disorder.

In one example, the disclosure provides a method of treating cancer in a subject in need thereof, comprising administering to the subject a composition comprising an antibody (e.g., scFv) or a CAR comprising an antibody (e.g., scFv) the antibody or CAR specifically binds to an antigen on a tumor cell. In aspects where the composition comprises a modified cell or cell population, the cell or cell population may be autologous or allogeneic.

In some aspects of the methods of treatment described herein, the treatment can be modified or terminated. Specifically, in aspects where the composition used for treatment comprises an inducible proapoptotic polypeptide, apoptosis may be selectively induced in the cell by contacting the cell with an induction agent. A treatment may be modified or terminated in response to, for example, a sign of recovery or a sign of decreasing disease severity/progression, a sign of disease remission/cessation, and/or the occurrence of an adverse event. In some aspects, the method comprises the step of administering an inhibitor of the induction agent to inhibit modification of the cell therapy, thereby restoring the function and/or efficacy of the cell therapy (for example, when a sign or symptom of the disease reappear or increase in severity and/or an adverse event is resolved).

Antibody/scFv Production, Screening and Purification

At least one antibody (e.g., monoclonal antibody, a chimeric antibody, a single domain antibody, a VHH, a VH, a single chain variable fragment (scFv), an antigen-binding fragment (Fab) or a Fab fragment) of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino acids from an scFv can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, an scFv can be engineered with retention of high affinity for the antigen and other favorable biological properties. To achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, i.e., the analysis of residues that influence the ability of the candidate scFv to bind its antigen. In this way, residues can be selected and combined from the parent and reference sequences so that the desired characteristic, such as affinity for the target antigen(s), is achieved. Alternatively, or in addition to, the above procedures, other suitable methods of engineering can be used.

Screening of an scFv for specific binding to similar proteins or fragments can be conveniently achieved using nucleotide (DNA or RNA display) or peptide display libraries, for example, in vitro display. This method involves the screening of large collections of peptides for individual members having the desired function or structure. The displayed nucleotide or peptide sequences can be from 3 to 5000 or more nucleotides or amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. WO 91/17271, WO 91/18980, WO 91/19818, and WO 93/08278.

Other systems for generating libraries of peptides have aspects of both in vitro chemical synthesis and recombinant methods. See, PCT Patent Publication Nos. WO 92/05258, WO 92/14843, and WO 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge Antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra.

An scFv of the disclosure can bind human or other mammalian proteins with a wide range of affinities (KD). In a preferred aspect, at least one scFv of the present disclosure can optionally bind to a target protein with high affinity, for example, with a KD equal to or less than about $10^{-7}$ M, such as but not limited to, 0.1-9.9 (or any range or value therein)$\times$ $10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art.

The affinity or avidity of a scFv for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular scFv-antigen interaction can vary if measured under different conditions (e.g., salt concentration, pH). Thus, measurements of affinity and other antigen-binding parameters (e.g., KD, Kon, Koff) are preferably made with standardized solutions of protein scaffold and antigen, and a standardized buffer, such as the buffer described herein.

Competitive assays can be performed with the scFv of the disclosure in order to determine what proteins, antibodies, and other antagonists compete for binding to a target protein with the scFv of the present disclosure and/or share the epitope region. These assays as readily known to those of ordinary skill in the art evaluate competition between antagonists or ligands for a limited number of binding sites on a protein. The protein and/or antibody is immobilized or insolubilized before or after the competition and the sample bound to the target protein is separated from the unbound sample, for example, by decanting (where the protein/antibody was pre-insolubilized) or by centrifuging (where the protein/antibody was precipitated after the competitive reaction). Also, the competitive binding may be determined by whether function is altered by the binding or lack of binding of the scFv to the target protein, e.g., whether the scFv molecule inhibits or potentiates the enzymatic activity of, for example, a label. ELISA and other functional assays may be used, as well known in the art.

Nucleic Acid Molecules

Nucleic acid molecules of the disclosure encoding an scFv can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the disclosure can include nucleic acid molecules comprising an open reading frame (ORF), optionally, with one or more introns, e.g., but not limited to, at least one specified portion of at least one scFv; nucleic acid molecules comprising the coding sequence for a protein scaffold or loop region that binds to the target protein; and nucleic acid molecules which comprise a nucleotide sequence substantially different from those described above but which, due to the degeneracy of the genetic code, still encode the protein scaffold as described herein and/or as known in the art. Of course, the genetic code is well known in the art. Thus, it would be routine for one skilled in the art to generate such degenerate nucleic acid variants that code for a specific scFv of the present disclosure. See, e.g., Ausubel, et al., supra, and such nucleic acid variants are included in the present disclosure.

As indicated herein, nucleic acid molecules of the disclosure which comprise a nucleic acid encoding a scFv can include, but are not limited to, those encoding the amino acid sequence of a scFv fragment, by itself, the coding sequence for the entire protein scaffold or a portion thereof; the coding sequence for a scFv, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding a protein scaffold can be fused to a marker sequence, such as a sequence encoding a peptide that facilitates purification of the fused protein scaffold comprising a protein scaffold fragment or portion.

Polynucleotides Selectively Hybridizing to a Polynucleotide as Described Herein

The disclosure provides isolated nucleic acids that hybridize under selective hybridization conditions to a polynucleotide disclosed herein. Thus, the polynucleotides can be used for isolating, detecting, and/or quantifying nucleic acids comprising such polynucleotides. For example, polynucleotides of the present disclosure can be used to identify, isolate, or amplify partial or full-length clones in a deposited library. The polynucleotides can be genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of a protein scaffold encoded by the polynucleotides described herein. The polynucleotides embrace nucleic acid sequences that can be employed for selective hybridization to a polynucleotide encoding a protein scaffold of the present disclosure. See, e.g., Ausubel, supra; Colligan, supra, each entirely incorporated herein by reference.

Construction of Nucleic Acids

The isolated nucleic acids of the disclosure can be made using (a) recombinant methods, (b) synthetic techniques, (c) purification techniques, and/or (d) combinations thereof, as well-known in the art.

The nucleic acids can conveniently comprise nucleotide sequences in addition to a polynucleotide of the present disclosure. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this disclosure, such as RNA, cDNA, genomic DNA, or any combination thereof, can be obtained from biological sources using any number of cloning methodologies known to those of skill in the art. In some aspects, oligonucleotide probes that selectively hybridize, under stringent conditions, to the polynucleotides of the present disclosure are used to identify the desired sequence in a cDNA or genomic DNA library. The isolation of RNA, and construction of cDNA and genomic libraries are well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the disclosure. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the disclosure can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The disclosure further provides recombinant expression cassettes comprising a nucleic acid of the disclosure. A nucleic acid sequence of the disclosure, for example, a cDNA or a genomic sequence encoding a protein scaffold of the disclosure, can be used to construct a recombinant expression cassette that can be introduced into at least one desired host cell. A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some aspects, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Expression Vectors and Host Cells

The disclosure also relates to vectors that include isolated nucleic acid molecules of the disclosure, host cells that are genetically engineered with the recombinant vectors, and the production of at least one protein scaffold by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), DIFR (encoding Dihydrofolate Reductase and conferring resistance to Methotrexate), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, "cluster of designation" or "classification determinant" proteins (often abbreviated as "CD") such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

At least one protein scaffold of the disclosure can be expressed in a modified form, such as a fusion protein, and can include not only secretion signals, but also additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the disclosure to facilitate purification. Such regions can be removed prior to final preparation of a protein scaffold or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the disclosure. Alternatively, nucleic acids of the disclosure can be expressed in a host cell by turning on (by manipulation) in a host cell that contains endogenous DNA encoding a protein scaffold of the disclosure. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the protein scaffolds, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a preferred aspect, the recombinant cell is a P3X63Ab8.653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present disclosure are known and/or available, for instance, from the American Type Culture Collection Catalogue of Cell Lines and Hybridomas (www.atcc.org) or other known or commercial sources.

When eukaryotic host cells are employed, polyadenylation or transcription terminator sequences are typically incorporated into the vector. An example of a terminator sequence is the polyadenylation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

scFv Purification

An scFv can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

An scFv of the disclosure include purified products, products of chemical synthetic procedures, and products produced by recombinant techniques from a prokaryotic or eukaryotic host, including, for example, E. coli, yeast, higher plant, insect and mammalian cells. Depending upon the host employed in a recombinant production procedure, the protein scaffold of the disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Amino Acid Codes

The amino acids that make up protein scaffolds of the disclosure are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). A protein scaffold of the disclosure can include one or more amino acid substitutions, deletions or additions, from spontaneous or mutations and/or human manipulation, as specified herein. Amino acids in a protein scaffold of the disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one neutralizing activity. Sites that are critical for protein scaffold binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

As those of skill will appreciate, the disclosure includes at least one biologically active protein scaffold of the disclosure. Biologically active protein scaffolds have a specific activity at least 20%, 30%, or 40%, and, preferably, at least 50%, 60%, or 70%, and, most preferably, at least 80%, 90%, or 95%-99% or more of the specific activity of the native (non-synthetic), endogenous or related and known protein scaffold. Methods of assaying and quantifying measures of enzymatic activity and substrate specificity are well known to those of skill in the art.

In another aspect, the disclosure relates to protein scaffolds and fragments, as described herein, which are modified by the covalent attachment of an organic moiety. Such modification can produce a protein scaffold fragment with improved pharmacokinetic properties (e.g., increased in vivo serum half-life). The organic moiety can be a linear or branched hydrophilic polymeric group, fatty acid group, or fatty acid ester group. In particular aspect, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified protein scaffolds and fragments of the disclosure can comprise one or more organic moieties that are covalently bonded, directly or indirectly, to the antibody. Each organic moiety that is bonded to a protein scaffold or fragment of the disclosure can independently be a hydrophilic polymeric group, a fatty acid group or a fatty acid ester group. As used herein, the term "fatty acid" encompasses mono-carboxylic acids and dicarboxylic acids. A "hydrophilic polymeric group," as the term is used herein, refers to an organic polymer that is more soluble in water than in octane. For example, polylysine is more soluble in water than in octane. Thus, a protein scaffold modified by the covalent attachment of polylysine is encompassed by the disclosure. Hydrophilic polymers suitable for modifying protein scaffolds of the disclosure can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the protein scaffold of the disclosure has a molecular weight of about 800 to about 150,000 Daltons as a separate molecular entity. For example, PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying protein scaffolds of the disclosure can be saturated or can contain one or more units of unsaturation. Fatty acids that are suitable for modifying protein scaffolds of the disclosure include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-Δ9-octadecanoate (C18, oleate), all cis-Δ5,8,11,14-eicosatetraenoate (C20, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably, one to about six, carbon atoms.

The modified protein scaffolds and fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, aminereactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom, such as oxygen, nitrogen or sulfur. Suitable linker moieties include, for example, tetraethylene glycol, —(CH2)3-, —NH—(CH2)6-NH—, —(CH2)2-NH— and —CH2-O—CH2-CH2-O—CH2-CH2-O—CH—NH—.

Modifying agents that comprise a linker moiety can be produced, for example, by reacting a mono-Boc-alkyl-diamine (e.g., mono-Boc-ethylenediamine, mono-Boc-diaminohexane) with a fatty acid in the presence of 1-ethyl- 3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimide derivative of the fatty acid. (See, for example, Thompson, et al., WO 92/16221, the entire teachings of which are incorporated herein by reference.)

The modified protein scaffolds of the disclosure can be produced by reacting a protein scaffold or fragment with a modifying agent. For example, the organic moieties can be bonded to the protein scaffold in a non-site specific manner by employing an amine-reactive modifying agent, for example, an NHS ester of PEG. Modified protein scaffolds and fragments comprising an organic moiety that is bonded to specific sites of a protein scaffold of the disclosure can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Definitions

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more standard deviations. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various aspects, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term "antibody" is used in the broadest sense and specifically covers single monoclonal antibodies (including agonist and antagonist antibodies) and antibody compositions with polyepitopic specificity. It is also within the scope hereof to use natural or synthetic analogs, mutants, variants, alleles, homologs and orthologs (herein collectively referred to as "analogs") of the antibodies hereof as defined herein. Thus, according to an aspect hereof, the term "antibody hereof" in its broadest sense also covers such analogs. Generally, in such analogs, one or more amino acid residues may have been replaced, deleted and/or added, compared to the antibodies hereof as defined herein.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g., CHI in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). The term further includes single domain antibodies ("sdAB") which generally refers to an antibody fragment having a single monomeric variable antibody domain, (for example, from camelids). Such antibody fragment types will be readily understood by a person having ordinary skill in the art.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Aspects defined by each of these transition terms are within the scope of this disclosure.

The term "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristylation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A method for directing proteins to a specific locus in a genome of an organism is disclosed. The method may comprise the steps of providing a DNA localization component and providing an effector molecule, wherein the DNA localization component and the effector molecule are capable of operatively linking via a non-covalent linkage.

The term "scFv" refers to a single-chain variable fragment. scFv is a fusion protein of the variable regions of the heavy (VH) and light chains (VL) of immunoglobulins, connected with a linker peptide. The linker peptide may be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. The term further includes a scFv that is an intrabody, an antibody that is stable in the cytoplasm of the cell, and which may bind to an intracellular protein.

The term "single domain antibody" means an antibody fragment having a single monomeric variable antibody domain which is able to bind selectively to a specific antigen. A single-domain antibody generally is a peptide chain of about 110 amino acids long, comprising one variable domain (VH) of a heavy-chain antibody, or of a common IgG, which generally have similar affinity to antigens as whole antibodies, but are more heat-resistant and stable towards detergents and high concentrations of urea. Examples are those derived from camelid or fish antibodies. Alternatively, single-domain antibodies can be made from common murine or human IgG with four chains.

The terms "specifically bind" and "specific binding" as used herein refer to the ability of an antibody, an antibody fragment or a nanobody to preferentially bind to a particular antigen that is present in a homogeneous mixture of different antigens. In some aspects, a specific binding interaction will discriminate between desirable and undesirable antigens in a sample. In some aspects, more than about ten- to 100-fold or more (e.g., more than about 1000- or 10,000-fold). "Specificity" refers to the ability of an immunoglobulin or an immunoglobulin fragment, such as a nanobody, to bind preferentially to one antigenic target versus a different antigenic target and does not necessarily imply high affinity.

A "target site" or "target sequence" is a nucleic acid sequence that defines a portion of a nucleic acid to which a binding molecule will bind, provided sufficient conditions for binding exist.

The terms "nucleic acid" or "oligonucleotide" or "poly-nucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Probes of the disclosure may comprise a single stranded nucleic acid that can hybridize to a target sequence under stringent hybridization conditions. Thus, nucleic acids of the disclosure may refer to a probe that hybridizes under stringent hybridization conditions.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, EF-1 Alpha promoter, CAG promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. A vector may comprise a combination of an amino acid with a DNA sequence, an RNA sequence, or both a DNA and an RNA sequence.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In an aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some aspects, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

| Conservative Substitutions I | | |
|---|---|---|
| Side chain characteristics | | Amino Acid |
| Aliphatic | Non-polar | G A P I L V F |
| | Polar - uncharged | C S T M N Q |
| | Polar - charged | D E K R |
| Aromatic | | H F W Y |
| Other | | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

| Conservative Substitutions II | | |
|---|---|---|
| Side Chain Characteristic | | Amino Acid |
| Non-polar | Aliphatic: | A L I V P |
| (hydrophobic) | Aromatic: | F W Y |
| | Sulfur-containing: | M |
| | Borderline: | G Y |

TABLE B -continued

| Conservative Substitutions II | | |
|---|---|---|
| Side Chain Characteristic | | Amino Acid |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

| Conservative Substitutions III | |
|---|---|
| Original Residue | Exemplary Substitution |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring.

Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the cell the polynucleotide construct in such a manner that the construct gains access to the interior of the host cell. The methods of the disclosure do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

EXAMPLES

Example 1: Generation of Humanized MUC1-C scFv Antibodies and Chimeric Antigen Receptors (CARs)

Figures 1A, 1B:
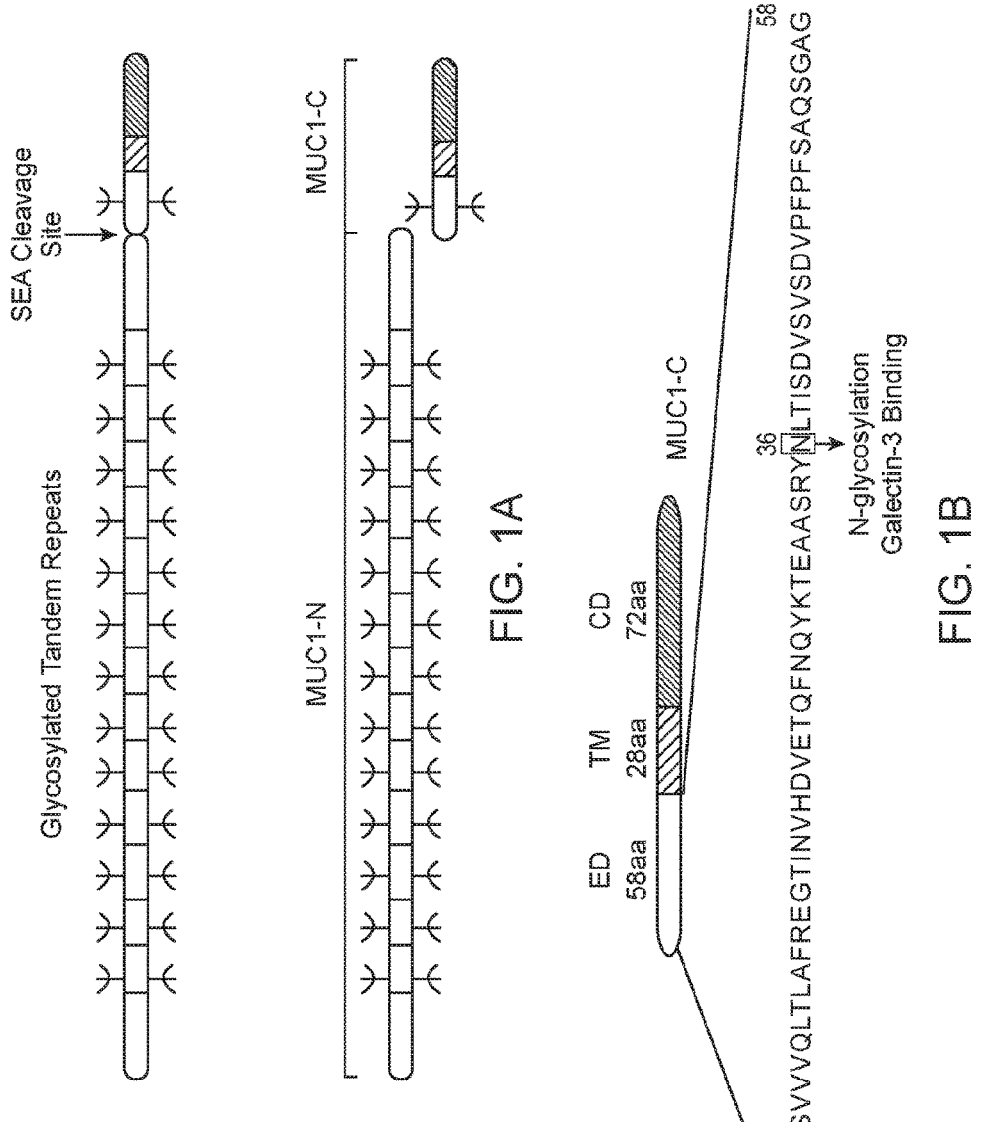
FIG. 1A-1B is a pair of schematic diagrams depicting the structure of a MUC1 heterodimer.

Chimeric antigen receptors (CARs) were generated having an antigen recognition region comprising a single chain antibody that specifically binds to an epitope of MUC1-C (FIGS. 1A and 1B).

Figures 2A, 2B:
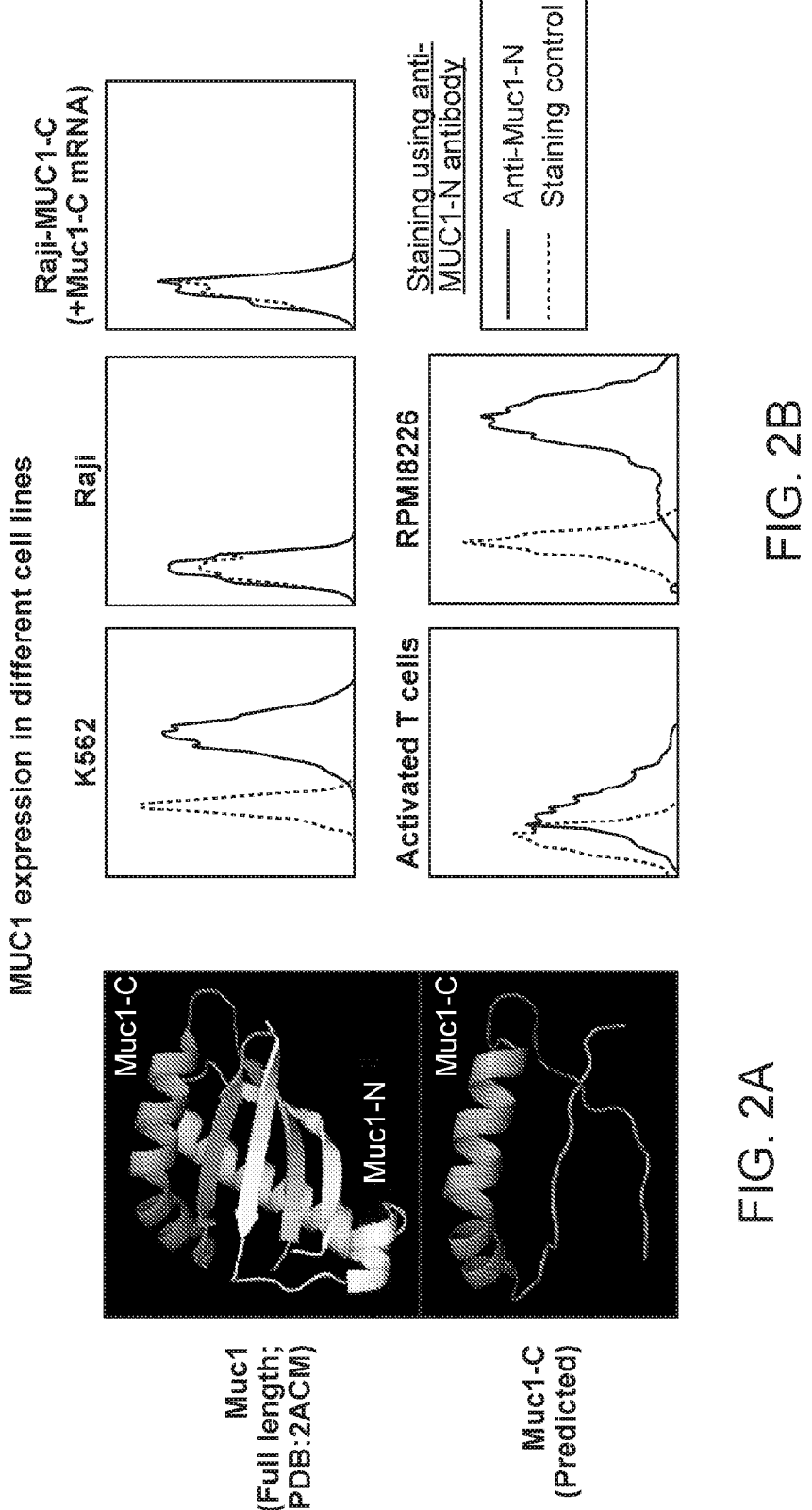
FIG. 2A is a pair of schematic diagrams depicting the ribbon structure of either full-length MUC1 (PDB:2ACM) or the predicted structure of a MUC1-C domain.
FIG. 2B is a series of graphs depicting MUC1 expression in different cell types.
Figure 3:
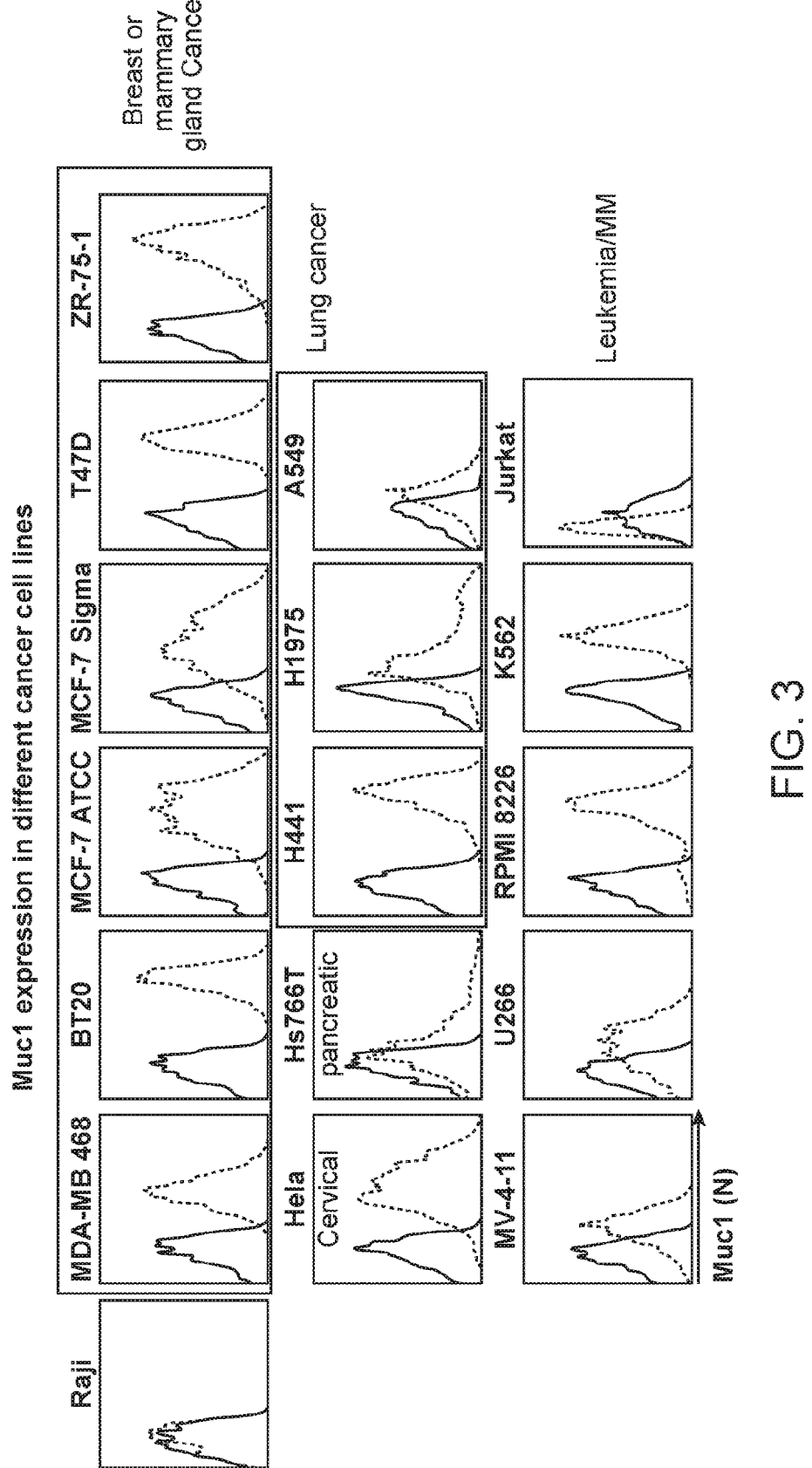
FIG. 3 is a series of flow cytometry graphs depicting Muc expression in different cancer cell lines.

As an initial study, MUC1 expression was assessed in different cell types (FIGS. 2A and 2B) including, K562 cells (immortalized human chronic myelogenous leukemia cells), Raji cells (human hematopoietic cell line used as a model of cancer), Raji cells modified to express MUC1-C, activated T cells and RPMI8226 cells (human peripheral blood B cell plasmacytoma/myeloma cell line). MUC1 expression in each of these cells was assessed by staining with an anti-MUC1-N antibody. For K562 cells, the staining control peak appears to the left of the anti-MUC1-N Ab peak. For Raji cells, the staining control peak overlaps with the anti-MUC1-N Ab peak, however, the anti-MUC1-N Ab peak is higher. For Raji cells modified to express MUC1-C, the staining control peak overlaps with the anti-MUC1-N Ab peak, however, the anti-MUC1-N Ab peak is higher. For activated T cells, the staining control peak appears to the left of the anti-MUC1-N Ab peak. For RPMI8226 cells, the staining control peak appears to the left of the anti-MUC1-N Ab peak. MUC-1C is also expressed on a panel of different cancer cell lines including breast or mammary gland cancer (MDA-MB 468, cervical cancer, pancreatic cancer, lung cancer, leukemia and multiple myeloma (FIG. 3).

Figures 5A, 5B:
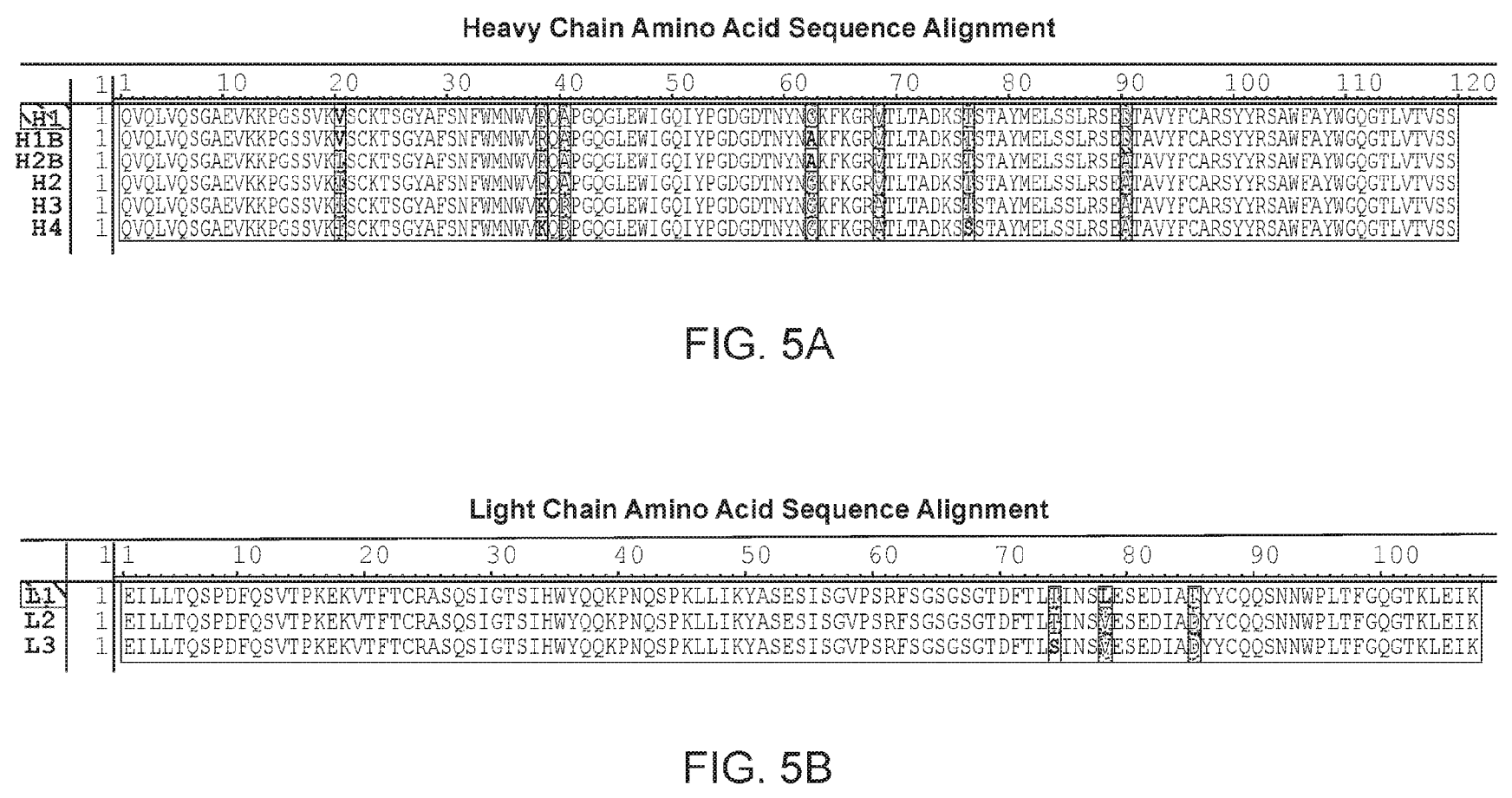

To generate humanized MUC1-C scFv CARs, in silico complementarity-determining region (CDR) grafting humanization of the variable regions of a mouse monoclonal antibody recognizing MUC1-C was performed. Computational modeling for the variable regions (both variable heavy (VH) and variable light (VL)) was performed and the most appropriate human VH/VL framework acceptor was identified without changing CDR regions; the most appropriate human VH and VL framework acceptor is IGHV1-69 08 and IGKV6-21 02, respectively. During the humanization process, mouse CDRs were grafted into the human framework acceptors. Residues in a human framework that are different from those in the mouse framework were studies. Back-mutations from human residues to mouse residues in the acceptor framework were designed if a new contact was created, if an old contact was lost, if a canonical mouse residue was made, or if instability was predicted within the antigen binding area. All resultant heavy chain (4+2 variants (H1B and H2B)) and light chain (3) sequences are displayed along with their alignments (FIGS. 5A and 5B).

Exemplary mouse CDR regions used to generate humanized MUC1-C scFv CARs comprise the following amino acid sequences:
CDRH1—NFWMN (SEQ ID NO: 69); CDRH2—QIYPGDGDTNYNGKFKG (SEQ ID NO: 70); CDRH3—SYYRSAWFAY (SEQ ID NO: 71); CDRL1—RASQSIGTSIH (SEQ ID NO: 72); CDRL2—YASESIS (SEQ ID NO: 73); CDRL3—QQSNNWPLT (SEQ ID NO: 74). In some cases, the CDRH2 regions were mutated to generate humanized MUC1-C scFv CARs. This includes a CDRH2 comprising the amino acid sequence of QIYPGDGDTNYNAKFKG (SEQ ID NO: 75).

Figure 4:
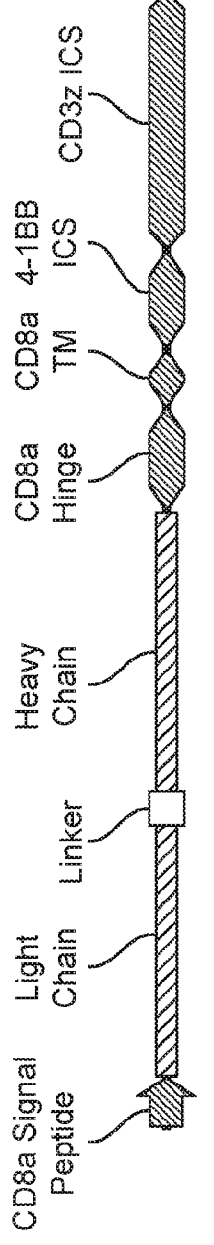
FIG. 4 is a schematic diagram depicting an exemplary construction of a humanized MUC1-C chimeric antigen receptor (CAR). Heavy chain (4+2 variants (H1B and H2B)) and light chain (3) sequences were assembled in different Light-Heavy chain combinations to construct 14 new candidate humanized MUC1-C CARs. The following humanized MUC1-C CAR structure was used: Signal peptide (CD8α)-Light Chain-Linker-Heavy Chain-Hinge (CD8α)-Transmembrane (CD8α)-Intracellular Signaling (4-1BB)-Intracellular Signaling (CD3ζ).

A diagram of an exemplary humanized MUC1-C-scFv CAR is depicted in FIG. 4. The following humanized MUC1-C CAR structure was used: Signal peptide (CD8α)-Light Chain-Linker-Heavy Chain-Hinge (CD8α)-Transmembrane (CD8α)-Intracellular Signaling (4-1BB)-Intracellular Signaling (CD3ζ).

Example 2—Functional Analysis of Humanized MUC1-C scFv CAR-T Cells

Figure 6:
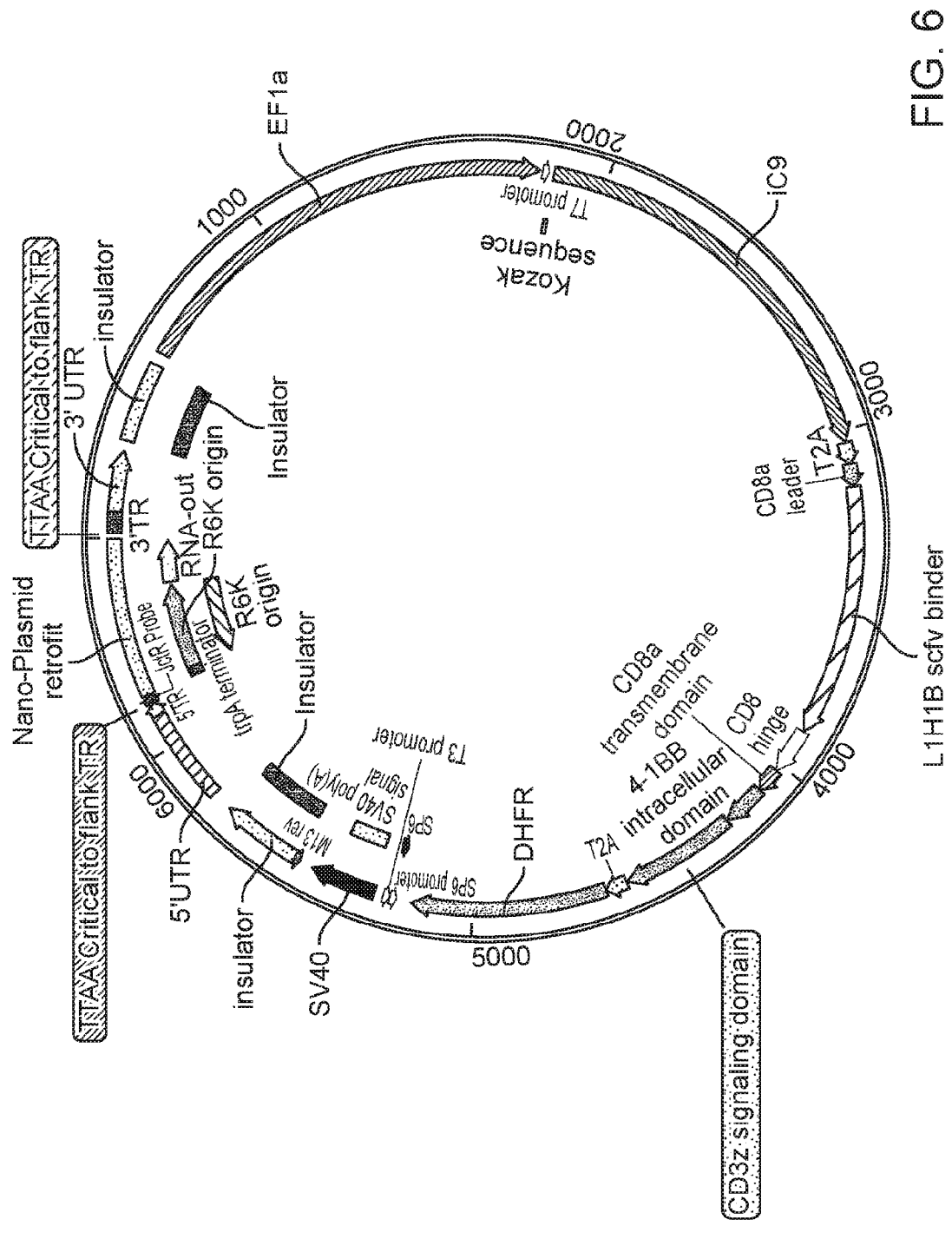
FIG. 6 is a schematic diagram of a piggyBac nanotransposon of the disclosure comprising a MUC-1C CAR. A MUC1-C CAR were subcloned into a tricistronic piggyBac transposon. The transposon contains an EFlalpha promoter-iC9 Safety Switch-T2A-MUC1-C CAR (L1-linker-H1B scFv)-T2A-DHFR selection gene construct.
Figure 7:
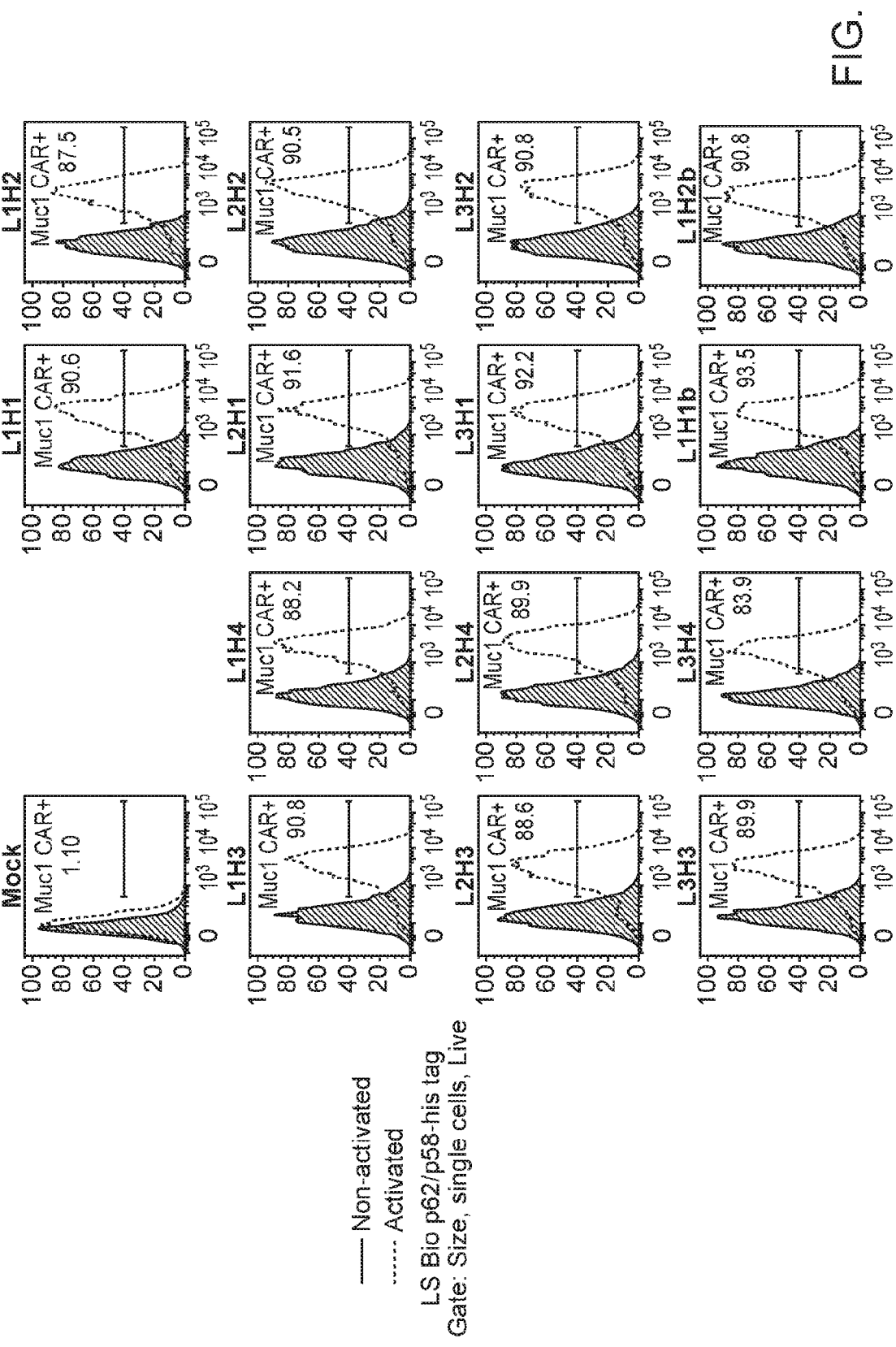
FIG. 7 is a series of flow cytometry graphs showing that candidate MUC1-C CARs are expressed on the surface of T cells. All candidate MUC1-C CARs were expressed and detected on the surface of piggyBac-produced CAR-T cells.

MUC1-C candidate CARs were subcloned into a tricistronic piggyBac transposon (EF1alpha promoter-iC9 Safety Switch-T2A-MUC1-C CAR-T2A-DHFR selection gene) and CAR-T cells were produced using pan T cells from a normal human blood donor as described herein (FIG. 6). Expression of each candidate CAR on the surface of piggyBac-modified cells was confirmed by FACS staining 19 days post-transposon delivery using an His-tagged p62/p58 MUC1 protein, followed by anti-His secondary antibody (FIG. 6). Specifically, cells were examined by flow cytometry for surface-expression of CAR on either mock transposed (blue) or anti-CD3/CD28 bead re-activated (red) cells (activation for 48 hours) that received transposon encoding CAR and data are shown as overlaid histograms; numbers represent percentage of cells expressing CAR on cell surface. All candidate MUC1-C CARs were expressed and detected on the surface of piggyBac-produced CAR-T cells (FIG. 7). Table 2 shows the mean fluorescence intensity (MFI) for CAR expression on the surface of non-activated and activated T cells.

TABLE 2

Surface Expression of CAR candidate MUC1-C CAR-T cells.

| MUC1-C CAR-T Candidate | Non-activated cells MFI | Activated cells MFI |
|---|---|---|
| no CAR (MOCK) | 733 | 796 |
| L3H4 | 695 | 1,963 |
| L1H4 | 737 | 2,512 |
| L3H3 | 696 | 2,585 |
| L2H3 | 770 | 2,881 |
| L1H2b | 714 | 2,994 |
| L2H4 | 729 | 3,016 |
| L1H2 | 720 | 3,030 |
| L1H3 | 743 | 3,321 |
| L1H1 | 734 | 3,562 |
| L3H2 | 726 | 3,615 |
| L1H1b | 739 | 3,753 |
| L2H2 | 717 | 3,834 |
| L3H1 | 723 | 4,046 |
| L2H1 | 756 | 4,052 |

Candidate MUC1-C CAR-T cells were produced using pan T cells from a normal human blood donor as described herein. CAR+ T cells were FACS stained 19 days post-transposon delivery for expression of surface CD45RA, CD45RO, and CD62L to define $T_{SCM}$, $T_{CM}$, $T_{EM}$, and $T_{EFF}$ cells; $T_{SCM}$ (CD45RA+/CD45RO−/CD62L+), $T_{CM}$ (CD45RA−/CD45RO+/CD62L+), $T_{EM}$ (CD45RA−/CD45RO+/CD62L−), TEFF (CD45RA+/CD45RO−/CD62L−). The results are shown in Table 3. All piggyBac-produced candidate MUC1-C CAR-T cell populations were comprised predominantly of exceptionally high levels of favorable $T_{SCM}$ and $T_{CM}$ cells.

TABLE 3

Proportion of TEFF, TSCM, TCM and TEM in CD8+ candidate MUC-1C CAR-T cells on Day 19

| MUC1-C CAR-T Candidate | $T_{SCM}$ | $T_{CM}$ | $T_{EM}$ | $T_{EFF}$ |
|---|---|---|---|---|
| L1H1b | 67.9 | 27.1 | 0.9 | 1.6 |
| L3H4 | 69.8 | 25.2 | 0.9 | 1.7 |
| L3H3 | 69.9 | 25.1 | 0.8 | 1.8 |
| L3H1 | 71.1 | 24.5 | 0.7 | 1.5 |
| L1H1 | 73.4 | 21.4 | 1 | 2.1 |
| L1H3 | 73.7 | 19.5 | 1.6 | 3.2 |
| L3H2 | 73.9 | 21.2 | 1.3 | 1.6 |
| L1H2b | 73.9 | 21.7 | 0.8 | 1.2 |
| L2H2 | 75.5 | 19 | 1.1 | 2.7 |
| L2H1 | 76.4 | 19.1 | 1 | 1.6 |
| L1H2 | 76.5 | 17.6 | 1.3 | 2.9 |
| L1H4 | 76.6 | 19.8 | 0.7 | 1.1 |
| L2H3 | 77.2 | 16.4 | 1.2 | 2.9 |
| L2H4 | 77.4 | 17.2 | 0.9 | 2.6 |

All piggyBac-produced candidate MUC1-C CAR-T cell populations were comprised predominantly of high levels of $T_{SCM}$ and $T_{CM}$ cells.

Figure 8:
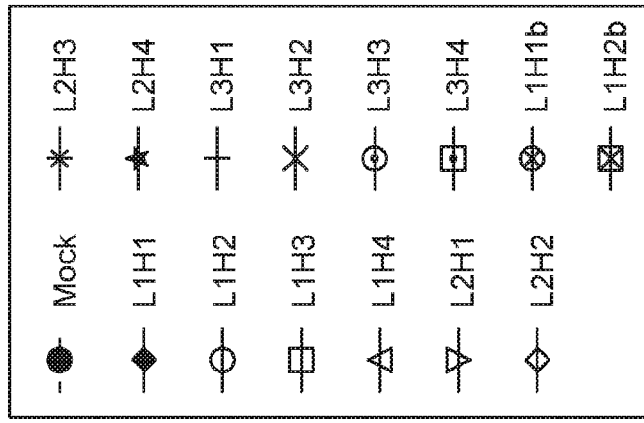
FIG. 8 is a graph showing specific killing of MUC1+ target cells by candidate MUC1-C CAR T-cells. Killing of MDA-MB-468 is shown for each CAR in the line graph. All CAR+ T cells expressed specific killing of MUC1+ MDA-MB-468 cells. Mock-transposed T cells did not specifically kill target cells (blue line).
Figure 8:
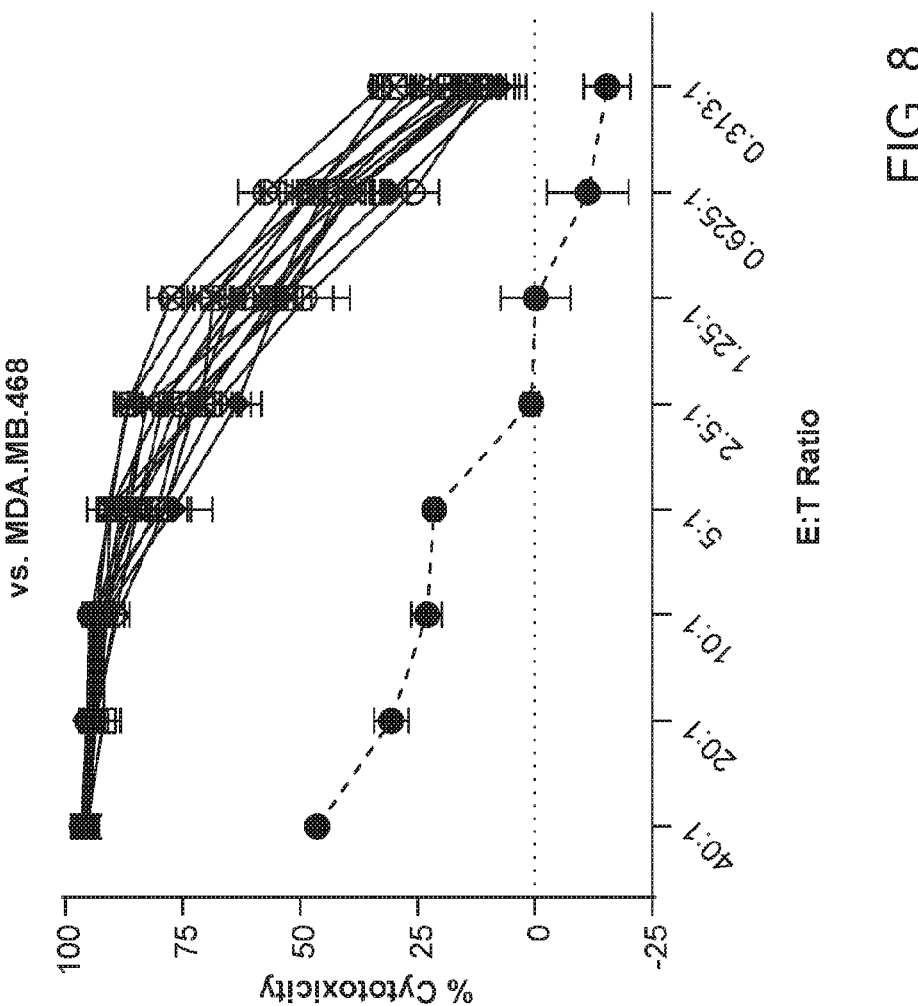

Candidate MUC1-C CAR-T cells were produced using pan T cells from a normal human blood donor as described herein. CAR-T cells were co-cultured with triple-negative breast cancer cell line MDA-MB-468.lucGFP (MDA-MB-468 expressing luciferase (luc) and green fluorescent protein (GFP)) for 24 hours at various E:T ratios (40:1, 20:1, 10:1, 5:1, 2.5:1, 1.25:1, 0.625:1, 0.313:1) (FIG. 8). Reporter signal was measured to determine cytotoxicity. Killing of MDA-MB-468 is shown for each CAR in the line graph. All CAR+ T cells expressed specific killing of MUC1+MDA-MB-468. Mock-transposed T cells did not specifically kill target cells (grey dotted line). Area under the curve with SEM (Standard Error of the Mean of samples run in triplicate) for killing of MDA-MB-468 at range of E:Ts is shown in Table 4 for each CAR. All CAR+ T cells expressed specific killing of MUC1+ MDA-MB-468.

TABLE 4

Area under the curve (AUC) of specific killing of MDA-MB-468 (MUC1+ target cells) by candidate MUC1-C CAR-T cells

| MUCIC CAR-T Candidate | Target cell killing area under the curve (AUC) |
|---|---|
| no CAR (MOCK) | 118 |
| L1H1 | 465 |
| L1H2 | 466 |
| L2H2 | 482 |
| L1H3 | 490 |
| L1H4 | 498 |
| 13H4 | 501 |
| 13H2 | 503 |
| L3H1 | 504 |
| L2H4 | 518 |
| L3H3 | 518 |
| L1H2b | 528 |
| L2H1 | 538 |
| L2H3 | 542 |
| L1H1b | 566 |

Figure 9:
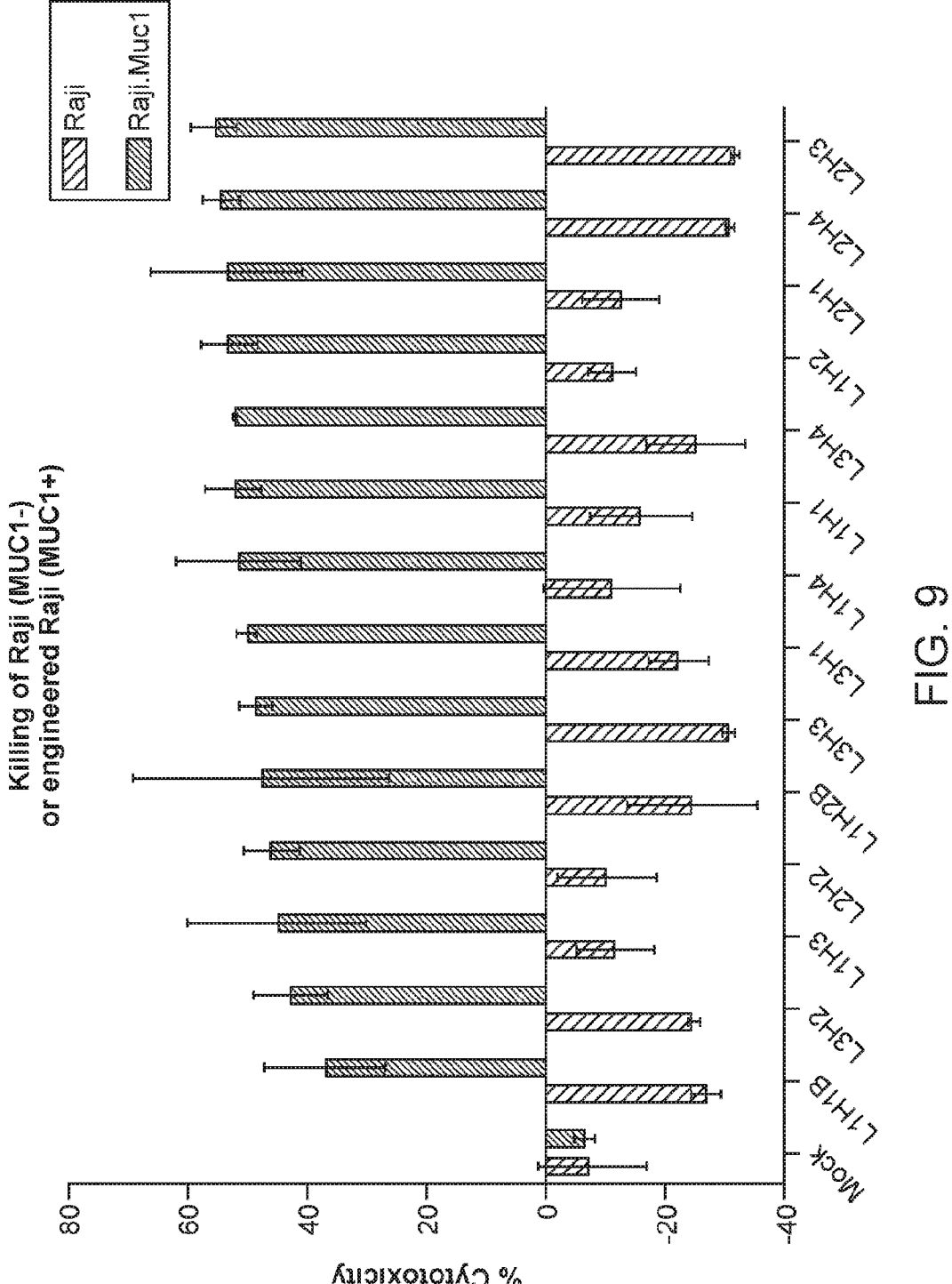
FIG. 9 is a graph showing specific killing of MUC1+ target cells by candidate MUC1-C CAR T cells. Killing of each cell line is shown for each CAR in the bar graph and error bars represent standard deviation of samples run in triplicate. All CAR+ T cells expressed specific killing of MUC1+ engineered Raji cell line, but not against MUC1-

Candidate MUC1-C CAR-T cells were produced using pan T cells from a normal human blood donor as described herein. CAR-T cells were co-cultured with Raji cell line (MUC1−; blue bars) or a Raji cell line engineered to express human MUC1 isoform 10 GenBank NP_001191215.1 (MUC1+; red bars), both expressing green fluorescent protein (GFP), for 24 hours at an E:T ratio of 10:1 (FIG. 9).

Reporter signal was measured to determine cytotoxicity. Killing of each cell line is shown for each CAR in the bar graph and error bars represent standard deviation of samples run in triplicate. All CAR+ T cells expressed specific killing of MUC1+ engineered Raji cell line, but not against MUC1– Raji cells. Mock-transposed T cells did not kill either Raji nor engineered Raji target cell lines.

Example 3—Preclinical Evaluation of Candidate Humanized MUC1-C CAR-T Cells at Stress Doses Using a Murine Xenograft Model A schematic diagram of a study design for preclinical evaluation of candidate humanized MUC1-C CAR-T cells at 'stress' doses using the Murine Xenograft Model is shown in FIG. 10. The murine xenograft model using a luciferase-expressing MDA-MB-468.lucGFP (MDA-MB-468) cell line at a dose of $5\times10^6$ cells injected subcutaneously (SC) into female NSG mice was utilized to assess in vivo anti-tumor efficacy of candidate MUC1-C CAR-T cells at a 'stress' dose ($4\times10^6$). A panel of total candidate CAR-T cells were chosen for this study. All CAR-T cells were produced using piggyBac (PB) delivery of candidate P-MUC1-C-101 transposons as described herein. Mice were injected in the axilla with MDA-MB-468 and treated when tumors were established (100-200 mm³ by caliper measurement). Table 5 shows preclinical evaluation of candidate humanized MUC1-C CAR-T cells at 'stress' doses using the murine xenograft model. Tumor volume assessment by caliper measurement for all treated animals were normalized to measurements from untreated group. Table 5 shows the tumor volumes by caliper in vehicle and treated groups.

TABLE 5

Tumor volumes measured by area under the curve (AUC) following treatment with candidate MUC1-C CAR-T cells

| MUC1C CAR-T Candidate | Area under the curve of tumor size (AUC) |
| --- | --- |
| no CAR-T (PBS) | 3,500 |
| L3H4 | 1,429 |
| L2H2 | 1,104 |
| L3H1 | 1,060 |
| L3H3 | 1,017 |
| L1H3 | 968 |
| L1H2b | 905 |
| L1H2 | 888 |
| L3H2 | 887 |
| L2H4 | 872 |
| L1H1B | 865 |
| L1H4 | 857 |

TABLE 5-continued

Tumor volumes measured by area under the curve (AUC) following treatment with candidate MUC1-C CAR-T cells

| MUC1C CAR-T Candidate | Area under the curve of tumor size (AUC) |
| --- | --- |
| L2H3 | 833 |
| L1H1 | 820 |
| L2H1 | 789 |

Mice were treated with a 'stress' doses ($4\times10^6$) of candidate P-MUC1-C-101 CAR-Ts by IV injection for greater resolution in detecting possible functional differences in efficacy among the different CAR candidates. Total T cells in blood of vehicle and treated mice were measured by TruCount staining. The Area Under the Curve (AUC) of T cells in blood of vehicle and treated mice were determined from blood draws and the results are shown in Table 6.

TABLE 6

Area Under the Curve of T cells (hCD45+) proliferation in blood following treatment with MUC1-C CART-T cell candidates.

| MUC1C CAR-T Candidate | T cell Area under the curve (AUC) |
| --- | --- |
| L3H3 | 1,337 |
| L1H4 | 1,393 |
| L2H4 | 1,596 |
| L2H3 | 1,680 |
| L3H2 | 2,731 |
| L1H2 | 3,861 |
| L1H1 | 5,415 |
| L1H2b | 6,133 |
| L3H1 | 6,216 |
| L2H1 | 6,270 |
| L2H2 | 7,870 |
| L1H3 | 7,979 |
| L3H4 | 9,397 |
| L1H1B | 10,170 |

The CD8+ T cell phenotypes of vehicle and treated mice were determined. Phenotype of CD8+ T cells in blood were measured by FACS staining for all animals and percentages are listed as group averages with error bars as SEM. Cells were stained for expression of surface CD45RA, CD45RO, and CD62L to define $T_{SCM}$, $T_{CM}$, $T_{EM}$, and $T_{EFF}$ cells; $T_{SCM}$ (CD45RA+/CD45RO–/CD62L+), $T_{CM}$ (CD45RA–/CD45RO+/CD62L+), $T_{EM}$ (CD45RA–/CD45RO+/CD62L–), TEFF (CD45RA+CD45RO–CD62L–). For all MUC-1C CAR-T cells tested, $T_{SCM}$ and $T_{CM}$ phenotype are more abundant than the $T_{EM}$ and TEFF phenotype on Day Pre-Infusion, Day 12 and Day 19.

What is claimed is:

1. A chimeric antigen receptor (CAR) comprising
(a) an ectodomain comprising an antigen recognition region, wherein the antigen recognition region comprises at least one anti-MUC1 single chain variable fragment (scFv) comprising a heavy chain variable region comprising the amino acid sequence of QVQLVQSGAEVKKPGSSVKVSCKTSG-YAFSNFWMNWVRQAPGOGLEWIGQIYPG DGDTNYNAKFKGRVTLTADKSTSTAYMELSSLRSED-TAVYFCARSYYRSAWFAYWGOGTLVTVSS (SEQ ID NO:4); and
a light chain variable region comprising the amino acid sequence of
EILLTOSPDFQSVTPKEKVTFT-CRASQSIGTSIHWYQQKPNQSPKLLIKYASESIS-GVPSRFSGSGSGTDFTLTINSLESEDI-ATYYCQQSNNWPLTFGOGTKLEIK (SEQ ID NO:9), wherein the scFv comprises a linker between the heavy chain variable region and the light chain variable region;
(b) a transmembrane domain, and
(c) an endodomain comprising at least one signal transduction domain.

2. The CAR of claim 1, wherein the linker comprises the amino acid sequence of SEQ ID NO: 59.

3. The CAR of claim 1, wherein the scFv comprises the amino acid sequence of SEQ ID NO: 125.

4. The CAR of claim 1, wherein the ectodomain further comprises a signal peptide.

5. The CAR of claim 4, wherein the signal peptide comprises the amino acid sequence of SEQ ID NO: 57.

6. The CAR of claim 1, wherein the CAR further comprises a hinge region between the antigen recognition region and the transmembrane domain.

7. The CAR of claim 6, wherein the hinge region comprises the amino acid sequence of SEQ ID NO: 61.

8. The CAR of claim 1, wherein the transmembrane domain comprises a sequence encoding a CD8 transmembrane domain.

9. The CAR of claim 8, wherein the CD8 transmembrane domain comprises the amino acid sequence of SEQ ID NO: 63.

10. The CAR of claim 1, wherein the at least one signal transduction domain comprises a CD3ζ intracellular signaling domain, a 4-1BB intracellular signaling domain, or a combination thereof.

11. The CAR of claim 1, wherein the at least one signal transduction domain comprises a CD3ζ intracellular signaling domain and a 4-1BB intracellular signaling domain, and wherein the 4-1BB intracellular signaling domain is located between the transmembrane domain and the CD3ζ costimulatory-intracellular signaling domain.

12. The CAR of claim 11, wherein the 4-1BB intracellular signaling domain comprises the amino acid sequence of SEQ ID NO: 65.

13. The CAR of claim 11, wherein the CD3ζ intracellular signaling domain comprises the amino acid sequence of SEQ ID NO: 67.

14. The CAR of claim 1, wherein
the ectodomain comprises a signal peptide,
the CAR further comprises a hinge region between the antigen recognition region and the transmembrane domain,
the transmembrane domain comprises a sequence comprising a CD8 transmembrane domain; and
the at least one signal transduction domain comprises a CD3ζ intracellular signaling domain and a 4-1BB intracellular signaling domain, and wherein the 4-1BB intracellular signaling domain is located between the transmembrane domain and the CD3ζ intracellular signaling domain.

15. The CAR of claim 14, wherein
the scFv comprises an amino acid sequence of SEQ ID NO: 125;
wherein the signal peptide comprises SEQ ID NO: 57;
wherein the hinge region comprises SEQ ID NO: 61;
wherein the CD8 transmembrane domain comprises SEQ ID NO: 63;
wherein the 4-1BB intracellular signaling domain comprises SEQ ID NO: 65; and
wherein the CD3ζ intracellular signaling domain comprises SEQ ID NO: 67.

16. The CAR of claim 14, wherein the CAR comprises the amino acid sequence of SEQ ID NO: 13.

17. The CAR of claim 14, wherein the amino acid sequence of the CAR is encoded by a polynucleotide comprising the nucleic acid sequence of SEQ ID NO: 31 or SEQ ID NO: 167.

18. The CAR of claim 17, wherein the amino acid sequence of the CAR is encoded by a polynucleotide comprising the nucleic acid sequence of SEQ ID NO: 167.

19. A polynucleotide comprising a nucleic acid sequence encoding the CAR of claim 1.

20. A vector comprising the polynucleotide of claim 19.

21. A cell comprising the CAR of claim 1.

22. A population of cells, wherein a plurality of the population of cells are modified to express the CAR of claim 1.

23. The population of cells of claim 22, wherein the plurality of modified cells is a plurality of modified immune cells.

24. The population of cells of claim 22, wherein the plurality of modified cells is a plurality of modified T-cells.

25. The population of cells of claim 22, wherein the plurality of the population of cells comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% of cells that express the CAR of claim 1.

26. A composition comprising the cell of claim 21.

27. A composition comprising the population of cells of claim 23.

28. A pharmaceutical composition comprising the composition of claim 26 and a pharmaceutically acceptable carrier.

29. A method of treating a MUC1 positive cancer in a subject in need thereof comprising administering a therapeutically effective amount of the composition of claim 27.

30. The method of claim 29, wherein the cancer is a MUC1-C positive cancer.

31. The method of claim 29, wherein the cancer is a lung cancer, a brain cancer, a head and neck cancer, a breast cancer, a skin cancer, a liver cancer, a pancreatic cancer, a stomach cancer, a colon cancer, a rectal cancer, a uterine cancer, a cervical cancer, an ovarian cancer, a prostate cancer, a testicular cancer, a skin cancer or an esophageal cancer.

32. The cell of claim 21 further comprising a a gene encoding a dihydrofolate reductase (DHFR) protein.

33. The cell of claim 32, wherein the gene encoding the DHFR protein comprises the sequence of SEQ ID NO: 93 or 174.

34. The cell of claim 32, wherein the DHFR protein comprises the sequence of SEQ ID NO: 92.

* * * * *

SEQUENCE LISTING

<160> NUMBER OF SEQ ID NOS: 181

<210> SEQ ID NO 1
<211> LENGTH: 119
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (20)..(20)
<223> OTHER INFORMATION: X is a Val or a Ile
<220> FEATURE:
<221> NAME/KEY: MISC_FEATURE -continued

```
<222> LOCATION: (38)..(38)
<223> OTHER INFORMATION: X is a Arg or a Lys
<220> FEATURE:
<221> NAME/KEY: MISC_FEATURE
<222> LOCATION: (40)..(40)
<223> OTHER INFORMATION: X is a Ala or a Arg
<220> FEATURE:
<221> NAME/KEY: MISC_FEATURE
<222> LOCATION: (62)..(62)
<223> OTHER INFORMATION: X is a Gly or a Ala
<220> FEATURE:
<221> NAME/KEY: MISC_FEATURE
<222> LOCATION: (68)..(68)
<223> OTHER INFORMATION: X is a Val or a Ala
<220> FEATURE:
<221> NAME/KEY: MISC_FEATURE
<222> LOCATION: (76)..(76)
<223> OTHER INFORMATION: X is a Thr or a Ser
<220> FEATURE:
<221> NAME/KEY: MISC_FEATURE
<222> LOCATION: (90)..(90)
<223> OTHER INFORMATION: X is a Asp or a Ala

<400> SEQUENCE: 1

Gln Val Gln Leu Val Gln Ser Gly Ala Glu Val Lys Lys Pro Gly Ser
1               5                   10                  15

Ser Val Lys Xaa Ser Cys Lys Thr Ser Gly Tyr Ala Phe Ser Asn Phe
            20                  25                  30

Trp Met Asn Trp Val Xaa Gln Xaa Pro Gly Gln Gly Leu Glu Trp Ile
        35                  40                  45

Gly Gln Ile Tyr Pro Gly Asp Gly Asp Thr Asn Tyr Asn Xaa Lys Phe
    50                  55                  60

Lys Gly Arg Xaa Thr Leu Thr Ala Asp Lys Ser Xaa Ser Thr Ala Tyr
65                  70                  75                  80

Met Glu Leu Ser Ser Leu Arg Ser Glu Xaa Thr Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (74)..(74)
<223> OTHER INFORMATION: X is a Thr or a Ser
<220> FEATURE:
<221> NAME/KEY: MISC_FEATURE
<222> LOCATION: (78)..(78)
<223> OTHER INFORMATION: X is a Leu or a Val
<220> FEATURE:
<221> NAME/KEY: MISC_FEATURE
<222> LOCATION: (85)..(85)
<223> OTHER INFORMATION: X is a Thr or a Asp

<400> SEQUENCE: 2

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45
```

-continued

```
Lys Tyr Ala Ser Glu Ser Ile Ser Gly Val Pro Ser Arg Phe Ser Gly
    50                  55                  60

Ser Gly Ser Gly Thr Asp Phe Thr Leu Xaa Ile Asn Ser Xaa Glu Ser
65                  70                  75                  80

Glu Asp Ile Ala Xaa Tyr Tyr Cys Gln Gln Ser Asn Asn Trp Pro Leu
                85                  90                  95

Thr Phe Gly Gln Gly Thr Lys Leu Glu Ile Lys
            100                 105
```

```
<210> SEQ ID NO 3
<211> LENGTH: 119
<212> TYPE: PRT
<213> ORGANISM: Artificial Sequence
<220> FEATURE:
<223> OTHER INFORMATION: Synthetic Polypeptide - "H1" humanized heavy
      chain variable region

<400> SEQUENCE: 3
```

```
Gln Val Gln Leu Val Gln Ser Gly Ala Glu Val Lys Lys Pro Gly Ser
1               5                   10                  15

Ser Val Lys Val Ser Cys Lys Thr Ser Gly Tyr Ala Phe Ser Asn Phe
                20                  25                  30

Trp Met Asn Trp Val Arg Gln Ala Pro Gly Gln Gly Leu Glu Trp Ile
            35                  40                  45

Gly Gln Ile Tyr Pro Gly Asp Gly Asp Thr Asn Tyr Asn Gly Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
            115
```

```
<210> SEQ ID NO 4
<211> LENGTH: 119
<212> TYPE: PRT
<213> ORGANISM: Artificial Sequence
<220> FEATURE:
<223> OTHER INFORMATION: Synthetic Polypeptide - "H1B" humanized heavy
      chain variable region

<400> SEQUENCE: 4
```

```
Gln Val Gln Leu Val Gln Ser Gly Ala Glu Val Lys Lys Pro Gly Ser
1               5                   10                  15

Ser Val Lys Val Ser Cys Lys Thr Ser Gly Tyr Ala Phe Ser Asn Phe
                20                  25                  30

Trp Met Asn Trp Val Arg Gln Ala Pro Gly Gln Gly Leu Glu Trp Ile
            35                  40                  45

Gly Gln Ile Tyr Pro Gly Asp Gly Asp Thr Asn Tyr Asn Ala Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Tyr Tyr Arg Ser Ala Trp Phe Ala Tyr Trp Gly Gln Gly
            100                 105                 110
```

-continued

```
Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: Synthetic Polypeptide - "H2" humanized heavy
      chain variable region

<400> SEQUENCE: 5

Gln Val Gln Leu Val Gln Ser Gly Ala Glu Val Lys Lys Pro Gly Ser
1               5                   10                  15

Ser Val Lys Ile Ser Cys Lys Thr Ser Gly Tyr Ala Phe Ser Asn Phe
            20                  25                  30

Trp Met Asn Trp Val Arg Gln Ala Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Ala Thr Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: Synthetic Polypeptide - "H2B" humanized heavy
      chain variable region

<400> SEQUENCE: 6

Gln Val Gln Leu Val Gln Ser Gly Ala Glu Val Lys Lys Pro Gly Ser
1               5                   10                  15

Ser Val Lys Ile Ser Cys Lys Thr Ser Gly Tyr Ala Phe Ser Asn Phe
            20                  25                  30

Trp Met Asn Trp Val Arg Gln Ala Pro Gly Gln Gly Leu Glu Trp Ile
        35                  40                  45

Gly Gln Ile Tyr Pro Gly Asp Gly Asp Thr Asn Tyr Asn Ala Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Ala Thr Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 7
<211> LENGTH: 119
<212> TYPE: PRT
<213> ORGANISM: Artificial Sequence
```

<220> FEATURE:
<223> OTHER INFORMATION: Synthetic Polypeptide - "H3" humanized heavy
      chain variable region

<400> SEQUENCE: 7

Gln Val Gln Leu Val Gln Ser Gly Ala Glu Val Lys Lys Pro Gly Ser
1               5                   10                  15

Ser Val Lys Ile Ser Cys Lys Thr Ser Gly Tyr Ala Phe Ser Asn Phe
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Ala Thr Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Synthetic Polypeptide - "H4" humanized heavy
      chain variable region

<400> SEQUENCE: 8

Gln Val Gln Leu Val Gln Ser Gly Ala Glu Val Lys Lys Pro Gly Ser
1               5                   10                  15

Ser Val Lys Ile Ser Cys Lys Thr Ser Gly Tyr Ala Phe Ser Asn Phe
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Arg Ala Thr Leu Thr Ala Asp Lys Ser Ser Ser Thr Ala Tyr
65                  70                  75                  80

Met Glu Leu Ser Ser Leu Arg Ser Glu Ala Thr Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Synthetic Polypeptide - "L1" humanized light
      chain variable region

<400> SEQUENCE: 9

Glu Ile Leu Leu Thr Gln Ser Pro Asp Phe Gln Ser Val Thr Pro Lys
1               5                   10                  15

```
Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ser
65                  70                  75                  80

Glu Asp Ile Ala Thr Tyr Tyr Cys Gln Gln Ser Asn Asn Trp Pro Leu
                85                  90                  95

Thr Phe Gly Gln Gly Thr Lys Leu Glu Ile Lys
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: Synthetic Polypeptide - "L2" humanized light
      chain variable region

<400> SEQUENCE: 10

```
Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys
            100                 105
```

<210> SEQ ID NO 11
<211> LENGTH: 107
<212> TYPE: PRT
<213> ORGANISM: Artificial Sequence
<220> FEATURE:
<223> OTHER INFORMATION: Synthetic Polypeptide - "L3" humanized light
      chain variable region

<400> SEQUENCE: 11

```
Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95
```

```
Thr Phe Gly Gln Gly Thr Lys Leu Glu Ile Lys
            100                 105

<210> SEQ ID NO 12
<211> LENGTH: 485
<212> TYPE: PRT
<213> ORGANISM: Artificial Sequence
<220> FEATURE:
<223> OTHER INFORMATION: Synthetic Polypeptide - "L1H1" CAR

<400> SEQUENCE: 12

Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
            20                  25                  30

Ser Val Thr Pro Lys Glu Lys Val Thr Phe Thr Cys Arg Ala Ser Gln
        35                  40                  45

Ser Ile Gly Thr Ser Ile His Trp Tyr Gln Gln Lys Pro Asn Gln Ser
    50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95

Asn Ser Leu Glu Ser Glu Asp Ile Ala Thr Tyr Tyr Cys Gln Gln Ser
            100                 105                 110

Asn Asn Trp Pro Leu Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ser Ser
145                 150                 155                 160

Val Lys Val Ser Cys Lys Thr Ser Gly Tyr Ala Phe Ser Asn Phe Trp
                165                 170                 175

Met Asn Trp Val Arg Gln Ala Pro Gly Gln Gly Leu Glu Trp Ile Gly
            180                 185                 190

Gln Ile Tyr Pro Gly Asp Gly Asp Thr Asn Tyr Asn Gly Lys Phe Lys
        195                 200                 205

Gly Arg Val Thr Leu Thr Ala Asp Lys Ser Thr Ser Thr Ala Tyr Met
    210                 215                 220

Glu Leu Ser Ser Leu Arg Ser Glu Asp Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350
```

-continued

```
Thr Gln Glu Glu Asp Gly Cys Ser Cys Arg Phe Pro Glu Glu Glu
        355             360             365

Gly Gly Cys Glu Leu Arg Val Lys Phe Ser Arg Ser Ala Asp Ala Pro
        370             375             380

Ala Tyr Lys Gln Gly Gln Asn Gln Leu Tyr Asn Glu Leu Asn Leu Gly
385             390             395             400

Arg Arg Glu Glu Tyr Asp Val Leu Asp Lys Arg Arg Gly Arg Asp Pro
                405             410             415

Glu Met Gly Gly Lys Pro Arg Arg Lys Asn Pro Gln Glu Gly Leu Tyr
                420             425             430

Asn Glu Leu Gln Lys Asp Lys Met Ala Glu Ala Tyr Ser Glu Ile Gly
        435             440             445

Met Lys Gly Glu Arg Arg Arg Gly Lys Gly His Asp Gly Leu Tyr Gln
        450             455             460

Gly Leu Ser Thr Ala Thr Lys Asp Thr Tyr Asp Ala Leu His Met Gln
465             470             475             480

Ala Leu Pro Pro Arg
                485
```

```
<210> SEQ ID NO 13
<211> LENGTH: 485
<212> TYPE: PRT
<213> ORGANISM: Artificial Sequence
<220> FEATURE:
<223> OTHER INFORMATION: Synthetic Polypeptide - "L1H1B" CAR

<400> SEQUENCE: 13

Met Ala Leu Pro Val Thr Ala Leu Leu Leu Pro Leu Ala Leu Leu Leu
1               5               10              15

His Ala Ala Arg Pro Glu Ile Leu Leu Thr Gln Ser Pro Asp Phe Gln
        20              25              30

Ser Val Thr Pro Lys Glu Lys Val Thr Phe Thr Cys Arg Ala Ser Gln
        35              40              45

Ser Ile Gly Thr Ser Ile His Trp Tyr Gln Gln Lys Pro Asn Gln Ser
    50              55              60

Pro Lys Leu Leu Ile Lys Tyr Ala Ser Glu Ser Ile Ser Gly Val Pro
65              70              75              80

Ser Arg Phe Ser Gly Ser Gly Ser Gly Thr Asp Phe Thr Leu Thr Ile
                85              90              95

Asn Ser Leu Glu Ser Glu Asp Ile Ala Thr Tyr Tyr Cys Gln Gln Ser
            100             105             110

Asn Asn Trp Pro Leu Thr Phe Gly Gln Gly Thr Lys Leu Glu Ile Lys
        115             120             125

Gly Gly Gly Gly Ser Gly Gly Gly Gly Ser Gly Gly Gly Gly Ser Gln
        130             135             140

Val Gln Leu Val Gln Ser Gly Ala Glu Val Lys Lys Pro Gly Ser Ser
145             150             155             160

Val Lys Val Ser Cys Lys Thr Ser Gly Tyr Ala Phe Ser Asn Phe Trp
                165             170             175

Met Asn Trp Val Arg Gln Ala Pro Gly Gln Gly Leu Glu Trp Ile Gly
            180             185             190

Gln Ile Tyr Pro Gly Asp Gly Asp Thr Asn Tyr Asn Ala Lys Phe Lys
        195             200             205

Gly Arg Val Thr Leu Thr Ala Asp Lys Ser Thr Ser Thr Ala Tyr Met
        210             215             220
```

```
Glu Leu Ser Ser Leu Arg Ser Glu Asp Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
                275                 280                 285

Cys Arg Pro Ala Ala Gly Gly Ala Val His Thr Arg Gly Leu Asp Phe
                290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
                355                 360                 365

Gly Gly Cys Glu Leu Arg Val Lys Phe Ser Arg Ser Ala Asp Ala Pro
                370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
                450                 455                 460

Gly Leu Ser Thr Ala Thr Lys Asp Thr Tyr Asp Ala Leu His Met Gln
465                 470                 475                 480

Ala Leu Pro Pro Arg
                485
```

```
<210> SEQ ID NO 14
<211> LENGTH: 485
<212> TYPE: PRT
<213> ORGANISM: Artificial Sequence
<220> FEATURE:
<223> OTHER INFORMATION: Synthetic Polypeptide - "L1H2" CAR

<400> SEQUENCE: 14

Met Ala Leu Pro Val Thr Ala Leu Leu Leu Pro Leu Ala Leu Leu Leu
1                   5                   10                  15

His Ala Ala Arg Pro Glu Ile Leu Leu Thr Gln Ser Pro Asp Phe Gln
                20                  25                  30

Ser Val Thr Pro Lys Glu Lys Val Thr Phe Thr Cys Arg Ala Ser Gln
                35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95
```

-continued

```
Asn Ser Leu Glu Ser Glu Asp Ile Ala Thr Tyr Tyr Cys Gln Gln Ser
         100                 105                 110

Asn Asn Trp Pro Leu Thr Phe Gly Gln Gly Thr Lys Leu Glu Ile Lys
         115                 120                 125

Gly Gly Gly Gly Ser Gly Gly Gly Gly Ser Gly Gly Gly Gly Ser Gln
         130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                 165                 170                 175

Met Asn Trp Val Arg Gln Ala Pro Gly Gln Gly Leu Glu Trp Ile Gly
         180                 185                 190

Gln Ile Tyr Pro Gly Asp Gly Asp Thr Asn Tyr Asn Gly Lys Phe Lys
         195                 200                 205

Gly Arg Val Thr Leu Thr Ala Asp Lys Ser Thr Ser Thr Ala Tyr Met
         210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                 245                 250                 255

Leu Val Thr Val Ser Ser Thr Thr Thr Pro Ala Pro Arg Pro Pro Thr
                 260                 265                 270

Pro Ala Pro Thr Ile Ala Ser Gln Pro Leu Ser Leu Arg Pro Glu Ala
         275                 280                 285

Cys Arg Pro Ala Ala Gly Gly Ala Val His Thr Arg Gly Leu Asp Phe
         290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                 325                 330                 335

Lys Leu Leu Tyr Ile Phe Lys Gln Pro Phe Met Arg Pro Val Gln Thr
         340                 345                 350

Thr Gln Glu Glu Asp Gly Cys Ser Cys Arg Phe Pro Glu Glu Glu Glu
         355                 360                 365

Gly Gly Cys Glu Leu Arg Val Lys Phe Ser Arg Ser Ala Asp Ala Pro
         370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                 405                 410                 415

Glu Met Gly Gly Lys Pro Arg Arg Lys Asn Pro Gln Glu Gly Leu Tyr
         420                 425                 430

Asn Glu Leu Gln Lys Asp Lys Met Ala Glu Ala Tyr Ser Glu Ile Gly
         435                 440                 445

Met Lys Gly Glu Arg Arg Arg Gly Lys Gly His Asp Gly Leu Tyr Gln
         450                 455                 460

Gly Leu Ser Thr Ala Thr Lys Asp Thr Tyr Asp Ala Leu His Met Gln
465                 470                 475                 480

Ala Leu Pro Pro Arg
                 485
```

```
<210> SEQ ID NO 15
<211> LENGTH: 485
<212> TYPE: PRT
```

<213> ORGANISM: Artificial Sequence
<220> FEATURE:
<223> OTHER INFORMATION: Synthetic Polypeptide - "L1H2B" CAR

<400> SEQUENCE: 15

```
Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
                20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95

Asn Ser Leu Glu Ser Glu Asp Ile Ala Thr Tyr Tyr Cys Gln Gln Ser
            100                 105                 110

Asn Asn Trp Pro Leu Thr Phe Gly Gln Gly Thr Lys Leu Glu Ile Lys
        115                 120                 125

Gly Gly Gly Gly Ser Gly Gly Gly Ser Gly Gly Gly Gly Ser Gln
    130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Arg Gln Ala Pro Gly Gln Gly Leu Glu Trp Ile Gly
            180                 185                 190

Gln Ile Tyr Pro Gly Asp Gly Asp Thr Asn Tyr Asn Ala Lys Phe Lys
        195                 200                 205

Gly Arg Val Thr Leu Thr Ala Asp Lys Ser Thr Ser Thr Ala Tyr Met
    210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
```

-continued

```
385                390                395                400
Arg Arg Glu Glu Tyr Asp Val Leu Asp Lys Arg Arg Gly Arg Asp Pro
                405                410                415

Glu Met Gly Gly Lys Pro Arg Arg Lys Asn Pro Gln Glu Gly Leu Tyr
            420                425                430

Asn Glu Leu Gln Lys Asp Lys Met Ala Glu Ala Tyr Ser Glu Ile Gly
        435                440                445

Met Lys Gly Glu Arg Arg Arg Gly Lys Gly His Asp Gly Leu Tyr Gln
    450                455                460

Gly Leu Ser Thr Ala Thr Lys Asp Thr Tyr Asp Ala Leu His Met Gln
465                470                475                480

Ala Leu Pro Pro Arg
                485
```

```
<210> SEQ ID NO 16
<211> LENGTH: 485
<212> TYPE: PRT
<213> ORGANISM: Artificial Sequence
<220> FEATURE:
<223> OTHER INFORMATION: Synthetic Polypeptide - "L1H3" CAR

<400> SEQUENCE: 16

Met Ala Leu Pro Val Thr Ala Leu Leu Leu Pro Leu Ala Leu Leu Leu
1                5                10                15

His Ala Ala Arg Pro Glu Ile Leu Leu Thr Gln Ser Pro Asp Phe Gln
                20                25                30

Ser Val Thr Pro Lys Glu Lys Val Thr Phe Thr Cys Arg Ala Ser Gln
            35                40                45

Ser Ile Gly Thr Ser Ile His Trp Tyr Gln Gln Lys Pro Asn Gln Ser
        50                55                60

Pro Lys Leu Leu Ile Lys Tyr Ala Ser Glu Ser Ile Ser Gly Val Pro
65                70                75                80

Ser Arg Phe Ser Gly Ser Gly Ser Gly Thr Asp Phe Thr Leu Thr Ile
                85                90                95

Asn Ser Leu Glu Ser Glu Asp Ile Ala Thr Tyr Tyr Cys Gln Gln Ser
            100                105                110

Asn Asn Trp Pro Leu Thr Phe Gly Gln Gly Thr Lys Leu Glu Ile Lys
            115                120                125

Gly Gly Gly Gly Ser Gly Gly Gly Gly Ser Gly Gly Gly Gly Ser Gln
        130                135                140

Val Gln Leu Val Gln Ser Gly Ala Glu Val Lys Lys Pro Gly Ser Ser
145                150                155                160

Val Lys Ile Ser Cys Lys Thr Ser Gly Tyr Ala Phe Ser Asn Phe Trp
                165                170                175

Met Asn Trp Val Lys Gln Arg Pro Gly Gln Gly Leu Glu Trp Ile Gly
            180                185                190

Gln Ile Tyr Pro Gly Asp Gly Asp Thr Asn Tyr Asn Gly Lys Phe Lys
            195                200                205

Gly Arg Ala Thr Leu Thr Ala Asp Lys Ser Thr Ser Thr Ala Tyr Met
        210                215                220

Glu Leu Ser Ser Leu Arg Ser Glu Ala Thr Ala Val Tyr Phe Cys Ala
225                230                235                240

Arg Ser Tyr Tyr Arg Ser Ala Trp Phe Ala Tyr Trp Gly Gln Gly Thr
                245                250                255

Leu Val Thr Val Ser Ser Thr Thr Thr Pro Ala Pro Arg Pro Pro Thr
```

-continued

```
              260               265               270

Pro Ala Pro Thr Ile Ala Ser Gln Pro Leu Ser Leu Arg Pro Glu Ala
          275               280               285

Cys Arg Pro Ala Ala Gly Gly Ala Val His Thr Arg Gly Leu Asp Phe
          290               295               300

Ala Cys Asp Ile Tyr Ile Trp Ala Pro Leu Ala Gly Thr Cys Gly Val
305               310               315               320

Leu Leu Leu Ser Leu Val Ile Thr Leu Tyr Cys Lys Arg Gly Arg Lys
              325               330               335

Lys Leu Leu Tyr Ile Phe Lys Gln Pro Phe Met Arg Pro Val Gln Thr
              340               345               350

Thr Gln Glu Glu Asp Gly Cys Ser Cys Arg Phe Pro Glu Glu Glu Glu
              355               360               365

Gly Gly Cys Glu Leu Arg Val Lys Phe Ser Arg Ser Ala Asp Ala Pro
          370               375               380

Ala Tyr Lys Gln Gly Gln Asn Gln Leu Tyr Asn Glu Leu Asn Leu Gly
385               390               395               400

Arg Arg Glu Glu Tyr Asp Val Leu Asp Lys Arg Arg Gly Arg Asp Pro
              405               410               415

Glu Met Gly Gly Lys Pro Arg Arg Lys Asn Pro Gln Glu Gly Leu Tyr
              420               425               430

Asn Glu Leu Gln Lys Asp Lys Met Ala Glu Ala Tyr Ser Glu Ile Gly
              435               440               445

Met Lys Gly Glu Arg Arg Arg Gly Lys Gly His Asp Gly Leu Tyr Gln
          450               455               460

Gly Leu Ser Thr Ala Thr Lys Asp Thr Tyr Asp Ala Leu His Met Gln
465               470               475               480

Ala Leu Pro Pro Arg
              485

<210> SEQ ID NO 17
<211> LENGTH: 485
<212> TYPE: PRT
<213> ORGANISM: Artificial Sequence
<220> FEATURE:
<223> OTHER INFORMATION: Synthetic Polypeptide - "L1H4" CAR

<400> SEQUENCE: 17

Met Ala Leu Pro Val Thr Ala Leu Leu Leu Pro Leu Ala Leu Leu Leu
1               5               10               15

His Ala Ala Arg Pro Glu Ile Leu Leu Thr Gln Ser Pro Asp Phe Gln
              20               25               30

Ser Val Thr Pro Lys Glu Lys Val Thr Phe Thr Cys Arg Ala Ser Gln
              35               40               45

Ser Ile Gly Thr Ser Ile His Trp Tyr Gln Gln Lys Pro Asn Gln Ser
      50               55               60

Pro Lys Leu Leu Ile Lys Tyr Ala Ser Glu Ser Ile Ser Gly Val Pro
65               70               75               80

Ser Arg Phe Ser Gly Ser Gly Ser Gly Thr Asp Phe Thr Leu Thr Ile
              85               90               95

Asn Ser Leu Glu Ser Glu Asp Ile Ala Thr Tyr Tyr Cys Gln Gln Ser
              100               105               110

Asn Asn Trp Pro Leu Thr Phe Gly Gln Gly Thr Lys Leu Glu Ile Lys
              115               120               125

Gly Gly Gly Gly Ser Gly Gly Gly Gly Ser Gly Gly Gly Gly Ser Gln
```

```
              130               135               140

Val Gln Leu Val Gln Ser Gly Ala Glu Val Lys Lys Pro Gly Ser Ser
145               150               155               160

Val Lys Ile Ser Cys Lys Thr Ser Gly Tyr Ala Phe Ser Asn Phe Trp
              165               170               175

Met Asn Trp Val Lys Gln Arg Pro Gly Gln Gly Leu Glu Trp Ile Gly
              180               185               190

Gln Ile Tyr Pro Gly Asp Gly Asp Thr Asn Tyr Asn Gly Lys Phe Lys
              195               200               205

Gly Arg Ala Thr Leu Thr Ala Asp Lys Ser Ser Ser Thr Ala Tyr Met
              210               215               220

Glu Leu Ser Ser Leu Arg Ser Glu Ala Thr Ala Val Tyr Phe Cys Ala
225               230               235               240

Arg Ser Tyr Tyr Arg Ser Ala Trp Phe Ala Tyr Trp Gly Gln Gly Thr
              245               250               255

Leu Val Thr Val Ser Ser Thr Thr Thr Pro Ala Pro Arg Pro Pro Thr
              260               265               270

Pro Ala Pro Thr Ile Ala Ser Gln Pro Leu Ser Leu Arg Pro Glu Ala
              275               280               285

Cys Arg Pro Ala Ala Gly Gly Ala Val His Thr Arg Gly Leu Asp Phe
              290               295               300

Ala Cys Asp Ile Tyr Ile Trp Ala Pro Leu Ala Gly Thr Cys Gly Val
305               310               315               320

Leu Leu Leu Ser Leu Val Ile Thr Leu Tyr Cys Lys Arg Gly Arg Lys
              325               330               335

Lys Leu Leu Tyr Ile Phe Lys Gln Pro Phe Met Arg Pro Val Gln Thr
              340               345               350

Thr Gln Glu Glu Asp Gly Cys Ser Cys Arg Phe Pro Glu Glu Glu Glu
              355               360               365

Gly Gly Cys Glu Leu Arg Val Lys Phe Ser Arg Ser Ala Asp Ala Pro
              370               375               380

Ala Tyr Lys Gln Gly Gln Asn Gln Leu Tyr Asn Glu Leu Asn Leu Gly
385               390               395               400

Arg Arg Glu Glu Tyr Asp Val Leu Asp Lys Arg Arg Gly Arg Asp Pro
              405               410               415

Glu Met Gly Gly Lys Pro Arg Arg Lys Asn Pro Gln Glu Gly Leu Tyr
              420               425               430

Asn Glu Leu Gln Lys Asp Lys Met Ala Glu Ala Tyr Ser Glu Ile Gly
              435               440               445

Met Lys Gly Glu Arg Arg Arg Gly Lys Gly His Asp Gly Leu Tyr Gln
              450               455               460

Gly Leu Ser Thr Ala Thr Lys Asp Thr Tyr Asp Ala Leu His Met Gln
465               470               475               480

Ala Leu Pro Pro Arg
              485

<210> SEQ ID NO 18
<211> LENGTH: 485
<212> TYPE: PRT
<213> ORGANISM: Artificial Sequence
<220> FEATURE:
<223> OTHER INFORMATION: Synthetic Polypeptide - "L2H1" CAR

<400> SEQUENCE: 18

Met Ala Leu Pro Val Thr Ala Leu Leu Leu Pro Leu Ala Leu Leu Leu
```

-continued

```
1                5                    10                   15

His Ala Ala Arg Pro Glu Ile Leu Leu Thr Gln Ser Pro Asp Phe Gln
            20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
    50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
            85                  90                  95

Asn Ser Val Glu Ser Glu Asp Ile Ala Asp Tyr Tyr Cys Gln Gln Ser
            100                 105                 110

Asn Asn Trp Pro Leu Thr Phe Gly Gln Gly Thr Lys Leu Glu Ile Lys
            115                 120                 125

Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ser Ser
145                 150                 155                 160

Val Lys Val Ser Cys Lys Thr Ser Gly Tyr Ala Phe Ser Asn Phe Trp
            165                 170                 175

Met Asn Trp Val Arg Gln Ala Pro Gly Gln Gly Leu Glu Trp Ile Gly
            180                 185                 190

Gln Ile Tyr Pro Gly Asp Gly Asp Thr Asn Tyr Asn Gly Lys Phe Lys
            195                 200                 205

Gly Arg Val Thr Leu Thr Ala Asp Lys Ser Thr Ser Thr Ala Tyr Met
    210                 215                 220

Glu Leu Ser Ser Leu Arg Ser Glu Asp Thr Ala Val Tyr Phe Cys Ala
225                 230                 235                 240

Arg Ser Tyr Tyr Arg Ser Ala Trp Phe Ala Tyr Trp Gly Gln Gly Thr
            245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
            325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
            405                 410                 415

Glu Met Gly Gly Lys Pro Arg Arg Lys Asn Pro Gln Glu Gly Leu Tyr
            420                 425                 430
```

-continued

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
        450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 19
<211> LENGTH: 485
<212> TYPE: PRT
<213> ORGANISM: Artificial Sequence
<220> FEATURE:
<223> OTHER INFORMATION: Synthetic Polypeptide - "L2H1B" CAR

<400> SEQUENCE: 19

Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
        20                  25                  30

Ser Val Thr Pro Lys Glu Lys Val Thr Phe Thr Cys Arg Ala Ser Gln
        35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95

Asn Ser Val Glu Ser Glu Asp Ile Ala Asp Tyr Tyr Cys Gln Gln Ser
        100                 105                 110

Asn Asn Trp Pro Leu Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
        130                 135                 140

Val Gln Leu Val Gln Ser Gly Ala Glu Val Lys Lys Pro Gly Ser Ser
145                 150                 155                 160

Val Lys Val Ser Cys Lys Thr Ser Gly Tyr Ala Phe Ser Asn Phe Trp
                165                 170                 175

Met Asn Trp Val Arg Gln Ala Pro Gly Gln Gly Leu Glu Trp Ile Gly
                180                 185                 190

Gln Ile Tyr Pro Gly Asp Gly Asp Thr Asn Tyr Asn Ala Lys Phe Lys
                195                 200                 205

Gly Arg Val Thr Leu Thr Ala Asp Lys Ser Thr Ser Thr Ala Tyr Met
        210                 215                 220

Glu Leu Ser Ser Leu Arg Ser Glu Asp Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
        290                 295                 300

-continued

```
Ala Cys Asp Ile Tyr Ile Trp Ala Pro Leu Ala Gly Thr Cys Gly Val
305                 310             315                 320

Leu Leu Leu Ser Leu Val Ile Thr Leu Tyr Cys Lys Arg Gly Arg Lys
                325             330             335

Lys Leu Leu Tyr Ile Phe Lys Gln Pro Phe Met Arg Pro Val Gln Thr
                340             345             350

Thr Gln Glu Glu Asp Gly Cys Ser Cys Arg Phe Pro Glu Glu Glu Glu
            355             360             365

Gly Gly Cys Glu Leu Arg Val Lys Phe Ser Arg Ser Ala Asp Ala Pro
        370             375             380

Ala Tyr Lys Gln Gly Gln Asn Gln Leu Tyr Asn Glu Leu Asn Leu Gly
385                 390             395                 400

Arg Arg Glu Glu Tyr Asp Val Leu Asp Lys Arg Arg Gly Arg Asp Pro
                405             410             415

Glu Met Gly Gly Lys Pro Arg Arg Lys Asn Pro Gln Glu Gly Leu Tyr
            420             425             430

Asn Glu Leu Gln Lys Asp Lys Met Ala Glu Ala Tyr Ser Glu Ile Gly
        435             440             445

Met Lys Gly Glu Arg Arg Arg Gly Lys Gly His Asp Gly Leu Tyr Gln
        450             455             460

Gly Leu Ser Thr Ala Thr Lys Asp Thr Tyr Asp Ala Leu His Met Gln
465                 470             475                 480

Ala Leu Pro Pro Arg
                485

<210> SEQ ID NO 20
<211> LENGTH: 485
<212> TYPE: PRT
<213> ORGANISM: Artificial Sequence
<220> FEATURE:
<223> OTHER INFORMATION: Synthetic Polypeptide - "L2H2" CAR

<400> SEQUENCE: 20

Met Ala Leu Pro Val Thr Ala Leu Leu Leu Pro Leu Ala Leu Leu Leu
1               5               10              15

His Ala Ala Arg Pro Glu Ile Leu Leu Thr Gln Ser Pro Asp Phe Gln
                20              25              30

Ser Val Thr Pro Lys Glu Lys Val Thr Phe Thr Cys Arg Ala Ser Gln
            35              40              45

Ser Ile Gly Thr Ser Ile His Trp Tyr Gln Gln Lys Pro Asn Gln Ser
        50              55              60

Pro Lys Leu Leu Ile Lys Tyr Ala Ser Glu Ser Ile Ser Gly Val Pro
65              70              75              80

Ser Arg Phe Ser Gly Ser Gly Ser Gly Thr Asp Phe Thr Leu Thr Ile
                85              90              95

Asn Ser Val Glu Ser Glu Asp Ile Ala Asp Tyr Tyr Cys Gln Gln Ser
            100             105             110

Asn Asn Trp Pro Leu Thr Phe Gly Gln Gly Thr Lys Leu Glu Ile Lys
        115             120             125

Gly Gly Gly Gly Ser Gly Gly Gly Gly Ser Gly Gly Gly Gly Ser Gln
        130             135             140

Val Gln Leu Val Gln Ser Gly Ala Glu Val Lys Lys Pro Gly Ser Ser
145             150             155             160

Val Lys Ile Ser Cys Lys Thr Ser Gly Tyr Ala Phe Ser Asn Phe Trp
                165             170             175
```

```
Met Asn Trp Val Arg Gln Ala Pro Gly Gln Gly Leu Glu Trp Ile Gly
            180                 185                 190

Gln Ile Tyr Pro Gly Asp Gly Asp Thr Asn Tyr Asn Gly Lys Phe Lys
            195                 200                 205

Gly Arg Val Thr Leu Thr Ala Asp Lys Ser Thr Ser Thr Ala Tyr Met
    210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485
```

<210> SEQ ID NO 21
<211> LENGTH: 485
<212> TYPE: PRT
<213> ORGANISM: Artificial Sequence
<220> FEATURE:
<223> OTHER INFORMATION: Synthetic Polypeptide - "L2H2B" CAR

<400> SEQUENCE: 21

```
Met Ala Leu Pro Val Thr Ala Leu Leu Leu Pro Leu Ala Leu Leu Leu
1                   5                   10                  15

His Ala Ala Arg Pro Glu Ile Leu Leu Thr Gln Ser Pro Asp Phe Gln
            20                  25                  30

Ser Val Thr Pro Lys Glu Lys Val Thr Phe Thr Cys Arg Ala Ser Gln
            35                  40                  45
```

-continued

```
Ser Ile Gly Thr Ser Ile His Trp Tyr Gln Gln Lys Pro Asn Gln Ser
    50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95

Asn Ser Val Glu Ser Glu Asp Ile Ala Asp Tyr Tyr Cys Gln Gln Ser
            100                 105                 110

Asn Asn Trp Pro Leu Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Arg Gln Ala Pro Gly Gln Gly Leu Glu Trp Ile Gly
            180                 185                 190

Gln Ile Tyr Pro Gly Asp Gly Asp Thr Asn Tyr Asn Ala Lys Phe Lys
        195                 200                 205

Gly Arg Val Thr Leu Thr Ala Asp Lys Ser Thr Ser Thr Ala Tyr Met
    210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460
```

```
Gly Leu Ser Thr Ala Thr Lys Asp Thr Tyr Asp Ala Leu His Met Gln
465                 470                 475                 480

Ala Leu Pro Pro Arg
                485

<210> SEQ ID NO 22
<211> LENGTH: 485
<212> TYPE: PRT
<213> ORGANISM: Artificial Sequence
<220> FEATURE:
<223> OTHER INFORMATION: Synthetic Polypeptide - "L2H3" CAR

<400> SEQUENCE: 22

Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
                20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95

Asn Ser Val Glu Ser Glu Asp Ile Ala Asp Tyr Tyr Cys Gln Gln Ser
                100                 105                 110

Asn Asn Trp Pro Leu Thr Phe Gly Gln Gly Thr Lys Leu Glu Ile Lys
                115                 120                 125

Gly Gly Gly Gly Ser Gly Gly Gly Gly Ser Gly Gly Gly Gly Ser Gln
            130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Lys Gln Arg Pro Gly Gln Gly Leu Glu Trp Ile Gly
                180                 185                 190

Gln Ile Tyr Pro Gly Asp Gly Asp Thr Asn Tyr Asn Gly Lys Phe Lys
                195                 200                 205

Gly Arg Ala Thr Leu Thr Ala Asp Lys Ser Thr Ser Thr Ala Tyr Met
        210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335
```

-continued

```
Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485
```

<210> SEQ ID NO 23
<211> LENGTH: 485
<212> TYPE: PRT
<213> ORGANISM: Artificial Sequence
<220> FEATURE:
<223> OTHER INFORMATION: Synthetic Polypeptide - "L2H4" CAR

<400> SEQUENCE: 23

```
Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
            20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
    50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Thr Ile
                85                  90                  95

Asn Ser Val Glu Ser Glu Asp Ile Ala Asp Tyr Tyr Cys Gln Gln Ser
            100                 105                 110

Asn Asn Trp Pro Leu Thr Phe Gly Gln Gly Thr Lys Leu Glu Ile Lys
            115                 120                 125

Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Lys Gln Arg Pro Gly Gln Gly Leu Glu Trp Ile Gly
            180                 185                 190

Gln Ile Tyr Pro Gly Asp Gly Asp Thr Asn Tyr Asn Gly Lys Phe Lys
            195                 200                 205
```

```
Gly Arg Ala Thr Leu Thr Ala Asp Lys Ser Ser Ser Thr Ala Tyr Met
210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
                275                 280                 285

Cys Arg Pro Ala Ala Gly Gly Ala Val His Thr Arg Gly Leu Asp Phe
                290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
                355                 360                 365

Gly Gly Cys Glu Leu Arg Val Lys Phe Ser Arg Ser Ala Asp Ala Pro
                370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
                450                 455                 460

Gly Leu Ser Thr Ala Thr Lys Asp Thr Tyr Asp Ala Leu His Met Gln
465                 470                 475                 480

Ala Leu Pro Pro Arg
                485
```

```
<210> SEQ ID NO 24
<211> LENGTH: 485
<212> TYPE: PRT
<213> ORGANISM: Artificial Sequence
<220> FEATURE:
<223> OTHER INFORMATION: Synthetic Polypeptide - "L3H1" CAR

<400> SEQUENCE: 24
```

```
Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
                20                  25                  30

Ser Val Thr Pro Lys Glu Lys Val Thr Phe Thr Cys Arg Ala Ser Gln
                35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80
```

-continued

```
Ser Arg Phe Ser Gly Ser Gly Ser Gly Thr Asp Phe Thr Leu Ser Ile
             85              90                  95

Asn Ser Val Glu Ser Glu Asp Ile Ala Asp Tyr Tyr Cys Gln Gln Ser
            100             105             110

Asn Asn Trp Pro Leu Thr Phe Gly Gln Gly Thr Lys Leu Glu Ile Lys
            115             120             125

Gly Gly Gly Gly Ser Gly Gly Gly Ser Gly Gly Gly Gly Ser Gln
    130             135             140

Val Gln Leu Val Gln Ser Gly Ala Glu Val Lys Lys Pro Gly Ser Ser
145             150             155                 160

Val Lys Val Ser Cys Lys Thr Ser Gly Tyr Ala Phe Ser Asn Phe Trp
            165             170             175

Met Asn Trp Val Arg Gln Ala Pro Gly Gln Gly Leu Glu Trp Ile Gly
            180             185             190

Gln Ile Tyr Pro Gly Asp Gly Asp Thr Asn Tyr Asn Gly Lys Phe Lys
            195             200             205

Gly Arg Val Thr Leu Thr Ala Asp Lys Ser Thr Ser Thr Ala Tyr Met
    210             215             220

Glu Leu Ser Ser Leu Arg Ser Glu Asp Thr Ala Val Tyr Phe Cys Ala
225             230             235                 240

Arg Ser Tyr Tyr Arg Ser Ala Trp Phe Ala Tyr Trp Gly Gln Gly Thr
            245             250             255

Leu Val Thr Val Ser Ser Thr Thr Thr Pro Ala Pro Arg Pro Pro Thr
            260             265             270

Pro Ala Pro Thr Ile Ala Ser Gln Pro Leu Ser Leu Arg Pro Glu Ala
            275             280             285

Cys Arg Pro Ala Ala Gly Gly Ala Val His Thr Arg Gly Leu Asp Phe
    290             295             300

Ala Cys Asp Ile Tyr Ile Trp Ala Pro Leu Ala Gly Thr Cys Gly Val
305             310             315                 320

Leu Leu Leu Ser Leu Val Ile Thr Leu Tyr Cys Lys Arg Gly Arg Lys
            325             330             335

Lys Leu Leu Tyr Ile Phe Lys Gln Pro Phe Met Arg Pro Val Gln Thr
            340             345             350

Thr Gln Glu Glu Asp Gly Cys Ser Cys Arg Phe Pro Glu Glu Glu Glu
            355             360             365

Gly Gly Cys Glu Leu Arg Val Lys Phe Ser Arg Ser Ala Asp Ala Pro
    370             375             380

Ala Tyr Lys Gln Gly Gln Asn Gln Leu Tyr Asn Glu Leu Asn Leu Gly
385             390             395                 400

Arg Arg Glu Glu Tyr Asp Val Leu Asp Lys Arg Arg Gly Arg Asp Pro
            405             410             415

Glu Met Gly Gly Lys Pro Arg Arg Lys Asn Pro Gln Glu Gly Leu Tyr
            420             425             430

Asn Glu Leu Gln Lys Asp Lys Met Ala Glu Ala Tyr Ser Glu Ile Gly
            435             440             445

Met Lys Gly Glu Arg Arg Arg Gly Lys Gly His Asp Gly Leu Tyr Gln
    450             455             460

Gly Leu Ser Thr Ala Thr Lys Asp Thr Tyr Asp Ala Leu His Met Gln
465             470             475                 480

Ala Leu Pro Pro Arg
            485
```

<210> SEQ ID NO 25
<211> LENGTH: 485
<212> TYPE: PRT
<213> ORGANISM: Artificial Sequence
<220> FEATURE:
<223> OTHER INFORMATION: Synthetic Polypeptide - "L3H1B" CAR

<400> SEQUENCE: 25

Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
                20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Ser Ile
                85                  90                  95

Asn Ser Val Glu Ser Glu Asp Ile Ala Asp Tyr Tyr Cys Gln Gln Ser
            100                 105                 110

Asn Asn Trp Pro Leu Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
        130                 135                 140

Val Gln Leu Val Gln Ser Gly Ala Glu Val Lys Lys Pro Gly Ser Ser
145                 150                 155                 160

Val Lys Val Ser Cys Lys Thr Ser Gly Tyr Ala Phe Ser Asn Phe Trp
                165                 170                 175

Met Asn Trp Val Arg Gln Ala Pro Gly Gln Gly Leu Glu Trp Ile Gly
                180                 185                 190

Gln Ile Tyr Pro Gly Asp Gly Asp Thr Asn Tyr Asn Ala Lys Phe Lys
            195                 200                 205

Gly Arg Val Thr Leu Thr Ala Asp Lys Ser Thr Ser Thr Ala Tyr Met
        210                 215                 220

Glu Leu Ser Ser Leu Arg Ser Glu Asp Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
        290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro

-continued

```
      370                375                380

Ala Tyr Lys Gln Gly Gln Asn Gln Leu Tyr Asn Glu Leu Asn Leu Gly
385                390                395                400

Arg Arg Glu Glu Tyr Asp Val Leu Asp Lys Arg Arg Gly Arg Asp Pro
                405                410                415

Glu Met Gly Gly Lys Pro Arg Arg Lys Asn Pro Gln Glu Gly Leu Tyr
                420                425                430

Asn Glu Leu Gln Lys Asp Lys Met Ala Glu Ala Tyr Ser Glu Ile Gly
                435                440                445

Met Lys Gly Glu Arg Arg Arg Gly Lys Gly His Asp Gly Leu Tyr Gln
        450                455                460

Gly Leu Ser Thr Ala Thr Lys Asp Thr Tyr Asp Ala Leu His Met Gln
465                470                475                480

Ala Leu Pro Pro Arg
                485

<210> SEQ ID NO 26
<211> LENGTH: 485
<212> TYPE: PRT
<213> ORGANISM: Artificial Sequence
<220> FEATURE:
<223> OTHER INFORMATION: Synthetic Polypeptide - "L3H2" CAR

<400> SEQUENCE: 26

Met Ala Leu Pro Val Thr Ala Leu Leu Leu Pro Leu Ala Leu Leu Leu
1                5                10                15

His Ala Ala Arg Pro Glu Ile Leu Leu Thr Gln Ser Pro Asp Phe Gln
                20                25                30

Ser Val Thr Pro Lys Glu Lys Val Thr Phe Thr Cys Arg Ala Ser Gln
                35                40                45

Ser Ile Gly Thr Ser Ile His Trp Tyr Gln Gln Lys Pro Asn Gln Ser
        50                55                60

Pro Lys Leu Leu Ile Lys Tyr Ala Ser Glu Ser Ile Ser Gly Val Pro
65                70                75                80

Ser Arg Phe Ser Gly Ser Gly Ser Gly Thr Asp Phe Thr Leu Ser Ile
                85                90                95

Asn Ser Val Glu Ser Glu Asp Ile Ala Asp Tyr Tyr Cys Gln Gln Ser
                100                105                110

Asn Asn Trp Pro Leu Thr Phe Gly Gln Gly Thr Lys Leu Glu Ile Lys
                115                120                125

Gly Gly Gly Gly Ser Gly Gly Gly Gly Ser Gly Gly Gly Gly Ser Gln
        130                135                140

Val Gln Leu Val Gln Ser Gly Ala Glu Val Lys Lys Pro Gly Ser Ser
145                150                155                160

Val Lys Ile Ser Cys Lys Thr Ser Gly Tyr Ala Phe Ser Asn Phe Trp
                165                170                175

Met Asn Trp Val Arg Gln Ala Pro Gly Gln Gly Leu Glu Trp Ile Gly
                180                185                190

Gln Ile Tyr Pro Gly Asp Gly Asp Thr Asn Tyr Asn Gly Lys Phe Lys
                195                200                205

Gly Arg Val Thr Leu Thr Ala Asp Lys Ser Thr Ser Thr Ala Tyr Met
        210                215                220

Glu Leu Ser Ser Leu Arg Ser Glu Ala Thr Ala Val Tyr Phe Cys Ala
225                230                235                240

Arg Ser Tyr Tyr Arg Ser Ala Trp Phe Ala Tyr Trp Gly Gln Gly Thr
```

-continued

```
                        245                     250                     255

Leu Val Thr Val Ser Ser Thr Thr Thr Pro Ala Pro Arg Pro Pro Thr
                260                     265                     270

Pro Ala Pro Thr Ile Ala Ser Gln Pro Leu Ser Leu Arg Pro Glu Ala
                275                     280                     285

Cys Arg Pro Ala Ala Gly Gly Ala Val His Thr Arg Gly Leu Asp Phe
        290                     295                     300

Ala Cys Asp Ile Tyr Ile Trp Ala Pro Leu Ala Gly Thr Cys Gly Val
305                     310                     315                     320

Leu Leu Leu Ser Leu Val Ile Thr Leu Tyr Cys Lys Arg Gly Arg Lys
                        325                     330                     335

Lys Leu Leu Tyr Ile Phe Lys Gln Pro Phe Met Arg Pro Val Gln Thr
                340                     345                     350

Thr Gln Glu Glu Asp Gly Cys Ser Cys Arg Phe Pro Glu Glu Glu Glu
                355                     360                     365

Gly Gly Cys Glu Leu Arg Val Lys Phe Ser Arg Ser Ala Asp Ala Pro
        370                     375                     380

Ala Tyr Lys Gln Gly Gln Asn Gln Leu Tyr Asn Glu Leu Asn Leu Gly
385                     390                     395                     400

Arg Arg Glu Glu Tyr Asp Val Leu Asp Lys Arg Arg Gly Arg Asp Pro
                        405                     410                     415

Glu Met Gly Gly Lys Pro Arg Arg Lys Asn Pro Gln Glu Gly Leu Tyr
                420                     425                     430

Asn Glu Leu Gln Lys Asp Lys Met Ala Glu Ala Tyr Ser Glu Ile Gly
                435                     440                     445

Met Lys Gly Glu Arg Arg Arg Gly Lys Gly His Asp Gly Leu Tyr Gln
        450                     455                     460

Gly Leu Ser Thr Ala Thr Lys Asp Thr Tyr Asp Ala Leu His Met Gln
465                     470                     475                     480

Ala Leu Pro Pro Arg
                485
```

```
<210> SEQ ID NO 27
<211> LENGTH: 485
<212> TYPE: PRT
<213> ORGANISM: Artificial Sequence
<220> FEATURE:
<223> OTHER INFORMATION: Synthetic Polypeptide - "L3H2B" CAR

<400> SEQUENCE: 27

Met Ala Leu Pro Val Thr Ala Leu Leu Leu Pro Leu Ala Leu Leu Leu
1               5                       10                      15

His Ala Ala Arg Pro Glu Ile Leu Leu Thr Gln Ser Pro Asp Phe Gln
                20                      25                      30

Ser Val Thr Pro Lys Glu Lys Val Thr Phe Thr Cys Arg Ala Ser Gln
        35                      40                      45

Ser Ile Gly Thr Ser Ile His Trp Tyr Gln Gln Lys Pro Asn Gln Ser
    50                      55                      60

Pro Lys Leu Leu Ile Lys Tyr Ala Ser Glu Ser Ile Ser Gly Val Pro
65                      70                      75                      80

Ser Arg Phe Ser Gly Ser Gly Ser Gly Thr Asp Phe Thr Leu Ser Ile
                85                      90                      95

Asn Ser Val Glu Ser Glu Asp Ile Ala Asp Tyr Tyr Cys Gln Gln Ser
                100                     105                     110

Asn Asn Trp Pro Leu Thr Phe Gly Gln Gly Thr Lys Leu Glu Ile Lys
```

-continued

```
              115                 120                 125
Gly Gly Gly Gly Ser Gly Gly Gly Gly Ser Gly Gly Gly Gly Ser Gln
    130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Arg Gln Ala Pro Gly Gln Gly Leu Glu Trp Ile Gly
            180                 185                 190

Gln Ile Tyr Pro Gly Asp Gly Asp Thr Asn Tyr Asn Ala Lys Phe Lys
        195                 200                 205

Gly Arg Val Thr Leu Thr Ala Asp Lys Ser Thr Ser Thr Ala Tyr Met
    210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 28
<211> LENGTH: 485
<212> TYPE: PRT
<213> ORGANISM: Artificial Sequence
<220> FEATURE:
<223> OTHER INFORMATION: Synthetic Polypeptide - "L3H3" CAR -continued

```
<400> SEQUENCE: 28

Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
                20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
        50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Ser Ile
                85                  90                  95

Asn Ser Val Glu Ser Glu Asp Ile Ala Asp Tyr Tyr Cys Gln Gln Ser
            100                 105                 110

Asn Asn Trp Pro Leu Thr Phe Gly Gln Gly Thr Lys Leu Glu Ile Lys
            115                 120                 125

Gly Gly Gly Gly Ser Gly Gly Gly Ser Gly Gly Gly Gly Ser Gln
        130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Lys Gln Arg Pro Gly Gln Gly Leu Glu Trp Ile Gly
            180                 185                 190

Gln Ile Tyr Pro Gly Asp Gly Asp Thr Asn Tyr Asn Gly Lys Phe Lys
            195                 200                 205

Gly Arg Ala Thr Leu Thr Ala Asp Lys Ser Thr Ser Thr Ala Tyr Met
        210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
        290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
        370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415
```

-continued

```
Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
            450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 29
<211> LENGTH: 485
<212> TYPE: PRT
<213> ORGANISM: Artificial Sequence
<220> FEATURE:
<223> OTHER INFORMATION: Synthetic Polypeptide - "L3H4" CAR

<400> SEQUENCE: 29

Met Ala Leu Pro Val Thr Ala Leu Leu Leu Pro Leu Ala Leu Leu Leu
1               5                   10                  15

His Ala Ala Arg Pro Glu Ile Leu Leu Thr Gln Ser Pro Asp Phe Gln
            20                  25                  30

Ser Val Thr Pro Lys Glu Lys Val Thr Phe Thr Cys Arg Ala Ser Gln
            35                  40                  45

Ser Ile Gly Thr Ser Ile His Trp Tyr Gln Gln Lys Pro Asn Gln Ser
            50                  55                  60

Pro Lys Leu Leu Ile Lys Tyr Ala Ser Glu Ser Ile Ser Gly Val Pro
65                  70                  75                  80

Ser Arg Phe Ser Gly Ser Gly Ser Gly Thr Asp Phe Thr Leu Ser Ile
                85                  90                  95

Asn Ser Val Glu Ser Glu Asp Ile Ala Asp Tyr Tyr Cys Gln Gln Ser
            100                 105                 110

Asn Asn Trp Pro Leu Thr Phe Gly Gln Gly Thr Lys Leu Glu Ile Lys
            115                 120                 125

Gly Gly Gly Gly Ser Gly Gly Gly Gly Ser Gly Gly Gly Gly Ser Gln
            130                 135                 140

Val Gln Leu Val Gln Ser Gly Ala Glu Val Lys Lys Pro Gly Ser Ser
145                 150                 155                 160

Val Lys Ile Ser Cys Lys Thr Ser Gly Tyr Ala Phe Ser Asn Phe Trp
                165                 170                 175

Met Asn Trp Val Lys Gln Arg Pro Gly Gln Gly Leu Glu Trp Ile Gly
            180                 185                 190

Gln Ile Tyr Pro Gly Asp Gly Asp Thr Asn Tyr Asn Gly Lys Phe Lys
            195                 200                 205

Gly Arg Ala Thr Leu Thr Ala Asp Lys Ser Ser Ser Thr Ala Tyr Met
            210                 215                 220

Glu Leu Ser Ser Leu Arg Ser Glu Ala Thr Ala Val Tyr Phe Cys Ala
225                 230                 235                 240

Arg Ser Tyr Tyr Arg Ser Ala Trp Phe Ala Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285
```

-continued

```
Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485
```

```
<210> SEQ ID NO 30
<211> LENGTH: 1455
<212> TYPE: DNA
<213> ORGANISM: Artificial Sequence
<220> FEATURE:
<223> OTHER INFORMATION: Synthetic Polynucleotide - "L1H1" CAR

<400> SEQUENCE: 30
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
agcagatttt ctggcagcgg aagcggcacc gacttcaccc tgaccatcaa cagcctggaa     300
tccgaggaca ttgccaccta ctactgccag cagtccaaca ctggcccct gacatttggc     360 cagggcacca agctggaaat caaaggcgga ggcggtagcg gtggcggagg tagcggaggt     420
ggtggatctc aggttcagct ggttcagtct ggcgccgaag tgaagaaacc tggcagcagc     480
gtgaaggtgt cctgcaagac aagcggctac gccttcagca cttctggat gaactgggtc     540 cgacaggccc ctggacaagg cctggaatgg atcggccaaa tctatcccgg cgacggcgac     600
accaactaca cggcaagtt caagggcaga gtgacactga ccgccgacaa gagcacaagc     660
accgcctaca tggaactgag cagcctgaga agcgaggata ccgccgtgta cttctgcgcc     720
cggtcctact acagaagcgc ttggtttgcc tattggggcc agggaaccct cgtgaccgtt     780
agctctacca acacccggc gcctagacct ccaacaccag ctcctacaat cgcgagtcag     840
cccctgtctc tcagacccga agcctgcagg ccagctgcag gaggagctgt gcacaccagg     900
```

-continued

```
ggcctggact tcgcctgcga catctacatt tgggcaccac tggccgggac ctgtggagtg      960
ctgctgctga gcctggtcat cacactgtac tgcaagagag gcaggaagaa actgctgtat     1020
attttcaaac agcccttcat gcgccccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
aagcccaggc gcaaaaaccc tcaggaaggc ctgtataacg agctgcagaa ggacaaaatg     1320
gcagaagcct attctgagat cggcatgaag ggggagcgac ggagaggcaa agggcacgat     1380
gggctgtacc agggactgag caccgccaca aaggacacct atgatgctct gcatatgcag     1440
gcactgcctc caagg                                                       1455
```

<210> SEQ ID NO 31
<211> LENGTH: 1455
<212> TYPE: DNA
<213> ORGANISM: Artificial Sequence
<220> FEATURE:
<223> OTHER INFORMATION: Synthetic Polynucleotide - "L1H1B" CAR

<400> SEQUENCE: 31

```
atggctctgc ctgtgacagc tctgcttctg cctctggcac tgcttcttca tgcggcgcgc       60
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgaccatcaa cagcctggaa      300
tccgaggaca ttgccaccta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaaggtgt cctgcaagac aagcggctac gccttcagca acttctggat gaactgggtc      540
cgacaggccc ctggacaagg cctggaatgg atcggccaaa tctatcccgg cgacggcgac      600
accaactaca cgccaagtt caagggcaga gtgacactga ccgccgacaa gagcacaagc      660
accgcctaca tggaactgag cagcctgaga agcgaggata ccgccgtgta cttctgcgcc      720
cggtcctact acagaagcgc ttggtttgcc tattggggcc agggaaccct cgtgaccgtt      780
agctctacca acacccggc gcctagacct ccaacaccac tcctacaat cgcgagtcag      840 cccctgtctc tcagacccga gcctgcagg ccagctgcag gaggagctgt gcacaccagg      900
ggcctggact tcgcctgcga catctacatt tgggcaccac tggccgggac ctgtggagtg      960
ctgctgctga gcctggtcat cacactgtac tgcaagagag gcaggaagaa actgctgtat     1020
attttcaaac agcccttcat gcgccccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
aagcccaggc gcaaaaaccc tcaggaaggc ctgtataacg agctgcagaa ggacaaaatg     1320
gcagaagcct attctgagat cggcatgaag ggggagcgac ggagaggcaa agggcacgat     1380
gggctgtacc agggactgag caccgccaca aaggacacct atgatgctct gcatatgcag     1440
```

-continued

```
gcactgcctc caagg                                                  1455

<210> SEQ ID NO 32
<211> LENGTH: 1455
<212> TYPE: DNA
<213> ORGANISM: Artificial Sequence
<220> FEATURE:
<223> OTHER INFORMATION: Synthetic Polynucleotide - "L1H2" CAR

<400> SEQUENCE: 32
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
agcagatttt ctggcagcgg aagcggcacc gacttcaccc tgaccatcaa cagcctggaa     300
tccgaggaca ttgccaccta ctactgccag cagtccaaca ctggcccct gacatttggc     360 cagggcacca agctggaaat caaaggcgga ggcggtagcg gtggcggagg tagcggaggt     420
ggtggatctc aggttcagct ggttcagtct ggcgccgaag tgaagaaacc tggcagcagc     480
gtgaagatca gctgcaagac aagcggctac gccttcagca cttctggat gaactgggtc     540 cgacaggccc ctggacaagg cctggaatgg atcggccaaa tctatcccgg cgacggcgac     600
accaactaca cggcaagtt caagggcaga gtgacactga ccgccgacaa gagcacaagc     660
accgcctaca tggaactgag cagcctgaga agcgaggcta ccgccgtgta cttctgtgcc     720
agaagctact acagaagcgc ttggtttgcc tactggggcc agggaacact cgtgaccgtt     780
agctctacca acaccggc gcctagacct ccaacaccag ctcctacaat cgcgagtcag     840
cccctgtctc tcagacccga agcctgcagg ccagctgcag gaggagctgt gcacaccagg     900
ggcctggact tcgcctgcga catctacatt tgggcaccac tggccgggac ctgtggagtg     960
ctgctgctga gcctggtcat cacactgtac tgcaagagag caggaagaa actgctgtat    1020 attttcaaac agcccttcat gcgccccgtg cagactaccc aggaggaaga cgggtgctcc    1080
tgtcgattcc ctgaggaaga ggaaggcggg tgtgagctgc gcgtgaagtt tagtcgatca    1140
gcagatgccc cagcttacaa acagggacag aaccagctgt ataacgagct gaatctgggc    1200
cgccgagagg aatatgacgt gctggataag cggagaggac gcgaccccga aatgggaggc    1260
aagcccaggc gcaaaaaccc tcaggaaggc ctgtataacg agctgcagaa ggacaaaatg    1320
gcagaagcct attctgagat cggcatgaag ggggagcgac ggagaggcaa agggcacgat    1380
gggctgtacc agggactgag caccgccaca aaggacacct atgatgctct gcatatgcag    1440
gcactgcctc caagg                                                 1455

<210> SEQ ID NO 33
<211> LENGTH: 1455
<212> TYPE: DNA
<213> ORGANISM: Artificial Sequence
<220> FEATURE:
<223> OTHER INFORMATION: Synthetic Polynucleotide - "L1H2B" CAR

<400> SEQUENCE: 33
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
```

-continued

```
agcagatttt ctggcagcgg aagcggcacc gacttcaccc tgaccatcaa cagcctggaa      300
tccgaggaca ttgccaccta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaagatca gctgcaagac aagcggctac gccttcagca acttctggat gaactgggtc      540
cgacaggccc ctggacaagg cctggaatgg atcggccaaa tctatcccgg cgacggcgac      600
accaactaca cgccaagtt caagggcaga gtgacactga ccgccgacaa gagcacaagc      660
accgcctaca tggaactgag cagcctgaga agcgaggcta ccgccgtgta cttctgtgcc      720
agaagctact acagaagcgc ttggtttgcc tactggggcc agggaacact cgtgaccgtt      780
agctctacca acacccggc gcctagacct ccaacaccag ctcctacaat cgcgagtcag      840
cccctgtctc tcagacccga agcctgcagg ccagctgcag gaggagctgt gcacaccagg      900
ggcctggact cgcctgcga catctacatt tgggcaccac tggccgggac ctgtggagtg      960
ctgctgctga gcctggtcat cacactgtac tgcaagagag gcaggaagaa actgctgtat     1020
attttcaaac agcccttcat gcgccccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
aagcccaggc gcaaaaaccc tcaggaaggc ctgtataacg agctgcagaa ggacaaaatg     1320
gcagaagcct attctgagat cggcatgaag ggggagcgac ggagaggcaa agggcacgat     1380
gggctgtacc agggactgag caccgccaca aaggacacct atgatgctct gcatatgcag     1440
gcactgcctc caagg                                                     1455
```

```
<210> SEQ ID NO 34
<211> LENGTH: 1455
<212> TYPE: DNA
<213> ORGANISM: Artificial Sequence
<220> FEATURE:
<223> OTHER INFORMATION: Synthetic Polynucleotide - "L1H3" CAR

<400> SEQUENCE: 34
atggctctgc ctgtgacagc tctgcttctg cctctggcac tgcttcttca tgcggcgcgc       60
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgaccatcaa cagcctggaa      300
tccgaggaca ttgccaccta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaagatca gctgcaagac aagcggctac gccttcagca acttctggat gaactgggtc      540
aagcagcggc caggccaagg cctggaatgg atcggacaaa tctatcccgg cgacggcgac      600
accaactaca cggcaagtt caagggcaga gctacactga ccgccgacaa gagcacaagc      660
accgcctaca tggaactgag cagcctgaga agcgaggcta ccgccgtgta cttctgtgcc      720
agaagctact acagaagcgc ttggtttgcc tactggggcc agggaacact cgtgaccgtt      780
```

-continued

```
agctctacca caacaccggc gcctagacct ccaacaccag ctcctacaat cgcgagtcag       840
cccctgtctc tcagacccga agcctgcagg ccagctgcag gaggagctgt gcacaccagg       900
ggcctggact tcgcctgcga catctacatt tgggcaccac tggccgggac ctgtggagtg       960
ctgctgctga gcctggtcat cacactgtac tgcaagagag gcaggaagaa actgctgtat      1020
attttcaaac agcccttcat gcgccccgtg cagactaccc aggaggaaga cgggtgctcc      1080
tgtcgattcc ctgaggaaga ggaaggcggg tgtgagctgc gcgtgaagtt tagtcgatca      1140
gcagatgccc cagcttacaa acagggacag aaccagctgt ataacgagct gaatctgggc      1200
cgccgagagg aatatgacgt gctggataag cggagaggac gcgaccccga aatgggaggc      1260
aagcccaggc gcaaaaaccc tcaggaaggc ctgtataacg agctgcagaa ggacaaaatg      1320
gcagaagcct attctgagat cggcatgaag ggggagcgac ggagaggcaa agggcacgat      1380
gggctgtacc agggactgag caccgccaca aaggacacct atgatgctct gcatatgcag      1440
gcactgcctc caagg                                                     1455

<210> SEQ ID NO 35
<211> LENGTH: 1455
<212> TYPE: DNA
<213> ORGANISM: Artificial Sequence
<220> FEATURE:
<223> OTHER INFORMATION: Synthetic Polynucleotide - "L1H4" CAR

<400> SEQUENCE: 35
atggctctgc ctgtgacagc tctgcttctg cctctggcac tgcttcttca tgcggcgcgc        60
cctgagattc tgctgacaca gagccctgac ttccagagcg tgacccctaa agaaaaagtg       120
accttcacct gtagagccag ccagagcatc ggcacctcca tccactggta tcagcagaag       180
cccaatcaga gccccaagct gctgattaag tacgccagcg agtccatcag cggcgtgcca       240
agcagatttt ctggcagcgg aagcggcacc gacttcaccc tgaccatcaa cagcctggaa       300
tccgaggaca ttgccaccta ctactgccag cagtccaaca ctggcccct gacatttggc        360 cagggcacca agctggaaat caaaggcgga ggcggtagcg gtggcggagg tagcggaggt       420
ggtggatctc aggttcagct ggttcagtct ggcgccgaag tgaagaaacc tggcagcagc       480
gtgaagatca gctgcaagac aagcggctac gccttcagca acttctggat gaactgggtc       540
aagcagcggc caggccaagg cctggaatgg atcggacaaa tctatcccgg cgacggcgac       600
accaactaca cggcaagtt caagggcaga gctacactga ccgccgacaa gagcagcagc        660
accgcctaca tggaactgag cagcctgaga agcgaggcta ccgccgtgta cttctgtgcc       720
agaagctact acagaagcgc ttggtttgcc tactggggcc agggaacact cgtgaccgtt       780
agctctacca caacaccggc gcctagacct ccaacaccag ctcctacaat cgcgagtcag       840
cccctgtctc tcagacccga agcctgcagg ccagctgcag gaggagctgt gcacaccagg       900
ggcctggact tcgcctgcga catctacatt tgggcaccac tggccgggac ctgtggagtg       960
ctgctgctga gcctggtcat cacactgtac tgcaagagag gcaggaagaa actgctgtat      1020
attttcaaac agcccttcat gcgccccgtg cagactaccc aggaggaaga cgggtgctcc      1080
tgtcgattcc ctgaggaaga ggaaggcggg tgtgagctgc gcgtgaagtt tagtcgatca      1140
gcagatgccc cagcttacaa acagggacag aaccagctgt ataacgagct gaatctgggc      1200
cgccgagagg aatatgacgt gctggataag cggagaggac gcgaccccga aatgggaggc      1260
aagcccaggc gcaaaaaccc tcaggaaggc ctgtataacg agctgcagaa ggacaaaatg      1320
gcagaagcct attctgagat cggcatgaag ggggagcgac ggagaggcaa agggcacgat      1380
```

-continued

```
gggctgtacc agggactgag caccgccaca aaggacacct atgatgctct gcatatgcag    1440
gcactgcctc caagg                                                     1455

<210> SEQ ID NO 36
<211> LENGTH: 1455
<212> TYPE: DNA
<213> ORGANISM: Artificial Sequence
<220> FEATURE:
<223> OTHER INFORMATION: Synthetic Polynucleotide - "L2H1" CAR

<400> SEQUENCE: 36
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
agcagatttt ctggcagcgg aagcggcacc gacttcaccc tgaccatcaa cagcgtggaa     300
tccgaggaca ttgccgacta ctactgccag cagtccaaca actggcccct gacatttggc     360
cagggcacca agctggaaat caaaggcgga ggcggtagcg gtggcggagg tagcggaggt     420
ggtggatctc aggttcagct ggttcagtct ggcgccgaag tgaagaaacc tggcagcagc     480
gtgaaggtgt cctgcaagac aagcggctac gccttcagca acttctggat gaactgggtc     540
cgacaggccc ctggacaagg cctggaatgg atcggccaaa tctatcccgg cgacggcgac     600
accaactaca cggcaagtt caagggcaga gtgacactga ccgccgacaa gagcacaagc     660
accgcctaca tggaactgag cagcctgaga agcgaggata ccgccgtgta cttctgcgcc     720
cggtcctact acagaagcgc ttggtttgcc tattgggggcc agggaaccct cgtgaccgtt     780
agctctacca acaccggc gcctagacct ccaacaccag ctcctacaat cgcgagtcag     840
cccctgtctc tcagacccga agcctgcagg ccagctgcag gaggagctgt gcacaccagg     900
ggcctggact cgcctgcga catctacatt tgggcaccac tggccgggac ctgtggagtg     960
ctgctgctga gcctggtcat cacactgtac tgcaagagag gcaggaagaa actgctgtat    1020
attttcaaac agcccttcat gcgccccgtg cagactaccc aggaggaaga cgggtgctcc    1080
tgtcgattcc ctgaggaaga ggaaggcggg tgtgagctgc gcgtgaagtt tagtcgatca    1140
gcagatgccc cagcttacaa acagggacag aaccagctgt ataacgagct gaatctgggc    1200
cgccgagagg aatatgacgt gctggataag cggagaggac gcgaccccga aatgggaggc    1260
aagcccaggc gcaaaaaccc tcaggaaggc ctgtataacg agctgcagaa ggacaaaatg    1320
gcagaagcct attctgagat cggcatgaag ggggagcgac ggagaggcaa agggcacgat    1380
gggctgtacc agggactgag caccgccaca aaggacacct atgatgctct gcatatgcag    1440
gcactgcctc caagg                                                     1455

<210> SEQ ID NO 37
<211> LENGTH: 1455
<212> TYPE: DNA
<213> ORGANISM: Artificial Sequence
<220> FEATURE:
<223> OTHER INFORMATION: Synthetic Polynucleotide - "L2H1B" CAR

<400> SEQUENCE: 37
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
```

```
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgaccatcaa cagcgtggaa      300
tccgaggaca ttgccgacta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaaggtgt cctgcaagac aagcggctac gccttcagca acttctggat gaactgggtc      540
cgacaggccc ctggacaagg cctggaatgg atcggccaaa tctatcccgg cgacggcgac      600
accaactaca acgccaagtt caagggcaga gtgacactga ccgccgacaa gagcacaagc      660
accgcctaca tggaactgag cagcctgaga agcgaggata ccgccgtgta cttctgcgcc      720
cggtcctact acagaagcgc ttggtttgcc tattggggcc agggaaccct cgtgaccgtt      780
agctctacca caacaccggc gcctagacct ccaacaccag ctcctacaat cgcgagtcag      840
cccctgtctc tcagacccga agcctgcagg ccagctgcag gaggagctgt gcacaccagg      900
ggcctggact cgcctgcga catctacatt tgggcaccac tggccgggac ctgtggagtg      960
ctgctgctga gcctggtcat cacactgtac tgcaagagag caggaagaa actgctgtat     1020 attttcaaac agcccttcat gcgccccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
aagcccaggc gcaaaaaccc tcaggaaggc ctgtataacg agctgcagaa ggacaaaatg     1320
gcagaagcct attctgagat cggcatgaag ggggagcgac ggagaggcaa agggcacgat     1380
gggctgtacc agggactgag caccgccaca aaggacacct atgatgctct gcatatgcag     1440
gcactgcctc caagg                                                     1455
```

```
<210> SEQ ID NO 38
<211> LENGTH: 1455
<212> TYPE: DNA
<213> ORGANISM: Artificial Sequence
<220> FEATURE:
<223> OTHER INFORMATION: Synthetic Polynucleotide - "L2H2" CAR

<400> SEQUENCE: 38
atggctctgc ctgtgacagc tctgcttctg cctctggcac tgcttcttca tgcggcgcgc       60
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgaccatcaa cagcgtggaa      300
tccgaggaca ttgccgacta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaagatca gctgcaagac aagcggctac gccttcagca acttctggat gaactgggtc      540
cgacaggccc ctggacaagg cctggaatgg atcggccaaa tctatcccgg cgacggcgac      600
accaactaca acgccaagtt caagggcaga gtgacactga ccgccgacaa gagcacaagc      660
accgcctaca tggaactgag cagcctgaga agcgaggcta ccgccgtgta cttctgtgcc      720
```

-continued

```
agaagctact acagaagcgc ttggtttgcc tactggggcc agggaacact cgtgaccgtt      780
agctctacca caacaccggc gcctagacct ccaacaccag ctcctacaat cgcgagtcag      840
cccctgtctc tcagacccga agcctgcagg ccagctgcag gaggagctgt gcacaccagg      900
ggcctggact tcgcctgcga catctacatt tgggcaccac tggccgggac ctgtggagtg      960
ctgctgctga gcctggtcat cacactgtac tgcaagagag gcaggaagaa actgctgtat     1020
attttcaaac agcccttcat cgcgccccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
aagcccaggc gcaaaaaccc tcaggaaggc ctgtataacg agctgcagaa ggacaaaatg     1320
gcagaagcct attctgagat cggcatgaag ggggagcgac ggagaggcaa agggcacgat     1380
gggctgtacc agggactgag caccgccaca aaggacacct atgatgctct gcatatgcag     1440
gcactgcctc caagg                                                       1455

<210> SEQ ID NO 39
<211> LENGTH: 1455
<212> TYPE: DNA
<213> ORGANISM: Artificial Sequence
<220> FEATURE:
<223> OTHER INFORMATION: Synthetic Polynucleotide - "L2H2B" CAR

<400> SEQUENCE: 39
atggctctgc ctgtgacagc tctgcttctg cctctggcac tgcttcttca tgcggcgcgc       60
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgaccatcaa cagcgtggaa      300
tccgaggaca ttgccgacta ctactgccag cagtccaaca ctggcccct gacatttggc      360 cagggcacca agctggaaat caaaggcgga ggcggtagcg tggcggagg tagcggaggt      420 ggtggatctc aggttcagct ggttcagtct ggcgccgaag tgaagaaacc tggcagcagc      480
gtgaagatca ctgcaagac aagcggctac gccttcagca acttctggat gaactgggtc      540
cgacaggccc ctggacaagg cctggaatgg atcggccaaa tctatcccgg cgacggcgac      600
accaactaca cgccaagtt caagggcaga gtgacactga ccgccgacaa gagcacaagc      660
accgcctaca tggaactgag cagcctgaga agcgaggcta ccgccgtgta cttctgtgcc      720
agaagctact acagaagcgc ttggtttgcc tactggggcc agggaacact cgtgaccgtt      780
agctctacca caacaccggc gcctagacct ccaacaccag ctcctacaat cgcgagtcag      840
cccctgtctc tcagacccga agcctgcagg ccagctgcag gaggagctgt gcacaccagg      900
ggcctggact tcgcctgcga catctacatt tgggcaccac tggccgggac ctgtggagtg      960
ctgctgctga gcctggtcat cacactgtac tgcaagagag gcaggaagaa actgctgtat     1020
attttcaaac agcccttcat cgcgccccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
```

-continued

```
aagcccaggc gcaaaaaccc tcaggaaggc ctgtataacg agctgcagaa ggacaaaatg    1320
gcagaagcct attctgagat cggcatgaag ggggagcgac ggagaggcaa agggcacgat    1380
gggctgtacc agggactgag caccgccaca aaggacacct atgatgctct gcatatgcag    1440
gcactgcctc caagg                                                     1455

<210> SEQ ID NO 40
<211> LENGTH: 1455
<212> TYPE: DNA
<213> ORGANISM: Artificial Sequence
<220> FEATURE:
<223> OTHER INFORMATION: Synthetic Polynucleotide - "L2H3" CAR

<400> SEQUENCE: 40
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
agcagatttt ctggcagcgg aagcggcacc gacttcaccc tgaccatcaa cagcgtggaa     300
tccgaggaca ttgccgacta ctactgccag cagtccaaca actggcccct gacatttggc     360
cagggcacca agctggaaat caaaggcgga ggcggtagcg tggcggagg tagcggaggt      420 ggtggatctc aggttcagct ggttcagtct ggcgccgaag tgaagaaacc tggcagcagc     480
gtgaagatca gctgcaagac aagcggctac gccttcagca acttctggat gaactgggtc     540
aagcagcggc aggccaagg cctggaatgg atcggacaaa tctatcccgg cgacggcgac      600
accaactaca cggcaagtt caagggcaga gctacactga ccgccgacaa gagcacaagc      660
accgcctaca tggaactgag cagcctgaga agcgaggcta ccgccgtgta cttctgtgcc     720
agaagctact acagaagcgc ttggtttgcc tactggggcc agggaacact cgtgaccgtt     780
agctctacca acaccggc gcctagacct ccaacaccag ctcctacaat cgcgagtcag      840
cccctgtctc tcagacccga agcctgcagg ccagctgcag gaggagctgt gcacaccagg     900
ggcctggact cgcctgcga catctacatt tgggcaccac tggccgggac ctgtggagtg      960
ctgctgctga gcctggtcat cacactgtac tgcaagagag gcaggaagaa actgctgtat    1020
attttcaaac agcccttcat cgcgccccgtg cagactaccc aggaggaaga cgggtgctcc    1080
tgtcgattcc ctgaggaaga ggaaggcggg tgtgagctgc gcgtgaagtt tagtcgatca    1140
gcagatgccc cagcttacaa acagggacag aaccagctgt ataacgagct gaatctgggc    1200
cgccgagagg aatatgacgt gctggataag cggagaggac gcgaccccga aatgggaggc    1260
aagcccaggc gcaaaaaccc tcaggaaggc ctgtataacg agctgcagaa ggacaaaatg    1320
gcagaagcct attctgagat cggcatgaag ggggagcgac ggagaggcaa agggcacgat    1380
gggctgtacc agggactgag caccgccaca aaggacacct atgatgctct gcatatgcag    1440
gcactgcctc caagg                                                     1455

<210> SEQ ID NO 41
<211> LENGTH: 1455
<212> TYPE: DNA
<213> ORGANISM: Artificial Sequence
<220> FEATURE:
<223> OTHER INFORMATION: Synthetic Polynucleotide - "L2H4" CAR

<400> SEQUENCE: 41
atggctctgc ctgtgacagc tctgcttctg cctctggcac tgcttcttca tgcggcgcgc      60
```

```
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgaccatcaa cagcgtggaa      300
tccgaggaca ttgccgacta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaagatca gctgcaagac aagcggctac gccttcagca acttctggat gaactgggtc      540
aagcagcggc caggccaagg cctggaatgg atcggacaaa tctatcccgg cgacggcgac      600
accaactaca cggcaagtt caagggcaga gctacactga ccgccgacaa gagcagcagc      660
accgcctaca tggaactgag cagcctgaga agcgaggcta ccgccgtgta cttctgtgcc      720
agaagctact acagaagcgc ttggtttgcc tactggggcc agggaacact cgtgaccgtt      780
agctctacca acaccggcgc cctagacct ccaacaccag ctcctacaat cgcgagtcag      840
cccctgtctc tcagacccga agcctgcagg ccagctgcag gaggagctgt gcacaccagg      900
ggcctggact cgcctgcga catctacatt tgggcaccac tggccgggac ctgtggagtg      960
ctgctgctga gcctggtcat cacactgtac tgcaagagag gcaggaagaa actgctgtat      1020
attttcaaac agcccttcat gcgcccgtg cagactaccc aggaggaaga cgggtgctcc      1080
tgtcgattcc ctgaggaaga ggaaggcggg tgtgagctgc gcgtgaagtt tagtcgatca      1140
gcagatgccc cagcttacaa acagggacag aaccagctgt ataacgagct gaatctgggc      1200
cgccgagagg aatatgacgt gctggataag cggagaggac gcgacccga aatgggaggc      1260 aagcccaggc gcaaaaaccc tcaggaaggc ctgtataacg agctgcagaa ggacaaaatg      1320
gcagaagcct attctgagat cggcatgaag ggggagcgac ggagaggcaa agggcacgat      1380
gggctgtacc agggactgag caccgccaca aaggacacct atgatgctct gcatatgcag      1440
gcactgcctc caagg                                                       1455
```

<210> SEQ ID NO 42
<211> LENGTH: 1455
<212> TYPE: DNA
<213> ORGANISM: Artificial Sequence
<220> FEATURE:
<223> OTHER INFORMATION: Synthetic Polynucleotide - "L3H1" CAR

<400> SEQUENCE: 42

```
atggctctgc ctgtgacagc tctgcttctg cctctggcac tgcttcttca tgcggcgcgc       60
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgtctatcaa cagcgtggaa      300
tccgaggaca ttgccgacta ctactgccag cagtccaaca actggcccct gacatttggc      360
cagggcacca agctggaaat caaaggcgga ggcggtagcg gtggcggagg tagcggaggt      420
ggtggatctc aggttcagct ggttcagtct ggcgccgaag tgaagaaacc tggcagcagc      480
gtgaaggtgt cctgcaagac aagcggctac gccttcagca acttctggat gaactgggtc      540
cgacaggccc ctggacaagg cctggaatgg atcggccaaa tctatcccgg cgacggcgac      600
```

-continued

```
accaactaca acggcaagtt caagggcaga gtgacactga ccgccgacaa gagcacaagc      660
accgcctaca tggaactgag cagcctgaga agcgaggata ccgccgtgta cttctgcgcc      720
cggtcctact acagaagcgc ttggtttgcc tattggggcc agggaaccct cgtgaccgtt      780
agctctacca caacaccggc gcctagacct ccaacaccag ctcctacaat cgcgagtcag      840
cccctgtctc tcagacccga agcctgcagg ccagctgcag gaggagctgt gcacaccagg      900
ggcctggact cgcctgcgca catctacatt tgggcaccac tggccgggac ctgtggagtg      960
ctgctgctga gcctggtcat cacactgtac tgcaagagag gcaggaagaa actgctgtat     1020
attttcaaac agcccttcat cgcgcccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
cgccgagagg aatatgacgt gctggataag cggagaggac gcgaccccga aatgggaggc     1260
aagcccaggc gcaaaaaccc tcaggaaggc ctgtataacg agctgcagaa ggacaaaatg     1320
gcagaagcct attctgagat cggcatgaag ggggagcgac ggagaggcaa agggcacgat     1380
gggctgtacc agggactgag caccgccaca aaggacacct atgatgctct gcatatgcag     1440
gcactgcctc caagg                                                     1455
```

<210> SEQ ID NO 43
<211> LENGTH: 1455
<212> TYPE: DNA
<213> ORGANISM: Artificial Sequence
<220> FEATURE:
<223> OTHER INFORMATION: Synthetic Polynucleotide - "L3H1B" CAR

<400> SEQUENCE: 43

```
atggctctgc ctgtgacagc tctgcttctg cctctggcac tgcttcttca tgcggcgcgc       60
cctgagattc tgctgacaca gagccctgac ttccagagcg tgacccctaa agaaaaagtg      120
accttcacct gtagagccag ccagagcatc ggcacctcca tccactggta tcagcagaag      180
cccaatcaga gccccaagct gctgattaag tacgccagcg agtccatcag cggcgtgcca      240
agcagatttt ctggcagcgg aagcggcacc gacttcaccc tgtctatcaa cagcgtggaa      300
tccgaggaca ttgccgacta ctactgccag cagtccaaca actggcccct gacatttggc      360
cagggcacca gctggaaat caaaggcgga ggcggtagcg gtggcggagg tagcggaggt      420
ggtggatctc aggttcagct ggttcagtct ggcgccgaag tgaagaaacc tggcagcagc      480
gtgaaggtgt cctgcaagac aagcggctac gccttcagca acttctggat gaactgggtc      540
cgacaggccc ctggacaagg cctggaatgg atcggccaaa tctatcccgg cgacggcgac      600
accaactaca acgccaagtt caagggcaga gtgacactga ccgccgacaa gagcacaagc      660
accgcctaca tggaactgag cagcctgaga agcgaggata ccgccgtgta cttctgcgcc      720
cggtcctact acagaagcgc ttggtttgcc tattggggcc agggaaccct cgtgaccgtt      780
agctctacca caacaccggc gcctagacct ccaacaccag ctcctacaat cgcgagtcag      840
cccctgtctc tcagacccga agcctgcagg ccagctgcag gaggagctgt gcacaccagg      900
ggcctggact cgcctgcgca catctacatt tgggcaccac tggccgggac ctgtggagtg      960
ctgctgctga gcctggtcat cacactgtac tgcaagagag gcaggaagaa actgctgtat     1020
attttcaaac agcccttcat cgcgcccgtg cagactaccc aggaggaaga cgggtgctcc     1080
tgtcgattcc ctgaggaaga ggaaggcggg tgtgagctgc gcgtgaagtt tagtcgatca     1140
gcagatgccc cagcttacaa acagggacag aaccagctgt ataacgagct gaatctgggc     1200
```

-continued

```
cgccgagagg aatatgacgt gctggataag cggagaggac gcgaccccga aatgggaggc      1260
aagcccaggc gcaaaaaccc tcaggaaggc ctgtataacg agctgcagaa ggacaaaatg      1320
gcagaagcct attctgagat cggcatgaag ggggagcgac ggagaggcaa agggcacgat      1380
gggctgtacc agggactgag caccgccaca aaggacacct atgatgctct gcatatgcag      1440
gcactgcctc caagg                                                       1455
```

```
<210> SEQ ID NO 44
<211> LENGTH: 1455
<212> TYPE: DNA
<213> ORGANISM: Artificial Sequence
<220> FEATURE:
<223> OTHER INFORMATION: Synthetic Polynucleotide - "L3H2" CAR

<400> SEQUENCE: 44
```

```
atggctctgc ctgtgacagc tctgcttctg cctctggcac tgcttcttca tgcggcgcgc        60
cctgagattc tgctgacaca gagccctgac ttccagagcg tgacccctaa agaaaaagtg       120
accttcacct gtagagccag ccagagcatc ggcacctcca tccactggta tcagcagaag       180
cccaatcaga gccccaagct gctgattaag tacgccagcg agtccatcag cggcgtgcca       240
agcagatttt ctggcagcgg aagcggcacc gacttcaccc tgtctatcaa cagcgtggaa       300
tccgaggaca ttgccgacta ctactgccag cagtccaaca actggcccct gacatttggc       360
cagggcacca agctggaaat caaaggcgga ggcggtagcg gtggcggagg tagcggaggt       420
ggtggatctc aggttcagct ggttcagtct ggcgccgaag tgaagaaacc tggcagcagc       480
gtgaagatca gctgcaagac aagcggctac gccttcagca acttctggat gaactgggtc       540
cgacaggccc ctggacaagg cctggaatgg atcggccaaa tctatcccgg cgacggcgac       600
accaactaca cggcaagtt caaggcagga gtgacactga ccgccgacaa gagcacaagc       660
accgcctaca tggaactgag cagcctgaga agcgaggcta ccgccgtgta cttctgtgcc       720
agaagctact acagaagcgc ttggtttgcc tactggggcc agggaacact cgtgaccgtt       780
agctctacca aacaccggc gcctagacct ccaacaccag ctcctacaat cgcgagtcag       840
cccctgtctc tcagacccga agcctgcagg ccagctgcag gaggagctgt gcacaccagg       900
ggcctggact cgcctgcga catctacatt tgggcaccac tggccgggac ctgtggagtg       960
ctgctgctga gcctggtcat cacactgtac tgcaagagag caggaagaa actgctgtat      1020 attttcaaac agcccttcat gcgccccgtg cagactaccc aggaggaaga cgggtgctcc      1080
tgtcgattcc ctgaggaaga ggaaggcggg tgtgagctgc gcgtgaagtt tagtcgatca      1140
gcagatgccc agcttacaa acagggacag aaccagctgt ataacgagct gaatctgggc      1200
cgccgagagg aatatgacgt gctggataag cggagaggac gcgaccccga aatgggaggc      1260
aagcccaggc gcaaaaaccc tcaggaaggc ctgtataacg agctgcagaa ggacaaaatg      1320
gcagaagcct attctgagat cggcatgaag ggggagcgac ggagaggcaa agggcacgat      1380
gggctgtacc agggactgag caccgccaca aaggacacct atgatgctct gcatatgcag      1440
gcactgcctc caagg                                                       1455
```

```
<210> SEQ ID NO 45
<211> LENGTH: 1455
<212> TYPE: DNA
<213> ORGANISM: Artificial Sequence
<220> FEATURE:
<223> OTHER INFORMATION: Synthetic Polynucleotide - "L3H2B" CAR
```

-continued

```
<400> SEQUENCE: 45
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
agcagatttt ctggcagcgg aagcggcacc gacttcaccc tgtctatcaa cagcgtggaa     300
tccgaggaca ttgccgacta ctactgccag cagtccaaca actggcccct gacatttggc     360
cagggcacca agctggaaat caaaggcgga ggcggtagcg gtggcggagg tagcggaggt     420
ggtggatctc aggttcagct ggttcagtct ggcgccgaag tgaagaaacc tggcagcagc     480
gtgaagatca gctgcaagac aagcggctac gccttcagca acttctggat gaactgggtc     540
cgacaggccc ctggacaagg cctggaatgg atcggccaaa tctatcccgg cgacggcgac     600
accaactaca cgccaagtt caagggcaga gtgacactga ccgccgacaa gagcacaagc     660
accgcctaca tggaactgag cagcctgaga agcgaggcta ccgccgtgta cttctgtgcc     720
agaagctact acagaagcgc ttggtttgcc tactggggcc agggaacact cgtgaccgtt     780
agctctacca acaccggc gcctagacct ccaacaccag ctcctacaat cgcgagtcag     840
cccctgtctc tcagacccga agcctgcagg ccagctgcag gaggagctgt gcacaccagg     900
ggcctggact cgcctgcga catctacatt tgggcaccac tggccgggac ctgtggagtg     960
ctgctgctga gcctggtcat cacactgtac tgcaagagag gcaggaagaa actgctgtat    1020
attttcaaac agcccttcat gcgccccgtg cagactaccc aggaggaaga cgggtgctcc    1080
tgtcgattcc ctgaggaaga ggaaggcggg tgtgagctgc gcgtgaagtt tagtcgatca    1140
gcagatgccc cagcttacaa acagggacag aaccagctgt ataacgagct gaatctgggc    1200
cgccgagagg aatatgacgt gctggataag cggagaggac gcgaccccga aatgggaggc    1260
aagcccaggc gcaaaaaccc tcaggaaggc ctgtataacg agctgcagaa ggacaaaatg    1320
gcagaagcct attctgagat cggcatgaag ggggagcgac ggagaggcaa agggcacgat    1380
gggctgtacc agggactgag caccgccaca aaggacacct atgatgctct gcatatgcag    1440
gcactgcctc caagg                                                    1455

<210> SEQ ID NO 46
<211> LENGTH: 1455
<212> TYPE: DNA
<213> ORGANISM: Artificial Sequence
<220> FEATURE:
<223> OTHER INFORMATION: Synthetic Polynucleotide - "L3H3" CAR

<400> SEQUENCE: 46
atggctctgc ctgtgacagc tctgcttctg cctctggcac tgcttcttca tgcggcgcgc      60
cctgagattc tgctgacaca gagccctgac ttccagagcg tgacccctaa agaaaaagtg     120
accttcacct gtagagccag ccagagcatc ggcacctcca tccactggta tcagcagaag     180
cccaatcaga gccccaagct gctgattaag tacgccagcg agtccatcag cggcgtgcca     240
agcagatttt ctggcagcgg aagcggcacc gacttcaccc tgtctatcaa cagcgtggaa     300
tccgaggaca ttgccgacta ctactgccag cagtccaaca actggcccct gacatttggc     360
cagggcacca agctggaaat caaaggcgga ggcggtagcg gtggcggagg tagcggaggt     420
ggtggatctc aggttcagct ggttcagtct ggcgccgaag tgaagaaacc tggcagcagc     480
gtgaagatca gctgcaagac aagcggctac gccttcagca acttctggat gaactgggtc     540
```

```
aagcagcggc caggccaagg cctggaatgg atcggacaaa tctatcccgg cgacggcgac        600
accaactaca acggcaagtt caagggcaga gctacactga ccgccgacaa gagcacaagc        660
accgcctaca tggaactgag cagcctgaga agcgaggcta ccgccgtgta cttctgtgcc        720
agaagctact acagaagcgc ttggtttgcc tactggggcc agggaacact cgtgaccgtt        780
agctctacca caacaccggc gcctagacct ccaacaccag ctcctacaat cgcgagtcag        840
cccctgtctc tcagacccga agcctgcagg ccagctgcag gaggagctgt gcacaccagg        900
ggcctggact tcgcctgcga catctacatt tgggcaccac tggccgggac ctgtggagtg        960
ctgctgctga gcctggtcat cacactgtac tgcaagagag gcaggaagaa actgctgtat       1020
attttcaaac agcccttcat gcgccccgtg cagactaccc aggaggaaga cgggtgctcc       1080
tgtcgattcc ctgaggaaga ggaaggcggg tgtgagctgc gcgtgaagtt tagtcgatca       1140
gcagatgccc cagcttacaa acagggacag aaccagctgt ataacgagct gaatctgggc       1200
cgccgagagg aatatgacgt gctggataag cggagaggac gcgaccccga aatgggaggc       1260
aagcccaggc gcaaaaaccc tcaggaaggc ctgtataacg agctgcagaa ggacaaaatg       1320
gcagaagcct attctgagat cggcatgaag ggggagcgac ggagaggcaa agggcacgat       1380
gggctgtacc agggactgag caccgccaca aaggacacct atgatgctct gcatatgcag       1440
gcactgcctc caagg                                                       1455
```

<210> SEQ ID NO 47
<211> LENGTH: 1455
<212> TYPE: DNA
<213> ORGANISM: Artificial Sequence
<220> FEATURE:
<223> OTHER INFORMATION: Synthetic Polynucleotide - "L3H4" CAR

<400> SEQUENCE: 47

```
atggctctgc ctgtgacagc tctgcttctg cctctggcac tgcttcttca tgcggcgcgc         60
cctgagattc tgctgacaca gagccctgac ttccagagcg tgacccctaa agaaaaagtg        120
accttcacct gtagagccag ccagagcatc ggcacctcca tccactggta tcagcagaag        180
cccaatcaga gccccaagct gctgattaag tacgccagcg agtccatcag cggcgtgcca        240
agcagatttt ctggcagcgg aagcggcacc gacttcaccc tgtctatcaa cagcgtggaa        300
tccgaggaca ttgccgacta ctactgccag cagtccaaca ctggcccct gacatttggc        360 cagggcacca agctggaaat caaaggcgga ggcggtagcg tggcggagg tagcggaggt        420 ggtggatctc aggttcagct ggttcagtct ggcgccgaag tgaagaaacc tggcagcagc        480
gtgaagatca gctgcaagac aagcggctac gccttcagca acttctggat gaactgggtc        540
aagcagcggc caggccaagg cctggaatgg atcggacaaa tctatcccgg cgacggcgac        600
accaactaca acggcaagtt caagggcaga gctacactga ccgccgacaa gagcagcagc        660
accgcctaca tggaactgag cagcctgaga agcgaggcta ccgccgtgta cttctgtgcc        720
agaagctact acagaagcgc ttggtttgcc tactggggcc agggaacact cgtgaccgtt        780
agctctacca caacaccggc gcctagacct ccaacaccag ctcctacaat cgcgagtcag        840
cccctgtctc tcagacccga agcctgcagg ccagctgcag gaggagctgt gcacaccagg        900
ggcctggact tcgcctgcga catctacatt tgggcaccac tggccgggac ctgtggagtg        960
ctgctgctga gcctggtcat cacactgtac tgcaagagag gcaggaagaa actgctgtat       1020
attttcaaac agcccttcat gcgccccgtg cagactaccc aggaggaaga cgggtgctcc       1080
```

-continued

```
tgtcgattcc ctgaggaaga ggaaggcggg tgtgagctgc gcgtgaagtt tagtcgatca      1140
gcagatgccc cagcttacaa acagggacag aaccagctgt ataacgagct gaatctgggc      1200
cgccgagagg aatatgacgt gctggataag cggagaggac gcgaccccga aatgggaggc      1260
aagcccaggc gcaaaaaccc tcaggaaggc ctgtataacg agctgcagaa ggacaaaatg      1320
gcagaagcct attctgagat cggcatgaag ggggagcgac ggagaggcaa agggcacgat      1380
gggctgtacc agggactgag caccgccaca aaggacacct atgatgctct gcatatgcag      1440
gcactgcctc caagg                                                       1455

<210> SEQ ID NO 48
<211> LENGTH: 357
<212> TYPE: DNA
<213> ORGANISM: Artificial Sequence
<220> FEATURE:
<223> OTHER INFORMATION: Synthetic Polynucleotide - "H1" humanized heavy
      chain variable region

<400> SEQUENCE: 48
caggttcagc tggttcagtc tggcgccgaa gtgaagaaac ctggcagcag cgtgaaggtg        60
tcctgcaaga caagcggcta cgccttcagc aacttctgga tgaactgggt ccgacaggcc       120
cctggacaag gcctggaatg gatcggccaa atctatcccg gcgacggcga caccaactac       180
aacggcaagt tcaagggcag agtgacactg accgccgaca gagcacaag caccgcctac        240 atggaactga gcagcctgag aagcgaggat accgccgtgt acttctgcgc ccggtcctac       300
tacagaagcg cttggtttgc ctattggggc cagggaaccc tcgtgaccgt tagctct         357

<210> SEQ ID NO 49
<211> LENGTH: 357
<212> TYPE: DNA
<213> ORGANISM: Artificial Sequence
<220> FEATURE:
<223> OTHER INFORMATION: Synthetic Polynucleotide - "H1B" humanized
      heavy chain variable region

<400> SEQUENCE: 49
caggttcagc tggttcagtc tggcgccgaa gtgaagaaac ctggcagcag cgtgaaggtg        60
tcctgcaaga caagcggcta cgccttcagc aacttctgga tgaactgggt ccgacaggcc       120
cctggacaag gcctggaatg gatcggccaa atctatcccg gcgacggcga caccaactac       180
aacgccaagt tcaagggcag agtgacactg accgccgaca gagcacaag caccgcctac        240 atggaactga gcagcctgag aagcgaggat accgccgtgt acttctgcgc ccggtcctac       300
tacagaagcg cttggtttgc ctattggggc cagggaaccc tcgtgaccgt tagctct         357

<210> SEQ ID NO 50
<211> LENGTH: 357
<212> TYPE: DNA
<213> ORGANISM: Artificial Sequence
<220> FEATURE:
<223> OTHER INFORMATION: Synthetic Polynucleotide - "H2" humanized heavy
      chain variable region

<400> SEQUENCE: 50
caggttcagc tggttcagtc tggcgccgaa gtgaagaaac ctggcagcag cgtgaagatc        60
agctgcaaga caagcggcta cgccttcagc aacttctgga tgaactgggt ccgacaggcc       120
cctggacaag gcctggaatg gatcggccaa atctatcccg gcgacggcga caccaactac       180
aacggcaagt tcaagggcag agtgacactg accgccgaca gagcacaag caccgcctac        240
```

-continued

```
atggaactga gcagcctgag aagcgaggct accgccgtgt acttctgtgc cagaagctac        300
tacagaagcg cttggtttgc ctactggggc cagggaacac tcgtgaccgt tagctct           357

<210> SEQ ID NO 51
<211> LENGTH: 357
<212> TYPE: DNA
<213> ORGANISM: Artificial Sequence
<220> FEATURE:
<223> OTHER INFORMATION: Synthetic Polynucleotide - "H2B" humanized
      heavy chain variable region

<400> SEQUENCE: 51
caggttcagc tggttcagtc tggcgccgaa gtgaagaaac ctggcagcag cgtgaagatc        60
agctgcaaga caagcggcta cgccttcagc aacttctgga tgaactgggt ccgacaggcc        120
cctggacaag gcctggaatg gatcggccaa atctatcccg gcgacggcga caccaactac        180
aacgccaagt tcaagggcag agtgacactg accgccgaca gagcacaag caccgcctac         240 atggaactga gcagcctgag aagcgaggct accgccgtgt acttctgtgc cagaagctac        300
tacagaagcg cttggtttgc ctactggggc cagggaacac tcgtgaccgt tagctct           357

<210> SEQ ID NO 52
<211> LENGTH: 357
<212> TYPE: DNA
<213> ORGANISM: Artificial Sequence
<220> FEATURE:
<223> OTHER INFORMATION: Synthetic Polynucleotide - "H3" humanized heavy
      chain variable region

<400> SEQUENCE: 52
caggttcagc tggttcagtc tggcgccgaa gtgaagaaac ctggcagcag cgtgaagatc        60
agctgcaaga caagcggcta cgccttcagc aacttctgga tgaactgggt caagcagcgg        120
ccaggccaag gcctggaatg gatcggacaa atctatcccg gcgacggcga caccaactac        180
aacggcaagt tcaagggcag agctacactg accgccgaca gagcacaag caccgcctac         240 atggaactga gcagcctgag aagcgaggct accgccgtgt acttctgtgc cagaagctac        300
tacagaagcg cttggtttgc ctactggggc cagggaacac tcgtgaccgt tagctct           357

<210> SEQ ID NO 53
<211> LENGTH: 357
<212> TYPE: DNA
<213> ORGANISM: Artificial Sequence
<220> FEATURE:
<223> OTHER INFORMATION: Synthetic Polynucleotide - "H4" humanized heavy
      chain variable region

<400> SEQUENCE: 53
caggttcagc tggttcagtc tggcgccgaa gtgaagaaac ctggcagcag cgtgaagatc        60
agctgcaaga caagcggcta cgccttcagc aacttctgga tgaactgggt caagcagcgg        120
ccaggccaag gcctggaatg gatcggacaa atctatcccg gcgacggcga caccaactac        180
aacggcaagt tcaagggcag agctacactg accgccgaca gagcagcag caccgcctac         240 atggaactga gcagcctgag aagcgaggct accgccgtgt acttctgtgc cagaagctac        300
tacagaagcg cttggtttgc ctactggggc cagggaacac tcgtgaccgt tagctct           357

<210> SEQ ID NO 54
<211> LENGTH: 321
<212> TYPE: DNA
<213> ORGANISM: Artificial Sequence
<220> FEATURE:
```

<223> OTHER INFORMATION: Synthetic Polynucleotide - "L1" humanized light
      chain variable region

<400> SEQUENCE: 54
gagattctgc tgacacagag ccctgacttc cagagcgtga cccctaaaga aaaagtgacc          60
ttcacctgta gagccagcca gagcatcggc acctccatcc actggtatca gcagaagccc         120
aatcagagcc ccaagctgct gattaagtac gccagcgagt ccatcagcgg cgtgccaagc         180
agattttctg gcagcggaag cggcaccgac ttcaccctga ccatcaacag cctggaatcc         240
gaggacattg ccacctacta ctgccagcag tccaacaact ggcccctgac atttggccag         300
ggcaccaagc tggaaatcaa a                                                    321

<210> SEQ ID NO 55
<211> LENGTH: 321
<212> TYPE: DNA
<213> ORGANISM: Artificial Sequence
<220> FEATURE:
<223> OTHER INFORMATION: Synthetic Polynucleotide - "L2" humanized light
      chain variable region

<400> SEQUENCE: 55
gagattctgc tgacacagag ccctgacttc cagagcgtga cccctaaaga aaaagtgacc          60
ttcacctgta gagccagcca gagcatcggc acctccatcc actggtatca gcagaagccc         120
aatcagagcc ccaagctgct gattaagtac gccagcgagt ccatcagcgg cgtgccaagc         180
agattttctg gcagcggaag cggcaccgac ttcaccctga ccatcaacag cgtggaatcc         240
gaggacattg ccgactacta ctgccagcag tccaacaact ggcccctgac atttggccag         300
ggcaccaagc tggaaatcaa a                                                    321

<210> SEQ ID NO 56
<211> LENGTH: 321
<212> TYPE: DNA
<213> ORGANISM: Artificial Sequence
<220> FEATURE:
<223> OTHER INFORMATION: Synthetic Polynucleotide - "L3" humanized light
      chain variable region

<400> SEQUENCE: 56
gagattctgc tgacacagag ccctgacttc cagagcgtga cccctaaaga aaaagtgacc          60
ttcacctgta gagccagcca gagcatcggc acctccatcc actggtatca gcagaagccc         120
aatcagagcc ccaagctgct gattaagtac gccagcgagt ccatcagcgg cgtgccaagc         180
agattttctg gcagcggaag cggcaccgac ttcaccctgt ctatcaacag cgtggaatcc         240
gaggacattg ccgactacta ctgccagcag tccaacaact ggcccctgac atttggccag         300
ggcaccaagc tggaaatcaa a                                                    321

<210> SEQ ID NO 57
<211> LENGTH: 21
<212> TYPE: PRT
<213> ORGANISM: Artificial Sequence
<220> FEATURE:
<223> OTHER INFORMATION: Synthetic Polypeptide - CD8a signal peptide

<400> SEQUENCE: 57

Met Ala Leu Pro Val Thr Ala Leu Leu Leu Pro Leu Ala Leu Leu Leu
1               5                   10                  15

His Ala Ala Arg Pro
            20

<210> SEQ ID NO 58
<211> LENGTH: 63
<212> TYPE: DNA
<213> ORGANISM: Artificial Sequence
<220> FEATURE:
<223> OTHER INFORMATION: Synthetic Polynucleotide - CD8a signal peptide

<400> SEQUENCE: 58
atggctctgc ctgtgacagc tctgcttctg cctctggcac tgcttcttca tgcggcgcgc      60
cct                                                                     63

<210> SEQ ID NO 59
<211> LENGTH: 15
<212> TYPE: PRT
<213> ORGANISM: Artificial Sequence
<220> FEATURE:
<223> OTHER INFORMATION: Synthetic Polypeptide - linker sequence

<400> SEQUENCE: 59

Gly Gly Gly Gly Ser Gly Gly Gly Gly Ser Gly Gly Gly Gly Ser
1               5                   10                  15

<210> SEQ ID NO 60
<211> LENGTH: 45
<212> TYPE: DNA
<213> ORGANISM: Artificial Sequence
<220> FEATURE:
<223> OTHER INFORMATION: Synthetic Polynucleotide - linker sequence

<400> SEQUENCE: 60
ggcggaggcg gtagcggtgg cggaggtagc ggaggtggtg gatct                       45

<210> SEQ ID NO 61
<211> LENGTH: 45
<212> TYPE: PRT
<213> ORGANISM: Artificial Sequence
<220> FEATURE:
<223> OTHER INFORMATION: Synthetic Polypeptide - CD8a hinge

<400> SEQUENCE: 61

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 62
<211> LENGTH: 135
<212> TYPE: DNA
<213> ORGANISM: Artificial Sequence
<220> FEATURE:
<223> OTHER INFORMATION: Synthetic Polynucleotide - CD8a hinge

<400> SEQUENCE: 62
accacaacac cggcgcctag acctccaaca ccagctccta caatcgcgag tcagcccctg      60
tctctcagac ccgaagcctg caggccagct gcaggaggag ctgtgcacac caggggcctg     120
gacttcgcct gcgac                                                       135

<210> SEQ ID NO 63
<211> LENGTH: 24
<212> TYPE: PRT
<213> ORGANISM: Artificial Sequence
<220> FEATURE:
<223> OTHER INFORMATION: Synthetic Polypeptide - CD8a transmembrane
      domain

<400> SEQUENCE: 63

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 64
<211> LENGTH: 72
<212> TYPE: DNA
<213> ORGANISM: Artificial Sequence
<220> FEATURE:
<223> OTHER INFORMATION: Synthetic Polynucleotide - CD8a transmembrane
      domain

<400> SEQUENCE: 64
atctacattt gggcaccact ggccgggacc tgtggagtgc tgctgctgag cctggtcatc      60
acactgtact gc                                                          72

<210> SEQ ID NO 65
<211> LENGTH: 42
<212> TYPE: PRT
<213> ORGANISM: Artificial Sequence
<220> FEATURE:
<223> OTHER INFORMATION: Synthetic Polypeptide - 41BB ICS

<400> SEQUENCE: 65

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 66
<211> LENGTH: 126
<212> TYPE: DNA
<213> ORGANISM: Artificial Sequence
<220> FEATURE:
<223> OTHER INFORMATION: Synthetic Polynucleotide - 41BB ICS

<400> SEQUENCE: 66
aagagaggca ggaagaaact gctgtatatt ttcaaacagc ccttcatgcg ccccgtgcag      60
actacccagg aggaagacgg gtgctcctgt cgattccctg aggaagagga aggcgggtgt     120
gagctg                                                               126

<210> SEQ ID NO 67
<211> LENGTH: 112
<212> TYPE: PRT
<213> ORGANISM: Artificial Sequence
<220> FEATURE:
<223> OTHER INFORMATION: Synthetic Polypeptide - CD3z ICS

<400> SEQUENCE: 67

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys

-continued

```
              35              40              45

Pro Arg Arg Lys Asn Pro Gln Glu Gly Leu Tyr Asn Glu Leu Gln Lys
     50              55              60

Asp Lys Met Ala Glu Ala Tyr Ser Glu Ile Gly Met Lys Gly Glu Arg
65              70              75              80

Arg Arg Gly Lys Gly His Asp Gly Leu Tyr Gln Gly Leu Ser Thr Ala
                85              90              95

Thr Lys Asp Thr Tyr Asp Ala Leu His Met Gln Ala Leu Pro Pro Arg
             100             105             110
```

```
<210> SEQ ID NO 68
<211> LENGTH: 336
<212> TYPE: DNA
<213> ORGANISM: Artificial Sequence
<220> FEATURE:
<223> OTHER INFORMATION: Synthetic Polynucleotide - CD3z ICS

<400> SEQUENCE: 68
cgcgtgaagt ttagtcgatc agcagatgcc ccagcttaca aacagggaca gaaccagctg      60
tataacgagc tgaatctggg ccgccgagag gaatatgacg tgctggataa gcggagagga     120
cgcgaccccg aaatgggagg caagcccagg cgcaaaaacc ctcaggaagg cctgtataac     180
gagctgcaga aggacaaaat ggcagaagcc tattctgaga tcggcatgaa gggggagcga     240
cggagaggca aagggcacga tgggctgtac cagggactga gcaccgccac aaaggacacc     300
tatgatgctc tgcatatgca ggcactgcct ccaagg                              336
```

```
<210> SEQ ID NO 69
<211> LENGTH: 5
<212> TYPE: PRT
<213> ORGANISM: Artificial Sequence
<220> FEATURE:
<223> OTHER INFORMATION: Synthetic Polypeptide - CDRH1

<400> SEQUENCE: 69

Asn Phe Trp Met Asn
1               5
```

```
<210> SEQ ID NO 70
<211> LENGTH: 17
<212> TYPE: PRT
<213> ORGANISM: Artificial Sequence
<220> FEATURE:
<223> OTHER INFORMATION: Synthetic Polypeptide - CDRH2

<400> SEQUENCE: 70

Gln Ile Tyr Pro Gly Asp Gly Asp Thr Asn Tyr Asn Gly Lys Phe Lys
1               5               10              15

Gly
```

```
<210> SEQ ID NO 71
<211> LENGTH: 10
<212> TYPE: PRT
<213> ORGANISM: Artificial Sequence
<220> FEATURE:
<223> OTHER INFORMATION: Synthetic Polypeptide - CDRH3

<400> SEQUENCE: 71

Ser Tyr Tyr Arg Ser Ala Trp Phe Ala Tyr
1               5               10
```

```
<210> SEQ ID NO 72
```

<211> LENGTH: 11
<212> TYPE: PRT
<213> ORGANISM: Artificial Sequence
<220> FEATURE:
<223> OTHER INFORMATION: Synthetic Polypeptide - CDRL1

<400> SEQUENCE: 72

Arg Ala Ser Gln Ser Ile Gly Thr Ser Ile His
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Synthetic Polypeptide - CDRL2

<400> SEQUENCE: 73

Tyr Ala Ser Glu Ser Ile Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Polypeptide - CDRL3

<400> SEQUENCE: 74

Gln Gln Ser Asn Asn Trp Pro Leu Thr
1               5

<210> SEQ ID NO 75
<211> LENGTH: 17
<212> TYPE: PRT
<213> ORGANISM: Artificial Sequence
<220> FEATURE:
<223> OTHER INFORMATION: Synthetic Polypeptide - CDRL3

<400> SEQUENCE: 75

Gln Ile Tyr Pro Gly Asp Gly Asp Thr Asn Tyr Asn Ala Lys Phe Lys
1               5                   10                  15

Gly

<210> SEQ ID NO 76
<211> LENGTH: 158
<212> TYPE: PRT
<213> ORGANISM: Homo Sapiens

<400> SEQUENCE: 76

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
                20                  25                  30

Ser Arg Tyr Asn Leu Thr Ile Ser Asp Val Ser Val Ser Asp Val Pro
            35                  40                  45

Phe Pro Phe Ser Ala Gln Ser Gly Ala Gly Val Pro Gly Trp Gly Ile
        50                  55                  60

Ala Leu Leu Val Leu Val Cys Val Leu Val Ala Leu Ala Ile Val Tyr
65                  70                  75                  80

Leu Ile Ala Leu Ala Val Cys Gln Cys Arg Arg Lys Asn Tyr Gly Gln
                85                  90                  95

Leu Asp Ile Phe Pro Ala Arg Asp Thr Tyr His Pro Met Ser Glu Tyr

```
                100                 105                 110
```

Pro Thr Tyr His Thr His Gly Arg Tyr Val Pro Pro Ser Ser Thr Asp
        115                 120                 125

Arg Ser Pro Tyr Glu Lys Val Ser Ala Gly Asn Gly Gly Ser Ser Leu
    130                 135                 140

Ser Tyr Thr Asn Pro Ala Val Ala Ala Thr Ser Ala Asn Leu
145                 150                 155

<210> SEQ ID NO 77
<211> LENGTH: 58
<212> TYPE: PRT
<213> ORGANISM: Homo Sapiens

<400> SEQUENCE: 77

Ser Val Val Val Gln Leu Thr Leu Ala Phe Arg Glu Gly Thr Ile Asn
1                   5                   10                  15

Val His Asp Val Glu Thr Gln Phe Asn Gln Tyr Lys Thr Glu Ala Ala
                20                  25                  30

Ser Arg Tyr Asn Leu Thr Ile Ser Asp Val Ser Val Ser Asp Val Pro
        35                  40                  45

Phe Pro Phe Ser Ala Gln Ser Gly Ala Gly
    50                  55

<210> SEQ ID NO 78
<211> LENGTH: 22
<212> TYPE: PRT
<213> ORGANISM: Artificial Sequence
<220> FEATURE:
<223> OTHER INFORMATION: Synthetic Polypeptide - MUC1C/ECD peptide

<400> SEQUENCE: 78

Ser Val Val Val Gln Leu Thr Leu Ala Phe Arg Glu Gly Thr Ile Asn
1                   5                   10                  15

Val His Asp Val Glu Thr
                20

<210> SEQ ID NO 79
<211> LENGTH: 22
<212> TYPE: PRT
<213> ORGANISM: Artificial Sequence
<220> FEATURE:
<223> OTHER INFORMATION: Synthetic Polypeptide - MUC1C/ECD peptide

<400> SEQUENCE: 79

Val Glu Thr Gln Phe Asn Gln Tyr Lys Thr Glu Ala Ala Ser Arg Tyr
1                   5                   10                  15

Asn Leu Thr Ile Ser Asp
                20

<210> SEQ ID NO 80
<211> LENGTH: 21
<212> TYPE: PRT
<213> ORGANISM: Artificial Sequence
<220> FEATURE:
<223> OTHER INFORMATION: Synthetic Polypeptide - MUC1C/ECD peptide

<400> SEQUENCE: 80

Thr Ile Ser Asp Val Ser Val Ser Asp Val Pro Phe Pro Phe Ser Ala
1                   5                   10                  15

Gln Ser Gly Ala Gly
                20

-continued

```
<210> SEQ ID NO 81
<211> LENGTH: 10
<212> TYPE: PRT
<213> ORGANISM: Artificial Sequence
<220> FEATURE:
<223> OTHER INFORMATION: Synthetic Polypeptide - MUC1C/ED peptide

<400> SEQUENCE: 81

Val His Asp Val Glu Thr Gln Phe Asn Gln
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic Polypeptide - MUC1C/ED peptide

<400> SEQUENCE: 82

Glu Ala Ala Ser Arg Tyr Asn
1               5

<210> SEQ ID NO 83
<211> LENGTH: 1053
<212> TYPE: PRT
<213> ORGANISM: Staphylococcus aureus

<400> SEQUENCE: 83

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240
```

-continued

```
Pro Glu Glu Leu Arg Ser Val Lys Tyr Ala Tyr Asn Ala Asp Leu Tyr
            245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
```

```
                    660             665             670
Val Lys Ser Ile Asn Gly Gly Phe Thr Ser Phe Leu Arg Arg Lys Trp
             675             680             685

Lys Phe Lys Lys Glu Arg Asn Lys Gly Tyr Lys His His Ala Glu Asp
        690             695             700

Ala Leu Ile Ile Ala Asn Ala Asp Phe Ile Phe Lys Glu Trp Lys Lys
705             710             715             720

Leu Asp Lys Ala Lys Lys Val Met Glu Asn Gln Met Phe Glu Glu Lys
             725             730             735

Gln Ala Glu Ser Met Pro Glu Ile Glu Thr Glu Gln Glu Tyr Lys Glu
             740             745             750

Ile Phe Ile Thr Pro His Gln Ile Lys His Ile Lys Asp Phe Lys Asp
             755             760             765

Tyr Lys Tyr Ser His Arg Val Asp Lys Lys Pro Asn Arg Glu Leu Ile
        770             775             780

Asn Asp Thr Leu Tyr Ser Thr Arg Lys Asp Asp Lys Gly Asn Thr Leu
785             790             795             800

Ile Val Asn Asn Leu Asn Gly Leu Tyr Asp Lys Asp Asn Asp Lys Leu
             805             810             815

Lys Lys Leu Ile Asn Lys Ser Pro Glu Lys Leu Leu Met Tyr His His
             820             825             830

Asp Pro Gln Thr Tyr Gln Lys Leu Lys Leu Ile Met Glu Gln Tyr Gly
             835             840             845

Asp Glu Lys Asn Pro Leu Tyr Lys Tyr Tyr Glu Glu Thr Gly Asn Tyr
        850             855             860

Leu Thr Lys Tyr Ser Lys Lys Asp Asn Gly Pro Val Ile Lys Lys Ile
865             870             875             880

Lys Tyr Tyr Gly Asn Lys Leu Asn Ala His Leu Asp Ile Thr Asp Asp
             885             890             895

Tyr Pro Asn Ser Arg Asn Lys Val Val Lys Leu Ser Leu Lys Pro Tyr
        900             905             910

Arg Phe Asp Val Tyr Leu Asp Asn Gly Val Tyr Lys Phe Val Thr Val
        915             920             925

Lys Asn Leu Asp Val Ile Lys Lys Glu Asn Tyr Tyr Glu Val Asn Ser
        930             935             940

Lys Cys Tyr Glu Glu Ala Lys Lys Leu Lys Lys Ile Ser Asn Gln Ala
945             950             955             960

Glu Phe Ile Ala Ser Phe Tyr Asn Asn Asp Leu Ile Lys Ile Asn Gly
             965             970             975

Glu Leu Tyr Arg Val Ile Gly Val Asn Asn Asp Leu Leu Asn Arg Ile
             980             985             990

Glu Val Asn Met Ile Asp Ile Thr  Tyr Arg Glu Tyr Leu  Glu Asn Met
             995             1000            1005

Asn Asp  Lys Arg Pro Pro Arg  Ile Ile Lys Thr Ile  Ala Ser Lys
        1010            1015            1020

Thr Gln  Ser Ile Lys Lys Tyr  Ser Thr Asp Ile Leu  Gly Asn Leu
        1025            1030            1035

Tyr Glu  Val Lys Ser Lys Lys  His Pro Gln Ile Ile  Lys Lys Gly
        1040            1045            1050

<210> SEQ ID NO 84
<211> LENGTH: 1053
<212> TYPE: PRT
<213> ORGANISM: Artificial Sequence
```

```
<220> FEATURE:
<223> OTHER INFORMATION: Synthetic Polypeptide - dSaCas9

<400> SEQUENCE: 84

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400
```

-continued

```
Asn Leu Ile Leu Asp Glu Leu Trp His Thr Asn Asp Asn Gln Ile Ala
            405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
            565                 570                 575

Gln Glu Glu Ala Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
            610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
            805                 810                 815
```

-continued

Lys Lys Leu Ile Asn Lys Ser Pro Glu Lys Leu Leu Met Tyr His His
                820             825             830

Asp Pro Gln Thr Tyr Gln Lys Leu Lys Leu Ile Met Glu Gln Tyr Gly
        835             840             845

Asp Glu Lys Asn Pro Leu Tyr Lys Tyr Glu Glu Thr Gly Asn Tyr
        850             855             860

Leu Thr Lys Tyr Ser Lys Lys Asp Asn Gly Pro Val Ile Lys Lys Ile
865             870             875             880

Lys Tyr Tyr Gly Asn Lys Leu Asn Ala His Leu Asp Ile Thr Asp Asp
                885             890             895

Tyr Pro Asn Ser Arg Asn Lys Val Val Lys Leu Ser Leu Lys Pro Tyr
                900             905             910

Arg Phe Asp Val Tyr Leu Asp Asn Gly Val Tyr Lys Phe Val Thr Val
        915             920             925

Lys Asn Leu Asp Val Ile Lys Lys Glu Asn Tyr Tyr Glu Val Asn Ser
        930             935             940

Lys Cys Tyr Glu Glu Ala Lys Lys Leu Lys Lys Ile Ser Asn Gln Ala
945             950             955             960

Glu Phe Ile Ala Ser Phe Tyr Asn Asn Asp Leu Ile Lys Ile Asn Gly
                965             970             975

Glu Leu Tyr Arg Val Ile Gly Val Asn Asn Asp Leu Leu Asn Arg Ile
                980             985             990

Glu Val Asn Met Ile Asp Ile Thr Tyr Arg Glu Tyr Leu Glu Asn Met
        995             1000            1005

Asn Asp Lys Arg Pro Pro Arg Ile Ile Lys Thr Ile Ala Ser Lys
        1010            1015            1020

Thr Gln Ser Ile Lys Lys Tyr Ser Thr Asp Ile Leu Gly Asn Leu
        1025            1030            1035

Tyr Glu Val Lys Ser Lys Lys His Pro Gln Ile Ile Lys Lys Gly
        1040            1045            1050

<210> SEQ ID NO 85
<211> LENGTH: 1368
<212> TYPE: PRT
<213> ORGANISM: Staphylococcus pyogenes
<220> FEATURE:
<221> NAME/KEY: misc_feature
<222> LOCATION: (1)..(1)
<223> OTHER INFORMATION: Xaa can be any naturally occurring amino acid

<400> SEQUENCE: 85

Xaa Asp Lys Lys Tyr Ser Ile Gly Leu Ala Ile Gly Thr Asn Ser Val
1               5               10              15

Gly Trp Ala Val Ile Thr Asp Glu Tyr Lys Val Pro Ser Lys Lys Phe
                20              25              30

Lys Val Leu Gly Asn Thr Asp Arg His Ser Ile Lys Lys Asn Leu Ile
        35              40              45

Gly Ala Leu Leu Phe Asp Ser Gly Glu Thr Ala Glu Ala Thr Arg Leu
        50              55              60

Lys Arg Thr Ala Arg Arg Arg Tyr Thr Arg Arg Lys Asn Arg Ile Cys
65              70              75              80

Tyr Leu Gln Glu Ile Phe Ser Asn Glu Met Ala Lys Val Asp Asp Ser
                85              90              95

Phe Phe His Arg Leu Glu Glu Ser Phe Leu Val Glu Glu Asp Lys Lys
                100             105             110

His Glu Arg His Pro Ile Phe Gly Asn Ile Val Asp Glu Val Ala Tyr

-continued

```
              115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540
```

-continued

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960
```

-continued

```
Lys Leu Val Ser Asp Phe Arg Lys Asp Phe Gln Phe Tyr Lys Val Arg
              965                 970                 975

Glu Ile Asn Asn Tyr His His Ala His Asp Ala Tyr Leu Asn Ala Val
              980                 985                 990

Val Gly Thr Ala Leu Ile Lys Lys  Tyr Pro Lys Leu Glu  Ser Glu Phe
         995              1000                 1005

Val Tyr  Gly Asp Tyr Lys Val  Tyr Asp Val Arg Lys  Met Ile Ala
    1010             1015              1020

Lys Ser  Glu Gln Glu Ile Gly  Lys Ala Thr Ala Lys  Tyr Phe Phe
    1025             1030              1035

Tyr Ser  Asn Ile Met Asn Phe  Phe Lys Thr Glu Ile  Thr Leu Ala
    1040             1045              1050

Asn Gly  Glu Ile Arg Lys Arg  Pro Leu Ile Glu Thr  Asn Gly Glu
    1055             1060              1065

Thr Gly  Glu Ile Val Trp Asp  Lys Gly Arg Asp Phe  Ala Thr Val
    1070             1075              1080

Arg Lys  Val Leu Ser Met Pro  Gln Val Asn Ile Val  Lys Lys Thr
    1085             1090              1095

Glu Val  Gln Thr Gly Gly Phe  Ser Lys Glu Ser Ile  Leu Pro Lys
    1100             1105              1110

Arg Asn  Ser Asp Lys Leu Ile  Ala Arg Lys Lys Asp  Trp Asp Pro
    1115             1120              1125

Lys Lys  Tyr Gly Gly Phe Asp  Ser Pro Thr Val Ala  Tyr Ser Val
    1130             1135              1140

Leu Val  Val Ala Lys Val Glu  Lys Gly Lys Ser Lys  Lys Leu Lys
    1145             1150              1155

Ser Val  Lys Glu Leu Leu Gly  Ile Thr Ile Met Glu  Arg Ser Ser
    1160             1165              1170

Phe Glu  Lys Asn Pro Ile Asp  Phe Leu Glu Ala Lys  Gly Tyr Lys
    1175             1180              1185

Glu Val  Lys Lys Asp Leu Ile  Ile Lys Leu Pro Lys  Tyr Ser Leu
    1190             1195              1200

Phe Glu  Leu Glu Asn Gly Arg  Lys Arg Met Leu Ala  Ser Ala Gly
    1205             1210              1215

Glu Leu  Gln Lys Gly Asn Glu  Leu Ala Leu Pro Ser  Lys Tyr Val
    1220             1225              1230

Asn Phe  Leu Tyr Leu Ala Ser  His Tyr Glu Lys Leu  Lys Gly Ser
    1235             1240              1245

Pro Glu  Asp Asn Glu Gln Lys  Gln Leu Phe Val Glu  Gln His Lys
    1250             1255              1260

His Tyr  Leu Asp Glu Ile Ile  Glu Gln Ile Ser Glu  Phe Ser Lys
    1265             1270              1275

Arg Val  Ile Leu Ala Asp Ala  Asn Leu Asp Lys Val  Leu Ser Ala
    1280             1285              1290

Tyr Asn  Lys His Arg Asp Lys  Pro Ile Arg Glu Gln  Ala Glu Asn
    1295             1300              1305

Ile Ile  His Leu Phe Thr Leu  Thr Asn Leu Gly Ala  Pro Ala Ala
    1310             1315              1320

Phe Lys  Tyr Phe Asp Thr Thr  Ile Asp Arg Lys Arg  Tyr Thr Ser
    1325             1330              1335

Thr Lys  Glu Val Leu Asp Ala  Thr Leu Ile His Gln  Ser Ile Thr
    1340             1345              1350

Gly Leu  Tyr Glu Thr Arg Ile  Asp Leu Ser Gln Leu  Gly Gly Asp
```

-continued

```
     1355              1360              1365
```

<210> SEQ ID NO 86
<211> LENGTH: 1368
<212> TYPE: PRT
<213> ORGANISM: Artificial Sequence
<220> FEATURE:
<223> OTHER INFORMATION: Synthetic Polypeptide - dCas9

<400> SEQUENCE: 86

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
```

```
             355                    360                    365

Gln Glu Glu Phe Tyr Lys Phe Ile Lys Pro Ile Leu Glu Lys Met Asp
    370                    375                    380

Gly Thr Glu Glu Leu Leu Val Lys Leu Asn Arg Glu Asp Leu Leu Arg
385                    390                    395                    400

Lys Gln Arg Thr Phe Asp Asn Gly Ser Ile Pro His Gln Ile His Leu
                    405                    410                    415

Gly Glu Leu His Ala Ile Leu Arg Arg Gln Glu Asp Phe Tyr Pro Phe
                420                    425                    430

Leu Lys Asp Asn Arg Glu Lys Ile Glu Lys Ile Leu Thr Phe Arg Ile
                435                    440                    445

Pro Tyr Tyr Val Gly Pro Leu Ala Arg Gly Asn Ser Arg Phe Ala Trp
    450                    455                    460

Met Thr Arg Lys Ser Glu Glu Thr Ile Thr Pro Trp Asn Phe Glu Glu
465                    470                    475                    480

Val Val Asp Lys Gly Ala Ser Ala Gln Ser Phe Ile Glu Arg Met Thr
                485                    490                    495

Asn Phe Asp Lys Asn Leu Pro Asn Glu Lys Val Leu Pro Lys His Ser
                500                    505                    510

Leu Leu Tyr Glu Tyr Phe Thr Val Tyr Asn Glu Leu Thr Lys Val Lys
                515                    520                    525

Tyr Val Thr Glu Gly Met Arg Lys Pro Ala Phe Leu Ser Gly Glu Gln
    530                    535                    540

Lys Lys Ala Ile Val Asp Leu Leu Phe Lys Thr Asn Arg Lys Val Thr
545                    550                    555                    560

Val Lys Gln Leu Lys Glu Asp Tyr Phe Lys Lys Ile Glu Cys Phe Asp
                565                    570                    575

Ser Val Glu Ile Ser Gly Val Glu Asp Arg Phe Asn Ala Ser Leu Gly
                580                    585                    590

Thr Tyr His Asp Leu Leu Lys Ile Ile Lys Asp Lys Asp Phe Leu Asp
                595                    600                    605

Asn Glu Glu Asn Glu Asp Ile Leu Glu Asp Ile Val Leu Thr Leu Thr
    610                    615                    620

Leu Phe Glu Asp Arg Glu Met Ile Glu Glu Arg Leu Lys Thr Tyr Ala
625                    630                    635                    640

His Leu Phe Asp Asp Lys Val Met Lys Gln Leu Lys Arg Arg Arg Tyr
                645                    650                    655

Thr Gly Trp Gly Arg Leu Ser Arg Lys Leu Ile Asn Gly Ile Arg Asp
                660                    665                    670

Lys Gln Ser Gly Lys Thr Ile Leu Asp Phe Leu Lys Ser Asp Gly Phe
                675                    680                    685

Ala Asn Arg Asn Phe Met Gln Leu Ile His Asp Asp Ser Leu Thr Phe
    690                    695                    700

Lys Glu Asp Ile Gln Lys Ala Gln Val Ser Gly Gln Gly Asp Ser Leu
705                    710                    715                    720

His Glu His Ile Ala Asn Leu Ala Gly Ser Pro Ala Ile Lys Lys Gly
                725                    730                    735

Ile Leu Gln Thr Val Lys Val Val Asp Glu Leu Val Lys Val Met Gly
                740                    745                    750

Arg His Lys Pro Glu Asn Ile Val Ile Glu Met Ala Arg Glu Asn Gln
                755                    760                    765

Thr Thr Gln Lys Gly Gln Lys Asn Ser Arg Glu Arg Met Lys Arg Ile
    770                    775                    780
```

```
Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
                805             810             815

Gln Asn Gly Arg Asp Met Tyr Val Asp Gln Glu Leu Asp Ile Asn Arg
        820             825             830

Leu Ser Asp Tyr Asp Val Asp Ala Ile Val Pro Gln Ser Phe Leu Lys
        835             840             845

Asp Asp Ser Ile Asp Asn Lys Val Leu Thr Arg Ser Asp Lys Asn Arg
    850             855             860

Gly Lys Ser Asp Asn Val Pro Ser Glu Glu Val Val Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
            915             920             925

Lys His Val Ala Gln Ile Leu Asp Ser Arg Met Asn Thr Lys Tyr Asp
    930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
        995             1000            1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185
```

```
Glu Val Lys Lys Asp Leu Ile  Ile Lys Leu Pro Lys  Tyr Ser Leu
    1190              1195              1200

Phe Glu Leu Glu Asn Gly Arg  Lys Arg Met Leu Ala  Ser Ala Gly
    1205              1210              1215

Glu Leu Gln Lys Gly Asn Glu  Leu Ala Leu Pro Ser  Lys Tyr Val
    1220              1225              1230

Asn Phe Leu Tyr Leu Ala Ser  His Tyr Glu Lys Leu  Lys Gly Ser
    1235              1240              1245

Pro Glu Asp Asn Glu Gln Lys  Gln Leu Phe Val Glu  Gln His Lys
    1250              1255              1260

His Tyr Leu Asp Glu Ile Ile  Glu Gln Ile Ser Glu  Phe Ser Lys
    1265              1270              1275

Arg Val Ile Leu Ala Asp Ala  Asn Leu Asp Lys Val  Leu Ser Ala
    1280              1285              1290

Tyr Asn Lys His Arg Asp Lys  Pro Ile Arg Glu Gln  Ala Glu Asn
    1295              1300              1305

Ile Ile His Leu Phe Thr Leu  Thr Asn Leu Gly Ala  Pro Ala Ala
    1310              1315              1320

Phe Lys Tyr Phe Asp Thr Thr  Ile Asp Arg Lys Arg  Tyr Thr Ser
    1325              1330              1335

Thr Lys Glu Val Leu Asp Ala  Thr Leu Ile His Gln  Ser Ile Thr
    1340              1345              1350

Gly Leu Tyr Glu Thr Arg Ile  Asp Leu Ser Gln Leu  Gly Gly Asp
    1355              1360              1365

<210> SEQ ID NO 87
<211> LENGTH: 199
<212> TYPE: PRT
<213> ORGANISM: Artificial Sequence
<220> FEATURE:
<223> OTHER INFORMATION: Synthetic Polypeptide - Clo051

<400> SEQUENCE: 87

Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
            20                  25                  30

Phe Asp Ser Lys Gln Asn Arg Leu Phe Glu Met Lys Val Leu Glu Leu
        35                  40                  45

Leu Val Asn Glu Tyr Gly Phe Lys Gly Arg His Leu Gly Gly Ser Arg
    50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                85                  90                  95

Ser Gln Ala Asp Glu Met Glu Arg Tyr Val Arg Glu Asn Ser Asn Arg
            100                 105                 110

Asp Glu Glu Val Asn Pro Asn Lys Trp Trp Glu Asn Phe Ser Glu Glu
        115                 120                 125

Val Lys Lys Tyr Tyr Phe Val Phe Ile Ser Gly Ser Phe Lys Gly Lys
    130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175
```

-continued

```
Ser Gly Glu Met Thr Ile Glu Glu Leu Glu Arg Ala Met Phe Asn Asn
            180                 185                 190

Ser Glu Phe Ile Leu Lys Tyr
        195

<210> SEQ ID NO 88
<211> LENGTH: 1591
<212> TYPE: PRT
<213> ORGANISM: Artificial Sequence
<220> FEATURE:
<223> OTHER INFORMATION: Synthetic Polypeptide - dCas9-Clo051

<400> SEQUENCE: 88

Met Ala Pro Lys Lys Lys Arg Lys Val Glu Gly Ile Lys Ser Asn Ile
1               5                   10                  15

Ser Leu Leu Lys Asp Glu Leu Arg Gly Gln Ile Ser His Ile Ser His
            20                  25                  30

Glu Tyr Leu Ser Leu Ile Asp Leu Ala Phe Asp Ser Lys Gln Asn Arg
        35                  40                  45

Leu Phe Glu Met Lys Val Leu Glu Leu Leu Val Asn Glu Tyr Gly Phe
    50                  55                  60

Lys Gly Arg His Leu Gly Gly Ser Arg Lys Pro Asp Gly Ile Val Tyr
65                  70                  75                  80

Ser Thr Thr Leu Glu Asp Asn Phe Gly Ile Ile Val Asp Thr Lys Ala
            85                  90                  95

Tyr Ser Glu Gly Tyr Ser Leu Pro Ile Ser Gln Ala Asp Glu Met Glu
            100                 105                 110

Arg Tyr Val Arg Glu Asn Ser Asn Arg Asp Glu Glu Val Asn Pro Asn
            115                 120                 125

Lys Trp Trp Glu Asn Phe Ser Glu Glu Val Lys Lys Tyr Tyr Phe Val
    130                 135                 140

Phe Ile Ser Gly Ser Phe Lys Gly Lys Phe Glu Glu Gln Leu Arg Arg
145                 150                 155                 160

Leu Ser Met Thr Thr Gly Val Asn Gly Ser Ala Val Asn Val Val Asn
            165                 170                 175

Leu Leu Leu Gly Ala Glu Lys Ile Arg Ser Gly Glu Met Thr Ile Glu
            180                 185                 190

Glu Leu Glu Arg Ala Met Phe Asn Asn Ser Glu Phe Ile Leu Lys Tyr
        195                 200                 205

Gly Gly Gly Gly Ser Asp Lys Lys Tyr Ser Ile Gly Leu Ala Ile Gly
    210                 215                 220

Thr Asn Ser Val Gly Trp Ala Val Ile Thr Asp Glu Tyr Lys Val Pro
225                 230                 235                 240

Ser Lys Lys Phe Lys Val Leu Gly Asn Thr Asp Arg His Ser Ile Lys
            245                 250                 255

Lys Asn Leu Ile Gly Ala Leu Leu Phe Asp Ser Gly Glu Thr Ala Glu
            260                 265                 270

Ala Thr Arg Leu Lys Arg Thr Ala Arg Arg Arg Tyr Thr Arg Arg Lys
            275                 280                 285

Asn Arg Ile Cys Tyr Leu Gln Glu Ile Phe Ser Asn Glu Met Ala Lys
    290                 295                 300

Val Asp Asp Ser Phe Phe His Arg Leu Glu Glu Ser Phe Leu Val Glu
305                 310                 315                 320

Glu Asp Lys Lys His Glu Arg His Pro Ile Phe Gly Asn Ile Val Asp
            325                 330                 335
```

-continued

```
Glu Val Ala Tyr His Glu Lys Tyr Pro Thr Ile Tyr His Leu Arg Lys
            340             345             350

Lys Leu Val Asp Ser Thr Asp Lys Ala Asp Leu Arg Leu Ile Tyr Leu
            355             360             365

Ala Leu Ala His Met Ile Lys Phe Arg Gly His Phe Leu Ile Glu Gly
            370             375             380

Asp Leu Asn Pro Asp Asn Ser Asp Val Asp Lys Leu Phe Ile Gln Leu
385             390             395             400

Val Gln Thr Tyr Asn Gln Leu Phe Glu Glu Asn Pro Ile Asn Ala Ser
                405             410             415

Gly Val Asp Ala Lys Ala Ile Leu Ser Ala Arg Leu Ser Lys Ser Arg
            420             425             430

Arg Leu Glu Asn Leu Ile Ala Gln Leu Pro Gly Glu Lys Lys Asn Gly
            435             440             445

Leu Phe Gly Asn Leu Ile Ala Leu Ser Leu Gly Leu Thr Pro Asn Phe
            450             455             460

Lys Ser Asn Phe Asp Leu Ala Glu Asp Ala Lys Leu Gln Leu Ser Lys
465             470             475             480

Asp Thr Tyr Asp Asp Asp Leu Asp Asn Leu Leu Ala Gln Ile Gly Asp
                485             490             495

Gln Tyr Ala Asp Leu Phe Leu Ala Ala Lys Asn Leu Ser Asp Ala Ile
            500             505             510

Leu Leu Ser Asp Ile Leu Arg Val Asn Thr Glu Ile Thr Lys Ala Pro
            515             520             525

Leu Ser Ala Ser Met Ile Lys Arg Tyr Asp Glu His His Gln Asp Leu
            530             535             540

Thr Leu Leu Lys Ala Leu Val Arg Gln Gln Leu Pro Glu Lys Tyr Lys
545             550             555             560

Glu Ile Phe Phe Asp Gln Ser Lys Asn Gly Tyr Ala Gly Tyr Ile Asp
                565             570             575

Gly Gly Ala Ser Gln Glu Glu Phe Tyr Lys Phe Ile Lys Pro Ile Leu
            580             585             590

Glu Lys Met Asp Gly Thr Glu Glu Leu Leu Val Lys Leu Asn Arg Glu
            595             600             605

Asp Leu Leu Arg Lys Gln Arg Thr Phe Asp Asn Gly Ser Ile Pro His
            610             615             620

Gln Ile His Leu Gly Glu Leu His Ala Ile Leu Arg Arg Gln Glu Asp
625             630             635             640

Phe Tyr Pro Phe Leu Lys Asp Asn Arg Glu Lys Ile Glu Lys Ile Leu
                645             650             655

Thr Phe Arg Ile Pro Tyr Tyr Val Gly Pro Leu Ala Arg Gly Asn Ser
            660             665             670

Arg Phe Ala Trp Met Thr Arg Lys Ser Glu Glu Thr Ile Thr Pro Trp
            675             680             685

Asn Phe Glu Glu Val Val Asp Lys Gly Ala Ser Ala Gln Ser Phe Ile
            690             695             700

Glu Arg Met Thr Asn Phe Asp Lys Asn Leu Pro Asn Glu Lys Val Leu
705             710             715             720

Pro Lys His Ser Leu Leu Tyr Glu Tyr Phe Thr Val Tyr Asn Glu Leu
                725             730             735

Thr Lys Val Lys Tyr Val Thr Glu Gly Met Arg Lys Pro Ala Phe Leu
            740             745             750

Ser Gly Glu Gln Lys Lys Ala Ile Val Asp Leu Leu Phe Lys Thr Asn
```

```
          755              760              765

Arg Lys Val Thr Val Lys Gln Leu Lys Glu Asp Tyr Phe Lys Lys Ile
    770              775              780

Glu Cys Phe Asp Ser Val Glu Ile Ser Gly Val Glu Asp Arg Phe Asn
785              790              795              800

Ala Ser Leu Gly Thr Tyr His Asp Leu Leu Lys Ile Ile Lys Asp Lys
                805              810              815

Asp Phe Leu Asp Asn Glu Glu Asn Glu Asp Ile Leu Glu Asp Ile Val
                820              825              830

Leu Thr Leu Thr Leu Phe Glu Asp Arg Glu Met Ile Glu Glu Arg Leu
                835              840              845

Lys Thr Tyr Ala His Leu Phe Asp Asp Lys Val Met Lys Gln Leu Lys
    850              855              860

Arg Arg Arg Tyr Thr Gly Trp Gly Arg Leu Ser Arg Lys Leu Ile Asn
865              870              875              880

Gly Ile Arg Asp Lys Gln Ser Gly Lys Thr Ile Leu Asp Phe Leu Lys
                885              890              895

Ser Asp Gly Phe Ala Asn Arg Asn Phe Met Gln Leu Ile His Asp Asp
                900              905              910

Ser Leu Thr Phe Lys Glu Asp Ile Gln Lys Ala Gln Val Ser Gly Gln
                915              920              925

Gly Asp Ser Leu His Glu His Ile Ala Asn Leu Ala Gly Ser Pro Ala
    930              935              940

Ile Lys Lys Gly Ile Leu Gln Thr Val Lys Val Val Asp Glu Leu Val
945              950              955              960

Lys Val Met Gly Arg His Lys Pro Glu Asn Ile Val Ile Glu Met Ala
                965              970              975

Arg Glu Asn Gln Thr Thr Gln Lys Gly Gln Lys Asn Ser Arg Glu Arg
                980              985              990

Met Lys Arg Ile Glu Glu Gly Ile  Lys Glu Leu Gly Ser  Gln Ile Leu
    995              1000              1005

Lys Glu  His Pro Val Glu Asn  Thr Gln Leu Gln Asn  Glu Lys Leu
    1010              1015              1020

Tyr Leu  Tyr Tyr Leu Gln Asn  Gly Arg Asp Met Tyr  Val Asp Gln
    1025              1030              1035

Glu Leu  Asp Ile Asn Arg Leu  Ser Asp Tyr Asp Val  Asp Ala Ile
    1040              1045              1050

Val Pro  Gln Ser Phe Leu Lys  Asp Asp Ser Ile Asp  Asn Lys Val
    1055              1060              1065

Leu Thr  Arg Ser Asp Lys Asn  Arg Gly Lys Ser Asp  Asn Val Pro
    1070              1075              1080

Ser Glu  Glu Val Val Lys Lys  Met Lys Asn Tyr Trp  Arg Gln Leu
    1085              1090              1095

Leu Asn  Ala Lys Leu Ile Thr  Gln Arg Lys Phe Asp  Asn Leu Thr
    1100              1105              1110

Lys Ala  Glu Arg Gly Gly Leu  Ser Glu Leu Asp Lys  Ala Gly Phe
    1115              1120              1125

Ile Lys  Arg Gln Leu Val Glu  Thr Arg Gln Ile Thr  Lys His Val
    1130              1135              1140

Ala Gln  Ile Leu Asp Ser Arg  Met Asn Thr Lys Tyr  Asp Glu Asn
    1145              1150              1155

Asp Lys  Leu Ile Arg Glu Val  Lys Val Ile Thr Leu  Lys Ser Lys
    1160              1165              1170
```

-continued

```
Leu Val Ser Asp Phe Arg Lys Asp Phe Gln Phe Tyr Lys Val Arg
1175            1180             1185

Glu Ile Asn Asn Tyr His His Ala His Asp Ala Tyr Leu Asn Ala
1190            1195             1200

Val Val Gly Thr Ala Leu Ile Lys Lys Tyr Pro Lys Leu Glu Ser
1205            1210             1215

Glu Phe Val Tyr Gly Asp Tyr Lys Val Tyr Asp Val Arg Lys Met
1220            1225             1230

Ile Ala Lys Ser Glu Gln Glu Ile Gly Lys Ala Thr Ala Lys Tyr
1235            1240             1245

Phe Phe Tyr Ser Asn Ile Met Asn Phe Phe Lys Thr Glu Ile Thr
1250            1255             1260

Leu Ala Asn Gly Glu Ile Arg Lys Arg Pro Leu Ile Glu Thr Asn
1265            1270             1275

Gly Glu Thr Gly Glu Ile Val Trp Asp Lys Gly Arg Asp Phe Ala
1280            1285             1290

Thr Val Arg Lys Val Leu Ser Met Pro Gln Val Asn Ile Val Lys
1295            1300             1305

Lys Thr Glu Val Gln Thr Gly Gly Phe Ser Lys Glu Ser Ile Leu
1310            1315             1320

Pro Lys Arg Asn Ser Asp Lys Leu Ile Ala Arg Lys Lys Asp Trp
1325            1330             1335

Asp Pro Lys Lys Tyr Gly Gly Phe Asp Ser Pro Thr Val Ala Tyr
1340            1345             1350

Ser Val Leu Val Val Ala Lys Val Glu Lys Gly Lys Ser Lys Lys
1355            1360             1365

Leu Lys Ser Val Lys Glu Leu Leu Gly Ile Thr Ile Met Glu Arg
1370            1375             1380

Ser Ser Phe Glu Lys Asn Pro Ile Asp Phe Leu Glu Ala Lys Gly
1385            1390             1395

Tyr Lys Glu Val Lys Lys Asp Leu Ile Ile Lys Leu Pro Lys Tyr
1400            1405             1410

Ser Leu Phe Glu Leu Glu Asn Gly Arg Lys Arg Met Leu Ala Ser
1415            1420             1425

Ala Gly Glu Leu Gln Lys Gly Asn Glu Leu Ala Leu Pro Ser Lys
1430            1435             1440

Tyr Val Asn Phe Leu Tyr Leu Ala Ser His Tyr Glu Lys Leu Lys
1445            1450             1455

Gly Ser Pro Glu Asp Asn Glu Gln Lys Gln Leu Phe Val Glu Gln
1460            1465             1470

His Lys His Tyr Leu Asp Glu Ile Ile Glu Gln Ile Ser Glu Phe
1475            1480             1485

Ser Lys Arg Val Ile Leu Ala Asp Ala Asn Leu Asp Lys Val Leu
1490            1495             1500

Ser Ala Tyr Asn Lys His Arg Asp Lys Pro Ile Arg Glu Gln Ala
1505            1510             1515

Glu Asn Ile Ile His Leu Phe Thr Leu Thr Asn Leu Gly Ala Pro
1520            1525             1530

Ala Ala Phe Lys Tyr Phe Asp Thr Thr Ile Asp Arg Lys Arg Tyr
1535            1540             1545

Thr Ser Thr Lys Glu Val Leu Asp Ala Thr Leu Ile His Gln Ser
1550            1555             1560
```

```
Ile Thr  Gly Leu Tyr Glu Thr  Arg Ile Asp Leu Ser  Gln Leu Gly
    1565                 1570                 1575

Gly Asp  Gly Ser Pro Lys Lys  Lys Arg Lys Val Ser  Ser
    1580                 1585                 1590
```

<210> SEQ ID NO 89
<211> LENGTH: 4776
<212> TYPE: DNA
<213> ORGANISM: Artificial Sequence
<220> FEATURE:
<223> OTHER INFORMATION: Synthetic Polynucleotide - dCas9-Clo051

<400> SEQUENCE: 89

```
atggcaccaa agaagaaaag aaaagtggag ggcatcaagt caaacatcag cctgctgaaa      60
gacgaactgc ggggacagat tagtcacatc agtcacgagt acctgtcact gattgatctg     120
gccttcgaca gcaagcagaa tagactgttt gagatgaaag tgctggaact gctggtcaac     180
gagtatggct tcaagggcag acatctgggc gggtctagga aacctgacgg catcgtgtac     240
agtaccacac tggaagacaa cttcggaatc attgtcgata ccaaggctta ttccgagggc     300
tactctctgc caattagtca ggcagatgag atggaaaggt acgtgcgcga aaactcaaat     360
agggacgagg aagtcaaccc caataagtgg tgggagaatt tcagcgagga agtgaagaaa     420
tactacttcg tctttatctc aggcagcttc aaagggagt ttgaggaaca gctgcggaga     480
ctgtccatga ctaccggggt gaacggatct gctgtcaacg tggtcaatct gctgctgggc     540
gcagaaaaga tcaggtccgg ggagatgaca attgaggaac tggaacgcgc catgttcaac     600
aattctgagt ttatcctgaa gtatggaggc gggggaagcg ataagaaata ctccatcgga     660
ctggccattg gcaccaattc cgtgggctgg gctgtcatca gacgagta caaggtgcca     720 agcaagaagt tcaaggtcct ggggaacacc gatcgccaca gtatcaagaa aaatctgatt     780
ggagccctgc tgttcgactc aggcgagact gctgaagcaa cccgactgaa gcggactgct     840
aggcgccgat atacccggag aaaaaatcgg atctgctacc tgcaggaaat tttcagcaac     900
gagatggcca aggtggacga tagtttcttt caccgcctgg aggaatcatt cctggtggag     960
gaagataaga aacacgagcg gcatcccatc tttggcaaca ttgtggacga agtcgcttat    1020
cacgagaagt accctactat ctatcatctg aggaagaaac tggtggactc caccgataag    1080
gcagacctgc gcctgatcta tctggccctg gctcacatga tcaagttccg ggggcatttt    1140
ctgatcgagg gagatctgaa ccctgacaat tctgatgtgg acaagctgtt catccagctg    1200
gtccagacat acaatcagct gtttgaggaa aacccaatta atgcctcagg cgtggacgca    1260
aaggccatcc tgagcgccag actgtccaaa tctaggcgcc tggaaaacct gatcgctcag    1320
ctgccaggag agaagaaaaa cggcctgttt gggaatctga ttgcactgtc cctgggcctg    1380
acacccaact tcaagtctaa ttttgatctg gccgaggacg ctaagctgca gctgtccaaa    1440
gacacttatg acgatgacct ggataacctg ctggctcaga tcggcgatca gtacgcagac    1500
ctgttcctgg ccgctaagaa tctgagtgac gccatcctgc tgtcagatat tctgcgcgtg    1560
aacacagaga ttactaaggc cccactgagt gcttcaatga tcaaaagata tgacgagcac    1620
catcaggatc tgaccctgct gaaggctctg gtgaggcagc agctgcccga aaatacaag    1680 gaaatcttct ttgatcagag caagaatgga tacgccggct atattgacgg cgggggcttcc    1740 caggaggagt ctacaagtt catcaagccc attctggaaa agatggacgg caccgaggaa    1800
ctgctggtga agctgaatcg ggaggacctg ctgagaaaac agaggacatt tgataacgga    1860
agcatccctc accagattca tctgggcgaa ctgcacgcca tcctgcgacg gcaggaggac    1920
```

-continued

```
ttctacccat ttctgaagga taaccgcgag aaaatcgaaa agatcctgac cttcagaatc   1980
ccctactatg tggggcctct ggcacgggga aatagtagat ttgcctggat gacaagaaag   2040
tcagaggaaa ctatcacccc ctggaacttc gaggaagtgg tcgataaagg cgctagcgca   2100
cagtccttca ttgaaaggat gacaaatttt gacaagaacc tgccaaatga gaaggtgctg   2160
cccaaacaca gcctgctgta cgaatatttc acagtgtata acgagctgac taaagtgaag   2220
tacgtcaccg aagggatgcg caagcccgca ttcctgtccg gagagcagaa gaaagccatc   2280
gtggacctgc tgtttaagac aaatcggaaa gtgactgtca aacagctgaa ggaagactat   2340
ttcaagaaaa ttgagtgttt cgattcagtg gaaatcagcg gcgtcgagga caggtttaac   2400
gcctccctgg ggacctacca cgatctgctg aagatcatca aggataagga cttcctggac   2460
aacgaggaaa atgaggacat cctggaggac attgtgctga cactgactct gtttgaggat   2520
cgcgaaatga tcgaggaacg actgaagact tatgcccatc tgttcgatga caaagtgatg   2580
aagcagctga aaagaaggcg ctacaccgga tggggacgcc tgagccgaaa actgatcaat   2640
gggattagag acaagcagag cggaaaaact atcctggact ttctgaagtc cgatggcttc   2700
gccaacagga acttcatgca gctgattcac gatgactctc tgaccttcaa ggaggacatc   2760
cagaaagcac aggtgtctgg ccaggggac agtctgcacg agcatatcgc aaacctggcc   2820
ggcagccccg ccatcaagaa aagggattct cagaccgtga aggtggtgga cgaactggtc   2880
aaggtcatgg gacgacacaa acctgagaac atcgtgattg agatggcccg cgaaaatcag   2940
acaactcaga agggccagaa aaacagtcga gaacggatga agagaatcga ggaaggcatc   3000
aaggagctgg ggtcacagat cctgaaggag catcctgtgg aaaacactca gctgcagaat   3060
gagaaactgt atctgtacta tctgcagaat ggacgggata tgtacgtgga ccaggagctg   3120
gatattaaca gactgagtga ttatgacgtg gatgccatcg tccctcagag cttcctgaag   3180
gatgactcca ttgacaacaa ggtgctgacc aggtccgaca agaaccgcgg caaatcagat   3240
aatgtgccaa gcgaggaagt ggtcaagaaa atgaagaact actggaggca gctgctgaat   3300
gccaagctga tcacacagcg gaaatttgat aacctgacta aggcagaaag aggaggcctg   3360
tctgagctgg acaaggccgg cttcatcaag cggcagctgg tggagacaag acagatcact   3420
aagcacgtcg ctcagattct ggatagcaga atgaacacaa agtacgatga aaacgacaag   3480
ctgatcaggg aggtgaaagt cattactctg aaatccaagc tggtgtctga ctttagaaag   3540
gatttccagt tttataaagt cagggagatc aacaactacc accatgctca tgacgcatac   3600
ctgaacgcag tggtcgggac cgccctgatt aagaaatacc ccaagctgga gtccgagttc   3660
gtgtacggag actataaagt gtacgatgtc cggaagatga tcgccaaatc tgagcaggaa   3720
attggcaagg ccaccgctaa gtatttcttt tacagtaaca tcatgaattt ctttaagacc   3780
gaaatcacac tggcaaatgg ggagatcaga aaaaggcctc tgattgagac caacggggag   3840
acaggagaaa tcgtgtggga caagggaagg gattttgcta ccgtgcgcaa agtcctgtcc   3900
atgccccaag tgaatattgt caagaaaact gaagtgcaga ccgggggatt ctctaaggag   3960
agtattctgc ctaagcgaaa ctctgataaa ctgatcgccc ggaagaaaga ctgggacccc   4020
aagaagtatg gcgggttcga ctctccaaca gtggcttaca gtgtcctggt ggtcgcaaag   4080
gtggaaaagg ggaagtccaa gaaactgaag tctgtcaaag agctgctggg aatcactatt   4140
atggaacgca gctccttcga gaagaatcct atcgatttc tggaagccaa gggctataaa   4200
gaggtgaaga aagacctgat cattaagctg ccaaaatact cactgtttga gctggaaaac   4260
```

```
ggacgaaagc gaatgctggc aagcgccgga gaactgcaga agggcaatga gctggccctg      4320
ccctccaaat acgtgaactt cctgtatctg gctagccact acgagaaact gaaggggtcc      4380
cctgaggata acgaacagaa gcagctgttt gtggagcagc acaaacatta tctggacgag      4440
atcattgaac agatttcaga gttcagcaag agagtgatcc tggctgacgc aaatctggat      4500
aaagtcctga gcgcatacaa caagcaccga gacaaaccaa tccgggagca ggccgaaaat      4560
atcattcatc tgttcaccct gacaaacctg ggcgccctg cagccttcaa gtattttgac      4620
accacaatcg atcggaagag atacacttct accaaagagg tgctggatgc taccctgatc      4680
caccagagta ttaccggcct gtatgagaca cgcatcgacc tgtcacagct gggaggcgat      4740
gggagcccca agaaaaagcg gaaggtgtct agttaa                                4776
```

```
<210> SEQ ID NO 90
<211> LENGTH: 1588
<212> TYPE: PRT
<213> ORGANISM: Artificial Sequence
<220> FEATURE:
<223> OTHER INFORMATION: Synthetic Polypeptide - dCas9-Clo051

<400> SEQUENCE: 90

Met Pro Lys Lys Lys Arg Lys Val Glu Gly Ile Lys Ser Asn Ile Ser
1               5                   10                  15

Leu Leu Lys Asp Glu Leu Arg Gly Gln Ile Ser His Ile Ser His Glu
                20                  25                  30

Tyr Leu Ser Leu Ile Asp Leu Ala Phe Asp Ser Lys Gln Asn Arg Leu
            35                  40                  45

Phe Glu Met Lys Val Leu Glu Leu Leu Val Asn Glu Tyr Gly Phe Lys
        50                  55                  60

Gly Arg His Leu Gly Gly Ser Arg Lys Pro Asp Gly Ile Val Tyr Ser
65                  70                  75                  80

Thr Thr Leu Glu Asp Asn Phe Gly Ile Ile Val Asp Thr Lys Ala Tyr
                85                  90                  95

Ser Glu Gly Tyr Ser Leu Pro Ile Ser Gln Ala Asp Glu Met Glu Arg
                100                 105                 110

Tyr Val Arg Glu Asn Ser Asn Arg Asp Glu Glu Val Asn Pro Asn Lys
            115                 120                 125

Trp Trp Glu Asn Phe Ser Glu Glu Val Lys Lys Tyr Tyr Phe Val Phe
        130                 135                 140

Ile Ser Gly Ser Phe Lys Gly Lys Phe Glu Glu Gln Leu Arg Arg Leu
145                 150                 155                 160

Ser Met Thr Thr Gly Val Asn Gly Ser Ala Val Asn Val Val Asn Leu
                165                 170                 175

Leu Leu Gly Ala Glu Lys Ile Arg Ser Gly Glu Met Thr Ile Glu Glu
                180                 185                 190

Leu Glu Arg Ala Met Phe Asn Asn Ser Glu Phe Ile Leu Lys Tyr Gly
            195                 200                 205

Gly Gly Gly Ser Asp Lys Lys Tyr Ser Ile Gly Leu Ala Ile Gly Thr
        210                 215                 220

Asn Ser Val Gly Trp Ala Val Ile Thr Asp Glu Tyr Lys Val Pro Ser
225                 230                 235                 240

Lys Lys Phe Lys Val Leu Gly Asn Thr Asp Arg His Ser Ile Lys Lys
                245                 250                 255

Asn Leu Ile Gly Ala Leu Leu Phe Asp Ser Gly Glu Thr Ala Glu Ala
                260                 265                 270
```

-continued

```
Thr Arg Leu Lys Arg Thr Ala Arg Arg Arg Tyr Thr Arg Arg Lys Asn
        275              280              285

Arg Ile Cys Tyr Leu Gln Glu Ile Phe Ser Asn Glu Met Ala Lys Val
        290              295              300

Asp Asp Ser Phe Phe His Arg Leu Glu Glu Ser Phe Leu Val Glu Glu
305              310              315              320

Asp Lys Lys His Glu Arg His Pro Ile Phe Gly Asn Ile Val Asp Glu
                325              330              335

Val Ala Tyr His Glu Lys Tyr Pro Thr Ile Tyr His Leu Arg Lys Lys
                340              345              350

Leu Val Asp Ser Thr Asp Lys Ala Asp Leu Arg Leu Ile Tyr Leu Ala
        355              360              365

Leu Ala His Met Ile Lys Phe Arg Gly His Phe Leu Ile Glu Gly Asp
        370              375              380

Leu Asn Pro Asp Asn Ser Asp Val Asp Lys Leu Phe Ile Gln Leu Val
385              390              395              400

Gln Thr Tyr Asn Gln Leu Phe Glu Glu Asn Pro Ile Asn Ala Ser Gly
                405              410              415

Val Asp Ala Lys Ala Ile Leu Ser Ala Arg Leu Ser Lys Ser Arg Arg
                420              425              430

Leu Glu Asn Leu Ile Ala Gln Leu Pro Gly Glu Lys Lys Asn Gly Leu
        435              440              445

Phe Gly Asn Leu Ile Ala Leu Ser Leu Gly Leu Thr Pro Asn Phe Lys
        450              455              460

Ser Asn Phe Asp Leu Ala Glu Asp Ala Lys Leu Gln Leu Ser Lys Asp
465              470              475              480

Thr Tyr Asp Asp Asp Leu Asp Asn Leu Leu Ala Gln Ile Gly Asp Gln
                485              490              495

Tyr Ala Asp Leu Phe Leu Ala Ala Lys Asn Leu Ser Asp Ala Ile Leu
        500              505              510

Leu Ser Asp Ile Leu Arg Val Asn Thr Glu Ile Thr Lys Ala Pro Leu
        515              520              525

Ser Ala Ser Met Ile Lys Arg Tyr Asp Glu His His Gln Asp Leu Thr
        530              535              540

Leu Leu Lys Ala Leu Val Arg Gln Gln Leu Pro Glu Lys Tyr Lys Glu
545              550              555              560

Ile Phe Phe Asp Gln Ser Lys Asn Gly Tyr Ala Gly Tyr Ile Asp Gly
                565              570              575

Gly Ala Ser Gln Glu Glu Phe Tyr Lys Phe Ile Lys Pro Ile Leu Glu
                580              585              590

Lys Met Asp Gly Thr Glu Glu Leu Leu Val Lys Leu Asn Arg Glu Asp
        595              600              605

Leu Leu Arg Lys Gln Arg Thr Phe Asp Asn Gly Ser Ile Pro His Gln
        610              615              620

Ile His Leu Gly Glu Leu His Ala Ile Leu Arg Arg Gln Glu Asp Phe
625              630              635              640

Tyr Pro Phe Leu Lys Asp Asn Arg Glu Lys Ile Glu Lys Ile Leu Thr
                645              650              655

Phe Arg Ile Pro Tyr Tyr Val Gly Pro Leu Ala Arg Gly Asn Ser Arg
                660              665              670

Phe Ala Trp Met Thr Arg Lys Ser Glu Glu Thr Ile Thr Pro Trp Asn
        675              680              685

Phe Glu Glu Val Val Asp Lys Gly Ala Ser Ala Gln Ser Phe Ile Glu
```

-continued

```
        690              695              700

Arg Met Thr Asn Phe Asp Lys Asn Leu Pro Asn Glu Lys Val Leu Pro
705                  710              715                  720

Lys His Ser Leu Leu Tyr Glu Tyr Phe Thr Val Tyr Asn Glu Leu Thr
                725              730                  735

Lys Val Lys Tyr Val Thr Glu Gly Met Arg Lys Pro Ala Phe Leu Ser
            740              745              750

Gly Glu Gln Lys Lys Ala Ile Val Asp Leu Leu Phe Lys Thr Asn Arg
        755              760              765

Lys Val Thr Val Lys Gln Leu Lys Glu Asp Tyr Phe Lys Lys Ile Glu
    770              775              780

Cys Phe Asp Ser Val Glu Ile Ser Gly Val Glu Asp Arg Phe Asn Ala
785              790              795                  800

Ser Leu Gly Thr Tyr His Asp Leu Leu Lys Ile Ile Lys Asp Lys Asp
                805              810              815

Phe Leu Asp Asn Glu Glu Asn Glu Asp Ile Leu Glu Asp Ile Val Leu
            820              825              830

Thr Leu Thr Leu Phe Glu Asp Arg Glu Met Ile Glu Glu Arg Leu Lys
            835              840              845

Thr Tyr Ala His Leu Phe Asp Asp Lys Val Met Lys Gln Leu Lys Arg
    850              855              860

Arg Arg Tyr Thr Gly Trp Gly Arg Leu Ser Arg Lys Leu Ile Asn Gly
865              870              875                  880

Ile Arg Asp Lys Gln Ser Gly Lys Thr Ile Leu Asp Phe Leu Lys Ser
                885              890              895

Asp Gly Phe Ala Asn Arg Asn Phe Met Gln Leu Ile His Asp Asp Ser
            900              905              910

Leu Thr Phe Lys Glu Asp Ile Gln Lys Ala Gln Val Ser Gly Gln Gly
            915              920              925

Asp Ser Leu His Glu His Ile Ala Asn Leu Ala Gly Ser Pro Ala Ile
    930              935              940

Lys Lys Gly Ile Leu Gln Thr Val Lys Val Val Asp Glu Leu Val Lys
945              950              955                  960

Val Met Gly Arg His Lys Pro Glu Asn Ile Val Ile Glu Met Ala Arg
                965              970              975

Glu Asn Gln Thr Thr Gln Lys Gly Gln Lys Asn Ser Arg Glu Arg Met
            980              985              990

Lys Arg Ile Glu Glu Gly Ile Lys  Glu Leu Gly Ser Gln  Ile Leu Lys
        995              1000                1005

Glu His  Pro Val Glu Asn Thr  Gln Leu Gln Asn Glu  Lys Leu Tyr
    1010              1015                1020

Leu Tyr  Tyr Leu Gln Asn Gly  Arg Asp Met Tyr Val  Asp Gln Glu
    1025              1030                1035

Leu Asp  Ile Asn Arg Leu Ser  Asp Tyr Asp Val Asp  Ala Ile Val
    1040              1045                1050

Pro Gln  Ser Phe Leu Lys Asp  Asp Ser Ile Asp Asn  Lys Val Leu
    1055              1060                1065

Thr Arg  Ser Asp Lys Asn Arg  Gly Lys Ser Asp Asn  Val Pro Ser
    1070              1075                1080

Glu Glu  Val Val Lys Lys Met  Lys Asn Tyr Trp Arg  Gln Leu Leu
    1085              1090                1095

Asn Ala  Lys Leu Ile Thr Gln  Arg Lys Phe Asp Asn  Leu Thr Lys
    1100              1105                1110
```

-continued

```
Ala Glu  Arg Gly Gly Leu Ser  Glu Leu Asp Lys Ala  Gly Phe Ile
    1115                1120                1125

Lys Arg  Gln Leu Val Glu Thr  Arg Gln Ile Thr Lys  His Val Ala
    1130                1135                1140

Gln Ile  Leu Asp Ser Arg Met  Asn Thr Lys Tyr Asp  Glu Asn Asp
    1145                1150                1155

Lys Leu  Ile Arg Glu Val Lys  Val Ile Thr Leu Lys  Ser Lys Leu
    1160                1165                1170

Val Ser  Asp Phe Arg Lys Asp  Phe Gln Phe Tyr Lys  Val Arg Glu
    1175                1180                1185

Ile Asn  Asn Tyr His His Ala  His Asp Ala Tyr Leu  Asn Ala Val
    1190                1195                1200

Val Gly  Thr Ala Leu Ile Lys  Lys Tyr Pro Lys Leu  Glu Ser Glu
    1205                1210                1215

Phe Val  Tyr Gly Asp Tyr Lys  Val Tyr Asp Val Arg  Lys Met Ile
    1220                1225                1230

Ala Lys  Ser Glu Gln Glu Ile  Gly Lys Ala Thr Ala  Lys Tyr Phe
    1235                1240                1245

Phe Tyr  Ser Asn Ile Met Asn  Phe Phe Lys Thr Glu  Ile Thr Leu
    1250                1255                1260

Ala Asn  Gly Glu Ile Arg Lys  Arg Pro Leu Ile Glu  Thr Asn Gly
    1265                1270                1275

Glu Thr  Gly Glu Ile Val Trp  Asp Lys Gly Arg Asp  Phe Ala Thr
    1280                1285                1290

Val Arg  Lys Val Leu Ser Met  Pro Gln Val Asn Ile  Val Lys Lys
    1295                1300                1305

Thr Glu  Val Gln Thr Gly Gly  Phe Ser Lys Glu Ser  Ile Leu Pro
    1310                1315                1320

Lys Arg  Asn Ser Asp Lys Leu  Ile Ala Arg Lys Lys  Asp Trp Asp
    1325                1330                1335

Pro Lys  Lys Tyr Gly Gly Phe  Asp Ser Pro Thr Val  Ala Tyr Ser
    1340                1345                1350

Val Leu  Val Val Ala Lys Val  Glu Lys Gly Lys Ser  Lys Lys Leu
    1355                1360                1365

Lys Ser  Val Lys Glu Leu Leu  Gly Ile Thr Ile Met  Glu Arg Ser
    1370                1375                1380

Ser Phe  Glu Lys Asn Pro Ile  Asp Phe Leu Glu Ala  Lys Gly Tyr
    1385                1390                1395

Lys Glu  Val Lys Lys Asp Leu  Ile Ile Lys Leu Pro  Lys Tyr Ser
    1400                1405                1410

Leu Phe  Glu Leu Glu Asn Gly  Arg Lys Arg Met Leu  Ala Ser Ala
    1415                1420                1425

Gly Glu  Leu Gln Lys Gly Asn  Glu Leu Ala Leu Pro  Ser Lys Tyr
    1430                1435                1440

Val Asn  Phe Leu Tyr Leu Ala  Ser His Tyr Glu Lys  Leu Lys Gly
    1445                1450                1455

Ser Pro  Glu Asp Asn Glu Gln  Lys Gln Leu Phe Val  Glu Gln His
    1460                1465                1470

Lys His  Tyr Leu Asp Glu Ile  Ile Glu Gln Ile Ser  Glu Phe Ser
    1475                1480                1485

Lys Arg  Val Ile Leu Ala Asp  Ala Asn Leu Asp Lys  Val Leu Ser
    1490                1495                1500
```

-continued

```
Ala Tyr  Asn Lys His Arg Asp  Lys Pro Ile Arg Glu  Gln Ala Glu
    1505              1510              1515

Asn Ile  Ile His Leu Phe Thr  Leu Thr Asn Leu Gly  Ala Pro Ala
    1520              1525              1530

Ala Phe  Lys Tyr Phe Asp Thr  Thr Ile Asp Arg Lys  Arg Tyr Thr
    1535              1540              1545

Ser Thr  Lys Glu Val Leu Asp  Ala Thr Leu Ile His  Gln Ser Ile
    1550              1555              1560

Thr Gly  Leu Tyr Glu Thr Arg  Ile Asp Leu Ser Gln  Leu Gly Gly
    1565              1570              1575

Asp Gly  Ser Pro Lys Lys Lys  Arg Lys Val
    1580              1585
```

```
<210> SEQ ID NO 91
<211> LENGTH: 4767
<212> TYPE: DNA
<213> ORGANISM: Artificial Sequence
<220> FEATURE:
<223> OTHER INFORMATION: Synthetic Polynucleotide - dCas9-Clo051

<400> SEQUENCE: 91
atgcctaaga agaagcggaa ggtggaaggc atcaaaagca acatctccct cctgaaagac      60
gaactccggg ggcagattag ccacattagt cacgaatacc tctccctcat cgacctggct     120
ttcgatagca agcagaacag gctctttgag atgaaagtgc tggaactgct cgtcaatgag     180
tacgggttca agggtcgaca cctcggcgga tctaggaaac agacggcat cgtgtatagt     240 accacactgg aagacaactt tgggatcatt gtggatcca aggcatactc tgagggttat      300
agtctgccca tttcacaggc cgacgagatg aacggtacg tgcgcgagaa ctcaaataga      360
gatgaggaag tcaaccctaa caagtggtgg gagaacttct ctgaggaagt gaagaaatac     420
tacttcgtct ttatcagcgg gtccttcaag ggtaaatttg aggaacagct caggagactg     480
agcatgacta ccggcgtgaa tggcagcgcc gtcaacgtgg tcaatctgct cctgggcgct     540
gaaaagattc ggagcggaga tgaccatc gaagagctgg agagggcaat gtttaataat     600
agcgagttta tcctgaaata cggtggcggt ggatccgata aaaagtattc tattggttta     660
gccatcggca ctaattccgt tggatgggct gtcataaccg atgaatacaa agtaccttca     720
aagaaattta aggtgttggg gaacacagac cgtcattcga ttaaaaagaa tcttatcggt     780
gccctcctat tcgatagtgg cgaaacggca gaggcgactc gcctgaaacg aaccgctcgg     840
agaaggtata cacgtcgcaa gaaccgaata tgttacttac aagaaatttt tagcaatgag     900
atggccaaag ttgacgattc tttctttcac cgtttggaag agtccttcct tgtcgaagag     960
gacaagaaac atgaacggca ccccatcttt ggaaacatag tagatgaggt ggcatatcat    1020
gaaaagtacc caacgattta tcacctcaga aaaaagctag ttgactcaac tgataaagcg    1080
gacctgaggt taatctactt ggctcttgcc catatgataa agttccgtgg cacttctc     1140 attgagggtg atctaaatcc ggacaactcg gatgtcgaca aactgttcat ccagttagta    1200
caaacctata atcagttgtt tgaagagaac cctataaatg caagtggcgt ggatgcgaag    1260
gctattctta gcgcccgcct ctctaaatcc gacggctag aaaacctgat cgcacaatta    1320
cccggagaga agaaaaatgg gttgttcggt aaccttatag cgctctcact aggcctgaca    1380
ccaaatttta gtcgaactt cgacttagct gaagatgcca aattgcagct tagtaaggac    1440
acgtacgatg acgatctcga caatctactg gcacaaattg agatcagta tgcggactta    1500 tttttggctg ccaaaaacct tagcgatgca atcctcctat ctgacatact gagagttaat    1560
```

```
actgagatta ccaaggcgcc gttatccgct tcaatgatca aaaggtacga tgaacatcac      1620
caagacttga cacttctcaa ggccctagtc cgtcagcaac tgcctgagaa atataaggaa      1680
atattctttg atcagtcgaa aaacgggtac gcaggttata ttgacggcgg agcgagtcaa      1740
gaggaattct acaagtttat caaacccata ttagagaaga tggatgggac ggaagagttg      1800
cttgtaaaac tcaatcgcga agatctactg cgaaagcagc ggactttcga caacggtagc      1860
attccacatc aaatccactt aggcgaattg catgctatac ttagaaggca ggaggatttt      1920
tatccgttcc tcaaagacaa tcgtgaaaag attgagaaaa tcctaacctt tcgcatacct      1980
tactatgtgg gacccctggc ccgagggaac tctcggttcg catggatgac aagaaagtcc      2040
gaagaaacga ttactccatg gaattttgag gaagttgtcg ataaaggtgc gtcagctcaa      2100
tcgttcatcg agaggatgac caactttgac aagaatttac cgaacgaaaa agtattgcct      2160
aagcacagtt tactttacga gtatttcaca gtgtacaatg aactcacgaa agttaagtat      2220
gtcactgagg gcatgcgtaa acccgccttt ctaagcggag aacagaagaa agcaatagta      2280
gatctgttat tcaagaccaa ccgcaaagtg acagttaagc aattgaaaga ggactacttt      2340
aagaaaattg aatgcttcga ttctgtcgag atctccgggg tagaagatcg atttaatgcg      2400
tcacttggta cgtatcatga cctcctaaag ataattaaag ataaggactt cctggataac      2460
gaagagaatg aagatatctt agaagatata gtgttgactc ttaccctctt tgaagatcgg      2520
gaaatgattg aggaaagact aaaaacatac gctcacctgt tcgacgataa ggttatgaaa      2580
cagttaaaga ggcgtcgcta tacgggctgg ggacgattgt cgcggaaact tatcaacggg      2640
ataagagaca agcaaagtgg taaaactatt ctcgattttc taaagagcga cggcttcgcc      2700
aataggaact ttatgcagct gatccatgat gactctttaa ccttcaaaga ggatatacaa      2760
aaggcacagg tttccggaca aggggactca ttgcacgaac atattgcgaa tcttgctggt      2820
tcgccagcca tcaaaaaggg catactccag acagtcaaag tagtggatga gctagttaag      2880
gtcatgggac gtcacaaacc ggaaaacatt gtaatcgaga tggcacgcga aaatcaaacg      2940
actcagaagg ggcaaaaaaa cagtcgagag cggatgaaga aatagaaga gggtattaaa      3000 gaactgggca gccagatctt aaaggagcat cctgtggaaa atacccaatt gcagaacgag      3060
aaactttacc tctattacct acaaaatgga agggacatgt atgttgatca ggaactggac      3120
ataaaccgtt tatctgatta cgacgtcgat gccattgtac cccaatcctt tttgaaggac      3180
gattcaatcg acaataaagt gcttacacgc tcggataaga accgagggaa aagtgacaat      3240
gttccaagcg aggaagtcgt aaagaaaatg aagaactatt ggcggcagct cctaaatgcg      3300
aaactgataa cgcaaagaaa gttcgataac ttaactaaag ctgagagggg tggcttgtct      3360
gaacttgaca aggccggatt tattaaacgt cagctcgtgg aaacccgcca aatcacaaag      3420
catgttgcac agatactaga ttcccgaatg aatacgaaat acgacgagaa cgataagctg      3480
attcgggaag tcaaagtaat cactttaaag tcaaaattgg tgtcggactt cagaaaggat      3540
tttcaattct ataaagttag ggagataaat aactaccacc atgcgcacga cgcttatctt      3600
aatgccgtcg tagggaccgc actcattaag aaatacccga agctagaaag tgagtttgtg      3660
tatggtgatt acaaagttta tgacgtccgt aagatgatcg cgaaaagcga acaggagata      3720
ggcaaggcta cagccaaata cttcttttat tctaacatta tgaatttctt taagacggaa      3780
atcactctgg caaacggaga gatacgcaaa cgacctttaa ttgaaaccaa tggggagaca      3840
ggtgaaatcg tatgggataa gggccgggac ttcgcgacgg tgagaaaagt tttgtccatg      3900
```

```
ccccaagtca acatagtaaa gaaaactgag gtgcagaccg gagggttttc aaaggaatcg   3960
attcttccaa aaaggaatag tgataagctc atcgctcgta aaaaggactg ggacccgaaa   4020
aagtacggtg gcttcgatag ccctacagtt gcctattctg tcctagtagt ggcaaaagtt   4080
gagaagggaa aatccaagaa actgaagtca gtcaaagaat tattggggat aacgattatg   4140
gagcgctcgt cttttgaaaa gaaccccatc gacttccttg aggcgaaagg ttacaaggaa   4200
gtaaaaaagg atctcataat taaactacca aagtatagtc tgtttgagtt agaaaatggc   4260
cgaaaacgga tgttggctag cgccggagag cttcaaaagg ggaacgaact cgcactaccg   4320
tctaaatacg tgaatttcct gtatttagcg tcccattacg agaagttgaa aggttcacct   4380
gaagataacg aacagaagca acttttttgtt gagcagcaca acattatct cgacgaaatc   4440 atagagcaaa tttcggaatt cagtaagaga gtcatcctag ctgatgccaa tctggacaaa   4500
gtattaagcg catacaacaa gcacagggat aaacccatac gtgagcaggc ggaaaatatt   4560
atccatttgt ttactcttac caacctcggc gctccagccg cattcaagta ttttgacaca   4620
acgatagatc gcaaacgata cacttctacc aaggaggtgc tagacgcgac actgattcac   4680
caatccatca cgggattata tgaaactcgg atagatttgt cacagcttgg gggtgacgga   4740
tcccccaaga agaagaggaa agtctga                                       4767
```

<210> SEQ ID NO 92
<211> LENGTH: 187
<212> TYPE: PRT
<213> ORGANISM: Artificial Sequence
<220> FEATURE:
<223> OTHER INFORMATION: Synthetic Polypeptide - DHFR mutein

<400> SEQUENCE: 92

```
Met Val Gly Ser Leu Asn Cys Ile Val Ala Val Ser Gln Asn Met Gly
1               5                   10                  15

Ile Gly Lys Asn Gly Asp Phe Pro Trp Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
        50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185
```

<210> SEQ ID NO 93
<211> LENGTH: 561

<212> TYPE: DNA
<213> ORGANISM: Artificial Sequence
<220> FEATURE:
<223> OTHER INFORMATION: Synthetic polynucleotide - DHFR mutein

<400> SEQUENCE: 93
atggtcgggt ctctgaattg tatcgtcgcc gtgagtcaga acatgggcat tgggaagaat        60
ggcgatttcc catggccacc tctgcgcaac gagtcccgat actttcagcg gatgacaact       120
acctcctctg tggaagggaa acagaatctg gtcatcatgg gaaagaaaac ttggttcagc       180
attccagaga agaaccggcc cctgaaaggc agaatcaatc tggtgctgtc ccgagaactg       240
aaggagccac cacagggagc tcactttctg agccggtccc tggacgatgc actgaagctg       300
acagaacagc ctgagctggc caacaaagtc gatatggtgt ggatcgtcgg gggaagttca       360
gtgtataagg aggccatgaa tcaccccggc catctgaaac tgttcgtcac acggatcatg       420
caggactttg agagcgatac tttcttcct gaaattgacc tggagaagta caaactgctg        480
cccgaatatc ctggcgtgct gtccgatgtc caggaagaga aaggcatcaa atacaagttc       540
gaggtctatg agaagaatga c                                                 561

<210> SEQ ID NO 94
<211> LENGTH: 18
<212> TYPE: PRT
<213> ORGANISM: Homo Sapiens

<400> SEQUENCE: 94

Glu Gly Arg Gly Ser Leu Leu Thr Cys Gly Asp Val Glu Glu Asn Pro
1               5                   10                  15

Gly Pro

<210> SEQ ID NO 95
<211> LENGTH: 21
<212> TYPE: PRT
<213> ORGANISM: Homo Sapiens

<400> SEQUENCE: 95

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 96
<211> LENGTH: 63
<212> TYPE: DNA
<213> ORGANISM: Homo Sapiens

<400> SEQUENCE: 96
ggatctggag agggaagggg aagcctgctg acctgtggag acgtggagga aaacccagga        60
cca                                                                      63

<210> SEQ ID NO 97
<211> LENGTH: 20
<212> TYPE: PRT
<213> ORGANISM: Homo Sapiens

<400> SEQUENCE: 97

Gln Cys Thr Asn Tyr Ala Leu Leu Lys Leu Ala Gly Asp Val Glu Ser
1               5                   10                  15

Asn Pro Gly Pro
            20

<210> SEQ ID NO 98
<211> LENGTH: 23
<212> TYPE: PRT
<213> ORGANISM: Homo Sapiens

<400> SEQUENCE: 98

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 99
<211> LENGTH: 22
<212> TYPE: PRT
<213> ORGANISM: Homo Sapiens

<400> SEQUENCE: 99

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 100
<211> LENGTH: 25
<212> TYPE: PRT
<213> ORGANISM: Homo Sapiens

<400> SEQUENCE: 100

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 101
<211> LENGTH: 19
<212> TYPE: PRT
<213> ORGANISM: Homo Sapiens

<400> SEQUENCE: 101

Ala Thr Asn Phe Ser Leu Leu Lys Gln Ala Gly Asp Val Glu Glu Asn
1               5                   10                  15

Pro Gly Pro

<210> SEQ ID NO 102
<211> LENGTH: 22
<212> TYPE: PRT
<213> ORGANISM: Homo Sapiens

<400> SEQUENCE: 102

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 103
<211> LENGTH: 594
<212> TYPE: PRT
<213> ORGANISM: Artificial Sequence
<220> FEATURE:
<223> OTHER INFORMATION: Synthetic Polypeptide - PB transposase

<400> SEQUENCE: 103

-continued

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
            195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Tyr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415
```

```
Leu Ser Ser Cys Asp Glu Asp Ala Ser Ile Asn Glu Ser Thr Gly Lys
            420             425             430

Pro Gln Met Val Met Tyr Tyr Asn Gln Thr Lys Gly Gly Val Asp Thr
        435             440             445

Leu Asp Gln Met Cys Ser Val Met Thr Cys Ser Arg Lys Thr Asn Arg
    450             455             460

Trp Pro Met Ala Leu Leu Tyr Gly Met Ile Asn Ile Ala Cys Ile Asn
465             470             475             480

Ser Phe Ile Ile Tyr Ser His Asn Val Ser Ser Lys Gly Glu Lys Val
            485             490             495

Gln Ser Arg Lys Lys Phe Met Arg Asn Leu Tyr Met Ser Leu Thr Ser
            500             505             510

Ser Phe Met Arg Lys Arg Leu Glu Ala Pro Thr Leu Lys Arg Tyr Leu
            515             520             525

Arg Asp Asn Ile Ser Asn Ile Leu Pro Asn Glu Val Pro Gly Thr Ser
        530             535             540

Asp Asp Ser Thr Glu Glu Pro Val Met Lys Lys Arg Thr Tyr Cys Thr
545             550             555             560

Tyr Cys Pro Ser Lys Ile Arg Arg Lys Ala Asn Ala Ser Cys Lys Lys
            565             570             575

Cys Lys Lys Val Ile Cys Arg Glu His Asn Ile Asp Met Cys Gln Ser
            580             585             590

Cys Phe
```

```
<210> SEQ ID NO 104
<211> LENGTH: 594
<212> TYPE: PRT
<213> ORGANISM: Artificial Sequence
<220> FEATURE:
<223> OTHER INFORMATION: Synthetic Polypeptide - SPB transposase

<400> SEQUENCE: 104

Met Gly Ser Ser Leu Asp Asp Glu His Ile Leu Ser Ala Leu Leu Gln
1               5               10              15

Ser Asp Asp Glu Leu Val Gly Glu Asp Ser Asp Ser Glu Val Ser Asp
            20              25              30

His Val Ser Glu Asp Asp Val Gln Ser Asp Thr Glu Glu Ala Phe Ile
        35              40              45

Asp Glu Val His Glu Val Gln Pro Thr Ser Ser Gly Ser Glu Ile Leu
    50              55              60

Asp Glu Gln Asn Val Ile Glu Gln Pro Gly Ser Ser Leu Ala Ser Asn
65              70              75              80

Arg Ile Leu Thr Leu Pro Gln Arg Thr Ile Arg Gly Lys Asn Lys His
            85              90              95

Cys Trp Ser Thr Ser Lys Ser Thr Arg Arg Ser Arg Val Ser Ala Leu
            100             105             110

Asn Ile Val Arg Ser Gln Arg Gly Pro Thr Arg Met Cys Arg Asn Ile
        115             120             125

Tyr Asp Pro Leu Leu Cys Phe Lys Leu Phe Phe Thr Asp Glu Ile Ile
    130             135             140

Ser Glu Ile Val Lys Trp Thr Asn Ala Glu Ile Ser Leu Lys Arg Arg
145             150             155             160

Glu Ser Met Thr Ser Ala Thr Phe Arg Asp Thr Asn Glu Asp Glu Ile
            165             170             175

Tyr Ala Phe Phe Gly Ile Leu Val Met Thr Ala Val Arg Lys Asp Asn
```

-continued

```
                  180              185              190
His Met Ser Thr Asp Asp Leu Phe Asp Arg Ser Leu Ser Met Val Tyr
              195              200              205

Val Ser Val Met Ser Arg Asp Arg Phe Asp Phe Leu Ile Arg Cys Leu
              210              215              220

Arg Met Asp Asp Lys Ser Ile Arg Pro Thr Leu Arg Glu Asn Asp Val
225              230              235              240

Phe Thr Pro Val Arg Lys Ile Trp Asp Leu Phe Ile His Gln Cys Ile
              245              250              255

Gln Asn Tyr Thr Pro Gly Ala His Leu Thr Ile Asp Glu Gln Leu Leu
              260              265              270

Gly Phe Arg Gly Arg Cys Pro Phe Arg Val Tyr Ile Pro Asn Lys Pro
              275              280              285

Ser Lys Tyr Gly Ile Lys Ile Leu Met Met Cys Asp Ser Gly Thr Lys
              290              295              300

Tyr Met Ile Asn Gly Met Pro Tyr Leu Gly Arg Gly Thr Gln Thr Asn
305              310              315              320

Gly Val Pro Leu Gly Glu Tyr Tyr Val Lys Glu Leu Ser Lys Pro Val
              325              330              335

His Gly Ser Cys Arg Asn Ile Thr Cys Asp Asn Trp Phe Thr Ser Ile
              340              345              350

Pro Leu Ala Lys Asn Leu Leu Gln Glu Pro Tyr Lys Leu Thr Ile Val
              355              360              365

Gly Thr Val Arg Ser Asn Lys Arg Glu Ile Pro Glu Val Leu Lys Asn
              370              375              380

Ser Arg Ser Arg Pro Val Gly Thr Ser Met Phe Cys Phe Asp Gly Pro
385              390              395              400

Leu Thr Leu Val Ser Tyr Lys Pro Lys Pro Ala Lys Met Val Tyr Leu
              405              410              415

Leu Ser Ser Cys Asp Glu Asp Ala Ser Ile Asn Glu Ser Thr Gly Lys
              420              425              430

Pro Gln Met Val Met Tyr Tyr Asn Gln Thr Lys Gly Gly Val Asp Thr
              435              440              445

Leu Asp Gln Met Cys Ser Val Met Thr Cys Ser Arg Lys Thr Asn Arg
              450              455              460

Trp Pro Met Ala Leu Leu Tyr Gly Met Ile Asn Ile Ala Cys Ile Asn
465              470              475              480

Ser Phe Ile Ile Tyr Ser His Asn Val Ser Ser Lys Gly Glu Lys Val
              485              490              495

Gln Ser Arg Lys Lys Phe Met Arg Asn Leu Tyr Met Ser Leu Thr Ser
              500              505              510

Ser Phe Met Arg Lys Arg Leu Glu Ala Pro Thr Leu Lys Arg Tyr Leu
              515              520              525

Arg Asp Asn Ile Ser Asn Ile Leu Pro Lys Glu Val Pro Gly Thr Ser
              530              535              540

Asp Asp Ser Thr Glu Glu Pro Val Met Lys Lys Arg Thr Tyr Cys Thr
545              550              555              560

Tyr Cys Pro Ser Lys Ile Arg Arg Lys Ala Asn Ala Ser Cys Lys Lys
              565              570              575

Cys Lys Lys Val Ile Cys Arg Glu His Asn Ile Asp Met Cys Gln Ser
              580              585              590

Cys Phe
```

-continued

<210> SEQ ID NO 105
<211> LENGTH: 340
<212> TYPE: PRT
<213> ORGANISM: Artificial Sequence
<220> FEATURE:
<223> OTHER INFORMATION: Synthetic Polypeptide - SB100x transposase

<400> SEQUENCE: 105

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
            195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
            325                 330                 335

Ala Thr Lys Tyr
            340

<210> SEQ ID NO 106
<211> LENGTH: 340

<212> TYPE: PRT
<213> ORGANISM: Artificial Sequence
<220> FEATURE:
<223> OTHER INFORMATION: Synthetic Polypeptide - hyperSB100x transposase

<400> SEQUENCE: 106

```
Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
                20                  25                  30

Ala Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

<210> SEQ ID NO 107
<211> LENGTH: 5296
<212> TYPE: DNA
<213> ORGANISM: Artificial Sequence
<220> FEATURE:

<223> OTHER INFORMATION: Synthetic Polynucleotide - Helraiser transposon

<400> SEQUENCE: 107

```
tcctatataa taaaagagaa acatgcaaat tgaccatccc tccgctacgc tcaagccacg      60
cccaccagcc aatcagaagt gactatgcaa attaacccaa caaagatggc agttaaattt     120
gcatacgcag gtgtcaagcg ccccaggagg caacggcggc cgcgggctcc caggaccttc     180
gctggccccg ggaggcgagg ccggccgcgc ctagccacac ccgcgggctc ccgggacctt     240
cgccagcaga gagcagagcg ggagagcggg cggagagcgg gaggtttgga ggacttggca     300
gagcaggagg ccgctggaca tagagcagag cgagagagag ggtggcttgg agggcgtggc     360
tccctctgtc accccagctt cctcatcaca gctgtggaaa ctgacagcag ggaggaggaa     420
gtcccacccc cacagaatca gccagaatca gccgttggtc agacagctct cagcggcctg     480
acagccagga ctctcattca cctgcatctc agaccgtgac agtagagagg tgggactatg     540
tctaaagaac aactgttgat acaacgtagc tctgcagccg aaagatgccg gcgttatcga     600
cagaaaatgt ctgcagagca acgtgcgtct gatcttgaaa gaaggcggcg cctgcaacag     660
aatgtatctg aagagcagct actggaaaaa cgtcgctctg aagccgaaaa acagcggcgt     720
catcgacaga aaatgtctaa agaccaacgt gcctttgaag ttgaaagaag gcggtggcga     780
cgacagaata tgtctagaga acagtcatca acaagtacta ccaataccgg taggaactgc     840
cttctcagca aaaatggagt acatgaggat gcaattctcg aacatagttg tggtggaatg     900
actgttcgat gtgaattttg cctatcacta aatttctctg atgaaaaacc atccgatggg     960
aaatttactc gatgttgtag caaagggaaa gtctgtccaa atgatataca ttttccagat    1020
tacccggcat atttaaaaag attaatgaca aacgaagatt ctgacagtaa aaatttcatg    1080
gaaaatattc gttccataaa tagttctttt gcttttgctt ccatgggtgc aaatattgca    1140
tcgccatcag gatatgggcc atactgtttt agaatacacg gacaagttta tcaccgtact    1200
ggaactttac atccttcgga tggtgtttct cggaagtttg ctcaactcta tattttggat    1260
acagccgaag ctacaagtaa aagattagca atgccagaaa accagggctg ctcagaaaga    1320
ctcatgatca acatcaacaa cctcatgcat gaaataaatg aattaacaaa atcgtacaag    1380
atgctacatg aggtagaaaa ggaagcccaa tctgaagcag cagcaaaagg tattgctccc    1440
acagaagtaa caatggcgat taaatacgat cgtaacagtg acccaggtag atataattct    1500
ccccgtgtaa ccgaggttgc tgtcatattc agaaacgaag atggagaacc tccttttgaa    1560
agggacttgc tcattcattg taaaccagat cccaataatc caaatgccac taaaaatgaaa    1620 caaatcagta tcctgtttcc tacattagat gcaatgacat atcctattct ttttccacat    1680
ggtgaaaaag gctggggaac agatattgca ttaagactca gagacaacag tgtaatcgac    1740
aataatacta gacaaaatgt aaggacacga gtcacacaaa tgcagtatta tggatttcat    1800
ctctctgtgc gggacacgtt caatcctatt ttaaatgcag gaaaattaac tcaacagttt    1860
attgtggatt catattcaaa aatggaggcc aatcggataa atttcatcaa agcaaaccaa    1920
tctaagttga gagttgaaaa atatagtggt ttgatggatt atctcaaatc tagatctgaa    1980
aatgacaatg tgccgattgg taaaatgata atacttccat catcttttga gggtagtccc    2040
agaaatatgc agcagcgata tcaggatgct atggcaattg taacgaagta tggcaagccc    2100
gatttattca taaccatgac atgcaacccc aaatgggcag atattacaaa caatttacaa    2160
cgctggcaaa aagttgaaaa cagacctgac ttggtagcca gagttttaa tattaagctg    2220 aatgctcttt taaatgatat atgtaaattc catttatttg gcaaagtaat agctaaaatt    2280
```

US 12,686,726 B2

261

262

-continued

```
catgtcattg aatttcagaa acgcggactg cctcacgctc acatattatt gatattagat   2340
agtgagtcca aattacgttc agaagatgac attgaccgta tagttaaggc agaaattcca   2400
gatgaagacc agtgtcctcg actttttcaa attgtaaaat caaatatggt acatggacca   2460
tgtggaatac aaaatccaaa tagtccatgt atggaaaatg gaaaatgttc aaagggatat   2520
ccaaaagaat ttcaaaatgc gaccattgga aatattgatg gatatcccaa atacaaacga   2580
agatctggta gcaccatgtc tattggaaat aaagttgtcg ataacacttg gattgtccct   2640
tataacccgt atttgtgcct taaatataac tgtcatataa atgttgaagt ctgtgcatca   2700
attaaaagtg tcaaatattt atttaaatac atctataaag ggcacgattg tgcaaatatt   2760
caaatttctg aaaaaaatat tatcaatcat gacgaagtac aggacttcat tgactccagg   2820
tatgtgagcg ctcctgaggc tgtttggaga ctttttgcaa tgcgaatgca tgaccaatct   2880
catgcaatca caagattagc tattcatttg ccaaatgatc agaatttgta ttttcatacc   2940
gatgattttg ctgaagtttt agataggget aaaaggcata actcgacttt gatggcttgg   3000
ttcttattga atagagaaga ttctgatgca cgtaattatt attattggga gattccacag   3060
cattatgtgt ttaataattc tttgtggaca aaacgccgaa agggtgggaa taaagtatta   3120
ggtagactgt tcactgtgag ctttagagaa ccagaacgat attaccttag acttttgctt   3180
ctgcatgtaa aaggtgcgat aagtttttgag gatctgcgaa ctgtaggagg tgtaacttat   3240
gatacatttc atgaagctgc taaacaccga ggattattac ttgatgacac tatctggaaa   3300
gatacgattg acgatgcaat catccttaat atgcccaaac aactacggca acttttttgca   3360 tatatatgtg tgtttggatg tccttctgct gcagacaaat tatgggatga gaataaatct   3420
cattttattg aagatttctg ttggaaatta caccgaagag aaggtgcctg tgtgaactgt   3480
gaaatgcatg cccttaacga aattcaggag gtattcacat tgcatggaat gaaatgttca   3540
catttcaaac ttccggacta tccttttatta atgaatgcaa atacatgtga tcaattgtac   3600
gagcaacaac aggcagaggt tttgataaat tctctgaatg atgaacagtt ggcagccttt   3660
cagactataa cttcagccat cgaagatcaa actgtacacc ccaaatgctt tttcttggat   3720
ggtccaggtg gtagtggaaa aacatatctg tataaagttt taacacatta tattagaggt   3780
cgtggtggta ctgttttacc cacagcatct acaggaattg ctgcaaattt acttcttggt   3840
ggaagaacct ttcattccca atataaatta ccaattccat taaatgaaac ttcaatttct   3900
agactcgata taaagagtga agttgctaaa accattaaaa aggcccaact tctcattatt   3960
gatgaatgca ccatggcatc cagtcatgct ataaacgcca tagatagatt actaagagaa   4020
attatgaatt tgaatgttgc atttggtggg aaagttctcc ttctcggagg ggattttcga   4080
caatgtctca gtattgtacc acatgctatg cgatcggcca tagtacaaac gagtttaaag   4140
tactgtaatg tttggggatg tttcagaaag ttgtctctta aaacaaatat gagatcagag   4200
gattctgctt atagtgaatg gttagtaaaa cttggagatg gcaaacttga tagcagtttt   4260
catttaggaa tggatattat tgaaatcccc catgaaatga tttgtaacgg atctattatt   4320
gaagctacct ttggaaatag tatatctata gataatatta aaaatatatc taaacgtgca   4380
attctttgtc caaaaaatga gcatgttcaa aaattaaatg aagaattttt ggatatactt   4440
gatggagatt ttcacacata tttgagtgat gattccattg attcaacaga tgatgctgaa   4500
aaggaaaatt ttcccatcga atttcttaat agtattactc cttcgggaat gccgtgtcat   4560
aaattaaaat tgaaagtggg tgcaatcatc atgctattga gaaatcttaa tagtaaatgg   4620
```

-continued

```
ggtctttgta atggtactag atttattatc aaaagattac gacctaacat tatcgaagct    4680
gaagtattaa caggatctgc agagggagag gttgttctga ttccaagaat tgatttgtcc    4740
ccatctgaca ctggcctccc atttaaatta attcgaagac agtttcccgt gatgccagca    4800
tttgcgatga ctattaataa atcacaagga caaactctag acagagtagg aatattccta    4860
cctgaacccg ttttcgcaca tggtcagtta tatgttgctt tctctcgagt tcgaagagca    4920
tgtgacgtta aagttaaagt tgtaaatact tcatcacaag ggaaattagt caagcactct    4980
gaaagtgttt ttactcttaa tgtggtatac agggagatat tagaataagt ttaatcactt    5040
tatcagtcat tgtttgcatc aatgttgttt ttatatcatg tttttgttgt ttttatatca    5100
tgtctttgtt gttgttatat catgttgtta ttgtttattt attaataaat ttatgtatta    5160
ttttcatata cattttactc atttcctttc atctctcaca cttctattat agagaaaggg    5220
caaatagcaa tattaaaata tttcctctaa ttaattccct ttcaatgtgc acgaatttcg    5280
tgcaccgggc cactag                                                    5296
```

<210> SEQ ID NO 108
<211> LENGTH: 1496
<212> TYPE: PRT
<213> ORGANISM: Artificial Sequence
<220> FEATURE:
<223> OTHER INFORMATION: Synthetic Polypeptide - Helitron transposase

<400> SEQUENCE: 108

```
Met Ser Lys Glu Gln Leu Leu Ile Gln Arg Ser Ser Ala Ala Glu Arg
1               5                   10                  15

Cys Arg Arg Tyr Arg Gln Lys Met Ser Ala Glu Gln Arg Ala Ser Asp
            20                  25                  30

Leu Glu Arg Arg Arg Arg Leu Gln Gln Asn Val Ser Glu Glu Gln Leu
        35                  40                  45

Leu Glu Lys Arg Arg Ser Glu Ala Glu Lys Gln Arg Arg His Arg Gln
    50                  55                  60

Lys Met Ser Lys Asp Gln Arg Ala Phe Glu Val Glu Arg Arg Arg Trp
65                  70                  75                  80

Arg Arg Gln Asn Met Ser Arg Glu Gln Ser Ser Thr Ser Thr Thr Asn
                85                  90                  95

Thr Gly Arg Asn Cys Leu Leu Ser Lys Asn Gly Val His Glu Asp Ala
            100                 105                 110

Ile Leu Glu His Ser Cys Gly Gly Met Thr Val Arg Cys Glu Phe Cys
        115                 120                 125

Leu Ser Leu Asn Phe Ser Asp Glu Lys Pro Ser Asp Gly Lys Phe Thr
    130                 135                 140

Arg Cys Cys Ser Lys Gly Lys Val Cys Pro Asn Asp Ile His Phe Pro
145                 150                 155                 160

Asp Tyr Pro Ala Tyr Leu Lys Arg Leu Met Thr Asn Glu Asp Ser Asp
                165                 170                 175

Ser Lys Asn Phe Met Glu Asn Ile Arg Ser Ile Asn Ser Ser Phe Ala
            180                 185                 190

Phe Ala Ser Met Gly Ala Asn Ile Ala Ser Pro Ser Gly Tyr Gly Pro
        195                 200                 205

Tyr Cys Phe Arg Ile His Gly Gln Val Tyr His Arg Thr Gly Thr Leu
    210                 215                 220

His Pro Ser Asp Gly Val Ser Arg Lys Phe Ala Gln Leu Tyr Ile Leu
225                 230                 235                 240
```

-continued

```
Asp Thr Ala Glu Ala Thr Ser Lys Arg Leu Ala Met Pro Glu Asn Gln
             245                 250                 255

Gly Cys Ser Glu Arg Leu Met Ile Asn Ile Asn Asn Leu Met His Glu
             260                 265                 270

Ile Asn Glu Leu Thr Lys Ser Tyr Lys Met Leu His Glu Val Glu Lys
             275                 280                 285

Glu Ala Gln Ser Glu Ala Ala Ala Lys Gly Ile Ala Pro Thr Glu Val
             290                 295                 300

Thr Met Ala Ile Lys Tyr Asp Arg Asn Ser Asp Pro Gly Arg Tyr Asn
305                 310                 315                 320

Ser Pro Arg Val Thr Glu Val Ala Val Ile Phe Arg Asn Glu Asp Gly
             325                 330                 335

Glu Pro Pro Phe Glu Arg Asp Leu Leu Ile His Cys Lys Pro Asp Pro
             340                 345                 350

Asn Asn Pro Asn Ala Thr Lys Met Lys Gln Ile Ser Ile Leu Phe Pro
             355                 360                 365

Thr Leu Asp Ala Met Thr Tyr Pro Ile Leu Phe Pro His Gly Glu Lys
             370                 375                 380

Gly Trp Gly Thr Asp Ile Ala Leu Arg Leu Arg Asp Asn Ser Val Ile
385                 390                 395                 400

Asp Asn Asn Thr Arg Gln Asn Val Arg Thr Arg Val Thr Gln Met Gln
             405                 410                 415

Tyr Tyr Gly Phe His Leu Ser Val Arg Asp Thr Phe Asn Pro Ile Leu
             420                 425                 430

Asn Ala Gly Lys Leu Thr Gln Gln Phe Ile Val Asp Ser Tyr Ser Lys
             435                 440                 445

Met Glu Ala Asn Arg Ile Asn Phe Ile Lys Ala Asn Gln Ser Lys Leu
             450                 455                 460

Arg Val Glu Lys Tyr Ser Gly Leu Met Asp Tyr Leu Lys Ser Arg Ser
465                 470                 475                 480

Glu Asn Asp Asn Val Pro Ile Gly Lys Met Ile Ile Leu Pro Ser Ser
             485                 490                 495

Phe Glu Gly Ser Pro Arg Asn Met Gln Gln Arg Tyr Gln Asp Ala Met
             500                 505                 510

Ala Ile Val Thr Lys Tyr Gly Lys Pro Asp Leu Phe Ile Thr Met Thr
             515                 520                 525

Cys Asn Pro Lys Trp Ala Asp Ile Thr Asn Asn Leu Gln Arg Trp Gln
             530                 535                 540

Lys Val Glu Asn Arg Pro Asp Leu Val Ala Arg Val Phe Asn Ile Lys
545                 550                 555                 560

Leu Asn Ala Leu Leu Asn Asp Ile Cys Lys Phe His Leu Phe Gly Lys
             565                 570                 575

Val Ile Ala Lys Ile His Val Ile Glu Phe Gln Lys Arg Gly Leu Pro
             580                 585                 590

His Ala His Ile Leu Leu Ile Leu Asp Ser Glu Ser Lys Leu Arg Ser
             595                 600                 605

Glu Asp Asp Ile Asp Arg Ile Val Lys Ala Glu Ile Pro Asp Glu Asp
             610                 615                 620

Gln Cys Pro Arg Leu Phe Gln Ile Val Lys Ser Asn Met Val His Gly
625                 630                 635                 640

Pro Cys Gly Ile Gln Asn Pro Asn Ser Pro Cys Met Glu Asn Gly Lys
             645                 650                 655

Cys Ser Lys Gly Tyr Pro Lys Glu Phe Gln Asn Ala Thr Ile Gly Asn
```

-continued

```
                660              665               670
Ile Asp Gly Tyr Pro Lys Tyr Lys Arg Arg Ser Gly Ser Thr Met Ser
            675              680               685

Ile Gly Asn Lys Val Val Asp Asn Thr Trp Ile Val Pro Tyr Asn Pro
690              695               700

Tyr Leu Cys Leu Lys Tyr Asn Cys His Ile Asn Val Glu Val Cys Ala
705              710               715               720

Ser Ile Lys Ser Val Lys Tyr Leu Phe Lys Tyr Ile Tyr Lys Gly His
            725              730               735

Asp Cys Ala Asn Ile Gln Ile Ser Glu Lys Asn Ile Ile Asn His Asp
            740              745               750

Glu Val Gln Asp Phe Ile Asp Ser Arg Tyr Val Ser Ala Pro Glu Ala
            755              760               765

Val Trp Arg Leu Phe Ala Met Arg Met His Asp Gln Ser His Ala Ile
770              775               780

Thr Arg Leu Ala Ile His Leu Pro Asn Asp Gln Asn Leu Tyr Phe His
785              790               795               800

Thr Asp Asp Phe Ala Glu Val Leu Asp Arg Ala Lys Arg His Asn Ser
            805              810               815

Thr Leu Met Ala Trp Phe Leu Leu Asn Arg Glu Asp Ser Asp Ala Arg
            820              825               830

Asn Tyr Tyr Tyr Trp Glu Ile Pro Gln His Tyr Val Phe Asn Asn Ser
            835              840               845

Leu Trp Thr Lys Arg Arg Lys Gly Gly Asn Lys Val Leu Gly Arg Leu
850              855               860

Phe Thr Val Ser Phe Arg Glu Pro Glu Arg Tyr Tyr Leu Arg Leu Leu
865              870               875               880

Leu Leu His Val Lys Gly Ala Ile Ser Phe Glu Asp Leu Arg Thr Val
            885              890               895

Gly Gly Val Thr Tyr Asp Thr Phe His Glu Ala Ala Lys His Arg Gly
            900              905               910

Leu Leu Leu Asp Asp Thr Ile Trp Lys Asp Thr Ile Asp Asp Ala Ile
            915              920               925

Ile Leu Asn Met Pro Lys Gln Leu Arg Gln Leu Phe Ala Tyr Ile Cys
930              935               940

Val Phe Gly Cys Pro Ser Ala Ala Asp Lys Leu Trp Asp Glu Asn Lys
945              950               955               960

Ser His Phe Ile Glu Asp Phe Cys Trp Lys Leu His Arg Arg Glu Gly
            965              970               975

Ala Cys Val Asn Cys Glu Met His Ala Leu Asn Glu Ile Gln Glu Val
            980              985               990

Phe Thr Leu His Gly Met Lys Cys  Ser His Phe Lys Leu  Pro Asp Tyr
            995              1000               1005

Pro Leu  Leu Met Asn Ala Asn  Thr Cys Asp Gln Leu  Tyr Glu Gln
    1010              1015               1020

Gln Gln  Ala Glu Val Leu Ile  Asn Ser Leu Asn Asp  Glu Gln Leu
    1025              1030               1035

Ala Ala  Phe Gln Thr Ile Thr  Ser Ala Ile Glu Asp  Gln Thr Val
    1040              1045               1050

His Pro  Lys Cys Phe Phe Leu  Asp Gly Pro Gly Gly  Ser Gly Lys
    1055              1060               1065

Thr Tyr  Leu Tyr Lys Val Leu  Thr His Tyr Ile Arg  Gly Arg Gly
    1070              1075               1080
```

-continued

```
Gly Thr Val Leu Pro Thr Ala  Ser Thr Gly Ile Ala  Ala Asn Leu
    1085              1090             1095

Leu Leu Gly Gly Arg Thr Phe  His Ser Gln Tyr Lys  Leu Pro Ile
    1100              1105             1110

Pro Leu Asn Glu Thr Ser Ile  Ser Arg Leu Asp Ile  Lys Ser Glu
    1115              1120             1125

Val Ala Lys Thr Ile Lys Lys  Ala Gln Leu Leu Ile  Ile Asp Glu
    1130              1135             1140

Cys Thr Met Ala Ser Ser His  Ala Ile Asn Ala Ile  Asp Arg Leu
    1145              1150             1155

Leu Arg Glu Ile Met Asn Leu  Asn Val Ala Phe Gly  Gly Lys Val
    1160              1165             1170

Leu Leu Leu Gly Gly Asp Phe  Arg Gln Cys Leu Ser  Ile Val Pro
    1175              1180             1185

His Ala Met Arg Ser Ala Ile  Val Gln Thr Ser Leu  Lys Tyr Cys
    1190              1195             1200

Asn Val Trp Gly Cys Phe Arg  Lys Leu Ser Leu Lys  Thr Asn Met
    1205              1210             1215

Arg Ser Glu Asp Ser Ala Tyr  Ser Glu Trp Leu Val  Lys Leu Gly
    1220              1225             1230

Asp Gly Lys Leu Asp Ser Ser  Phe His Leu Gly Met  Asp Ile Ile
    1235              1240             1245

Glu Ile Pro His Glu Met Ile  Cys Asn Gly Ser Ile  Ile Glu Ala
    1250              1255             1260

Thr Phe Gly Asn Ser Ile Ser  Ile Asp Asn Ile Lys  Asn Ile Ser
    1265              1270             1275

Lys Arg Ala Ile Leu Cys Pro  Lys Asn Glu His Val  Gln Lys Leu
    1280              1285             1290

Asn Glu Glu Ile Leu Asp Ile  Leu Asp Gly Asp Phe  His Thr Tyr
    1295              1300             1305

Leu Ser Asp Asp Ser Ile Asp  Ser Thr Asp Asp Ala  Glu Lys Glu
    1310              1315             1320

Asn Phe Pro Ile Glu Phe Leu  Asn Ser Ile Thr Pro  Ser Gly Met
    1325              1330             1335

Pro Cys His Lys Leu Lys Leu  Lys Val Gly Ala Ile  Ile Met Leu
    1340              1345             1350

Leu Arg Asn Leu Asn Ser Lys  Trp Gly Leu Cys Asn  Gly Thr Arg
    1355              1360             1365

Phe Ile Ile Lys Arg Leu Arg  Pro Asn Ile Ile Glu  Ala Glu Val
    1370              1375             1380

Leu Thr Gly Ser Ala Glu Gly  Glu Val Val Leu Ile  Pro Arg Ile
    1385              1390             1395

Asp Leu Ser Pro Ser Asp Thr  Gly Leu Pro Phe Lys  Leu Ile Arg
    1400              1405             1410

Arg Gln Phe Pro Val Met Pro  Ala Phe Ala Met Thr  Ile Asn Lys
    1415              1420             1425

Ser Gln Gly Gln Thr Leu Asp  Arg Val Gly Ile Phe  Leu Pro Glu
    1430              1435             1440

Pro Val Phe Ala His Gly Gln  Leu Tyr Val Ala Phe  Ser Arg Val
    1445              1450             1455

Arg Arg Ala Cys Asp Val Lys  Val Lys Val Val Asn  Thr Ser Ser
    1460              1465             1470
```

```
Gln Gly Lys Leu Val Lys His Ser Glu Ser Val Phe Thr Leu Asn
    1475            1480                1485

Val Val Tyr Arg Glu Ile Leu Glu
    1490            1495

<210> SEQ ID NO 109
<211> LENGTH: 4682
<212> TYPE: DNA
<213> ORGANISM: Artificial Sequence
<220> FEATURE:
<223> OTHER INFORMATION: Synthetic Polynucleotide - Tol2 transposon

<400> SEQUENCE: 109
cagaggtgta aagtacttga gtaattttac ttgattactg tacttaagta ttatttttgg      60
ggatttttac tttacttgag tacaattaaa aatcaatact tttactttta cttaattaca     120
tttttttaga aaaaaaagta cttttttactc cttacaattt tatttacagt caaaaagtac    180
ttattttttg gagatcactt cattctattt tcccttgcta ttaccaaacc aattgaattg     240
cgctgatgcc cagtttaatt taaatgttat ttattctgcc tatgaaaatc gttttcacat     300
tatatgaaat tggtcagaca tgttcattgg tcctttggaa gtgacgtcat gtcacatcta     360
ttaccacaat gcacagcacc ttgacctgga aattagggaa attataacag tcaatcagtg     420
gaagaaaatg gaggaagtat gtgattcatc agcagctgcg agcagcacag tccaaaatca     480
gccacaggat caagagcacc cgtggccgta tcttcgcgaa ttcttttctt taagtggtgt     540
aaataaagat tcattcaaga tgaaatgtgt cctctgtctc ccgcttaata aagaaatatc     600
ggccttcaaa agttcgccat caaacctaag gaagcatatt gaggtaagta cattaagtat     660
tttgttttac tgatagtttt tttttttttt tttttttttt tttttgggtg tgcatgtttt     720
gacgttgatg gcgcgccttt tatatgtgta gtaggcctat tttcactaat gcatgcgatt     780
gacaatataa ggctcacgta ataaaatgct aaaatgcatt tgtaattggt aacgttaggt     840
ccacgggaaa tttggcgcct attgcagctt tgaataatca ttatcattcc gtgctctcat     900
tgtgtttgaa ttcatgcaaa acacaagaaa accaagcgag aaattttttt ccaaacatgt     960
tgtattgtca aaacggtaac actttacaat gaggttgatt agttcatgta ttaactaaca    1020
ttaaataacc atgagcaata catttgttac tgtatctgtt aatctttgtt aacgttagtt    1080
aatagaaata cagatgttca ttgtttgttc atgttagttc acagtgcatt aactaatgtt    1140
aacaagatat aaagtattag taaatgttga aattaacatg tatacgtgca gttcattatt    1200
agttcatgtt aactaatgta gttaactaac gaaccttatt gtaaaagtgt taccatcaaa    1260
actaatgtaa tgaaatcaat tcaccctgtc atgtcagcct tacagtcctg tgtttttgtc    1320
aatataatca gaaataaaat taatgtttga ttgtcactaa atgctactgt atttctaaaa    1380
tcaacaagta tttaacatta taaagtgtgc aattggctgc aaatgtcagt tttattaaag    1440
ggttagttca cccaaaaatg aaaataatgt cattaatgac tcgccctcat gtcgttccaa    1500
gcccgtaaga cctccgttca tcttcagaac acagtttaag atattttaga tttagtccga    1560
gagctttctg tgcctccatt gagaatgtat gtacggtata ctgtccatgt ccagaaaggt    1620
aataaaaaca tcaaagtagt ccatgtgaca tcagtgggtt agttagaatt ttttgaagca    1680
tcgaatacat tttggtccaa aaataacaaa acctacgact ttattcggca ttgtattctc    1740
ttccgggtct gttgtcaatc cgcgttcacg acttcgcagt gacgctacaa tgctgaataa    1800
agtcgtaggt tttgttattt ttggaccaaa atgtattttc gatgcttcaa ataattctac    1860
ctaacccact gatgtcacat ggactacttt gatgttttta ttacctttct ggacatggac    1920
```

-continued

```
agtataccgt acatacattt tcagtggagg gacagaaagc tctcggacta aatctaaaat    1980
atcttaaact gtgttccgaa gatgaacgga ggtgttacgg gcttggaacg acatgagggt    2040
gagtcattaa tgacatcttt tcatttttgg gtgaactaac cctttaatgc tgtaatcaga    2100
gagtgtatgt gtaattgtta catttattgc atacaatata aatatttatt tgttgttttt    2160
acagagaatg cacccaaatt acctcaaaaa ctactctaaa ttgacagcac agaagagaaa    2220
gatcgggacc tccacccatg cttccagcag taagcaactg aaagttgact cagttttccc    2280
agtcaaacat gtgtctccag tcactgtgaa caaagctata ttaaggtaca tcattcaagg    2340
acttcatcct ttcagcactg ttgatctgcc atcatttaaa gagctgatta gtacactgca    2400
gcctggcatt tctgtcatta caaggcctac tttacgctcc aagatagctg aagctgctct    2460
gatcatgaaa cagaaagtga ctgctgccat gagtgaagtt gaatggattg caaccacaac    2520
ggattgttgg actgcacgta gaaagtcatt cattggtgta actgctcact ggatcaaccc    2580
tggaagtctt gaaagacatt ccgctgcact tgcctgcaaa agattaatgg gctctcatac    2640
ttttgaggta ctggccagtg ccatgaatga tatccactca gagtatgaaa tacgtgacaa    2700
ggttgtttgc acaaccacag acagtggttc caactttatg aaggctttca gagttttttgg    2760 tgtggaaaac aatgatatcg agactgaggc aagaaggtgt gaaagtgatg acactgattc    2820
tgaaggctgt ggtgagggaa gtgatggtgt ggaattccaa gatgcctcac gagtcctgga    2880
ccaagacgat ggcttcgaat tccagctacc aaaacatcaa aagtgtgcct gtcacttact    2940
taacctagtc tcaagcgttg atgcccaaaa agctctctca aatgaacact acaagaaact    3000
ctacagatct gtctttggca aatgccaagc tttatggaat aaaagcagcc gatcggctct    3060
agcagctgaa gctgttgaat cagaaagccg gcttcagctt ttaaggccaa accaaacgcg    3120
gtggaattca acttttatgg ctgttgacag aattcttcaa atttgcaaag aagcaggaga    3180
aggcgcactt cggaatatat gcacctctct tgaggttcca atgtaagtgt ttttcccctc    3240
tatcgatgta aacaaatgtg ggttgttttt gtttaatact ctttgattat gctgatttct    3300
cctgtaggtt taatccagca gaaatgctgt tcttgacaga gtgggccaac acaatgcgtc    3360
cagttgcaaa agtactcgac atcttgcaag cggaaacgaa tacacagctg gggtggctgc    3420
tgcctagtgt ccatcagtta agcttgaaac ttcagcgact ccaccattct ctcaggtact    3480
gtgacccact tgtggatgcc ctacaacaag gaatccaaac acgattcaag catatgtttg    3540
aagatcctga gatcatagca gctgccatcc ttctccctaa atttcggacc tcttggacaa    3600
atgatgaaac catcataaaa cgaggtaaat gaatgcaagc aacatacact tgacgaattc    3660
taatctgggc aacctttgag ccataccaaa attattcttt tatttattta tttttgcact    3720
ttttaggaat gttatatccc atctttggct gtgatctcaa tatgaatatt gatgtaaagt    3780
attcttgcag caggttgtag ttatccctca gtgtttcttg aaaccaaact catatgtatc    3840
atatgtggtt tggaaatgca gttagatttt atgctaaaat aagggatttg catgatttta    3900
gatgtagatg actgcacgta aatgtagtta atgacaaaat ccataaaatt tgttcccagt    3960
cagaagcccc tcaaccaaac ttttctttgt gtctgctcac tgtgcttgta ggcatggact    4020
acatcagagt gcatctggag cctttggacc acaagaagga attggccaac agttcatctg    4080
atgatgaaga tttttttcgct tctttgaaac cgacaacaca tgaagccagc aaagagttgg    4140
atggatatct ggcctgtgtt tcagacacca gggagtctct gctcacgttt cctgctattt    4200
gcagcctctc tatcaagact aatacacctc ttcccgcatc ggctgcctgt gagaggcttt    4260
```

-continued

```
tcagcactgc aggattgctt ttcagcccca aaagagctag gcttgacact aacaattttg    4320
agaatcagct tctactgaag ttaaatctga ggtttacaa cttttgagtag cgtgtactgg    4380 cattagattg tctgtcttat agtttgataa ttaaatacaa acagttctaa agcaggataa    4440
aaccttgtat gcatttcatt taatgttttt tgagattaaa agcttaaaca agaatctcta    4500
gttttctttc ttgcttttac ttttacttcc ttaatactca agtacaattt taatggagta    4560 ctttttttact tttactcaag taagattcta gccagatact tttactttta attgagtaaa    4620
atttttccta agtacttgta ctttcacttg agtaaaattt ttgagtactt tttacacctc    4680
tg                                                                    4682
```

```
<210> SEQ ID NO 110
<211> LENGTH: 649
<212> TYPE: PRT
<213> ORGANISM: Artificial Sequence
<220> FEATURE:
<223> OTHER INFORMATION: Synthetic Polypeptide - Tol2 transposase

<400> SEQUENCE: 110

Met Glu Glu Val Cys Asp Ser Ser Ala Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285
```

```
Thr Asp Ser Glu Gly Cys Gly Glu Gly Ser Asp Gly Val Glu Phe Gln
    290             295             300

Asp Ala Ser Arg Val Leu Asp Gln Asp Asp Gly Phe Glu Phe Gln Leu
305             310             315             320

Pro Lys His Gln Lys Cys Ala Cys His Leu Leu Asn Leu Val Ser Ser
                325             330             335

Val Asp Ala Gln Lys Ala Leu Ser Asn Glu His Tyr Lys Lys Leu Tyr
            340             345             350

Arg Ser Val Phe Gly Lys Cys Gln Ala Leu Trp Asn Lys Ser Ser Arg
            355             360             365

Ser Ala Leu Ala Ala Glu Ala Val Glu Ser Glu Ser Arg Leu Gln Leu
    370             375             380

Leu Arg Pro Asn Gln Thr Arg Trp Asn Ser Thr Phe Met Ala Val Asp
385             390             395             400

Arg Ile Leu Gln Ile Cys Lys Glu Ala Gly Glu Gly Ala Leu Arg Asn
            405             410             415

Ile Cys Thr Ser Leu Glu Val Pro Met Phe Asn Pro Ala Glu Met Leu
            420             425             430

Phe Leu Thr Glu Trp Ala Asn Thr Met Arg Pro Val Ala Lys Val Leu
            435             440             445

Asp Ile Leu Gln Ala Glu Thr Asn Thr Gln Leu Gly Trp Leu Leu Pro
    450             455             460

Ser Val His Gln Leu Ser Leu Lys Leu Gln Arg Leu His His Ser Leu
465             470             475             480

Arg Tyr Cys Asp Pro Leu Val Asp Ala Leu Gln Gln Gly Ile Gln Thr
            485             490             495

Arg Phe Lys His Met Phe Glu Asp Pro Glu Ile Ile Ala Ala Ala Ile
            500             505             510

Leu Leu Pro Lys Phe Arg Thr Ser Trp Thr Asn Asp Glu Thr Ile Ile
            515             520             525

Lys Arg Gly Met Asp Tyr Ile Arg Val His Leu Glu Pro Leu Asp His
    530             535             540

Lys Lys Glu Leu Ala Asn Ser Ser Ser Asp Asp Glu Asp Phe Phe Ala
545             550             555             560

Ser Leu Lys Pro Thr Thr His Glu Ala Ser Lys Glu Leu Asp Gly Tyr
            565             570             575

Leu Ala Cys Val Ser Asp Thr Arg Glu Ser Leu Leu Thr Phe Pro Ala
            580             585             590

Ile Cys Ser Leu Ser Ile Lys Thr Asn Thr Pro Leu Pro Ala Ser Ala
            595             600             605

Ala Cys Glu Arg Leu Phe Ser Thr Ala Gly Leu Leu Phe Ser Pro Lys
    610             615             620

Arg Ala Arg Leu Asp Thr Asn Asn Phe Glu Asn Gln Leu Leu Leu Lys
625             630             635             640

Leu Asn Leu Arg Phe Tyr Asn Phe Glu
            645
```

<210> SEQ ID NO 111
<211> LENGTH: 636
<212> TYPE: PRT
<213> ORGANISM: Artificial Sequence
<220> FEATURE:
<223> OTHER INFORMATION: Synthetic Polynucleotide - TcBuster transposase

<400> SEQUENCE: 111

```
Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
            35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
            115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Asp Thr Thr Ile
            180                 185                 190

Ser Arg Arg Ile Glu Asp Met Ser Tyr Phe Cys Glu Ala Val Leu Val
            195                 200                 205

Asn Arg Leu Glu Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
            275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
            325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
            355                 360                 365

Lys Asn Leu Leu Leu His Thr Glu Val Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415
```

```
Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Glu Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
            515                 520                 525

Asp Thr Leu Pro Ile Lys Glu Arg Glu Gln Leu Ile Asp Ile Arg Thr
        530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
            565                 570                 575

Lys Glu Leu Met Pro Phe Val Thr Thr Tyr Leu Cys Glu Lys Ser Phe
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635
```

```
<210> SEQ ID NO 112
<211> LENGTH: 1911
<212> TYPE: DNA
<213> ORGANISM: Artificial Sequence
<220> FEATURE:
<223> OTHER INFORMATION: Synthetic Polynucleotide - TcBuster transposase

<400> SEQUENCE: 112
atgatgttga attggctgaa aagtggaaag cttgaaagtc aatcacagga acagagttcc      60
tgctaccttg agaactctaa ctgcctgcca ccaacgctcg attctacaga tattatcggt     120
gaagagaaca aagctggtac cacctctcgc aagaagcgga aatatgacga ggactatctg     180
aacttcggtt ttacatggac tggcgacaag gatgagccca cggactttg tgtgatttgc      240 gagcaggtag tcaacaattc ctcacttaac ccggccaaac tgaaacgcca tttggacaca     300
aagcatccga cgcttaaagg caagagcgaa tacttcaaaa gaaaatgtaa cgagctcaat     360
caaaagaagc atactttga gcgatacgta agggacgata acaagaacct cctgaaagct      420
tcttatctcg tcagtttgag aatagctaaa caggcgagg catataccat agcggagaag      480
ttgatcaagc cttgcaccaa ggatctgaca acttgcgtat ttggagaaaa attcgcgagc     540
aaagttgatc tcgtcccct gtccgacacg actatttcaa ggcgaatcga agacatgagt      600
tacttctgtg aagccgtgct ggtgaacagg ttgaaaaatg ctaaatgtgg gtttacgctg     660
cagatggacg agtcaacaga tgttgccggt cttgcaatcc tgcttgtgtt tgttaggtac     720
atacatgaaa gctcttttga ggaggatatg ttgttctgca aagcacttcc cactcagacg     780
acaggggagg agattttcaa tcttctcaat gcctatttcg aaaagcactc catcccatgg     840
```

```
aatctgtgtt accacatttg cacagacggt gccaaggcaa tggtaggagt tattaaagga      900
gtcatagcga gaataaaaaa actcgtccct gatataaaag ctagccactg ttgcctgcat      960
cgccacgctt tggctgtaaa gcgaataccg aatgcattgc acgaggtgct caatgacgct     1020
gttaaaatga tcaacttcat caagtctcgg ccgttgaatg cgcgcgtctt cgctttgctg     1080
tgtgacgatt tggggagcct gcataaaaat cttcttcttc ataccgaagt gaggtggctg     1140
tctagaggaa aggtgctgac ccgattttgg gaactgagag atgaaattag aattttcttc     1200
aacgaaaggg aatttgccgg gaaattgaac gacaccagtt ggttgcaaaa tttggcatat     1260
atagctgaca tattcagtta tctgaatgaa gttaatcttt ccctgcaagg gccgaatagc     1320
acaatcttca aggtaaatag ccgcattaac agtattaaat caaagttgaa gttgtgggaa     1380
gagtgtataa cgaaaaataa cactgagtgt tttgcgaacc tcaacgattt tttgaaact      1440 tcaaacactg cgttggatcc aaacctgaag tctaatattt tggaacatct caacggtctt     1500
aagaacacct ttctggagta ttttccacct acgtgtaata atatctcctg ggtggagaat     1560
cctttcaatg aatgcggtaa cgtcgataca ctcccaataa aagagaggga acaattgatt     1620
gacatacgga ctgatacgac attgaaatct tcattcgtgc ctgatggtat aggaccattc     1680
tggatcaaac tgatggacga atttccagaa attagcaaac gagctgtcaa agagctcatg     1740
ccatttgtaa ccacttacct ctgtgagaaa tcattttccg tctatgtagc cacaaaaaca     1800
aaatatcgaa atagacttga tgctgaagac gatatgcgac tccaacttac tactatccat     1860
ccagacattg acaacctttg taacaacaag caggctcaga aatcccactg a               1911
```

<210> SEQ ID NO 113
<211> LENGTH: 107
<212> TYPE: PRT
<213> ORGANISM: Artificial Sequence
<220> FEATURE:
<223> OTHER INFORMATION: Synthetic Polypeptide - FKBP12

<400> SEQUENCE: 113

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 114
<211> LENGTH: 321
<212> TYPE: DNA
<213> ORGANISM: Artificial Sequence
<220> FEATURE:
<223> OTHER INFORMATION: Synthetic Polynucleotide - FKBP12

<400> SEQUENCE: 114

```
ggggtccagg tcgagactat ttcaccaggg gatgggcgaa catttccaaa aaggggccag       60
```

-continued

```
acttgcgtcg tgcattacac cgggatgctg gaggacggga agaaagtgga cagctccagg          120
gatcgcaaca agcccttcaa gttcatgctg ggaaagcagg aagtgatccg aggatgggag          180
gaaggcgtgg cacagatgtc agtcggccag cgggccaaac tgaccattag ccctgactac          240
gcttatggag caacaggcca cccagggatc attcccccctc atgccaccct ggtcttcgat          300
gtggaactgc tgaagctgga g                                                    321
```

<210> SEQ ID NO 115
<211> LENGTH: 5
<212> TYPE: PRT
<213> ORGANISM: Artificial Sequence
<220> FEATURE:
<223> OTHER INFORMATION: Synthetic Polypeptide - linker

<400> SEQUENCE: 115

```
Gly Gly Gly Gly Ser
1               5
```

<210> SEQ ID NO 116
<211> LENGTH: 15
<212> TYPE: DNA
<213> ORGANISM: Artificial Sequence
<220> FEATURE:
<223> OTHER INFORMATION: Synthetic Polynucleotide - linker

<400> SEQUENCE: 116

```
ggaggaggag gatcc                                                           15
```

<210> SEQ ID NO 117
<211> LENGTH: 282
<212> TYPE: PRT
<213> ORGANISM: Artificial Sequence
<220> FEATURE:
<223> OTHER INFORMATION: Synthetic Polypeptide - truncated Cas9

<400> SEQUENCE: 117

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
            115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175
```

-continued

```
Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
            195                 200                 205

Val Ser Tyr Ser Thr Phe Pro Gly Phe Val Ser Trp Arg Asp Pro Lys
            210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
            275                 280
```

```
<210> SEQ ID NO 118
<211> LENGTH: 843
<212> TYPE: DNA
<213> ORGANISM: Artificial Sequence
<220> FEATURE:
<223> OTHER INFORMATION: Synthetic Polynucleotide - truncated Cas9

<400> SEQUENCE: 118
tttggggacg tggggggccct ggagtctctg cgaggaaatg ccgatctggc ttacatcctg      60
agcatggaac cctgcggcca ctgtctgatc attaacaatg tgaacttctg cagagaaagc     120
ggactgcgaa cacggactgg ctccaatatt gactgtgaga agctgcggag aaggttctct     180
agtctgcact ttatggtcga agtgaaaggg gatctgaccg ccaagaaaat ggtgctggcc     240
ctgctggagc tggctcagca ggaccatgga gctctggatt gctgcgtggt cgtgatcctg     300
tcccacgggt gccaggcttc tcatctgcag ttccccggag cagtgtacgg aacagacggc     360
tgtcctgtca gcgtggagaa gatcgtcaac atcttcaacg gcacttcttg ccctagtctg     420
gggggaaagc caaaactgtt ctttatccag gcctgtggcg gggaacagaa agatcacggc     480
ttcgaggtgg ccagcaccag ccctgaggac gaatcaccag ggagcaaccc tgaaccagat     540
gcaactccat tccaggaggg actgaggacc tttgaccagc tggatgctat ctcaagcctg     600
cccactccta gtgacatttt cgtgtcttac agtaccttcc caggctttgt ctcatggcgc     660
gatcccaagt cagggagctg gtacgtggag acactgacg acatctttga acagtgggcc     720
cattcagagg acctgcagag cctgctgctg cgagtggcaa acgctgtctc tgtgaagggc     780
atctacaaac agatgcccgg gtgcttcaat tttctgagaa agaaactgtt ctttaagact     840
tcc                                                                    843
```

```
<210> SEQ ID NO 119
<211> LENGTH: 394
<212> TYPE: PRT
<213> ORGANISM: Artificial Sequence
<220> FEATURE:
<223> OTHER INFORMATION: Synthetic Polypeptide

<400> SEQUENCE: 119
```

```
Gly Val Gln Val Glu Thr Ile Ser Pro Gly Asp Gly Arg Thr Phe Pro
1                   5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
            35                  40                  45
```

```
Met Leu Gly Lys Gln Glu Val Ile Arg Gly Trp Glu Glu Gly Val Ala
    50              55              60

Gln Met Ser Val Gly Gln Arg Ala Lys Leu Thr Ile Ser Pro Asp Tyr
65              70              75              80

Ala Tyr Gly Ala Thr Gly His Pro Gly Ile Ile Pro Pro His Ala Thr
                85              90              95

Leu Val Phe Asp Val Glu Leu Leu Lys Leu Glu Gly Gly Gly Gly Ser
            100             105             110

Gly Phe Gly Asp Val Gly Ala Leu Glu Ser Leu Arg Gly Asn Ala Asp
        115             120             125

Leu Ala Tyr Ile Leu Ser Met Glu Pro Cys Gly His Cys Leu Ile Ile
    130             135             140

Asn Asn Val Asn Phe Cys Arg Glu Ser Gly Leu Arg Thr Arg Thr Gly
145             150             155             160

Ser Asn Ile Asp Cys Glu Lys Leu Arg Arg Arg Phe Ser Ser Leu His
            165             170             175

Phe Met Val Glu Val Lys Gly Asp Leu Thr Ala Lys Lys Met Val Leu
            180             185             190

Ala Leu Leu Glu Leu Ala Gln Gln Asp His Gly Ala Leu Asp Cys Cys
        195             200             205

Val Val Val Ile Leu Ser His Gly Cys Gln Ala Ser His Leu Gln Phe
    210             215             220

Pro Gly Ala Val Tyr Gly Thr Asp Gly Cys Pro Val Ser Val Glu Lys
225             230             235             240

Ile Val Asn Ile Phe Asn Gly Thr Ser Cys Pro Ser Leu Gly Gly Lys
            245             250             255

Pro Lys Leu Phe Phe Ile Gln Ala Cys Gly Gly Glu Gln Lys Asp His
            260             265             270

Gly Phe Glu Val Ala Ser Thr Ser Pro Glu Asp Glu Ser Pro Gly Ser
        275             280             285

Asn Pro Glu Pro Asp Ala Thr Pro Phe Gln Glu Gly Leu Arg Thr Phe
    290             295             300

Asp Gln Leu Asp Ala Ile Ser Ser Leu Pro Thr Pro Ser Asp Ile Phe
305             310             315             320

Val Ser Tyr Ser Thr Phe Pro Gly Phe Val Ser Trp Arg Asp Pro Lys
            325             330             335

Ser Gly Ser Trp Tyr Val Glu Thr Leu Asp Asp Ile Phe Glu Gln Trp
            340             345             350

Ala His Ser Glu Asp Leu Gln Ser Leu Leu Leu Arg Val Ala Asn Ala
        355             360             365

Val Ser Val Lys Gly Ile Tyr Lys Gln Met Pro Gly Cys Phe Asn Phe
    370             375             380

Leu Arg Lys Lys Leu Phe Phe Lys Thr Ser
385             390
```

```
<210> SEQ ID NO 120
<211> LENGTH: 1182
<212> TYPE: DNA
<213> ORGANISM: Artificial Sequence
<220> FEATURE:
<223> OTHER INFORMATION: Synthetic Polynucleotide

<400> SEQUENCE: 120
ggggtccagg tcgagactat ttcaccaggg gatgggcgaa catttccaaa aagggggccag        60
```

-continued

```
acttgcgtcg tgcattacac cgggatgctg gaggacggga agaaagtgga cagctccagg     120
gatcgcaaca agcccttcaa gttcatgctg ggaaagcagg aagtgatccg aggatgggag     180
gaaggcgtgg cacagatgtc agtcggccag cgggccaaac tgaccattag ccctgactac     240
gcttatggag caacaggcca cccagggatc attcccctc atgccaccct ggtcttcgat      300
gtggaactgc tgaagctgga gggaggagga ggatccggat ttggggacgt ggggggccctg   360 gagtctctgc gaggaaatgc cgatctggct tacatcctga gcatggaacc ctgcggccac     420
tgtctgatca ttaacaatgt gaacttctgc agagaaagcg gactgcgaac acggactggc     480
tccaatattg actgtgagaa gctgcggaga aggttctcta gtctgcactt tatggtcgaa     540
gtgaaagggg atctgaccgc caagaaaatg gtgctggccc tgctggagct ggctcagcag     600
gaccatggag ctctggattg ctgcgtggtc gtgatcctgt cccacgggtg ccaggcttct     660
catctgcagt tccccggagc agtgtacgga acagacggct gtcctgtcag cgtggagaag    720
atcgtcaaca tcttcaacgg cacttcttgc cctagtctgg ggggaaagcc aaaactgttc    780
tttatccagg cctgtggcgg ggaacagaaa gatcacggct cgaggtggc cagcaccagc      840 cctgaggacg aatcaccagg gagcaaccct gaaccagatg caactccatt ccaggaggga    900
ctgaggacct ttgaccagct ggatgctatc tcaagcctgc ccactcctag tgacattttc    960
gtgtcttaca gtaccttccc aggctttgtc tcatggcgcg atcccaagtc agggagctgg   1020
tacgtggaga cactggacga catctttgaa cagtgggccc attcagagga cctgcagagc   1080
ctgctgctgc gagtggcaaa cgctgtctct gtgaagggca tctacaaaca gatgcccggg   1140
tgcttcaatt ttctgagaaa gaaactgttc tttaagactt cc                       1182
```

<210> SEQ ID NO 121
<211> LENGTH: 463
<212> TYPE: PRT
<213> ORGANISM: Artificial Sequence
<220> FEATURE:
<223> OTHER INFORMATION: Synthetic Polypeptide - CSR-CD2z

<400> SEQUENCE: 121

```
Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
```

-continued

```
                        165                      170                      175

Thr Thr Ser Leu Ser Ala Lys Phe Lys Cys Thr Ala Gly Asn Lys Val
            180                      185                      190

Ser Lys Glu Ser Ser Val Glu Pro Val Ser Cys Pro Glu Lys Gly Leu
            195                      200                      205

Asp Ile Tyr Leu Ile Ile Gly Ile Cys Gly Gly Ser Leu Leu Met
        210                      215                      220

Val Phe Val Ala Leu Leu Val Phe Tyr Ile Thr Lys Arg Lys Lys Gln
225                      230                      235                      240

Arg Ser Arg Arg Asn Asp Glu Glu Leu Glu Thr Arg Ala His Arg Val
            245                      250                      255

Ala Thr Glu Glu Arg Gly Arg Lys Pro His Gln Ile Pro Ala Ser Thr
            260                      265                      270

Pro Gln Asn Pro Ala Thr Ser Gln His Pro Pro Pro Pro Gly His
            275                      280                      285

Arg Ser Gln Ala Pro Ser His Arg Pro Pro Pro Gly His Arg Val
        290                      295                      300

Gln His Gln Pro Gln Lys Arg Pro Pro Ala Pro Ser Gly Thr Gln Val
305                      310                      315                      320

His Gln Gln Lys Gly Pro Pro Leu Pro Arg Pro Arg Val Gln Pro Lys
            325                      330                      335

Pro Pro His Gly Ala Ala Glu Asn Ser Leu Ser Pro Ser Ser Asn Arg
            340                      345                      350

Val Lys Phe Ser Arg Ser Ala Asp Ala Pro Ala Tyr Lys Gln Gly Gln
            355                      360                      365

Asn Gln Leu Tyr Asn Glu Leu Asn Leu Gly Arg Arg Glu Glu Tyr Asp
        370                      375                      380

Val Leu Asp Lys Arg Arg Gly Arg Asp Pro Glu Met Gly Gly Lys Pro
385                      390                      395                      400

Arg Arg Lys Asn Pro Gln Glu Gly Leu Tyr Asn Glu Leu Gln Lys Asp
            405                      410                      415

Lys Met Ala Glu Ala Tyr Ser Glu Ile Gly Met Lys Gly Glu Arg Arg
            420                      425                      430

Arg Gly Lys Gly His Asp Gly Leu Tyr Gln Gly Leu Ser Thr Ala Thr
            435                      440                      445

Lys Asp Thr Tyr Asp Ala Leu His Met Gln Ala Leu Pro Pro Arg
        450                      455                      460
```

```
<210> SEQ ID NO 122
<211> LENGTH: 184
<212> TYPE: PRT
<213> ORGANISM: Artificial Sequence
<220> FEATURE:
<223> OTHER INFORMATION: Synthetic Polypeptide - CD2 ECD with D111H

<400> SEQUENCE: 122

Lys Glu Ile Thr Asn Ala Leu Glu Thr Trp Gly Ala Leu Gly Gln Asp
1               5                       10                      15

Ile Asn Leu Asp Ile Pro Ser Phe Gln Met Ser Asp Ile Asp Asp
            20                      25                      30

Ile Lys Trp Glu Lys Thr Ser Asp Lys Lys Ile Ala Gln Phe Arg
            35                      40                      45

Lys Glu Lys Glu Thr Phe Lys Glu Lys Asp Thr Tyr Lys Leu Phe Lys
        50                      55                      60

Asn Gly Thr Leu Lys Ile Lys His Leu Lys Thr Asp Asp Gln Asp Ile
```

-continued

```
65                   70                   75                   80

Tyr Lys Val Ser Ile Tyr His Thr Lys Gly Lys Asn Val Leu Glu Lys
                85                   90                   95

Ile Phe Asp Leu Lys Ile Gln Glu Arg Val Ser Lys Pro Lys Ile Ser
                100                  105                  110

Trp Thr Cys Ile Asn Thr Thr Leu Thr Cys Glu Val Met Asn Gly Thr
                115                  120                  125

Asp Pro Glu Leu Asn Leu Tyr Gln Asp Gly Lys His Leu Lys Leu Ser
    130                  135                  140

Gln Arg Val Ile Thr His Lys Trp Thr Thr Ser Leu Ser Ala Lys Phe
145                  150                  155                  160

Lys Cys Thr Ala Gly Asn Lys Val Ser Lys Glu Ser Ser Val Glu Pro
                165                  170                  175

Val Ser Cys Pro Glu Lys Gly Leu
                180

<210> SEQ ID NO 123
<211> LENGTH: 463
<212> TYPE: PRT
<213> ORGANISM: Artificial Sequence
<220> FEATURE:
<223> OTHER INFORMATION: Synthetic Polypeptide - CSR-CD2z with D111H

<400> SEQUENCE: 123

Met Ser Phe Pro Cys Lys Phe Val Ala Ser Phe Leu Leu Ile Phe Asn
1               5                    10                   15

Val Ser Ser Lys Gly Ala Val Ser Lys Glu Ile Thr Asn Ala Leu Glu
                20                   25                   30

Thr Trp Gly Ala Leu Gly Gln Asp Ile Asn Leu Asp Ile Pro Ser Phe
                35                   40                   45

Gln Met Ser Asp Asp Ile Asp Asp Ile Lys Trp Glu Lys Thr Ser Asp
    50                   55                   60

Lys Lys Lys Ile Ala Gln Phe Arg Lys Glu Lys Glu Thr Phe Lys Glu
65                   70                   75                   80

Lys Asp Thr Tyr Lys Leu Phe Lys Asn Gly Thr Leu Lys Ile Lys His
                85                   90                   95

Leu Lys Thr Asp Asp Gln Asp Ile Tyr Lys Val Ser Ile Tyr His Thr
                100                  105                  110

Lys Gly Lys Asn Val Leu Glu Lys Ile Phe Asp Leu Lys Ile Gln Glu
                115                  120                  125

Arg Val Ser Lys Pro Lys Ile Ser Trp Thr Cys Ile Asn Thr Thr Leu
    130                  135                  140

Thr Cys Glu Val Met Asn Gly Thr Asp Pro Glu Leu Asn Leu Tyr Gln
145                  150                  155                  160

Asp Gly Lys His Leu Lys Leu Ser Gln Arg Val Ile Thr His Lys Trp
                165                  170                  175

Thr Thr Ser Leu Ser Ala Lys Phe Lys Cys Thr Ala Gly Asn Lys Val
                180                  185                  190

Ser Lys Glu Ser Ser Val Glu Pro Val Ser Cys Pro Glu Lys Gly Leu
                195                  200                  205

Asp Ile Tyr Leu Ile Ile Gly Ile Cys Gly Gly Gly Ser Leu Leu Met
    210                  215                  220

Val Phe Val Ala Leu Leu Val Phe Tyr Ile Thr Lys Arg Lys Lys Gln
225                  230                  235                  240

Arg Ser Arg Arg Asn Asp Glu Glu Leu Glu Thr Arg Ala His Arg Val
```

-continued

```
                    245                 250                 255
Ala Thr Glu Glu Arg Gly Arg Lys Pro His Gln Ile Pro Ala Ser Thr
                260                 265                 270

Pro Gln Asn Pro Ala Thr Ser Gln His Pro Pro Pro Pro Gly His
        275                 280                 285

Arg Ser Gln Ala Pro Ser His Arg Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn Arg
        340                 345                 350

Val Lys Phe Ser Arg Ser Ala Asp Ala Pro Ala Tyr Lys Gln Gly Gln
        355                 360                 365

Asn Gln Leu Tyr Asn Glu Leu Asn Leu Gly Arg Arg Glu Glu Tyr Asp
        370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
                420                 425                 430

Arg Gly Lys Gly His Asp Gly Leu Tyr Gln Gly Leu Ser Thr Ala Thr
                435                 440                 445

Lys Asp Thr Tyr Asp Ala Leu His Met Gln Ala Leu Pro Pro Arg
    450                 455                 460
```

```
<210> SEQ ID NO 124
<211> LENGTH: 241
<212> TYPE: PRT
<213> ORGANISM: Artificial Sequence
<220> FEATURE:
<223> OTHER INFORMATION: Synthetic Polypeptide - "L1H1" scFv

<400> SEQUENCE: 124

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
                20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ser
65                  70                  75                  80

Glu Asp Ile Ala Thr Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Gly Ser Gln Val Gln Leu Val Gln
        115                 120                 125

Ser Gly Ala Glu Val Lys Lys Pro Gly Ser Ser Val Lys Val Ser Cys
    130                 135                 140

Lys Thr Ser Gly Tyr Ala Phe Ser Asn Phe Trp Met Asn Trp Val Arg
```

-continued

```
145              150              155              160

Gln Ala Pro Gly Gln Gly Leu Glu Trp Ile Gly Gln Ile Tyr Pro Gly
                165              170              175

Asp Gly Asp Thr Asn Tyr Asn Gly Lys Phe Lys Gly Arg Val Thr Leu
                180              185              190

Thr Ala Asp Lys Ser Thr Ser Thr Ala Tyr Met Glu Leu Ser Ser Leu
                195              200              205

Arg Ser Glu Asp Thr Ala Val Tyr Phe Cys Ala Arg Ser Tyr Tyr Arg
        210              215              220

Ser Ala Trp Phe Ala Tyr Trp Gly Gln Gly Thr Leu Val Thr Val Ser
225              230              235              240

Ser
```

```
<210> SEQ ID NO 125
<211> LENGTH: 241
<212> TYPE: PRT
<213> ORGANISM: Artificial Sequence
<220> FEATURE:
<223> OTHER INFORMATION: Synthetic Polypeptide - "L1H1B" scFv

<400> SEQUENCE: 125

Glu Ile Leu Leu Thr Gln Ser Pro Asp Phe Gln Ser Val Thr Pro Lys
1                5               10               15

Glu Lys Val Thr Phe Thr Cys Arg Ala Ser Gln Ser Ile Gly Thr Ser
                20               25               30

Ile His Trp Tyr Gln Gln Lys Pro Asn Gln Ser Pro Lys Leu Leu Ile
        35               40               45

Lys Tyr Ala Ser Glu Ser Ile Ser Gly Val Pro Ser Arg Phe Ser Gly
    50               55               60

Ser Gly Ser Gly Thr Asp Phe Thr Leu Thr Ile Asn Ser Leu Glu Ser
65               70               75               80

Glu Asp Ile Ala Thr Tyr Tyr Cys Gln Gln Ser Asn Asn Trp Pro Leu
                85               90               95

Thr Phe Gly Gln Gly Thr Lys Leu Glu Ile Lys Gly Gly Gly Gly Ser
                100              105              110

Gly Gly Gly Gly Ser Gly Gly Gly Gly Ser Gln Val Gln Leu Val Gln
        115              120              125

Ser Gly Ala Glu Val Lys Lys Pro Gly Ser Ser Val Lys Val Ser Cys
        130              135              140

Lys Thr Ser Gly Tyr Ala Phe Ser Asn Phe Trp Met Asn Trp Val Arg
145              150              155              160

Gln Ala Pro Gly Gln Gly Leu Glu Trp Ile Gly Gln Ile Tyr Pro Gly
                165              170              175

Asp Gly Asp Thr Asn Tyr Asn Ala Lys Phe Lys Gly Arg Val Thr Leu
                180              185              190

Thr Ala Asp Lys Ser Thr Ser Thr Ala Tyr Met Glu Leu Ser Ser Leu
                195              200              205

Arg Ser Glu Asp Thr Ala Val Tyr Phe Cys Ala Arg Ser Tyr Tyr Arg
        210              215              220

Ser Ala Trp Phe Ala Tyr Trp Gly Gln Gly Thr Leu Val Thr Val Ser
225              230              235              240

Ser
```

```
<210> SEQ ID NO 126
<211> LENGTH: 241
```

-continued

<212> TYPE: PRT
<213> ORGANISM: Artificial Sequence
<220> FEATURE:
<223> OTHER INFORMATION: Synthetic Polypeptide - "L1H2" scFv

<400> SEQUENCE: 126

```
Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ser
65                  70                  75                  80

Glu Asp Ile Ala Thr Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ser Ser Val Lys Ile Ser Cys
    130                 135                 140

Lys Thr Ser Gly Tyr Ala Phe Ser Asn Phe Trp Met Asn Trp Val Arg
145                 150                 155                 160

Gln Ala Pro Gly Gln Gly Leu Glu Trp Ile Gly Gln Ile Tyr Pro Gly
            165                 170                 175

Asp Gly Asp Thr Asn Tyr Asn Gly Lys Phe Lys Gly Arg Val Thr Leu
            180                 185                 190

Thr Ala Asp Lys Ser Thr Ser Thr Ala Tyr Met Glu Leu Ser Ser Leu
            195                 200                 205

Arg Ser Glu Ala Thr Ala Val Tyr Phe Cys Ala Arg Ser Tyr Tyr Arg
    210                 215                 220

Ser Ala Trp Phe Ala Tyr Trp Gly Gln Gly Thr Leu Val Thr Val Ser
225                 230                 235                 240

Ser
```

<210> SEQ ID NO 127
<211> LENGTH: 241
<212> TYPE: PRT
<213> ORGANISM: Artificial Sequence
<220> FEATURE:
<223> OTHER INFORMATION: Synthetic Polypeptide - "L1H2B" scFv

<400> SEQUENCE: 127

```
Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ser
65                  70                  75                  80
```

-continued

```
Glu Asp Ile Ala Thr Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ser Ser Val Lys Ile Ser Cys
    130                 135                 140

Lys Thr Ser Gly Tyr Ala Phe Ser Asn Phe Trp Met Asn Trp Val Arg
145                 150                 155                 160

Gln Ala Pro Gly Gln Gly Leu Glu Trp Ile Gly Gln Ile Tyr Pro Gly
                165                 170                 175

Asp Gly Asp Thr Asn Tyr Asn Ala Lys Phe Lys Gly Arg Val Thr Leu
                180                 185                 190

Thr Ala Asp Lys Ser Thr Ser Thr Ala Tyr Met Glu Leu Ser Ser Leu
                195                 200                 205

Arg Ser Glu Ala Thr Ala Val Tyr Phe Cys Ala Arg Ser Tyr Tyr Arg
    210                 215                 220

Ser Ala Trp Phe Ala Tyr Trp Gly Gln Gly Thr Leu Val Thr Val Ser
225                 230                 235                 240

Ser
```

<210> SEQ ID NO 128
<211> LENGTH: 241
<212> TYPE: PRT
<213> ORGANISM: Artificial Sequence
<220> FEATURE:
<223> OTHER INFORMATION: Synthetic Polypeptide - "L1H3" scFv

<400> SEQUENCE: 128

```
Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
            35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ser
65                  70                  75                  80

Glu Asp Ile Ala Thr Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ser Ser Val Lys Ile Ser Cys
    130                 135                 140

Lys Thr Ser Gly Tyr Ala Phe Ser Asn Phe Trp Met Asn Trp Val Lys
145                 150                 155                 160

Gln Arg Pro Gly Gln Gly Leu Glu Trp Ile Gly Gln Ile Tyr Pro Gly
                165                 170                 175

Asp Gly Asp Thr Asn Tyr Asn Gly Lys Phe Lys Gly Arg Ala Thr Leu
                180                 185                 190

Thr Ala Asp Lys Ser Thr Ser Thr Ala Tyr Met Glu Leu Ser Ser Leu
```

-continued

```
        195              200              205
Arg Ser Glu Ala Thr Ala Val Tyr Phe Cys Ala Arg Ser Tyr Tyr Arg
    210              215              220

Ser Ala Trp Phe Ala Tyr Trp Gly Gln Gly Thr Leu Val Thr Val Ser
225              230              235              240

Ser

<210> SEQ ID NO 129
<211> LENGTH: 241
<212> TYPE: PRT
<213> ORGANISM: Artificial Sequence
<220> FEATURE:
<223> OTHER INFORMATION: Synthetic Polypeptide - "L1H4" scFv

<400> SEQUENCE: 129

Glu Ile Leu Leu Thr Gln Ser Pro Asp Phe Gln Ser Val Thr Pro Lys
1               5               10               15

Glu Lys Val Thr Phe Thr Cys Arg Ala Ser Gln Ser Ile Gly Thr Ser
        20              25              30

Ile His Trp Tyr Gln Gln Lys Pro Asn Gln Ser Pro Lys Leu Leu Ile
        35              40              45

Lys Tyr Ala Ser Glu Ser Ile Ser Gly Val Pro Ser Arg Phe Ser Gly
    50              55              60

Ser Gly Ser Gly Thr Asp Phe Thr Leu Thr Ile Asn Ser Leu Glu Ser
65              70              75              80

Glu Asp Ile Ala Thr Tyr Tyr Cys Gln Gln Ser Asn Asn Trp Pro Leu
                85              90              95

Thr Phe Gly Gln Gly Thr Lys Leu Glu Ile Lys Gly Gly Gly Gly Ser
        100             105             110

Gly Gly Gly Gly Ser Gly Gly Gly Gly Ser Gln Val Gln Leu Val Gln
        115             120             125

Ser Gly Ala Glu Val Lys Lys Pro Gly Ser Ser Val Lys Ile Ser Cys
    130             135             140

Lys Thr Ser Gly Tyr Ala Phe Ser Asn Phe Trp Met Asn Trp Val Lys
145             150             155             160

Gln Arg Pro Gly Gln Gly Leu Glu Trp Ile Gly Gln Ile Tyr Pro Gly
        165             170             175

Asp Gly Asp Thr Asn Tyr Asn Gly Lys Phe Lys Gly Arg Ala Thr Leu
        180             185             190

Thr Ala Asp Lys Ser Ser Ser Thr Ala Tyr Met Glu Leu Ser Ser Leu
        195             200             205

Arg Ser Glu Ala Thr Ala Val Tyr Phe Cys Ala Arg Ser Tyr Tyr Arg
    210             215             220

Ser Ala Trp Phe Ala Tyr Trp Gly Gln Gly Thr Leu Val Thr Val Ser
225             230             235             240

Ser

<210> SEQ ID NO 130
<211> LENGTH: 241
<212> TYPE: PRT
<213> ORGANISM: Artificial Sequence
<220> FEATURE:
<223> OTHER INFORMATION: Synthetic Polypeptide - "L2H1" scFv

<400> SEQUENCE: 130

Glu Ile Leu Leu Thr Gln Ser Pro Asp Phe Gln Ser Val Thr Pro Lys
1               5               10               15
```

```
Glu Lys Val Thr Phe Thr Cys Arg Ala Ser Gln Ser Ile Gly Thr Ser
        20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ser Ser Val Lys Val Ser Cys
    130                 135                 140

Lys Thr Ser Gly Tyr Ala Phe Ser Asn Phe Trp Met Asn Trp Val Arg
145                 150                 155                 160

Gln Ala Pro Gly Gln Gly Leu Glu Trp Ile Gly Gln Ile Tyr Pro Gly
            165                 170                 175

Asp Gly Asp Thr Asn Tyr Asn Gly Lys Phe Lys Gly Arg Val Thr Leu
            180                 185                 190

Thr Ala Asp Lys Ser Thr Ser Thr Ala Tyr Met Glu Leu Ser Ser Leu
            195                 200                 205

Arg Ser Glu Asp Thr Ala Val Tyr Phe Cys Ala Arg Ser Tyr Tyr Arg
    210                 215                 220

Ser Ala Trp Phe Ala Tyr Trp Gly Gln Gly Thr Leu Val Thr Val Ser
225                 230                 235                 240

Ser
```

<210> SEQ ID NO 131
<211> LENGTH: 241
<212> TYPE: PRT
<213> ORGANISM: Artificial Sequence
<220> FEATURE:
<223> OTHER INFORMATION: Synthetic Polypeptide - "L2H1B" scFv

<400> SEQUENCE: 131

```
Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
        20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125
```

```
Ser Gly Ala Glu Val Lys Lys Pro Gly Ser Ser Val Lys Val Ser Cys
    130             135             140

Lys Thr Ser Gly Tyr Ala Phe Ser Asn Phe Trp Met Asn Trp Val Arg
145             150             155             160

Gln Ala Pro Gly Gln Gly Leu Glu Trp Ile Gly Gln Ile Tyr Pro Gly
            165             170             175

Asp Gly Asp Thr Asn Tyr Asn Ala Lys Phe Lys Gly Arg Val Thr Leu
            180             185             190

Thr Ala Asp Lys Ser Thr Ser Thr Ala Tyr Met Glu Leu Ser Ser Leu
            195             200             205

Arg Ser Glu Asp Thr Ala Val Tyr Phe Cys Ala Arg Ser Tyr Tyr Arg
    210             215             220

Ser Ala Trp Phe Ala Tyr Trp Gly Gln Gly Thr Leu Val Thr Val Ser
225             230             235             240

Ser
```

```
<210> SEQ ID NO 132
<211> LENGTH: 241
<212> TYPE: PRT
<213> ORGANISM: Artificial Sequence
<220> FEATURE:
<223> OTHER INFORMATION: Synthetic Polypeptide - "L2H2" scFv

<400> SEQUENCE: 132

Glu Ile Leu Leu Thr Gln Ser Pro Asp Phe Gln Ser Val Thr Pro Lys
1               5               10              15

Glu Lys Val Thr Phe Thr Cys Arg Ala Ser Gln Ser Ile Gly Thr Ser
            20              25              30

Ile His Trp Tyr Gln Gln Lys Pro Asn Gln Ser Pro Lys Leu Leu Ile
        35              40              45

Lys Tyr Ala Ser Glu Ser Ile Ser Gly Val Pro Ser Arg Phe Ser Gly
    50              55              60

Ser Gly Ser Gly Thr Asp Phe Thr Leu Thr Ile Asn Ser Val Glu Ser
65              70              75              80

Glu Asp Ile Ala Asp Tyr Tyr Cys Gln Gln Ser Asn Asn Trp Pro Leu
            85              90              95

Thr Phe Gly Gln Gly Thr Lys Leu Glu Ile Lys Gly Gly Gly Gly Ser
            100             105             110

Gly Gly Gly Gly Ser Gly Gly Gly Gly Ser Gln Val Gln Leu Val Gln
        115             120             125

Ser Gly Ala Glu Val Lys Lys Pro Gly Ser Ser Val Lys Ile Ser Cys
    130             135             140

Lys Thr Ser Gly Tyr Ala Phe Ser Asn Phe Trp Met Asn Trp Val Arg
145             150             155             160

Gln Ala Pro Gly Gln Gly Leu Glu Trp Ile Gly Gln Ile Tyr Pro Gly
            165             170             175

Asp Gly Asp Thr Asn Tyr Asn Gly Lys Phe Lys Gly Arg Val Thr Leu
            180             185             190

Thr Ala Asp Lys Ser Thr Ser Thr Ala Tyr Met Glu Leu Ser Ser Leu
            195             200             205

Arg Ser Glu Ala Thr Ala Val Tyr Phe Cys Ala Arg Ser Tyr Tyr Arg
    210             215             220

Ser Ala Trp Phe Ala Tyr Trp Gly Gln Gly Thr Leu Val Thr Val Ser
225             230             235             240

Ser
```

<210> SEQ ID NO 133
<211> LENGTH: 241
<212> TYPE: PRT
<213> ORGANISM: Artificial Sequence
<220> FEATURE:
<223> OTHER INFORMATION: Synthetic Polypeptide - "L2H2B" scFv

<400> SEQUENCE: 133

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ser Ser Val Lys Ile Ser Cys
    130                 135                 140

Lys Thr Ser Gly Tyr Ala Phe Ser Asn Phe Trp Met Asn Trp Val Arg
145                 150                 155                 160

Gln Ala Pro Gly Gln Gly Leu Glu Trp Ile Gly Gln Ile Tyr Pro Gly
                165                 170                 175

Asp Gly Asp Thr Asn Tyr Asn Ala Lys Phe Lys Gly Arg Val Thr Leu
            180                 185                 190

Thr Ala Asp Lys Ser Thr Ser Thr Ala Tyr Met Glu Leu Ser Ser Leu
        195                 200                 205

Arg Ser Glu Ala Thr Ala Val Tyr Phe Cys Ala Arg Ser Tyr Tyr Arg
    210                 215                 220

Ser Ala Trp Phe Ala Tyr Trp Gly Gln Gly Thr Leu Val Thr Val Ser
225                 230                 235                 240

Ser

<210> SEQ ID NO 134
<211> LENGTH: 241
<212> TYPE: PRT
<213> ORGANISM: Artificial Sequence
<220> FEATURE:
<223> OTHER INFORMATION: Synthetic Polypeptide - "L2H3" scFv

<400> SEQUENCE: 134

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Val Gln
            115                 120                 125

Ser Gly Ala Glu Val Lys Lys Pro Gly Ser Ser Val Lys Ile Ser Cys
        130                 135                 140

Lys Thr Ser Gly Tyr Ala Phe Ser Asn Phe Trp Met Asn Trp Val Lys
145                 150                 155                 160

Gln Arg Pro Gly Gln Gly Leu Glu Trp Ile Gly Gln Ile Tyr Pro Gly
                165                 170                 175

Asp Gly Asp Thr Asn Tyr Asn Gly Lys Phe Lys Gly Arg Ala Thr Leu
            180                 185                 190

Thr Ala Asp Lys Ser Thr Ser Thr Ala Tyr Met Glu Leu Ser Ser Leu
            195                 200                 205

Arg Ser Glu Ala Thr Ala Val Tyr Phe Cys Ala Arg Ser Tyr Tyr Arg
        210                 215                 220

Ser Ala Trp Phe Ala Tyr Trp Gly Gln Gly Thr Leu Val Thr Val Ser
225                 230                 235                 240

Ser

<210> SEQ ID NO 135
<211> LENGTH: 241
<212> TYPE: PRT
<213> ORGANISM: Artificial Sequence
<220> FEATURE:
<223> OTHER INFORMATION: Synthetic Polypeptide - "L2H4" scFv

<400> SEQUENCE: 135

Glu Ile Leu Leu Thr Gln Ser Pro Asp Phe Gln Ser Val Thr Pro Lys
1                   5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ser Ser Val Lys Ile Ser Cys
        130                 135                 140

Lys Thr Ser Gly Tyr Ala Phe Ser Asn Phe Trp Met Asn Trp Val Lys
145                 150                 155                 160

Gln Arg Pro Gly Gln Gly Leu Glu Trp Ile Gly Gln Ile Tyr Pro Gly
                165                 170                 175

-continued

Asp Gly Asp Thr Asn Tyr Asn Gly Lys Phe Lys Gly Arg Ala Thr Leu
                180                 185                 190

Thr Ala Asp Lys Ser Ser Ser Thr Ala Tyr Met Glu Leu Ser Ser Leu
            195                 200                 205

Arg Ser Glu Ala Thr Ala Val Tyr Phe Cys Ala Arg Ser Tyr Tyr Arg
        210                 215                 220

Ser Ala Trp Phe Ala Tyr Trp Gly Gln Gly Thr Leu Val Thr Val Ser
225                 230                 235                 240

Ser

<210> SEQ ID NO 136
<211> LENGTH: 241
<212> TYPE: PRT
<213> ORGANISM: Artificial Sequence
<220> FEATURE:
<223> OTHER INFORMATION: Synthetic Polypeptide - "L3H1" scFv

<400> SEQUENCE: 136

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
                20                  25                  30

Ile His Trp Tyr Gln Gln Lys Pro Asn Gln Ser Pro Lys Leu Leu Ile
            35                  40                  45

Lys Tyr Ala Ser Glu Ser Ile Ser Gly Val Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ser Ser Val Lys Val Ser Cys
        130                 135                 140

Lys Thr Ser Gly Tyr Ala Phe Ser Asn Phe Trp Met Asn Trp Val Arg
145                 150                 155                 160

Gln Ala Pro Gly Gln Gly Leu Glu Trp Ile Gly Gln Ile Tyr Pro Gly
                165                 170                 175

Asp Gly Asp Thr Asn Tyr Asn Gly Lys Phe Lys Gly Arg Val Thr Leu
                180                 185                 190

Thr Ala Asp Lys Ser Thr Ser Thr Ala Tyr Met Glu Leu Ser Ser Leu
            195                 200                 205

Arg Ser Glu Asp Thr Ala Val Tyr Phe Cys Ala Arg Ser Tyr Tyr Arg
        210                 215                 220

Ser Ala Trp Phe Ala Tyr Trp Gly Gln Gly Thr Leu Val Thr Val Ser
225                 230                 235                 240

Ser

<210> SEQ ID NO 137
<211> LENGTH: 241
<212> TYPE: PRT
<213> ORGANISM: Artificial Sequence
<220> FEATURE:
<223> OTHER INFORMATION: Synthetic Polypeptide - "L3H1B" scFv -continued

<400> SEQUENCE: 137

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Val Gln
            115                 120                 125

Ser Gly Ala Glu Val Lys Lys Pro Gly Ser Ser Val Lys Val Ser Cys
    130                 135                 140

Lys Thr Ser Gly Tyr Ala Phe Ser Asn Phe Trp Met Asn Trp Val Arg
145                 150                 155                 160

Gln Ala Pro Gly Gln Gly Leu Glu Trp Ile Gly Gln Ile Tyr Pro Gly
            165                 170                 175

Asp Gly Asp Thr Asn Tyr Asn Ala Lys Phe Lys Gly Arg Val Thr Leu
            180                 185                 190

Thr Ala Asp Lys Ser Thr Ser Thr Ala Tyr Met Glu Leu Ser Ser Leu
            195                 200                 205

Arg Ser Glu Asp Thr Ala Val Tyr Phe Cys Ala Arg Ser Tyr Tyr Arg
    210                 215                 220

Ser Ala Trp Phe Ala Tyr Trp Gly Gln Gly Thr Leu Val Thr Val Ser
225                 230                 235                 240

Ser

<210> SEQ ID NO 138
<211> LENGTH: 241
<212> TYPE: PRT
<213> ORGANISM: Artificial Sequence
<220> FEATURE:
<223> OTHER INFORMATION: Synthetic Polypeptide - "L3H2" scFv

<400> SEQUENCE: 138

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

-continued

```
Gly Gly Gly Gly Ser Gly Gly Gly Gly Ser Gln Val Gln Leu Val Gln
        115             120             125

Ser Gly Ala Glu Val Lys Lys Pro Gly Ser Ser Val Lys Ile Ser Cys
    130             135             140

Lys Thr Ser Gly Tyr Ala Phe Ser Asn Phe Trp Met Asn Trp Val Arg
145             150             155             160

Gln Ala Pro Gly Gln Gly Leu Glu Trp Ile Gly Gln Ile Tyr Pro Gly
                165             170             175

Asp Gly Asp Thr Asn Tyr Asn Gly Lys Phe Lys Gly Arg Val Thr Leu
            180             185             190

Thr Ala Asp Lys Ser Thr Ser Thr Ala Tyr Met Glu Leu Ser Ser Leu
        195             200             205

Arg Ser Glu Ala Thr Ala Val Tyr Phe Cys Ala Arg Ser Tyr Tyr Arg
    210             215             220

Ser Ala Trp Phe Ala Tyr Trp Gly Gln Gly Thr Leu Val Thr Val Ser
225             230             235             240

Ser
```

```
<210> SEQ ID NO 139
<211> LENGTH: 241
<212> TYPE: PRT
<213> ORGANISM: Artificial Sequence
<220> FEATURE:
<223> OTHER INFORMATION: Synthetic Polypeptide - "L3H2B" scFv

<400> SEQUENCE: 139
```

```
Glu Ile Leu Leu Thr Gln Ser Pro Asp Phe Gln Ser Val Thr Pro Lys
1               5               10              15

Glu Lys Val Thr Phe Thr Cys Arg Ala Ser Gln Ser Ile Gly Thr Ser
        20              25              30

Ile His Trp Tyr Gln Gln Lys Pro Asn Gln Ser Pro Lys Leu Leu Ile
        35              40              45

Lys Tyr Ala Ser Glu Ser Ile Ser Gly Val Pro Ser Arg Phe Ser Gly
    50              55              60

Ser Gly Ser Gly Thr Asp Phe Thr Leu Ser Ile Asn Ser Val Glu Ser
65              70              75              80

Glu Asp Ile Ala Asp Tyr Tyr Cys Gln Gln Ser Asn Asn Trp Pro Leu
            85              90              95

Thr Phe Gly Gln Gly Thr Lys Leu Glu Ile Lys Gly Gly Gly Gly Ser
        100             105             110

Gly Gly Gly Gly Ser Gly Gly Gly Gly Ser Gln Val Gln Leu Val Gln
        115             120             125

Ser Gly Ala Glu Val Lys Lys Pro Gly Ser Ser Val Lys Ile Ser Cys
    130             135             140

Lys Thr Ser Gly Tyr Ala Phe Ser Asn Phe Trp Met Asn Trp Val Arg
145             150             155             160

Gln Ala Pro Gly Gln Gly Leu Glu Trp Ile Gly Gln Ile Tyr Pro Gly
                165             170             175

Asp Gly Asp Thr Asn Tyr Asn Ala Lys Phe Lys Gly Arg Val Thr Leu
            180             185             190

Thr Ala Asp Lys Ser Thr Ser Thr Ala Tyr Met Glu Leu Ser Ser Leu
        195             200             205

Arg Ser Glu Ala Thr Ala Val Tyr Phe Cys Ala Arg Ser Tyr Tyr Arg
    210             215             220
```

-continued

```
Ser Ala Trp Phe Ala Tyr Trp Gly Gln Gly Thr Leu Val Thr Val Ser
225                 230                 235                 240

Ser

<210> SEQ ID NO 140
<211> LENGTH: 241
<212> TYPE: PRT
<213> ORGANISM: Artificial Sequence
<220> FEATURE:
<223> OTHER INFORMATION: Synthetic Polypeptide - "L3H3" scFv

<400> SEQUENCE: 140

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ser Ser Val Lys Ile Ser Cys
    130                 135                 140

Lys Thr Ser Gly Tyr Ala Phe Ser Asn Phe Trp Met Asn Trp Val Lys
145                 150                 155                 160

Gln Arg Pro Gly Gln Gly Leu Glu Trp Ile Gly Gln Ile Tyr Pro Gly
                165                 170                 175

Asp Gly Asp Thr Asn Tyr Asn Gly Lys Phe Lys Gly Arg Ala Thr Leu
            180                 185                 190

Thr Ala Asp Lys Ser Thr Ser Thr Ala Tyr Met Glu Leu Ser Ser Leu
            195                 200                 205

Arg Ser Glu Ala Thr Ala Val Tyr Phe Cys Ala Arg Ser Tyr Tyr Arg
    210                 215                 220

Ser Ala Trp Phe Ala Tyr Trp Gly Gln Gly Thr Leu Val Thr Val Ser
225                 230                 235                 240

Ser

<210> SEQ ID NO 141
<211> LENGTH: 241
<212> TYPE: PRT
<213> ORGANISM: Artificial Sequence
<220> FEATURE:
<223> OTHER INFORMATION: Synthetic Polypeptide - "L3H4" scFv

<400> SEQUENCE: 141

Glu Ile Leu Leu Thr Gln Ser Pro Asp Phe Gln Ser Val Thr Pro Lys
1               5                   10                  15

Glu Lys Val Thr Phe Thr Cys Arg Ala Ser Gln Ser Ile Gly Thr Ser
            20                  25                  30

Ile His Trp Tyr Gln Gln Lys Pro Asn Gln Ser Pro Lys Leu Leu Ile
```

-continued

```
              35              40              45

Lys Tyr Ala Ser Glu Ser Ile Ser Gly Val Pro Ser Arg Phe Ser Gly
    50              55              60

Ser Gly Ser Gly Thr Asp Phe Thr Leu Ser Ile Asn Ser Val Glu Ser
65              70              75              80

Glu Asp Ile Ala Asp Tyr Tyr Cys Gln Gln Ser Asn Asn Trp Pro Leu
                85              90              95

Thr Phe Gly Gln Gly Thr Lys Leu Glu Ile Lys Gly Gly Gly Gly Ser
            100             105             110

Gly Gly Gly Gly Ser Gly Gly Gly Ser Gln Val Gln Leu Val Gln
        115             120             125

Ser Gly Ala Glu Val Lys Lys Pro Gly Ser Ser Val Lys Ile Ser Cys
    130             135             140

Lys Thr Ser Gly Tyr Ala Phe Ser Asn Phe Trp Met Asn Trp Val Lys
145             150             155             160

Gln Arg Pro Gly Gln Gly Leu Glu Trp Ile Gly Gln Ile Tyr Pro Gly
            165             170             175

Asp Gly Asp Thr Asn Tyr Asn Gly Lys Phe Lys Gly Arg Ala Thr Leu
            180             185             190

Thr Ala Asp Lys Ser Ser Ser Thr Ala Tyr Met Glu Leu Ser Ser Leu
            195             200             205

Arg Ser Glu Ala Thr Ala Val Tyr Phe Cys Ala Arg Ser Tyr Tyr Arg
    210             215             220

Ser Ala Trp Phe Ala Tyr Trp Gly Gln Gly Thr Leu Val Thr Val Ser
225             230             235             240

Ser
```

```
<210> SEQ ID NO 142
<211> LENGTH: 723
<212> TYPE: DNA
<213> ORGANISM: Artificial Sequence
<220> FEATURE:
<223> OTHER INFORMATION: Synthetic Polynucleotide - "L1H1" scFv

<400> SEQUENCE: 142
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180 agatttctg gcagcggaag cggcaccgac ttcaccctga ccatcaacag cctggaatcc     240
gaggacattg ccacctacta ctgccagcag tccaacaact ggcccctgac atttggccag     300
ggcaccaagc tggaaatcaa aggcggaggc ggtagcggtg cggaggtag cggaggtggt     360 ggatctcagg ttcagctggt tcagtctggc gccgaagtga agaaacctgg cagcagcgtg     420
aaggtgtcct gcaagacaag cggctacgcc ttcagcaact ctggatgaa ctgggtccga     480 caggcccctg acaaggcct ggaatggatc ggccaaatct atcccggcga cggcgacacc     540
aactacaacg gcaagttcaa gggcagagtg acactgaccg ccgacaagag cacaagcacc     600
gcctacatgg aactgagcag cctgagaagc gaggataccg ccgtgtactt ctgcgcccgg     660
tcctactaca gaagcgcttg gtttgcctat tggggccagg gaaccctcgt gaccgttagc     720
tct                                                                    723
```

```
<210> SEQ ID NO 143
<211> LENGTH: 723
```

-continued

```
<212> TYPE: DNA
<213> ORGANISM: Artificial Sequence
<220> FEATURE:
<223> OTHER INFORMATION: Synthetic Polynucleotide - "L1H1B" scFv

<400> SEQUENCE: 143
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctga ccatcaacag cctggaatcc     240
gaggacattg ccacctacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aaggtgtcct gcaagacaag cggctacgcc ttcagcaact tctggatgaa ctgggtccga     480
caggcccctg gacaaggcct ggaatggatc ggccaaatct atcccggcga cggcgacacc     540
aactacaacg ccaagttcaa gggcagagtg acactgaccg ccgacaagag cacaagcacc     600
gcctacatgg aactgagcag cctgagaagc gaggataccg ccgtgtactt ctgcgcccgg     660
tcctactaca gaagcgcttg gtttgcctat tggggccagg gaaccctcgt gaccgttagc     720
tct                                                                     723

<210> SEQ ID NO 144
<211> LENGTH: 723
<212> TYPE: DNA
<213> ORGANISM: Artificial Sequence
<220> FEATURE:
<223> OTHER INFORMATION: Synthetic Polynucleotide - "L1H2" scFv

<400> SEQUENCE: 144
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctga ccatcaacag cctggaatcc     240
gaggacattg ccacctacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aagatcagct gcaagacaag cggctacgcc ttcagcaact tctggatgaa ctgggtccga     480
caggcccctg gacaaggcct ggaatggatc ggccaaatct atcccggcga cggcgacacc     540
aactacaacg gcaagttcaa gggcagagtg acactgaccg ccgacaagag cacaagcacc     600
gcctacatgg aactgagcag cctgagaagc gaggctaccg ccgtgtactt ctgtgccaga     660
agctactaca gaagcgcttg gtttgcctac tggggccagg gaacactcgt gaccgttagc     720
tct                                                                     723

<210> SEQ ID NO 145
<211> LENGTH: 723
<212> TYPE: DNA
<213> ORGANISM: Artificial Sequence
<220> FEATURE:
<223> OTHER INFORMATION: Synthetic Polynucleotide - "L1H2B" scFv

<400> SEQUENCE: 145
```

-continued

```
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctga ccatcaacag cctggaatcc     240
gaggacattg ccacctacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aagatcagct gcaagacaag cggctacgcc ttcagcaact ctggatgaa ctgggtccga     480 caggcccctg acaaggcct ggaatggatc ggccaaatct atcccggcga cggcgacacc     540
aactacaacg ccaagttcaa gggcagagtg acactgaccg ccgacaagag cacaagcacc     600
gcctacatgg aactgagcag cctgagaagc gaggctaccg ccgtgtactt ctgtgccaga     660
agctactaca gaagcgcttg gtttgcctac tggggccagg gaacactcgt gaccgttagc     720
tct                                                                    723
```

```
<210> SEQ ID NO 146
<211> LENGTH: 723
<212> TYPE: DNA
<213> ORGANISM: Artificial Sequence
<220> FEATURE:
<223> OTHER INFORMATION: Synthetic Polynucleotide - "L1H3" scFv

<400> SEQUENCE: 146
```

```
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctga ccatcaacag cctggaatcc     240
gaggacattg ccacctacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aagatcagct gcaagacaag cggctacgcc ttcagcaact ctggatgaa ctgggtcaag     480 cagcggccag gccaaggcct ggaatggatc ggacaaatct atcccggcga cggcgacacc     540
aactacaacg gcaagttcaa gggcagagct acactgaccg ccgacaagag cacaagcacc     600
gcctacatgg aactgagcag cctgagaagc gaggctaccg ccgtgtactt ctgtgccaga     660
agctactaca gaagcgcttg gtttgcctac tggggccagg gaacactcgt gaccgttagc     720
tct                                                                    723
```

```
<210> SEQ ID NO 147
<211> LENGTH: 723
<212> TYPE: DNA
<213> ORGANISM: Artificial Sequence
<220> FEATURE:
<223> OTHER INFORMATION: Synthetic Polynucleotide - "L1H4" scFv

<400> SEQUENCE: 147
```

```
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctga ccatcaacag cctggaatcc     240
```

-continued

```
gaggacattg ccacctacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
aagatcagct gcaagacaag cggctacgcc ttcagcaact tctggatgaa ctgggtcaag      480
cagcggccag ccaaggcct ggaatggatc ggacaaatct atcccggcga cggcgacacc       540
aactacaacg gcaagttcaa gggcagagct acactgaccg ccgacaagag cagcagcacc      600
gcctacatgg aactgagcag cctgagaagc gaggctaccg ccgtgtactt ctgtgccaga      660
agctactaca aagcgcttg gtttgcctac tggggccagg gaacactcgt gaccgttagc       720
tct                                                                    723

<210> SEQ ID NO 148
<211> LENGTH: 723
<212> TYPE: DNA
<213> ORGANISM: Artificial Sequence
<220> FEATURE:
<223> OTHER INFORMATION: Synthetic Polynucleotide - "L2H1" scFv

<400> SEQUENCE: 148
gagattctgc tgacacagag ccctgacttc cagagcgtga cccctaaaga aaaagtgacc       60
ttcacctgta gagccagcca gagcatcggc acctccatcc actggtatca gcagaagccc      120
aatcagagcc ccaagctgct gattaagtac gccagcgagt ccatcagcgg cgtgccaagc      180
agattttctg gcagcggaag cggcaccgac ttcaccctga ccatcaacag cgtggaatcc      240
gaggacattg ccgactacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
aaggtgtcct gcaagacaag cggctacgcc ttcagcaact tctggatgaa ctgggtccga      480
caggcccctg acaaggcct ggaatggatc ggccaaatct atcccggcga cggcgacacc       540
aactacaacg gcaagttcaa gggcagagtg acactgaccg ccgacaagag cacaagcacc      600
gcctacatgg aactgagcag cctgagaagc gaggatacsg ccgtgtactt ctgcgcccgg      660
tcctactaca aagcgcttg gtttgcctat tggggccagg gaacccctcgt gaccgttagc      720 tct                                                                    723

<210> SEQ ID NO 149
<211> LENGTH: 723
<212> TYPE: DNA
<213> ORGANISM: Artificial Sequence
<220> FEATURE:
<223> OTHER INFORMATION: Synthetic Polynucleotide - "L2H1B" scFv

<400> SEQUENCE: 149
gagattctgc tgacacagag ccctgacttc cagagcgtga cccctaaaga aaaagtgacc       60
ttcacctgta gagccagcca gagcatcggc acctccatcc actggtatca gcagaagccc      120
aatcagagcc ccaagctgct gattaagtac gccagcgagt ccatcagcgg cgtgccaagc      180
agattttctg gcagcggaag cggcaccgac ttcaccctga ccatcaacag cgtggaatcc      240
gaggacattg ccgactacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
```

-continued

```
aaggtgtcct gcaagacaag cggctacgcc ttcagcaact tctggatgaa ctgggtccga    480
caggcccctg gacaaggcct ggaatggatc ggccaaatct atcccggcga cggcgacacc    540
aactacaacg ccaagttcaa gggcagagtg acactgaccg ccgacaagag cacaagcacc    600
gcctacatgg aactgagcag cctgagaagc gaggataccg ccgtgtactt ctgcgcccgg    660
tcctactaca gaagcgcttg gtttgcctat tggggccagg gaaccctcgt gaccgttagc    720
tct                                                                  723
```

<210> SEQ ID NO 150
<211> LENGTH: 723
<212> TYPE: DNA
<213> ORGANISM: Artificial Sequence
<220> FEATURE:
<223> OTHER INFORMATION: Synthetic Polynucleotide - "L2H2" scFv

<400> SEQUENCE: 150

```
gagattctgc tgacacagag ccctgacttc cagagcgtga cccctaaaga aaaagtgacc     60
ttcacctgta gagccagcca gagcatcggc acctccatcc actggtatca gcagaagccc    120
aatcagagcc ccaagctgct gattaagtac gccagcgagt ccatcagcgg cgtgccaagc    180
agattttctg gcagcggaag cggcaccgac ttcaccctga ccatcaacag cgtggaatcc    240
gaggacattg ccgactacta ctgccagcag tccaacaact ggcccctgac atttggccag    300
ggcaccaagc tggaaatcaa aggcggaggc ggtagcggtg gcggaggtag cggaggtggt    360
ggatctcagg ttcagctggt tcagtctggc gccgaagtga agaaacctgg cagcagcgtg    420
aagatcagct gcaagacaag cggctacgcc ttcagcaact tctggatgaa ctgggtccga    480
caggcccctg gacaaggcct ggaatggatc ggccaaatct atcccggcga cggcgacacc    540
aactacaacg gcaagttcaa gggcagagtg acactgaccg ccgacaagag cacaagcacc    600
gcctacatgg aactgagcag cctgagaagc gaggctaccg ccgtgtactt ctgtgccaga    660
agctactaca gaagcgcttg gtttgcctac tggggccagg gaacactcgt gaccgttagc    720
tct                                                                  723
```

<210> SEQ ID NO 151
<211> LENGTH: 723
<212> TYPE: DNA
<213> ORGANISM: Artificial Sequence
<220> FEATURE:
<223> OTHER INFORMATION: Synthetic Polynucleotide - "L2H2B" scFv

<400> SEQUENCE: 151

```
gagattctgc tgacacagag ccctgacttc cagagcgtga cccctaaaga aaaagtgacc     60
ttcacctgta gagccagcca gagcatcggc acctccatcc actggtatca gcagaagccc    120
aatcagagcc ccaagctgct gattaagtac gccagcgagt ccatcagcgg cgtgccaagc    180
agattttctg gcagcggaag cggcaccgac ttcaccctga ccatcaacag cgtggaatcc    240
gaggacattg ccgactacta ctgccagcag tccaacaact ggcccctgac atttggccag    300
ggcaccaagc tggaaatcaa aggcggaggc ggtagcggtg gcggaggtag cggaggtggt    360
ggatctcagg ttcagctggt tcagtctggc gccgaagtga agaaacctgg cagcagcgtg    420
aagatcagct gcaagacaag cggctacgcc ttcagcaact tctggatgaa ctgggtccga    480
caggcccctg gacaaggcct ggaatggatc ggccaaatct atcccggcga cggcgacacc    540
aactacaacg ccaagttcaa gggcagagtg acactgaccg ccgacaagag cacaagcacc    600
gcctacatgg aactgagcag cctgagaagc gaggctaccg ccgtgtactt ctgtgccaga    660
```
agctactaca gaagcgcttg gtttgcctac tggggccagg gaacactcgt gaccgttagc      720
tct                                                                   723

<210> SEQ ID NO 152
<211> LENGTH: 723
<212> TYPE: DNA
<213> ORGANISM: Artificial Sequence
<220> FEATURE:
<223> OTHER INFORMATION: Synthetic Polynucleotide - "L2H3" scFv

<400> SEQUENCE: 152
gagattctgc tgacacagag ccctgacttc cagagcgtga cccctaaaga aaaagtgacc       60
ttcacctgta gagccagcca gagcatcggc acctccatcc actggtatca gcagaagccc      120
aatcagagcc ccaagctgct gattaagtac gccagcgagt ccatcagcgg cgtgccaagc      180
agattttctg gcagcggaag cggcaccgac ttcaccctga ccatcaacag cgtggaatcc      240
gaggacattg ccgactacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
aagatcagct gcaagacaag cggctacgcc ttcagcaact ctggatgaa ctgggtcaag      480 cagcggccag gccaaggcct ggaatggatc ggacaaatct atcccggcga cggcgacacc      540
aactacaacg gcaagttcaa gggcagagct acactgaccg ccgacaagag cacaagcacc      600
gcctacatgg aactgagcag cctgagaagc gaggctaccg ccgtgtactt ctgtgccaga      660
agctactaca gaagcgcttg gtttgcctac tggggccagg gaacactcgt gaccgttagc      720
tct                                                                   723

<210> SEQ ID NO 153
<211> LENGTH: 723
<212> TYPE: DNA
<213> ORGANISM: Artificial Sequence
<220> FEATURE:
<223> OTHER INFORMATION: Synthetic Polynucleotide - "L2H4" scFv

<400> SEQUENCE: 153
gagattctgc tgacacagag ccctgacttc cagagcgtga cccctaaaga aaaagtgacc       60
ttcacctgta gagccagcca gagcatcggc acctccatcc actggtatca gcagaagccc      120
aatcagagcc ccaagctgct gattaagtac gccagcgagt ccatcagcgg cgtgccaagc      180
agattttctg gcagcggaag cggcaccgac ttcaccctga ccatcaacag cgtggaatcc      240
gaggacattg ccgactacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
aagatcagct gcaagacaag cggctacgcc ttcagcaact ctggatgaa ctgggtcaag      480 cagcggccag gccaaggcct ggaatggatc ggacaaatct atcccggcga cggcgacacc      540
aactacaacg gcaagttcaa gggcagagct acactgaccg ccgacaagag cagcagcacc      600
gcctacatgg aactgagcag cctgagaagc gaggctaccg ccgtgtactt ctgtgccaga      660
agctactaca gaagcgcttg gtttgcctac tggggccagg gaacactcgt gaccgttagc      720
tct                                                                   723

<210> SEQ ID NO 154

-continued

```
<211> LENGTH: 723
<212> TYPE: DNA
<213> ORGANISM: Artificial Sequence
<220> FEATURE:
<223> OTHER INFORMATION: Synthetic Polynucleotide - "L3H1" scFv

<400> SEQUENCE: 154
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctgt ctatcaacag cgtggaatcc     240
gaggacattg ccgactacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aaggtgtcct gcaagacaag cggctacgcc ttcagcaact ctggatgaa ctgggtccga     480 caggcccctg acaaggcct ggaatggatc ggccaaatct atcccggcga cggcgacacc     540
aactacaacg gcaagttcaa gggcagagtg acactgaccg ccgacaagag cacaagcacc     600
gcctacatgg aactgagcag cctgagaagc gaggataccg ccgtgtactt ctgcgcccgg     660
tcctactaca gaagcgcttg gtttgcctat tggggccagg gaaccctcgt gaccgttagc     720
tct                                                                    723

<210> SEQ ID NO 155
<211> LENGTH: 723
<212> TYPE: DNA
<213> ORGANISM: Artificial Sequence
<220> FEATURE:
<223> OTHER INFORMATION: Synthetic Polynucleotide - "L3H1B" scFv

<400> SEQUENCE: 155
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctgt ctatcaacag cgtggaatcc     240
gaggacattg ccgactacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aaggtgtcct gcaagacaag cggctacgcc ttcagcaact ctggatgaa ctgggtccga     480 caggcccctg acaaggcct ggaatggatc ggccaaatct atcccggcga cggcgacacc     540
aactacaacg ccaagttcaa gggcagagtg acactgaccg ccgacaagag cacaagcacc     600
gcctacatgg aactgagcag cctgagaagc gaggataccg ccgtgtactt ctgcgcccgg     660
tcctactaca gaagcgcttg gtttgcctat tggggccagg gaaccctcgt gaccgttagc     720
tct                                                                    723

<210> SEQ ID NO 156
<211> LENGTH: 723
<212> TYPE: DNA
<213> ORGANISM: Artificial Sequence
<220> FEATURE:
<223> OTHER INFORMATION: Synthetic Polynucleotide - "L3H2" scFv

<400> SEQUENCE: 156
```

```
gagattctgc tgacacagag ccctgacttc cagagcgtga cccctaaaga aaaagtgacc      60
ttcacctgta gagccagcca gagcatcggc acctccatcc actggtatca gcagaagccc     120
aataatccga ggacattgcc gactactact gccagcagtc caacaactgg cccctgacat     180
ttggccaggg caccaagctg gaaatcaaag cggaggcgg tagcggtggc ggaggtagcg      240
gagcagagcc ccaagctgct gattaagtac gccagcgagt ccatcagcgg cgtgccaagc     300
agattttctg gcagcggaag cggcaccgac ttcaccctgt ctatcaacag cgtgggtggt     360
ggatctcagg ttcagctggt tcagtctggc gccgaagtga agaaacctgg cagcagcgtg     420
aagatcagct gcaagacaag cggctacgcc ttcagcaact tctggatgaa ctgggtccga     480
caggcccctg acaaggcct ggaatggatc ggccaaatct atcccggcga cggcgacacc      540
aactacaacg gcaagttcaa gggcagagtg acactgaccg ccgacaagag cacaagcacc     600
gcctacatgg aactgagcag cctgagaagc gaggctaccg ccgtgtactt ctgtgccaga     660
agctactaca gaagcgcttg gtttgcctac tggggccagg gaacactcgt gaccgttagc     720
tct                                                                    723

<210> SEQ ID NO 157
<211> LENGTH: 723
<212> TYPE: DNA
<213> ORGANISM: Artificial Sequence
<220> FEATURE:
<223> OTHER INFORMATION: Synthetic Polynucleotide - "L3H2B" scFv

<400> SEQUENCE: 157
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
agattttctg gcagcggaag cggcaccgac ttcaccctgt ctatcaacag cgtggaatcc     240
gaggacattg ccgactacta ctgccagcag tccaacaact ggcccctgac atttggccag     300
ggcaccaagc tggaaatcaa aggcggaggc ggtagcggtg gcggaggtag cggaggtggt     360
ggatctcagg ttcagctggt tcagtctggc gccgaagtga agaaacctgg cagcagcgtg     420
aagatcagct gcaagacaag cggctacgcc ttcagcaact tctggatgaa ctgggtccga     480
caggcccctg acaaggcct ggaatggatc ggccaaatct atcccggcga cggcgacacc      540
aactacaacg ccaagttcaa gggcagagtg acactgaccg ccgacaagag cacaagcacc     600
gcctacatgg aactgagcag cctgagaagc gaggctaccg ccgtgtactt ctgtgccaga     660
agctactaca gaagcgcttg gtttgcctac tggggccagg gaacactcgt gaccgttagc     720
tct                                                                    723

<210> SEQ ID NO 158
<211> LENGTH: 723
<212> TYPE: DNA
<213> ORGANISM: Artificial Sequence
<220> FEATURE:
<223> OTHER INFORMATION: Synthetic Polynucleotide - "L3H3" scFv

<400> SEQUENCE: 158
gagattctgc tgacacagag ccctgacttc cagagcgtga cccctaaaga aaaagtgacc      60
ttcacctgta gagccagcca gagcatcggc acctccatcc actggtatca gcagaagccc     120
aatcagagcc ccaagctgct gattaagtac gccagcgagt ccatcagcgg cgtgccaagc     180
```

```
agattttctg gcagcggaag cggcaccgac ttcaccctgt ctatcaacag cgtggaatcc      240
gaggacattg ccgactacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
aagatcagct gcaagacaag cggctacgcc ttcagcaact ctggatgaa ctgggtcaag       480 cagcggccag gccaaggcct ggaatggatc ggacaaatct atcccggcga cggcgacacc      540
aactacaacg gcaagttcaa gggcagagct acactgaccg ccgacaagag cacaagcacc      600
gcctacatgg aactgagcag cctgagaagc gaggctaccg ccgtgtactt ctgtgccaga      660
agctactaca gaagcgcttg gtttgcctac tggggccagg gaacactcgt gaccgttagc      720
tct                                                                    723
```

```
<210> SEQ ID NO 159
<211> LENGTH: 723
<212> TYPE: DNA
<213> ORGANISM: Artificial Sequence
<220> FEATURE:
<223> OTHER INFORMATION: Synthetic Polynucleotide - "L3H4" scFv

<400> SEQUENCE: 159
gagattctgc tgacacagag ccctgacttc cagagcgtga cccctaaaga aaaagtgacc       60
ttcacctgta gagccagcca gagcatcggc acctccatcc actggtatca gcagaagccc      120
aatcagagcc ccaagctgct gattaagtac gccagcgagt ccatcagcgg cgtgccaagc      180
agattttctg gcagcggaag cggcaccgac ttcaccctgt ctatcaacag cgtggaatcc      240
gaggacattg ccgactacta ctgccagcag tccaacaact ggcccctgac atttggccag      300
ggcaccaagc tggaaatcaa aggcggaggc ggtagcggtg gcggaggtag cggaggtggt      360
ggatctcagg ttcagctggt tcagtctggc gccgaagtga agaaacctgg cagcagcgtg      420
aagatcagct gcaagacaag cggctacgcc ttcagcaact ctggatgaa ctgggtcaag       480 cagcggccag gccaaggcct ggaatggatc ggacaaatct atcccggcga cggcgacacc      540
aactacaacg gcaagttcaa gggcagagct acactgaccg ccgacaagag cagcagcacc      600
gcctacatgg aactgagcag cctgagaagc gaggctaccg ccgtgtactt ctgtgccaga      660
agctactaca gaagcgcttg gtttgcctac tggggccagg gaacactcgt gaccgttagc      720
tct                                                                    723
```

```
<210> SEQ ID NO 160
<211> LENGTH: 1255
<212> TYPE: PRT
<213> ORGANISM: Homo Sapiens

<400> SEQUENCE: 160

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80
```

-continued

```
Ala Pro Ala Thr Glu Pro Ala Ser Gly Ser Ala Ala Thr Trp Gly Gln
             85              90                  95

Asp Val Thr Ser Val Pro Val Thr Arg Pro Ala Leu Gly Ser Thr Thr
             100             105             110

Pro Pro Ala His Asp Val Thr Ser Ala Pro Asp Asn Lys Pro Ala Pro
             115             120             125

Gly Ser Thr Ala Pro Pro Ala His Gly Val Thr Ser Ala Pro Asp Thr
             130             135             140

Arg Pro Ala Pro Gly Ser Thr Ala Pro Pro Ala His Gly Val Thr Ser
145                 150             155                 160

Ala Pro Asp Thr Arg Pro Ala Pro Gly Ser Thr Ala Pro Pro Ala His
             165             170             175

Gly Val Thr Ser Ala Pro Asp Thr Arg Pro Ala Pro Gly Ser Thr Ala
             180             185             190

Pro Pro Ala His Gly Val Thr Ser Ala Pro Asp Thr Arg Pro Ala Pro
             195             200             205

Gly Ser Thr Ala Pro Pro Ala His Gly Val Thr Ser Ala Pro Asp Thr
             210             215             220

Arg Pro Ala Pro Gly Ser Thr Ala Pro Pro Ala His Gly Val Thr Ser
225                 230             235                 240

Ala Pro Asp Thr Arg Pro Ala Pro Gly Ser Thr Ala Pro Pro Ala His
             245             250             255

Gly Val Thr Ser Ala Pro Asp Thr Arg Pro Ala Pro Gly Ser Thr Ala
             260             265             270

Pro Pro Ala His Gly Val Thr Ser Ala Pro Asp Thr Arg Pro Ala Pro
             275             280             285

Gly Ser Thr Ala Pro Pro Ala His Gly Val Thr Ser Ala Pro Asp Thr
             290             295             300

Arg Pro Ala Pro Gly Ser Thr Ala Pro Pro Ala His Gly Val Thr Ser
305                 310             315                 320

Ala Pro Asp Thr Arg Pro Ala Pro Gly Ser Thr Ala Pro Pro Ala His
             325             330             335

Gly Val Thr Ser Ala Pro Asp Thr Arg Pro Ala Pro Gly Ser Thr Ala
             340             345             350

Pro Pro Ala His Gly Val Thr Ser Ala Pro Asp Thr Arg Pro Ala Pro
             355             360             365

Gly Ser Thr Ala Pro Pro Ala His Gly Val Thr Ser Ala Pro Asp Thr
             370             375             380

Arg Pro Ala Pro Gly Ser Thr Ala Pro Pro Ala His Gly Val Thr Ser
385                 390             395                 400

Ala Pro Asp Thr Arg Pro Ala Pro Gly Ser Thr Ala Pro Pro Ala His
             405             410             415

Gly Val Thr Ser Ala Pro Asp Thr Arg Pro Ala Pro Gly Ser Thr Ala
             420             425             430

Pro Pro Ala His Gly Val Thr Ser Ala Pro Asp Thr Arg Pro Ala Pro
             435             440             445

Gly Ser Thr Ala Pro Pro Ala His Gly Val Thr Ser Ala Pro Asp Thr
             450             455             460

Arg Pro Ala Pro Gly Ser Thr Ala Pro Pro Ala His Gly Val Thr Ser
465                 470             475                 480

Ala Pro Asp Thr Arg Pro Ala Pro Gly Ser Thr Ala Pro Pro Ala His
             485             490             495

Gly Val Thr Ser Ala Pro Asp Thr Arg Pro Ala Pro Gly Ser Thr Ala
```

-continued

```
                  500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
        530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
        610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
                660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
        690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
        770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
        850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
        915                 920                 925
```

-continued

```
Gly Ser Thr Ala Pro Pro Ala His Gly Val Thr Ser Ala Pro Asp Asn
    930             935             940

Arg Pro Ala Leu Gly Ser Thr Ala Pro Pro Val His Asn Val Thr Ser
945             950             955             960

Ala Ser Gly Ser Ala Ser Gly Ser Ala Ser Thr Leu Val His Asn Gly
            965             970             975

Thr Ser Ala Arg Ala Thr Thr Thr Pro Ala Ser Lys Ser Thr Pro Phe
            980             985             990

Ser Ile Pro Ser His His Ser Asp  Thr Pro Thr Thr Leu  Ala Ser His
        995             1000            1005

Ser Thr  Lys Thr Asp Ala Ser  Ser Thr His His Ser  Ser Val Pro
    1010            1015            1020

Pro Leu  Thr Ser Ser Asn His  Ser Thr Ser Pro Gln  Leu Ser Thr
    1025            1030            1035

Gly Val  Ser Phe Phe Phe Leu  Ser Phe His Ile Ser  Asn Leu Gln
    1040            1045            1050

Phe Asn  Ser Ser Leu Glu Asp  Pro Ser Thr Asp Tyr  Tyr Gln Glu
    1055            1060            1065

Leu Gln  Arg Asp Ile Ser Glu  Met Phe Leu Gln Ile  Tyr Lys Gln
    1070            1075            1080

Gly Gly  Phe Leu Gly Leu Ser  Asn Ile Lys Phe Arg  Pro Gly Ser
    1085            1090            1095

Val Val  Val Gln Leu Thr Leu  Ala Phe Arg Glu Gly  Thr Ile Asn
    1100            1105            1110

Val His  Asp Val Glu Thr Gln  Phe Asn Gln Tyr Lys  Thr Glu Ala
    1115            1120            1125

Ala Ser  Arg Tyr Asn Leu Thr  Ile Ser Asp Val Ser  Val Ser Asp
    1130            1135            1140

Val Pro  Phe Pro Phe Ser Ala  Gln Ser Gly Ala Gly  Val Pro Gly
    1145            1150            1155

Trp Gly  Ile Ala Leu Leu Val  Leu Val Cys Val Leu  Val Ala Leu
    1160            1165            1170

Ala Ile  Val Tyr Leu Ile Ala  Leu Ala Val Cys Gln  Cys Arg Arg
    1175            1180            1185

Lys Asn  Tyr Gly Gln Leu Asp  Ile Phe Pro Ala Arg  Asp Thr Tyr
    1190            1195            1200

His Pro  Met Ser Glu Tyr Pro  Thr Tyr His Thr His  Gly Arg Tyr
    1205            1210            1215

Val Pro  Pro Ser Ser Thr Asp  Arg Ser Pro Tyr Glu  Lys Val Ser
    1220            1225            1230

Ala Gly  Asn Gly Gly Ser Ser  Leu Ser Tyr Thr Asn  Pro Ala Val
    1235            1240            1245

Ala Ala  Thr Ser Ala Asn Leu
    1250            1255

<210> SEQ ID NO 161
<211> LENGTH: 1074
<212> TYPE: PRT
<213> ORGANISM: Homo Sapiens

<400> SEQUENCE: 161

Ser Gly His Ala Ser Ser Thr Pro Gly Gly Glu Lys Glu Thr Ser Ala
1               5               10              15

Thr Gln Arg Ser Ser Val Pro Ser Ser Thr Glu Lys Asn Ala Val Ser
```

-continued

```
                    20                25                30
Met Thr Ser Ser Val Leu Ser Ser His Ser Pro Gly Ser Gly Ser Ser
                35                40                45
Thr Thr Gln Gly Gln Asp Val Thr Leu Ala Pro Ala Thr Glu Pro Ala
        50                55                60
Ser Gly Ser Ala Ala Thr Trp Gly Gln Asp Val Thr Ser Val Pro Val
65                70                75                80
Thr Arg Pro Ala Leu Gly Ser Thr Thr Pro Pro Ala His Asp Val Thr
                85                90                95
Ser Ala Pro Asp Asn Lys Pro Ala Pro Gly Ser Thr Ala Pro Pro Ala
                100                105                110
His Gly Val Thr Ser Ala Pro Asp Thr Arg Pro Ala Pro Gly Ser Thr
                115                120                125
Ala Pro Pro Ala His Gly Val Thr Ser Ala Pro Asp Thr Arg Pro Ala
        130                135                140
Pro Gly Ser Thr Ala Pro Pro Ala His Gly Val Thr Ser Ala Pro Asp
145                150                155                160
Thr Arg Pro Ala Pro Gly Ser Thr Ala Pro Pro Ala His Gly Val Thr
                165                170                175
Ser Ala Pro Asp Thr Arg Pro Ala Pro Gly Ser Thr Ala Pro Pro Ala
                180                185                190
His Gly Val Thr Ser Ala Pro Asp Thr Arg Pro Ala Pro Gly Ser Thr
                195                200                205
Ala Pro Pro Ala His Gly Val Thr Ser Ala Pro Asp Thr Arg Pro Ala
        210                215                220
Pro Gly Ser Thr Ala Pro Pro Ala His Gly Val Thr Ser Ala Pro Asp
225                230                235                240
Thr Arg Pro Ala Pro Gly Ser Thr Ala Pro Pro Ala His Gly Val Thr
                245                250                255
Ser Ala Pro Asp Thr Arg Pro Ala Pro Gly Ser Thr Ala Pro Pro Ala
                260                265                270
His Gly Val Thr Ser Ala Pro Asp Thr Arg Pro Ala Pro Gly Ser Thr
                275                280                285
Ala Pro Pro Ala His Gly Val Thr Ser Ala Pro Asp Thr Arg Pro Ala
        290                295                300
Pro Gly Ser Thr Ala Pro Pro Ala His Gly Val Thr Ser Ala Pro Asp
305                310                315                320
Thr Arg Pro Ala Pro Gly Ser Thr Ala Pro Pro Ala His Gly Val Thr
                325                330                335
Ser Ala Pro Asp Thr Arg Pro Ala Pro Gly Ser Thr Ala Pro Pro Ala
                340                345                350
His Gly Val Thr Ser Ala Pro Asp Thr Arg Pro Ala Pro Gly Ser Thr
                355                360                365
Ala Pro Pro Ala His Gly Val Thr Ser Ala Pro Asp Thr Arg Pro Ala
        370                375                380
Pro Gly Ser Thr Ala Pro Pro Ala His Gly Val Thr Ser Ala Pro Asp
385                390                395                400
Thr Arg Pro Ala Pro Gly Ser Thr Ala Pro Pro Ala His Gly Val Thr
                405                410                415
Ser Ala Pro Asp Thr Arg Pro Ala Pro Gly Ser Thr Ala Pro Pro Ala
                420                425                430
His Gly Val Thr Ser Ala Pro Asp Thr Arg Pro Ala Pro Gly Ser Thr
                435                440                445
```

-continued

```
Ala Pro Pro Ala His Gly Val Thr Ser Ala Pro Asp Thr Arg Pro Ala
    450             455             460

Pro Gly Ser Thr Ala Pro Pro Ala His Gly Val Thr Ser Ala Pro Asp
465             470             475             480

Thr Arg Pro Ala Pro Gly Ser Thr Ala Pro Pro Ala His Gly Val Thr
            485             490             495

Ser Ala Pro Asp Thr Arg Pro Ala Pro Gly Ser Thr Ala Pro Pro Ala
            500             505             510

His Gly Val Thr Ser Ala Pro Asp Thr Arg Pro Ala Pro Gly Ser Thr
        515             520             525

Ala Pro Pro Ala His Gly Val Thr Ser Ala Pro Asp Thr Arg Pro Ala
    530             535             540

Pro Gly Ser Thr Ala Pro Pro Ala His Gly Val Thr Ser Ala Pro Asp
545             550             555             560

Thr Arg Pro Ala Pro Gly Ser Thr Ala Pro Pro Ala His Gly Val Thr
            565             570             575

Ser Ala Pro Asp Thr Arg Pro Ala Pro Gly Ser Thr Ala Pro Pro Ala
            580             585             590

His Gly Val Thr Ser Ala Pro Asp Thr Arg Pro Ala Pro Gly Ser Thr
        595             600             605

Ala Pro Pro Ala His Gly Val Thr Ser Ala Pro Asp Thr Arg Pro Ala
    610             615             620

Pro Gly Ser Thr Ala Pro Pro Ala His Gly Val Thr Ser Ala Pro Asp
625             630             635             640

Thr Arg Pro Ala Pro Gly Ser Thr Ala Pro Pro Ala His Gly Val Thr
            645             650             655

Ser Ala Pro Asp Thr Arg Pro Ala Pro Gly Ser Thr Ala Pro Pro Ala
            660             665             670

His Gly Val Thr Ser Ala Pro Asp Thr Arg Pro Ala Pro Gly Ser Thr
        675             680             685

Ala Pro Pro Ala His Gly Val Thr Ser Ala Pro Asp Thr Arg Pro Ala
    690             695             700

Pro Gly Ser Thr Ala Pro Pro Ala His Gly Val Thr Ser Ala Pro Asp
705             710             715             720

Thr Arg Pro Ala Pro Gly Ser Thr Ala Pro Pro Ala His Gly Val Thr
            725             730             735

Ser Ala Pro Asp Thr Arg Pro Ala Pro Gly Ser Thr Ala Pro Pro Ala
            740             745             750

His Gly Val Thr Ser Ala Pro Asp Thr Arg Pro Ala Pro Gly Ser Thr
        755             760             765

Ala Pro Pro Ala His Gly Val Thr Ser Ala Pro Asp Thr Arg Pro Ala
    770             775             780

Pro Gly Ser Thr Ala Pro Pro Ala His Gly Val Thr Ser Ala Pro Asp
785             790             795             800

Thr Arg Pro Ala Pro Gly Ser Thr Ala Pro Pro Ala His Gly Val Thr
            805             810             815

Ser Ala Pro Asp Thr Arg Pro Ala Pro Gly Ser Thr Ala Pro Pro Ala
            820             825             830

His Gly Val Thr Ser Ala Pro Asp Thr Arg Pro Ala Pro Gly Ser Thr
        835             840             845

Ala Pro Pro Ala His Gly Val Thr Ser Ala Pro Asp Thr Arg Pro Ala
    850             855             860
```

-continued

```
Pro Gly Ser Thr Ala Pro Pro Ala His Gly Val Thr Ser Ala Pro Asp
865                 870                 875                 880

Thr Arg Pro Ala Pro Gly Ser Thr Ala Pro Pro Ala His Gly Val Thr
                885                 890                 895

Ser Ala Pro Asp Thr Arg Pro Ala Pro Gly Ser Thr Ala Pro Pro Ala
                900                 905                 910

His Gly Val Thr Ser Ala Pro Asp Asn Arg Pro Ala Leu Gly Ser Thr
                915                 920                 925

Ala Pro Pro Val His Asn Val Thr Ser Ala Ser Gly Ser Ala Ser Gly
        930                 935                 940

Ser Ala Ser Thr Leu Val His Asn Gly Thr Ser Ala Arg Ala Thr Thr
945                 950                 955                 960

Thr Pro Ala Ser Lys Ser Thr Pro Phe Ser Ile Pro Ser His His Ser
                965                 970                 975

Asp Thr Pro Thr Thr Leu Ala Ser His Ser Thr Lys Thr Asp Ala Ser
                980                 985                 990

Ser Thr His His Ser Ser Val Pro Pro Leu Thr Ser Ser Asn His Ser
        995                 1000                1005

Thr Ser Pro Gln Leu Ser Thr Gly Val Ser Phe Phe Phe Leu Ser
    1010                1015                1020

Phe His Ile Ser Asn Leu Gln Phe Asn Ser Ser Leu Glu Asp Pro
    1025                1030                1035

Ser Thr Asp Tyr Tyr Gln Glu Leu Gln Arg Asp Ile Ser Glu Met
    1040                1045                1050

Phe Leu Gln Ile Tyr Lys Gln Gly Gly Phe Leu Gly Leu Ser Asn
    1055                1060                1065

Ile Lys Phe Arg Pro Gly
    1070
```

```
<210> SEQ ID NO 162
<211> LENGTH: 98
<212> TYPE: PRT
<213> ORGANISM: Homo Sapiens

<400> SEQUENCE: 162

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Thr Ile Ser Trp Val Arg Gln Ala Pro Gly Gln Gly Leu Glu Trp Met
            35                  40                  45

Gly Arg Ile Ile Pro Ile Leu Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

```
<210> SEQ ID NO 163
<211> LENGTH: 95
<212> TYPE: PRT
<213> ORGANISM: Homo Sapiens

<400> SEQUENCE: 163

Glu Ile Val Leu Thr Gln Ser Pro Asp Phe Gln Ser Val Thr Pro Lys
```

-continued

```
1               5              10              15

Glu Lys Val Thr Ile Thr Cys Arg Ala Ser Gln Ser Ile Gly Ser Ser
              20              25              30

Leu His Trp Tyr Gln Gln Lys Pro Asp Gln Ser Pro Lys Leu Leu Ile
        35              40              45

Lys Tyr Ala Ser Gln Ser Ile Ser Gly Val Pro Ser Arg Phe Ser Gly
     50              55              60

Ser Gly Ser Gly Thr Asp Phe Thr Leu Thr Ile Asn Ser Leu Glu Ala
65              70              75              80

Glu Asp Ala Ala Thr Tyr Tyr Cys His Gln Ser Ser Ser Leu Pro
              85              90              95
```

```
<210> SEQ ID NO 164
<211> LENGTH: 357
<212> TYPE: DNA
<213> ORGANISM: Artificial Sequence
<220> FEATURE:
<223> OTHER INFORMATION: H1B VH polynucleotide sequence

<400> SEQUENCE: 164
caggttcagc tggttcagtc tggcgccgaa gtgaagaaac ctggcagcag cgtgaaggtg      60
tcctgcaaga caagcggcta cgccttcagc aacttctgga tgaactgggt ccgacaggcc     120
cctggacaag cctggaatg gatcggccaa atctatcccg cgacggcga caccaactac        180 aacgccaagt tcaagggcag agtgacactg accgccgaca gagcacaag caccgcctac        240 atggaactgt ccagcctgag aagcgaggat acagccgtgt acttctgcgc ccggtcctac      300
tacagaagcg cttggtttgc ctattggggc cagggaaccc tggtcaccgt gtctagt         357
```

```
<210> SEQ ID NO 165
<211> LENGTH: 321
<212> TYPE: DNA
<213> ORGANISM: Artificial Sequence
<220> FEATURE:
<223> OTHER INFORMATION: L1 VL polynucleotide sequence

<400> SEQUENCE: 165
gagattctgc tgacacagag ccctgacttc cagagcgtga cccctaaaga aaaagtgacc      60
ttcacctgtc gcgccagcca gagcatcggc acctccatcc actggtatca gcagaagccc     120
aatcagagcc ccaagctgct gattaagtac gccagcgagt ccatcagcgg cgtgccaagc     180
agattttctg gcagcggctc tggcaccgac ttcaccctga ccatcaacag cctggaatcc     240
gaggatatcg ccacctacta ctgccagcag tccaacaact ggcccctgac atttggccag     300
ggcaccaagc tggaaatcaa a                                                321
```

```
<210> SEQ ID NO 166
<211> LENGTH: 723
<212> TYPE: DNA
<213> ORGANISM: Artificial Sequence
<220> FEATURE:
<223> OTHER INFORMATION: L1H1B scFv polynucleotide sequence

<400> SEQUENCE: 166
gagattctgc tgacacagag ccctgacttc cagagcgtga cccctaaaga aaaagtgacc      60
ttcacctgtc gcgccagcca gagcatcggc acctccatcc actggtatca gcagaagccc     120
aatcagagcc ccaagctgct gattaagtac gccagcgagt ccatcagcgg cgtgccaagc     180
agattttctg gcagcggctc tggcaccgac ttcaccctga ccatcaacag cctggaatcc     240
```

-continued

```
gaggatatcg ccacctacta ctgccagcag tccaacaact ggcccctgac atttggccag        300
ggcaccaagc tggaaatcaa aggcggaggc ggtagcggtg gcggaggtag cggaggtggt        360
ggatctcagg ttcagctggt tcagtctggc gccgaagtga agaaacctgg cagcagcgtg        420
aaggtgtcct gcaagacaag cggctacgcc ttcagcaact ctggatgaa ctgggtccga         480 caggcccctg acaaggcct  ggaatggatc ggccaaatct atcccggcga cggcgacacc        540
aactacaacg ccaagttcaa gggcagagtg acactgaccg ccgacaagag cacaagcacc        600
gcctacatgg aactgtccag cctgagaagc gaggatacag ccgtgtactt ctgcgcccgg        660
tcctactaca gaagcgcttg gtttgcctat tggggccagg gaaccctggt caccgtgtct        720
agt                                                                       723
```

```
<210> SEQ ID NO 167
<211> LENGTH: 1455
<212> TYPE: DNA
<213> ORGANISM: Artificial Sequence
<220> FEATURE:
<223> OTHER INFORMATION: L1H1B CAR polynucleotide sequence

<400> SEQUENCE: 167
atggctctgc ctgtgacagc tctgcttctg cctctggcac tgcttcttca tgcggcgcgc         60
cctgagattc tgctgacaca gagccctgac ttccagagcg tgaccctaa agaaaaagtg        120 accttcacct gtcgcgccag ccagagcatc ggcacctcca tccactggta tcagcagaag        180
cccaatcaga gccccaagct gctgattaag tacgccagcg agtccatcag cggcgtgcca        240
agcagatttt ctggcagcgg ctctggcacc gacttcaccc tgaccatcaa cagcctggaa        300
tccgaggata tcgccaccta ctactgccag cagtccaaca actggcccct gacatttggc        360
cagggcacca agctggaaat caaaggcgga ggcggtagcg tggcggagg tagcggaggt        420 ggtggatctc aggttcagct ggttcagtct ggcgccgaag tgaagaaacc tggcagcagc        480
gtgaaggtgt cctgcaagac aagcggctac gccttcagca cttctggat gaactgggtc        540 cgacaggccc ctggacaagg cctggaatgg atcggccaaa tctatcccgg cgacggcgac        600
accaactaca acgccaagtt caagggcaga gtgacactga ccgccgacaa gagcacaagc        660
accgcctaca tggaactgtc cagcctgaga agcgaggata cagccgtgta cttctgcgcc        720
cggtcctact acagaagcgc ttggtttgcc tattggggcc agggaaccct ggtcaccgtg        780
tctagtacaa caacaccggc gcctcggcct ccaacaccag ctcctacaat tgctagccag        840
ccactgtctc tgaggcccga ggcttgtaga cctgctgctg cgggagctgt gcacacaaga        900
ggactggatt tcgcctgcga catctatatc tgggcccctc tggccggaac atgtggcgtt        960
ctgctgctca gcctggtcat caccctgtac tgcaagcggg gcagaaagaa gctgctgtac       1020
atctttaagc agcccttcat gaggcccgtg cagaccacac aagaagagga cggctgctcc       1080
tgccgcttcc ccgaggaaga agaaggcggt gcgaactga gagtgaagtt cagcagatcc       1140
gccgacgcac ccgcctataa gcagggacag aatcagctgt acaacgagct gaatctgggg       1200
cgcagagaag agtacgacgt gctggacaag agaagaggca gggaccctga gatgggcggc       1260
aagcccagaa gaaagaaccc tcaagagggc ctgtataatg agctgcagaa agacaagatg       1320
gccgaggcct acagcgagat cggaatgaag ggcgagcgca agagaggcaa gggtcacgat       1380
ggactgtacc agggcctgag caccgccacc aaggatacct atgatgccct gcacatgcag       1440
gccctgcctc caaga                                                        1455
```

<210> SEQ ID NO 168
<211> LENGTH: 135
<212> TYPE: DNA
<213> ORGANISM: Artificial Sequence
<220> FEATURE:
<223> OTHER INFORMATION: CD8a hinge polynucleotide sequence

<400> SEQUENCE: 168
acaacaacac cggcgcctcg gcctccaaca ccagctccta caattgctag ccagccactg      60
tctctgaggc ccgaggcttg tagacctgct gctggcggag ctgtgcacac aagaggactg     120
gatttcgcct gcgac                                                       135

<210> SEQ ID NO 169
<211> LENGTH: 72
<212> TYPE: DNA
<213> ORGANISM: Artificial Sequence
<220> FEATURE:
<223> OTHER INFORMATION: CD8a transmembrane polynucleotide sequence

<400> SEQUENCE: 169
atctatatct gggcccctct ggccggaaca tgtggcgttc tgctgctcag cctggtcatc      60
accctgtact gc                                                          72

<210> SEQ ID NO 170
<211> LENGTH: 126
<212> TYPE: DNA
<213> ORGANISM: Artificial Sequence
<220> FEATURE:
<223> OTHER INFORMATION: 41BB polynucleotide sequence

<400> SEQUENCE: 170
aagcggggca gaaagaagct gctgtacatc tttaagcagc ccttcatgag gcccgtgcag      60
accacacaag aagaggacgg ctgctcctgc cgcttccccg aggaagaaga aggcggttgc     120
gaactg                                                                126

<210> SEQ ID NO 171
<211> LENGTH: 336
<212> TYPE: DNA
<213> ORGANISM: Artificial Sequence
<220> FEATURE:
<223> OTHER INFORMATION: CD3z polynucleotide sequence

<400> SEQUENCE: 171
agagtgaagt tcagcagatc cgccgacgca cccgcctata agcagggaca gaatcagctg      60
tacaacgagc tgaatctggg cgcgcagagaa gagtacgacg tgctggacaa gagaagaggc     120
agggaccctg agatgggcgg caagcccaga agaaagaacc ctcaagaggg cctgtataat     180
gagctgcaga aagacaagat ggccgaggcc tacagcgaga tcggaatgaa gggcgagcgc     240
agaagaggca agggtcacga tggactgtac cagggcctga gcaccgccac caaggatacc     300
tatgatgccc tgcacatgca ggccctgcct ccaaga                              336

<210> SEQ ID NO 172
<211> LENGTH: 395
<212> TYPE: PRT
<213> ORGANISM: Artificial Sequence
<220> FEATURE:
<223> OTHER INFORMATION: ic9 polypeptide sequence

<400> SEQUENCE: 172

Met Gly Val Gln Val Glu Thr Ile Ser Pro Gly Asp Gly Arg Thr Phe
1               5                   10                  15

-continued

```
Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
            35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Gly Gly
            100                 105                 110

Ser Gly Phe Gly Asp Val Gly Ala Leu Glu Ser Leu Arg Gly Asn Ala
            115                 120                 125

Asp Leu Ala Tyr Ile Leu Ser Met Glu Pro Cys Gly His Cys Leu Ile
    130                 135                 140

Ile Asn Asn Val Asn Phe Cys Arg Glu Ser Gly Leu Arg Thr Arg Thr
145                 150                 155                 160

Gly Ser Asn Ile Asp Cys Glu Lys Leu Arg Arg Arg Phe Ser Ser Leu
                165                 170                 175

His Phe Met Val Glu Val Lys Gly Asp Leu Thr Ala Lys Lys Met Val
            180                 185                 190

Leu Ala Leu Leu Glu Leu Ala Gln Gln Asp His Gly Ala Leu Asp Cys
            195                 200                 205

Cys Val Val Val Ile Leu Ser His Gly Cys Gln Ala Ser His Leu Gln
    210                 215                 220

Phe Pro Gly Ala Val Tyr Gly Thr Asp Gly Cys Pro Val Ser Val Glu
225                 230                 235                 240

Lys Ile Val Asn Ile Phe Asn Gly Thr Ser Cys Pro Ser Leu Gly Gly
                245                 250                 255

Lys Pro Lys Leu Phe Phe Ile Gln Ala Cys Gly Gly Glu Gln Lys Asp
            260                 265                 270

His Gly Phe Glu Val Ala Ser Thr Ser Pro Glu Asp Glu Ser Pro Gly
            275                 280                 285

Ser Asn Pro Glu Pro Asp Ala Thr Pro Phe Gln Glu Gly Leu Arg Thr
    290                 295                 300

Phe Asp Gln Leu Asp Ala Ile Ser Ser Leu Pro Thr Pro Ser Asp Ile
305                 310                 315                 320

Phe Val Ser Tyr Ser Thr Phe Pro Gly Phe Val Ser Trp Arg Asp Pro
                325                 330                 335

Lys Ser Gly Ser Trp Tyr Val Glu Thr Leu Asp Asp Ile Phe Glu Gln
            340                 345                 350

Trp Ala His Ser Glu Asp Leu Gln Ser Leu Leu Leu Arg Val Ala Asn
            355                 360                 365

Ala Val Ser Val Lys Gly Ile Tyr Lys Gln Met Pro Gly Cys Phe Asn
    370                 375                 380

Phe Leu Arg Lys Lys Leu Phe Phe Lys Thr Ser
385                 390                 395
```

<210> SEQ ID NO 173
<211> LENGTH: 1185
<212> TYPE: DNA
<213> ORGANISM: Artificial Sequence
<220> FEATURE:

<223> OTHER INFORMATION: ic9 polynucleotide sequence

<400> SEQUENCE: 173
atgggcgtgc aggtcgagac aatttctcct ggcgacggcc ggacattccc taagcgagga     60
cagacatgcg tggtgcacta caccggcatg ctggaagatg gcaagaaggt ggacagcagc    120
cgggacagaa acaagccctt caagttcatg ctgggcaagc aagaagtgat cagaggctgg    180
gaagagggcg tcgcccagat gtctgttgga cagagagcca agctgacaat cagccccgat    240
tacgcctatg gcgccacagg acaccctggc atcattcctc acatgccac actggtgttc     300 gacgtggaac tgctgaagct ggaaggcggc ggaggatctg gctttggaga tgtgggagcc    360
ctggaaagcc tgagaggcaa tgccgatctg gcctacatcc tgagcatgga accttgcggc    420
cactgcctga ttatcaacaa cgtgaacttc tgcagagaga gcggcctgag aaccagaacc    480
ggcagcaaca tcgactgcga gaagctgcgg agaagattca gcagcctgca cttcatggtg    540
gaagtgaagg gcgacctgac cgccaagaaa atggtgctgg ctctgctgga actggcccag    600
caagatcatg gcgccctgga ttgctgtgtg gtcgtgatcc tgtctcacgg ctgtcaggcc    660
agccatctgc aattccctgg cgccgtgtat ggcaccgatg gctgtcctgt gtccgtggaa    720
aagatcgtga acatcttcaa cggcaccagc tgtcctagcc tcggcggaaa gcccaagctg    780
ttcttcatcc aagcctgtgg cggcgagcag aaggatcacg gatttgaggt ggccagcaca    840
agccccgagg atgagtctcc tggaagcaac cctgagcctg acgccacacc tttccaagag    900
ggactgagaa ccttcgacca gctggacgct atcagctccc tgcctacacc tagcgacatc    960
ttcgtgtcct acagcacatt ccccggcttt gtgtcttggc gggaccctaa gtctggctct   1020
tggtatgtgg aaaccctgga cgatatcttc gagcagtggg cccatagcga ggacctgcaa   1080
tctctgctgc tgagagtggc caatgccgtg tccgtgaagg gcatctacaa gcagatgcct   1140
ggctgcttca acttcctgcg gaagaagctg tttttcaaga ccagc                    1185

<210> SEQ ID NO 174
<211> LENGTH: 561
<212> TYPE: DNA
<213> ORGANISM: Artificial Sequence
<220> FEATURE:
<223> OTHER INFORMATION: DHFR polynucleotide sequence

<400> SEQUENCE: 174
atggtcggaa gcctgaactg catcgtggcc gtgtctcaga acatgggcat cggcaagaac     60
ggcgacttcc cttggcctcc tctgagaaac gagagccgct acttccagcg gatgaccacc    120
acaagctccg tggaaggcaa gcagaacctc gtgatcatgg gcaagaaaac ctggttcagc    180
atccctgaga gaacagacc cctgaagggc agaatcaacc tggtgctgag cagagagctg    240
aaagagcctc tcaaggcgc ccacttcctg agcagatctc tggacgatgc cctgaagctg     300
accgagcagc cagaactggc caacaaagtg gacatggtct ggatcgtcgg cggcagctcc    360
gtgtacaaag aagccatgaa tcaccccggc cacctgaaac tgttcgtgac cagaatcatg    420
caggacttcg agagcgacac attcttcccg gagatcgacc tggaaaagta caaactgctg    480
cctgagtacc ccggcgtgct gagcgacgtg caagaggaaa agggcatcaa gtacaagttc    540
gaggtgtacg agaagaacga c                                              561

<210> SEQ ID NO 175
<211> LENGTH: 6616
<212> TYPE: DNA
<213> ORGANISM: Artificial Sequence -continued

```
<220> FEATURE:
<223> OTHER INFORMATION: L1H1B transposon polynucleotide sequence

<400> SEQUENCE: 175
tgtacataga ttaaccctag aaagataatc atattgtgac gtacgttaaa gataatcatg      60
cgtaaaattg acgcatgtgt tttatcggtc tgtatatcga ggtttattta ttaatttgaa     120
tagatattaa gttttattat atttacactt acatactaat aataaattca acaaacaatt     180
tatttatgtt tatttattta ttaaaaaaaa acaaaaactc aaaatttctt ctataaagta     240
acaaaacttt tatcgaatac ctgcagcccg ggggatgcag agggacagcc cccccccaaa     300
gcccccaggg atgtaattac gtccctcccc cgctaggggg cagcagcgag ccgcccgggg     360
ctccgctccg gtccggcgct ccccccgcat ccccgagccg gcagcgtgcg gggacagccc     420
gggcacgggg aaggtggcac gggatcgctt tcctctgaac gcttctcgct gctctttgag     480
cctgcagaca cctgggggga tacggggaaa agttgactgt gcctttcgat cgaaccatgg     540
acagttagct ttgcaaagat ggataaagtt ttaaacagag aggaatcttt gcagctaatg     600
gaccttctag gtcttgaaag gagtgggaat tggctccggt gcccgtcagt gggcagagcg     660
cacatcgccc acagtccccg agaagttggg gggaggggtc ggcaattgaa ccggtgccta     720
gagaaggtgg cgcggggtaa actgggaaag tgatgtcgtg tactggctcc gccttttttcc    780 cgagggtggg ggagaaccgt atataagtgc agtagtcgcc gtgaacgttc tttttcgcaa     840
cgggtttgcc gccagaacac aggtaagtgc cgtgtgtggt tcccgcgggc ctggcctctt     900
tacgggttat ggcccttgcg tgccttgaat tacttccacc tggctgcagt acgtgattct     960
tgatcccgag cttcgggttg gaagtgggtg ggagagttcg aggccttgcg cttaaggagc    1020
cccttcgcct cgtgcttgag ttgaggcctg gcctgggcgc tggggccgcc gcgtgcgaat    1080
ctggtggcac cttcgcgcct gtctcgctgc tttcgataag tctctagcca tttaaaattt    1140
ttgatgacct gctgcgacgc tttttttctg gcaagatagt cttgtaaatg cgggccaaga    1200
tctgcacact ggtatttcgg tttttggggc cgcgggcggc gacggggccc gtgcgtccca    1260
gcgcacatgt tcggcgaggc ggggcctgcg agcgcggcca ccgagaatcg gacgggggta    1320
gtctcaagct ggccggcctg ctctggtgcc tggcctcgcg ccgccgtgta tcgccccgcc    1380
ctgggcggca aggctggccc ggtcggcacc agttgcgtga gcggaaagat ggccgcttcc    1440
cggccctgct gcagggagct caaaatggag gacgcggcgc tcgggagagc gggcgggtga    1500
gtcacccaca caaaggaaaa gggcctttcc gtcctcagcc gtcgcttcat gtgactccac    1560
ggagtaccgg gcgccgtcca ggcacctcga ttagttctcg agcttttgga gtacgtcgtc    1620
tttaggttgg ggggaggggt tttatgcgat ggagtttccc cacactgagt gggtggagac    1680
tgaagttagg ccagcttggc acttgatgta attctccttg gaatttgccc tttttgagtt    1740
tggatcttgg ttcattctca agcctcagac agtggttcaa agtttttttc ttccatttca    1800
ggtgtcgtga gaattctaat acgactcact ataggggtgcg gccgccacca tgggcgtgca    1860
ggtcgagaca atttctcctg gcgacggccg gacattccct aagcgaggac agacatgcgt    1920
ggtgcactac accggcatgc tggaagatgg caagaaggtg gacagcagcc gggacagaaa    1980
caagcccttc aagttcatgc tgggcaagca agaagtgatc agaggctggg aagagggcgt    2040
cgcccagatg tctgttggac agagagccaa gctgacaatc agccccgatt acgcctatgg    2100
cgccacagga caccctggca tcattcctcc acatgccaca ctggtgttcg acgtggaact    2160
gctgaagctg gaaggcggcg gaggatctgg ctttggagat gtgggagccc tggaaagcct    2220
```

-continued

```
gagaggcaat gccgatctgg cctacatcct gagcatggaa ccttgcggcc actgcctgat    2280
tatcaacaac gtgaacttct gcagagagag cggcctgaga accagaaccg gcagcaacat    2340
cgactgcgag aagctgcgga gaagattcag cagcctgcac ttcatggtgg aagtgaaggg    2400
cgacctgacc gccaagaaaa tggtgctggc tctgctggaa ctggcccagc aagatcatgg    2460
cgccctggat tgctgtgtgg tcgtgatcct gtctcacggc tgtcaggcca gccatctgca    2520
attccctggc gccgtgtatg gcaccgatgg ctgtcctgtg tccgtggaaa agatcgtgaa    2580
catcttcaac ggcaccagct gtcctagcct cggcggaaag cccaagctgt tcttcatcca    2640
agcctgtggc ggcgagcaga aggatcacgg atttgaggtg gccagcacaa gccccgagga    2700
tgagtctcct ggaagcaacc ctgagcctga cgccacacct ttccaagagg gactgagaac    2760
cttcgaccag ctggacgcta tcagctccct gcctacacct agcgacatct tcgtgtccta    2820
cagcacattc cccggctttg tgtcttggcg ggaccctaag tctggctctt ggtatgtgga    2880
aaccctggac gatatcttcg agcagtgggc ccatagcgag gacctgcaat ctctgctgct    2940
gagagtggcc aatgccgtgt ccgtgaaggg catctacaag cagatgcctg gctgcttcaa    3000
cttcctgcgg aagaagctgt ttttcaagac cagcggcagc ggcgaaggca gaggatccct    3060
tttgacatgc ggcgacgtcg aagagaaccc cggacctatg gctctgcctg tgacagctct    3120
gcttctgcct ctggcactgc ttcttcatgc ggcgcgccct gagattctgc tgacacagag    3180
ccctgacttc cagagcgtga cccctaaaga aaaagtgacc ttcacctgtc gcgccagcca    3240
gagcatcggc acctccatcc actggtatca gcagaagccc aatcagagcc ccaagctgct    3300
gattaagtac gccagcgagt ccatcagcgg cgtgccaagc agattttctg gcagcggctc    3360
tggcaccgac ttcaccctga ccatcaacag cctggaatcc gaggatatcg ccacctacta    3420
ctgccagcag tccaacaact ggcccctgac atttggccag ggcaccaagc tggaaatcaa    3480
aggcggaggc ggtagcggtg gcggaggtag cggaggtggt ggatctcagg ttcagctggt    3540
tcagtctggc gccgaagtga agaaacctgg cagcagcgtg aaggtgtcct gcaagacaag    3600
cggctacgcc ttcagcaact tctggatgaa ctgggtccga caggcccctg acaaggcct    3660 ggaatggatc ggccaaatct atcccggcga cggcgacacc aactacaacg ccaagttcaa    3720
gggcagagtg acactgaccg ccgacaagag cacaagcacc gcctacatgg aactgtccag    3780
cctgagaagc gaggatacag ccgtgtactt ctgcgcccgg tcctactaca gaagcgcttg    3840
gtttgcctat tggggccagg gaaccctggt caccgtgtct agtacaacaa caccggcgcc    3900
tcggcctcca acaccagctc ctacaattgc tagccagcca ctgtctctga ggcccgaggc    3960
ttgtagacct gctgctggcg gagctgtgca cacaagagga ctggatttcg cctgcgacat    4020
ctatatctgg gcccctctgg ccggaacatg tggcgttctg ctgctcagcc tggtcatcac    4080
cctgtactgc aagcggggca gaaagaagct gctgtacatc tttaagcagc ccttcatgag    4140
gcccgtgcag accacacaag aagaggacgg ctgctcctgc cgcttccccg aggaagaaga    4200
aggcggttgc gaactgagag tgaagttcag cagatccgcc gacgcacccg cctataagca    4260
gggacagaat cagctgtaca acgagctgaa tctggggcgc agagaagagt acgacgtgct    4320
ggacaagaga gagaggcaggg accctgagat gggcggcaag cccagaagaa agaaccctca    4380
agagggcctg tataatgagc tgcagaaaga caagatggcc gaggcctaca gcgagatcgg    4440
aatgaagggc gagcgcagaa gaggcaaggg tcacgatgga ctgtaccagg gcctgagcac    4500
cgccaccaag gataccatg atgccctgca catgcaggcc ctgcctccaa gaggaagtgg    4560
cgaaggacgg ggatctcttc tcacgtgcgg ggatgttgaa gagaatcctg gtccaatggt    4620
```

-continued

```
cggaagcctg aactgcatcg tggccgtgtc tcagaacatg ggcatcggca agaacggcga     4680
cttcccttgg cctcctctga gaaacgagag ccgctacttc cagcggatga ccaccacaag     4740
ctccgtggaa ggcaagcaga acctcgtgat catgggcaag aaaacctggt tcagcatccc     4800
tgagaagaac agacccctga agggcagaat caacctggtg ctgagcagag agctgaaaga     4860
gcctcctcaa ggcgcccact tcctgagcag atctctggac gatgccctga agctgaccga     4920
gcagccagaa ctggccaaca aagtggacat ggtctggatc gtcggcggca gctccgtgta     4980
caaagaagcc atgaatcacc ccggccacct gaaactgttc gtgaccagaa tcatgcagga     5040
cttcgagagc gacacattct tcccggagat cgacctggaa aagtacaaac tgctgcctga     5100
gtaccccggc gtgctgagcg acgtgcaaga ggaaaagggc atcaagtaca agttcgaggt     5160
gtacgagaag aacgactaat aaggtaccga tcacatatgc ctttaattaa acactagttc     5220
tatagtgtca cctaaattcc ctttagtgag ggttaatggc cgtaggccgc cagaattggg     5280
tccagacatg ataagataca ttgatgagtt tggacaaacc acaactagaa tgcagtgaaa     5340
aaaatgcttt atttgtgaaa tttgtgatgc tattgcttta tttgtaacca ttataagctg     5400
caataaacaa gttaacaaca caattgcat tcattttatg tttcaggttc aggggggaggt     5460 gtgggaggtt ttttcggact ctaggacctg cgcatgcgct tggcgtaatc atggtcatag     5520
ctgtttcctg ttttccccgt atccccccag gtgtctgcag gctcaaagag cagcgagaag     5580
cgttcagagg aaagcgatcc cgtgccacct tccccgtgcc cgggctgtcc ccgcacgctg     5640
ccggctcggg gatgcggggg gagcgccgga ccggagcgga gccccgggcg gctcgctgct     5700
gccccctagc gggggaggga cgtaattaca tccctggggg ctttgggggg gggctgtccc     5760
tctcaccgcg gtggagctcc agcttttgtt cgaattgggg cccccctcg agggtatcga     5820 tgatatctat aacaagaaaa tatatatata ataagttatc acgtaagtag aacatgaaat     5880
aacaatataa ttatcgtatg agttaaatct taaaagtcac gtaaaagata atcatgcgtc     5940
attttgactc acgcggtcgt tatagttcaa aatcagtgac acttaccgca ttgacaagca     6000
cgcctcacgg gagctccaag cggcgactga gatgtcctaa atgcacagcg acggattcgc     6060
gctatttaga aagagagagc aatatttcaa gaatgcatgc gtcaatttta cgcagactat     6120
ctttctaggg ttaatctagc tagccttaag ggcgcagccc gcctaatgag cgggcttttt     6180
tttggcttgt tgtccacaac cgttaaacct taaaagcttt aaaagcctta tatattcttt     6240
tttttcttat aaaacttaaa accttagagg ctatttaagt tgctgattta tattaatttt     6300
attgttcaaa catgagagct tagtacgtga aacatgagag cttagtacgt tagccatgag     6360
agcttagtac gttagccatg agggtttagt tcgttaaaca tgagagctta gtacgttaaa     6420
catgagagct tagtacgtac tatcaacagg ttgaactgct gatccacgtt gtggtagaat     6480
tggtaaagag agtcgtgtaa aatatcgagt tcgcacatct tgttgtctga ttattgattt     6540
ttggcgaaac catttgatca tatgacaaga tgtgtatcta ccttaactta atgattttga     6600
taaaaatcat taggta                                                      6616
```

<210> SEQ ID NO 176
<211> LENGTH: 107
<212> TYPE: PRT
<213> ORGANISM: Artificial Sequence
<220> FEATURE:
<223> OTHER INFORMATION: synthetic polypeptide sequence

<400> SEQUENCE: 176

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Phe Trp
            20                  25                  30

Met Asn Trp Val Arg Gln Ala Pro Gly Gln Gly Leu Glu Trp Met Gly
        35                  40                  45

Gln Ile Tyr Pro Gly Asp Gly Asp Thr Asn Tyr Asn Ala Lys Phe Lys
    50                  55                  60

Gly Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Tyr Tyr Arg Ser Ala Trp Phe Ala Tyr
            100                 105
```

```
<210> SEQ ID NO 177
<211> LENGTH: 97
<212> TYPE: PRT
<213> ORGANISM: Artificial Sequence
<220> FEATURE:
<223> OTHER INFORMATION: synthetic polypeptide sequence

<400> SEQUENCE: 177
```

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr
```

```
<210> SEQ ID NO 178
<211> LENGTH: 119
<212> TYPE: PRT
<213> ORGANISM: Artificial Sequence
<220> FEATURE:
<223> OTHER INFORMATION: synthetic polypeptide sequence

<400> SEQUENCE: 178
```

```
Gln Val Gln Leu Gln Gln Ser Gly Ala Glu Leu Val Arg Pro Gly Ser
1               5                   10                  15

Ser Val Lys Ile Ser Cys Lys Thr Ser Gly Tyr Ala Phe Ser Asn Phe
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Ala Ser Ala Val Tyr Phe Cys
                85                  90                  95
```

```
Ala Arg Ser Tyr Tyr Arg Ser Ala Trp Phe Ala Tyr Trp Gly Gln Gly
            100                 105                 110

Thr Leu Val Ser Val Ser Ala
        115

<210> SEQ ID NO 179
<211> LENGTH: 107
<212> TYPE: PRT
<213> ORGANISM: Artificial Sequence
<220> FEATURE:
<223> OTHER INFORMATION: Synthetic polypeptide sequence

<400> SEQUENCE: 179

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Ala Gly Thr Lys Leu Glu Leu Lys
            100                 105

<210> SEQ ID NO 180
<211> LENGTH: 119
<212> TYPE: PRT
<213> ORGANISM: Artificial Sequence
<220> FEATURE:
<223> OTHER INFORMATION: synthetic polypeptide sequence

<400> SEQUENCE: 180

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Phe
            20                  25                  30

Trp Met Asn Trp Val Arg Gln Met Pro Gly Lys Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Leu
        115

<210> SEQ ID NO 181
<211> LENGTH: 107
<212> TYPE: PRT
<213> ORGANISM: Artificial Sequence
<220> FEATURE:
<223> OTHER INFORMATION: synthetic polypeptide sequence
```

-continued

```
<400> SEQUENCE: 181

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr Phe Gly Gln Gly Thr Lys Val Glu Ile Lys
                100                 105
```